(12) United States Patent
Shinohata et al.

(10) Patent No.: US 8,168,812 B2
(45) Date of Patent: May 1, 2012

(54) PROCESS FOR PRODUCING ALKYL TIN ALKOXIDE COMPOUND AND PROCESS FOR PRODUCING CARBONIC ACID ESTER USING SAID COMPOUND

(75) Inventors: Masaaki Shinohata, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 87 days.

(21) Appl. No.: 12/811,335

(22) PCT Filed: Mar. 31, 2009

(86) PCT No.: PCT/JP2009/056756
§ 371 (c)(1),
(2), (4) Date: Jun. 30, 2010

(87) PCT Pub. No.: WO2010/016297
PCT Pub. Date: Feb. 11, 2010

(65) Prior Publication Data
US 2010/0292496 A1   Nov. 18, 2010

(30) Foreign Application Priority Data

Aug. 8, 2008   (JP) ................. 2008-206205

(51) Int. Cl.
*C07F 7/00* (2006.01)
*C07C 69/96* (2006.01)

(52) U.S. Cl. ............................ 556/83; 556/89; 558/260
(58) Field of Classification Search ............. 556/83, 556/89; 558/206
See application file for complete search history.

(56) References Cited

U.S. PATENT DOCUMENTS

| 5,545,600 | A | 8/1996 | Knudsen et al. |
| 6,414,174 | B1 * | 7/2002 | Boyle .................. 556/83 |
| 7,541,482 | B2 * | 6/2009 | Miyake et al. ............ 556/89 |
| 2005/0080274 | A1 | 4/2005 | Miyake et al. |
| 2005/0240045 | A1 | 10/2005 | Miyake et al. |
| 2008/0275262 | A1 | 11/2008 | Miyake et al. |
| 2010/0041908 | A1 | 2/2010 | Shinohata et al. |

FOREIGN PATENT DOCUMENTS

| JP | 2005-298433 | 10/2005 |
| JP | 2006-028066 | 2/2006 |
| WO | WO 03/055840 | 7/2003 |
| WO | WO 2004/014840 | 2/2004 |
| WO | WO 2005/111049 | 11/2005 |
| WO | WO 2008/044575 | 4/2008 |

OTHER PUBLICATIONS

Gerrard, et al., "Alkyltin Route to Alkylboron and Alkyltin Halides and Compounds Prepared therefrom", Journal of Chemical Society, pp. 740-745, 1964.
Encyclopedia Chimica, Koyoritsu Publishing Co., Ltd., 2003.

* cited by examiner

*Primary Examiner* — Porfirio Nazario Gonzalez
(74) *Attorney, Agent, or Firm* — Morgan, Lewis & Bockius LLP

(57) ABSTRACT

The present invention provides a process for producing: a compound represented by $XOR^2$; a dialkyl tin dialkoxide compound having one tin atom, two $Sn-R^1$ bonds and two $Sn-OR^2$ bonds; and/or a tetraalkyl dialkoxy distannoxane compound having one Sn—O—Sn bond, in which each tin atom of the tetraalkyl dialkoxy distannoxane compound has two $Sn-R^1$ bonds and one $Sn-OR^2$ bond.

20 Claims, 8 Drawing Sheets

PROCESS FOR PRODUCING ALKYL TIN ALKOXIDE COMPOUND AND PROCESS FOR PRODUCING CARBONIC ACID ESTER USING SAID COMPOUND

CROSS-REFERENCE TO RELATED APPLICATIONS

The present application is a U.S. National Phase Application of International Application PCT/JP2009/056756 filed Mar. 31, 2009, which claims the benefit of Japanese Patent Application No. 2008-206205, filed Aug. 8, 2008, which are hereby incorporated by reference in their entirety.

TECHNICAL FIELD

The present invention relates to a production of a dialkyl tin dialkoxide compound and/or tetraalkyl dialkoxy distannoxane compound as a catalyst used in the production of esters and carbonic acid esters, and to a production of an ester and carbonic acid ester using the dialkyl tin dialkoxide compound and/or tetraalkyl dialkoxy distannoxane compound.

BACKGROUND ART

Dialkyl tin dialkoxide compounds and tetraalkyl dialkoxy distannoxane compounds are extremely useful as catalysts such as ester synthesis catalysts, carbonic acid ester synthesis catalysts, transesterification reaction catalysts and silicone polymer or urethane curing catalysts. In particular, in addition to carbonic acid esters being used as additives such as gasoline additives for improving octane value and diesel fuel additives for reducing particle levels in exhaust gas, these useful compounds are also used as alkylation agents, carbonylation agents or solvents and the like during synthesis of polycarbonates, urethanes, pharmaceuticals, agricultural chemicals and other organic compounds, or as lithium battery electrolytes, lubricating oil raw materials and raw materials of deoxygenating agents for rust prevention of boiler pipes. Dialkyl tin dialkoxide compounds and tetraalkyl dialkoxy distannoxane compounds are particularly attracting attention as synthesis catalysts. For example, Patent document 1 (International Publication No. WO 2003/055840) discloses a process for producing a carbonic acid ester comprising reacting an organometallic compound containing dialkyl tin dialkoxide with carbon dioxide followed by thermal decomposition of the formed addition product.

Various methods are known for producing dialkyl tin dialkoxide compounds and tetraalkyl dialkoxy distannoxane compounds.

For example, Patent document 2 (U.S. Pat. No. 5,545,600) discloses a process comprising carrying out a dehydration reaction on a dialkyl tin oxide and an alcohol and removing the resulting low boiling point component that contains water from the reaction liquid. This reaction is presumed to be a sequential equilibrium reaction accompanying dehydration as shown in formulas (1) and (2) below, and in order to obtain dialkyl tin dialkoxide at high yield, the dialkyl tin dialkoxide is produced while extracting the water formed by each dehydration reaction outside the system. Moreover, since this reaction is disadvantageous in terms of energy, it is necessary to carry out the reaction for a long time at a high temperature (for example, 180° C.), and there are cases in which thermal denaturation reactions occur in the products in the form of dialkyl tin dialkoxide compounds and tetraalkyl dialkoxy distannoxane compounds due to this heating for a long period of time at high temperatures. Since the dialkyl tin compound is a solid, there are cases in which handling difficulties occur during production by a continuous process.

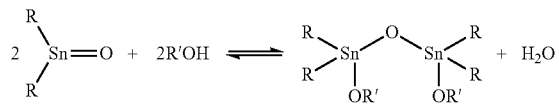
(1)

(wherein each of R and R' independently represents an alkyl group.)

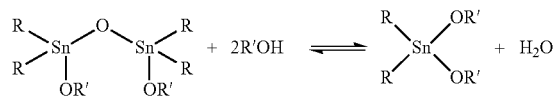
(2)

(wherein each of R and R' independently represent an alkyl group.)

In addition, Non-Patent document 1 (Journal of Chemical Society, p. 740, 1964) discloses a process for producing diethyl tin dibutoxide by reacting diethyl dichloro tin and sodium butoxide. In this reaction, since a byproduct in the form of sodium chloride is formed as a solid, the liquid after the reaction is in the form of a slurry, thus resulting in the possibility of handling difficulties when purifying the tin compound and the like.

On the other hand, Patent document 3 (International Patent Publication No. WO 2008/044575) describes a process in which a deactivated composition of a tin catalyst formed in the production process of carbonic acid ester is regenerated and again used as a catalyst in the production of carbonic acid ester. This regeneration process produces a dialkyl tin compound by heat-treating a compound produced by reacting a composition containing a deactivated form of a dialkyl tin alkoxide compound formed in the production process of carbonic acid ester with acid and/or acid anhydride, and the dialkyl tin compound is further regenerated to a dialkyl tin alkoxide compound.

PRIOR ART REFERENCES

Patent Documents

Patent document 1: International Publication No. WO 2003/055840
Patent document 2: U.S. Pat. No. 5,545,600
Patent document 3: International Patent Publication No. WO 2008/044575

Non-Patent Documents

Non-Patent document 1: Journal of Chemical Society, p. 740, 1964

DISCLOSURE OF INVENTION

Problems to be Solved by the Invention

However, in a step for regenerating the dialkyl tin compound to the dialkyl tin dialkoxide compound, a composition containing dialkyl tin oxide is obtained by reacting the dialkyl tin compound with an aqueous alkaline solution, the composition is reacted with an alcohol, and a component containing the formed water is removed from the reaction liquid, and since this is accompanied by a dehydration reaction as represented by formulas (1) and (2) above, there are cases in which this step may be accompanied by a thermal denaturation reaction of the dialkyl tin dialkoxide compound and tetraalkyl dialkoxy distannoxane compound as previously described. Moreover, since the dialkyl tin oxide is a solid in this step, steps involving the handling of a liquid and steps involving the handling of a solid are both present, thereby resulting in difficulty with respect to industrial implementation.

As has been described above, the problem of developing a technology for easily producing the dialkyl tin dialkoxide compound and/or tetraalkyl dialkoxy distannoxane compound without having to handle compounds in a solid state remains unsolved at the present.

Therefore, an object of the present invention is to provide a process for producing dialkyl tin alkoxide compounds without involving the handling of solid tin compounds. Another object of the present invention is to provide a method for using the dialkyl tin alkoxide compounds produced in the production of carbonic acid esters.

Means for Solving the Problems

As a result of conducting extensive studies on the above-mentioned problems, the inventors of the present invention found that the above-mentioned problems can be solved by producing a dialkyl tin alkoxide compound and/or tetraalkyl dialkoxy distannoxane compound by reacting a specific dialkyl tin compound and/or tetraalkyl distannoxane compound with a carbonic acid ester and/or an alcohol, thereby leading to completion of the present invention.

Namely, the present invention provides:

[1] a process for producing a compound represented by $XOR^2$;
  a dialkyl tin dialkoxide compound having one tin atom, two $Sn-R^1$ bonds and two $Sn-OR^2$ bonds; and/or
  a tetraalkyl dialkoxy distannoxane compound having one $Sn-O-Sn$ bond, in which each tin atom of the tetraalkyl dialkoxy distannoxane compound has two $Sn-R^1$ bonds and one $Sn-OR^2$ bond,
  comprising reacting in the absence of a catalyst at least one alkyl tin compound selected from the group consisting of i) and ii) below:
  i) a dialkyl tin compound having one tin atom, two $Sn-R^1$ (wherein $R^1$ represents an alkyl group) bonds, and two $Sn-OX$ bonds (wherein OX is a group in which HOX that is a conjugate acid of OX is a Bronsted acid having a pKa of from 0 to 6.8); and
  ii) a tetraalkyl distannoxane compound having one $Sn-O-Sn$ bond, in which each tin atom of the tetraalkyl distannoxane compound has two $Sn-R^1$ bonds and one $Sn-OX$ bond (wherein OX is a group in which HOX that is a conjugate acid of OX is a Bronsted acid having a pKa of from 0 to 6.8); and
  a carbonic acid ester represented by $R^2OCOOR^2$ (wherein $R^2$ represents a linear or branched, saturated or unsaturated hydrocarbon group, a hydrocarbon group having a saturated or unsaturated cyclic hydrocarbon substituent, or a $Y-CH_2-$ group (wherein Y represents an alkyl polyalkylene group, an aromatic group or a cyclic saturated or unsaturated alkylene ether group)), and/or
  an alcohol represented by $R^2OH$ (wherein $R^2$ is the same as defined above),

[2] the process according to item [1], wherein, in the carbonic acid ester $R^2OCOOR^2$ and/or the alcohol $R^2OH$, $R^2$ represents a linear or branched, saturated or unsaturated hydrocarbon group, or a hydrocarbon group having an unsaturated or saturated cyclic hydrocarbon substituent,

[3] the process according to item [1] or [2], wherein, in the carbonic dialkyl ester $R^2OCOOR^2$ and/or the alcohol $R^2OH$, $R^2$ represents a linear or branched alkyl group having 1 to 8 carbon atoms,

[4] the process according to any of items [1] to [3], wherein the dialkyl tin compound is a compound represented by the following formula (3):

(3)

(wherein
  each of $R^1$ independently represents a linear or branched alkyl group having 1 to 12 carbon atoms,
  O represents an oxygen atom,
  $OX^1$ and $OX^2$ are $OX^1$ and $OX^2$ in which $HOX^1$ and $HOX^2$ that are conjugate acids of $OX^1$ and $OX^2$ are Bronsted acids having a pKa of from 0 to 6.8, and
  a and b are integers of from 0 to 2, respectively, and a+b=2),

[5] the process according to any one of items [1] to [4], wherein the tetraalkyl distannoxane compound is a compound represented by the following formula (4):

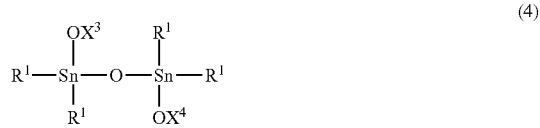

(4)

(wherein
  each of $R^1$ independently represents a linear or branched alkyl group having 1 to 12 carbon atoms,
  O represents an oxygen atom, and
  $OX^3$ and $OX^4$ are $OX^3$ and $OX^4$ in which $HOX^3$ and $HOX^4$ that are conjugate acids of $OX^3$ and $OX^4$ are Bronsted acids having a pKa of from 0 to 6.8),

[6] the process according to any one of items [1] to [5], wherein the group OX represents an acyloxyl group,

[7] the process according to any one of items [1] to [6], wherein the reaction of the dialkyl tin compound and/or the tetraalkyl distannoxane compound and the carbonic acid ester and/or the alcohol is carried out at a temperature of from 20 to 250° C.,

[8] the process according to item [1], wherein the dialkyl tin dialkoxide compound is a compound represented by the following formula (5):

(5)

(wherein
  each of $R^1$ independently represents a linear or branched alkyl group having 1 to 12 carbon atoms, which is derived from a dialkyl tin compound and/or a tetraalkyl distannoxane compound, and each of R² independently represents a linear or branched, unsaturated or saturated hydrocarbon group, a hydrocarbon group having a saturated or unsaturated cyclic hydrocarbon substituent, or a Y—CH₂— group (wherein Y represents an alkyl polyalkylene group, an aromatic group, or a cyclic saturated or unsaturated alkylene ether group), which is derived from a carbonic acid ester and/or an alcohol),

[9] the process according to any one of items [1] to [8], wherein the tetraalkyl dialkoxy distannoxane compound is a compound represented by the following formula (6):

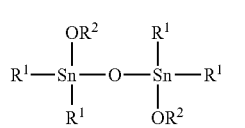

(6)

(wherein each of R¹ independently represents a linear or branched alkyl group having 1 to 12 carbon atoms, which is derived from a dialkyl tin compound and/or a tetraalkyl distannoxane compound, and each of R² independently represents a linear or branched, unsaturated or saturated hydrocarbon group, a hydrocarbon group having a saturated or unsaturated cyclic hydrocarbon substituent, or a Y—CH₂— group (wherein Y represents an alkyl polyalkylene group, an aromatic group, or a cyclic saturated or unsaturated alkylene ether group), which is derived from a carbonic acid ester and/or an alcohol),

[10] the process according to any one of items [1] to [9], wherein the dialkyl tin compound and/or the tetraalkyl distannoxane compound are compounds produced according to a process which comprises:

a step (1) of reacting an alkyl tin composition, containing a monoalkyl tin alkoxide compound and a trialkyl tin alkoxide compound, which are produced by a disproportionation reaction of at least one alkyl tin alkoxide compound selected from the group consisting of a dialkyl tin dialkoxide compound having one tin atom, two Sn—R¹ bonds and two Sn—OR² bonds and/or a tetraalkyl dialkoxy distannoxane compound having one Sn—O—Sn bond, in which each tin atom of the tetraalkyl distannoxane compound has two Sn—R¹ bonds and one Sn—OR² bond, (wherein the number of two R¹ groups bound to tin is disproportionated between two molecules in the case of a dialkyl tin alkoxide compound, or disproportionated intramolecularly and/or intermolecularly in the case of a tetraalkyl dialkoxy distannoxane compound, so as to convert to a monoalkyl tin alkoxide compound having one Sn—R¹ bond and a trialkyl tin alkoxide compound having three Sn—R¹ bonds) with an acid represented by the general formula HOX (Bronsted acid having a pKa of from 0 to 6.8) and/or an acid anhydride represented by the general formula XOX (wherein OX represents a group in which HOX that is a conjugate acid of OX is a Bronsted acid having a pKa of from 0 to 6.8, so as to produce a mixture of organic tin compounds having a group (OX group), which is derived from the acid and/or the acid anhydride; and a step (2) of carrying out an alkyl group redistribution reaction by heat-treating the mixture of the organic tin compounds obtained in step (1), so as to obtain from the monoalkyl tin alkoxide compound and the trialkyl tin alkoxide compound in the alkyl tin composition at least one alkyl tin compound selected from the group consisting of:

i) a dialkyl tin compound having one tin atom, the one tin atom having two Sn—R¹ (wherein R¹ represents an alkyl group) bonds, and two Sn—OX bonds (wherein OX is a group in which HOX that is a conjugate acid of OX is a Bronsted acid having a pKa of from 0 to 6.8), and ii) a tetraalkyl distannoxane compound having one Sn—O—Sn bond, in which each tin atom of the tetraalkyl distannoxane compound has two Sn—R¹ bonds and one Sn—OX bond (wherein OX is a group in which HOX that is a conjugate acid of OX is a Bronsted acid having a pKa of from 0 to 6.8); provided that, R¹ which directly bound to tin of the dialkyl tin compound, the tetraalkyl distannoxane compound, the dialkyl tin dialkoxide compound, the tetraalkyl dialkoxy distannoxane compound, the monoalkyl tin alkoxide compound and the trialkyl tin alkoxide, is the same alkyl group,

[11] the process according to item [10], wherein the alkyl tin composition is an alkyl tin composition formed during the production of the carbonic acid ester obtained by sequentially carrying out:

a step (a) of obtaining a reaction liquid containing a carbonic acid ester and the tetraalkyl dialkoxy distannoxane represented by the following general formula (8) and/or a conjugate of the tetraalkyl dialkoxy distannoxane and carbon dioxide by reacting the dialkyl tin dialkoxide represented by the following general formula (7) and carbon dioxide:

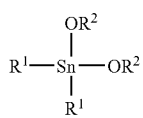

(7)

(wherein each of R¹ independently represents a linear or branched alkyl group having 1 to 12 carbon atoms, and each of R² independently represents a linear or branched, unsaturated or saturated hydrocarbon group, a hydrocarbon group having a saturated or unsaturated cyclic hydrocarbon substituent, or a Y—CH₂— group (wherein Y represents an alkyl polyalkylene group, an aromatic group, or a cyclic saturated or unsaturated alkylene ether group));

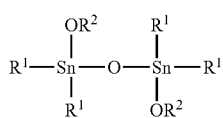

(8)

(wherein

R¹ represents a linear or branched alkyl group having 1 to 12 carbon atoms, and

R² represents a linear or branched, unsaturated or saturated hydrocarbon group, a hydrocarbon group having a saturated or unsaturated cyclic hydrocarbon substituent, or a Y—CH₂— group (wherein Y represents an alkyl polyalkylene group, an aromatic group, or a cyclic saturated or unsaturated alkylene ether group));

a step (b) of obtaining a residual liquid containing the tetraalkyl dialkoxy distannoxane and/or a conjugate of the tetraalkyl dialkoxy distannoxane and carbon dioxide by separating the carbonic acid ester from the reaction liquid by distillation; and a step (c) of reacting the residual liquid with an alcohol represented by the following general formula (9), so as to remove a water formed as a by-product to regenerate the dialkyl tin dialkoxide, and using the dialkyl tin dialkoxide as the dialkyl tin dialkoxide of step (a):

WOH (9)

(wherein

W represents a linear or branched, unsaturated or saturated hydrocarbon groups, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group)),

[12] the process according to item [11], wherein the step for carrying out the process according to claim 10 for regenerating the dialkyl tin dialkoxide and/or tetraalkyl dialkoxy distannoxane from the alkyl tin composition formed during the production of the carbonic acid ester is carried out after step (b) and/or step (c) according to Claim 11, and uses the regenerated dialkyl tin dialkoxide and/or tetraalkyl dialkoxy distannoxane as the dialkyl tin dialkoxide of step (a), and as the raw material of step (c) by mixing with the residual liquid of step (b),

[13] a process for producing a carbonic acid ester comprising following steps (A) to (B) further into the process according to item [1]:

step (A): obtaining a reaction liquid containing a carbonic acid ester and a tetraalkyl dialkoxy distannoxane compound and/or a conjugate of the tetraalkyl dialkoxy distannoxane compound and carbon dioxide by reacting the dialkyl tin dialkoxide compound and/or tetraalkyl dialkoxy distannoxane compound according to Claim 1 with carbon dioxide; and step (B): obtaining a residual liquid containing a tetraalkyl dialkoxy distannoxane and/or a conjugate of the tetraalkyl dialkoxy distannoxane and carbon dioxide by separating the carbonic acid ester from the reaction liquid by distillation,

[14] a process for producing the carbonic acid ester further comprising a following step (C) into the process according to item [13] and using an alkyl tin compound produced in the step (C) for the alkyl tin compound according to item [1]:

step (C): producing at least one alkyl tin compound selected from the group consisting of the following i) and ii) by reacting the residual liquid of the step (B) with an acid represented by the general formula HOX (Bronsted acid having a pKa of from 0 to 6.8) and/or an acid anhydride represented by the general formula XOX (wherein OX represents a group in which HOX that is a conjugate acid of OX is a Bronsted acid having a pKa of from 0 to 6.8);

i) a dialkyl tin compound having one tin atom, two Sn—R$^1$ (wherein R$^1$ represents an alkyl group), and two Sn—OX bonds (wherein OX is a group in which HOX that is a conjugate acid of OX is a Bronsted acid having a pKa of from 0 to 6.8); and ii) a tetraalkyl distannoxane compound having one Sn—O—Sn bond, in which each tin atom of the tetraalkyl distannoxane compound has two Sn—R$^1$ bonds and one Sn—OX bond (wherein OX is a group in which HOX that is a conjugate acid of OX is a Bronsted acid having a pKa of from 0 to 6.8),

[15] the process according to item [1], wherein the dialkyl tin compound and/or the tetraalkyl distannoxane compound are compounds produced according to a process comprising:

a step (I) of reacting a dialkyl tin dialkoxide represented by the following general formula (10) with carbon dioxide, so as to obtain a reaction liquid containing carbonic acid ester and a tetraalkyl dialkoxy distannoxane represented by the following general formula (11) and/or a conjugate of the tetraalkyl dialkoxiy distannoxane and carbon dioxide;

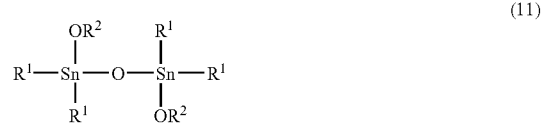

(10)

(wherein each of R$^1$ independently represents a linear or branched alkyl group having 1 to 12 carbon atoms, and each of R$^2$ independently represents a linear or branched, unsaturated or saturated hydrocarbon group, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group));

(11)

(wherein each of R$^1$ independently represents a linear or branched alkyl group having 1 to 12 carbon atoms, and each of R$^2$ independently represents a linear or branched, unsaturated or saturated hydrocarbon group, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group));

a step (II) of separating the carbonic acid ester from the reaction liquid by distillation so as to obtain a residual liquid containing the tetraalkyl dialkoxy distannoxane and/or a conjugate of the tetraalkyl dialkoxy distannoxane and carbon dioxide; and a step (III) of reacting the residual liquid of the step (II) with an acid represented by the general formula HOX (Bronsted acid having a pKa of from 0 to 6.8) and/or acid anhydride represented by the general formula XOX (wherein OX represents a group in which HOX that is a conjugate acid of OX is a Bronsted acid having a pKa of from 0 to 6.8), so as to produce a compound having a group (OX group), which is derived from the acid and/or the acid anhydride, and which is a dialkoxy tin compound represented by the following general formula (12) and/or a tetraalkyl distannoxane compound represented by the following general formula (13):

(12)

(wherein each of R$^1$ independently represents a linear or branched alkyl group having 1 to 12 carbon atoms, O represents an oxygen atom, and OX represents a group OX in which HOX that is a conjugate acid of OX is a Bronsted acid having a pKa of from 0 to 6.8);

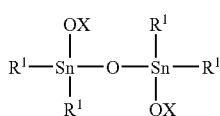

(13)

(wherein
each of $R^1$ independently represents a linear or branched alkyl group having 1 to 12 carbon atoms,
O represents an oxygen atom, and
OX represents a group OX in which HOX that is a conjugate acid of OX is a Bronsted acid having a pKa of from 0 to 6.8),
[16] the process according to any one of items [1] to [15], wherein the alkyl group $R^1$ represents a linear alkyl group having 1 to 8 carbon atoms,
[17] the process according to item [16], wherein the alkyl group $R^1$ represents an n-butyl group or an n-octyl group,
[18] the process according to any one of items [10], [14] and [15], wherein the acid HOX represents a carboxylic acid,
[19] the process according to item [18], wherein the carboxylic acid is selected from the group consisting of acetic acid, propionic acid and maleic acid,
[20] the process according to any one of items [10], [14] and [15], wherein the acid anhydride XOX represents an acid anhydride selected from the group consisting of acetic anhydride, propionic anhydride and maleic anhydride.

ADVANTAGEOUS EFFECTS OF THE INVENTION

According to the present invention, the dialkyl tin compound and/or the tetraalkyl distannoxane compound can easily be converted to the dialkyl tin alkoxide compound and/or the tetraalkyl dialkoxy distannoxane compound without involving the handling of solid tin compounds. The dialkyl tin alkoxide compound and/or the tetraalkyl dialkoxy distannoxane compound can be used as a catalyst for production of carbonic acid esters. In addition, since useful components in the form of dialkyl tin dialkoxide compounds and/or tetraalkyl dialkoxy distannoxane compounds can be produced from monoalkyl tin alkoxide compounds and tetraalkyl tin alkoxide compounds formed by an alkyl group disproportionation reaction of the dialkyl tin dialkoxide compound and/or the tetraalkyl dialkoxy distannoxane compound used to produce carbonic acid ester, and these useful compounds can be reused to produce carbonic acid esters, the present invention is very useful in industrial fields.

DETAIL DESCRIPTION OF THE INVENTION

Figure 1:
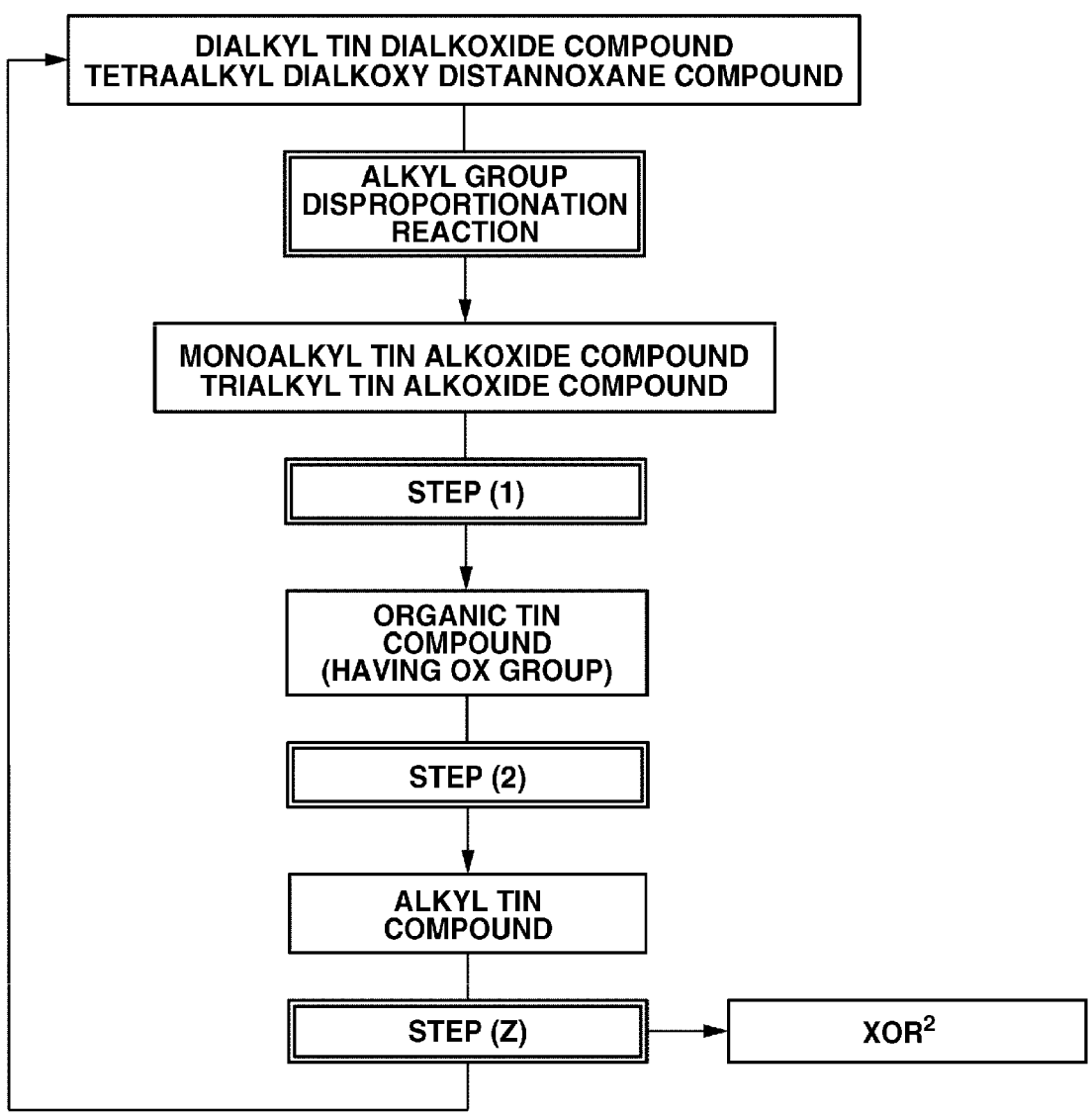
FIG. 1 shows a flow chart for explaining a process for regenerating a monoalkyl tin alkoxide compound and a trialkyl tin alkoxide compound formed by an alkyl group disproportionation reaction of a dialkyl tin dialkoxide compound and/or a tetraalkyl dialkoxy distannoxane compound as a dialkyl tin dialkoxide compound and/or a tetraalkyl dialkoxy distannoxane compound in the present embodiment.

The following provides a detailed explanation of preferred embodiments of the present invention (to be referred to as the present embodiments). Furthermore, the present invention is not limited to the following embodiments, but rather can be carried out without departing from the spirit and scope thereof.

The process of the present embodiment provides: a process for producing a compound represented by $XOR^2$;
a dialkyl tin dialkoxide compound having one tin atom, two Sn—$R^1$ bonds and two Sn—$OR^2$ bonds; and/or
a tetraalkyl dialkoxy distannoxane compound having one Sn—O—Sn bond, in which each tin atom of the tetraalkyl dialkoxy distannoxane compound has two Sn—$R^1$ bonds and one Sn—$OR^2$ bond,
comprising reacting in the absence of a catalyst at least one alkyl tin compound selected from the group consisting of i) and ii) below:
i) a dialkyl tin compound having one tin atom, two Sn—$R^1$ (wherein $R^1$ represents an alkyl group) bonds, and two Sn—OX bonds (wherein OX is a group in which HOX that is a conjugate acid of OX is a Bronsted acid having a pKa of from 0 to 6.8); and
ii) a tetraalkyl distannoxane compound having one Sn—O—Sn bond, in which each tin atom of the tetraalkyl distannoxane compound has two Sn—$R^1$ bonds and one Sn—OX bond (wherein OX is a group in which HOX that is a conjugate acid of OX is a Bronsted acid having a pKa of from 0 to 6.8); and
a carbonic acid ester represented by $R^2OCOOR^2$ (wherein $R^2$ represents a linear or branched, saturated or unsaturated hydrocarbon group, a hydrocarbon group having a saturated or unsaturated cyclic hydrocarbon substituent, or a Y—$CH_2$— group (wherein Y represents an alkyl polyalkylene group, an aromatic group or a cyclic saturated or unsaturated alkylene ether group)), and/or
an alcohol represented by $R^2OH$ (wherein $R^2$ is the same as defined above), <Dialkyl Tin Compound>

First, an explanation is provided of the dialkyl tin compound belonging to i).

The dialkyl tin compound is a compound represented by the following formula (14):

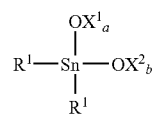

(14)

(wherein
each of $R^1$ independently represents a linear or branched alkyl group having 1 to 12 carbon atoms,
O represents an oxygen atom,
$OX^1$ and $OX^2$ are $OX^1$ and $OX^2$ in which conjugate acids of $OX^1$ and $OX^2$ in the form of $HOX^1$ and $HOX^2$ are Bronsted acids having a pKa of from 0 to 6.8, and
a and b are integers of 0 to 2, respectively, and a+b=2).

Examples of $R^1$ in the formula (14) may include alkyl groups in the form of aliphatic hydrocarbon groups in which the number of carbon atoms that constitute the groups is a number selected from an integer of 1 to 12, such as a methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof may include linear or branched alkyl groups in which the number of carbon atoms that constitute the groups is a number selected from an integer of 1 to 8. Although a dialkyl tin compound can be used in which the groups are alkyl groups in which the number of carbon atoms that constitute the groups is outside the indicated range, fluidity may become poor and productivity may be impaired. The alkyl groups are more preferably n-butyl groups or n-octyl groups in consideration of ease of acquisition during industrial production.

Although there are no particular limitations on $OX^1$ and $OX^2$ in the formula (14) provided their conjugate acids in the form of $HOX^1$ and $HOX^2$ are Bronsted acids and the pKa of the conjugate acids are 0 to 6.8, they are preferably at least one type of substituent selected from the group consisting of acyloxyl groups and aryloxy groups, and the pKa of conjugate acids thereof are 0 to 6.8. More preferably, $OX^1$ and $OX^2$ are groups in which the number of carbon atoms that constitute the groups is a number selected from integers of 0 to 12. Specific examples of such groups may include acyloxyl groups composed of a linear or branched, saturated alkyl group, a carbonyl group and an oxygen atom, such as an acetoxy group, propionyloxy group, butyryloxy group, valeryloxy group or lauroyloxy group; and aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a dimethylphenoxy group (including isomers), a methylethylphenoxy group (including isomers), a methylpropylphenoxy group (including isomers), a methylbutylphenoxy group (including isomers), a methylpentylphenoxy group (including isomers), a diethylphenoxy group (including isomers), an ethylpropylphenoxy group (including isomers), an ethylbutylphenoxy group (including isomers), a dipropylphenoxy group (including isomers), a trimethylphenoxy group (including isomers), a dimethylethylphenoxy group (including isomers), a dimethylpropylphenoxy group (including isomers), a dimethylbutylphenoxy group (including isomers), a methylethylpropylphenoxy group (including isomers), a methyldimethylphenoxy group (including isomers) or a triethylphenoxy group (including isomers).

Specific examples of dialkyl tin compounds represented by the formula (14) may include dialkyl-diacyloxy tin compounds such as dimethyl-diacetoxy tin, dimethyl-dipropionyloxy tin (including isomers), dimethyl-dibutyryloxy tin (including isomers), dimethyl-valeryloxy tin (including isomers), dimethyl-dilauroyloxy tin (including isomers), dibutyl-acetoxy tin (including isomers), dibutyl-dipropionyloxy tin (including isomers), dibutyl-dibuturyloxy tin (including isomers), dibutyl-divaleryloxy tin (including isomers), dibutyl-dilauroyloxy tin (including isomers), dioctyl-diacetoxy tin (including isomers), dioctyl-dipropionyloxy tin (including isomers), dioctyl-butyryloxy tin (including isomers), dioctyl-divaleryloxy tin (including isomers) or dioctyl-dilauroyloxy tin (including isomers); and, alkyl-diaryloxy tin compounds such as dimethyl-diphenoxy tin, dimethyl-di(methylphenoxy)tin (including isomers), dimethyl-di(ethylphenoxy)tin (including isomers), dimethyl-di(propylphenoxy)tin (including isomers), dimethyl-di(butylphenoxy)tin (including isomers), dimethyl-di(pentylphenoxy)tin (including isomers), dimethyl-di(hexylphenoxy)tin (including isomers), dimethyl-bis(dimethylphenoxy)tin (including isomers), dimethyl-di(methylethylphenoxy)tin (including isomers), dimethyl-di(methylpropylphenoxy)tin (including isomers), dimethyl-di(methylbutylphenoxy)tin (including isomers), dimethyl-di(methylpentylphenoxy)tin (including isomers), dimethyl-bis(diethylphenoxy)tin (including isomers), dimethyl-di(ethylpropylphenoxy)tin (including isomers), dimethyl-di(ethylbutylphenoxy)tin (including isomers), dimethyl-di(dipropylphenoxy)tin (including isomers), dimethyl-di(trimethylphenoxy)tin (including isomers), dimethyl-bis(dimethylethylphenoxy)tin (including isomers), dimethyl-bis(diethylpropylphenoxy)tin (including isomers), dimethyl-bis(dimethylbutylphenoxy)tin (including isomers), dimethyl-di(methylethylpropylphenoxy)tin (including isomers), dimethyl-di(ethyldimethylphenoxy)tin (including isomers), dimethyl-di(triethylphenoxy)tin (including isomers), dibutyl-diphenoxy tin (including isomers), dibutyl-di(methylphenoxy)tin (including isomers), dibutyl-di(ethylphenoxy)tin (including isomers), dibutyl-di(propylphenoxy)tin (including isomers), dibutyl-di(butylphenoxy)tin (including isomers), dibutyl-di(pentylphenoxy)tin (including isomers), dibutyl-di(hexylphenoxy)tin (including isomers), dibutyl-bis(dimethylphenoxy)tin (including isomers), dibutyl-di(methylethylphenoxy)tin (including isomers), dibutyl-di(methylpropylphenoxy)tin (including isomers), dibutyl-di(methylbutylphenoxy)tin (including isomers), dibutyl-di(methylpentylphenoxy)tin (including isomers), dibutyl-bis(diethylphenoxy)tin (including isomers), dibutyl-di(ethylpropylphenoxy)tin (including isomers), dibutyl-di(ethylbutylphenoxy)tin (including isomers), dibutyl-di(dipropylphenoxy)tin (including isomers), dibutyl-di(trimethylphenoxy)tin (including isomers), dibutyl-bis(dimethylethylphenoxy)tin (including isomers), dibutyl-bis(dimethylpropylphenoxy)tin (including isomers), dibutyl-bis(dimethylbutylphenoxy)tin (including isomers), dibutyl-di(methylethylpropylphenoxy)tin (including isomers), dibutyl-di(ethyldimethylphenoxy)tin (including isomers), dibutyl-di(triethylphenoxy)tin (including isomers), dioctyl-diphenoxy tin (including isomers), dioctyl-di(methylphenoxy)tin (including isomers), dioctyl-di(ethylphenoxy)tin (including isomers), dioctyl-di(propylphenoxy)tin (including isomers), dioctyl-di(butylphenoxy)tin (including isomers), dioctyl-di(pentylphenoxy)tin (including isomers), dioctyl-di(hexylphenoxy)tin (including isomers), diocty-bis(dimethylphenoxy)tin (including isomers), dioctyl-di(methylethylphenoxy)tin (including isomers), dioctyl-di(methylpropylphenoxy)tin (including isomers), dioctyl-di(methylbutylphenoxy)tin (including isomers), dioctyl-di(methylpentylphenoxy)tin (including isomers), dioctyl-bis(diethylphenoxy)tin (including isomers), dioctyl-di(ethylpropylphenoxy)tin (including isomers), dioctyl-di(ethylbutylphenoxy)tin (including isomers), dioctyl-di(dipropylphenoxy)tin (including isomers), dioctyl-di(trimethylphenoxy)tin (including isomers), dioctyl-bis (dimethylethylphenoxy)tin (including isomers), dioctyl-bis (dimethylpropylphenoxy)tin (including isomers), dioctyl-bis (dimethylbutylphenoxy)tin (including isomers), dioctyl-di (methylethylpropylphenoxy)tin (including isomers), dioctyl-di(ethyldimethylphenoxy)tin (including isomers) or dioctyl-di(triethylphenoxy)tin (including isomers).

<Tetraalkyl Distannoxane Compound>

Next, an explanation is provided of the tetraalkyl distannoxane compound belonging to ii).

The tetraalkyl distannoxane compound is a compound represented by the following formula (15):

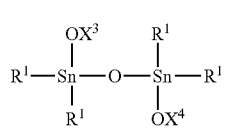

(15)

(wherein each of $R^1$ independently represents a linear or branched alkyl group having 1 to 12 carbon atoms, O represents an oxygen atom, and $OX^3$ and $OX^4$ are $OX^3$ and $OX^4$ in which conjugate acids of $OX^3$ and $OX^4$ in the form of $HOX^3$ and $HOX^4$ are Bronsted acids having a pKa of from 0 to 6.8).

Examples of $R^1$ in the formula (15) may include alkyl groups in the form of aliphatic hydrocarbon groups in which the number of carbon atoms that constitute the groups is a number selected from an integer of 1 to 12, such as a methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof may include linear or branched alkyl groups in which the number of carbon atoms that constitute the groups is a number selected from an integer of 1 to 8. Although a tetraalkyl distannoxane compound can be used in which the groups are alkyl groups in which the number of carbon atoms that constitute the groups is outside the indicated range, fluidity may become poor and productivity may be impaired. The alkyl groups are more preferably n-butyl groups or n-octyl groups in consideration of ease of acquisition during industrial production.

Although there are no particular limitations on $OX^3$ and $OX^4$ in the formula (15) provided their conjugate acids in the form of $HOX^3$ and $HOX^4$ are Bronsted acids and the pKa of the conjugate acids are 0 to 6.8, they are preferably at least one type of substituent selected from the group consisting of acyloxyl groups and aryloxy groups, and the pKa of conjugate acids thereof are 0 to 6.8. More preferably, $OX^1$ and $OX^2$ are groups in which the number of carbon atoms that constitute the groups is a number selected from integers of 0 to 12. Specific examples of such groups may include acyloxyl groups composed of a linear or branched, saturated alkyl group, a carbonyl group and an oxygen atom, such as an acetoxy group, a propionyloxy group, a butyryloxy group, a valeryloxy group or a lauroyloxy group; and aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a dimethylphenoxy group (including isomers), a methylethylphenoxy group (including isomers), a methylpropylphenoxy group (including isomers), a methylbutylphenoxy group (including isomers), a methylpentylphenoxy group (including isomers), a diethylphenoxy group (including isomers), an ethylpropylphenoxy group (including isomers), an ethylbutylphenoxy group (including isomers), a dipropylphenoxy group (including isomers), a trimethylphenoxy group (including isomers), a dimethylethylphenoxy group (including isomers), a dimethylpropylphenoxy group (including isomers), a dimethylbutylphenoxy group (including isomers), a methylethylpropylphenoxy group, a methyldimethylphenoxy group or a triethylphenoxy group (including isomers).

Specific examples of compounds represented by the formula (15) may include 1,1,3,3-tetraallkyl-1,3-diacyloxy distannoxanes such as 1,1,3,3-tetramethyl-1,3-diacetoxy distannoxane, 1,1,3,3-tetramethyl-1,3-dipropionyloxy distannoxane (including isomers), 1,1,3,3-tetramethyl-1,3-dibutyryloxy distannoxane (including isomers), 1,1,3,3-tetramethyl-1,3-divaleryloxy distannoxane (including isomers), 1,1,3,3-tetramethyl-1,3-dilauroyloxy distannoxane (including isomers), 1,1,3,3-tetrabutyl-1,3-diacetoxy distannoxane (including isomers), 1,1,3,3-tetrabutyl-1,3-dipropionyloxy distannoxane (including isomers), 1,1,3,3-tetrabutyl-1,3-dibutyryloxy distannoxane (including isomers), 1,1,3,3-tetrabutyl-1,3-divaleryloxy distannoxane (including isomers), 1,1,3,3-tetrabutyl-1,3-dilauroyloxy distannoxane (including isomers), 1,1,3,3-tetraoctyl-1,3-diacetoxy distannoxane (including isomers), 1,1,3,3-tetraoctyl-1,3-dipropionyloxy distannoxane (including isomers), 1,1,3,3-tetraoctyl-1,3-dibutyryloxy distannoxane (including isomers), 1,1,3,3-tetraoctyl-1,3-divaleryloxy distannoxane (including isomers) or 1,1,3,3-tetraoctyl-1,3-dilauroyloxy distannoxane (including isomers); and 1,1,3,3-tetraalkyl-1,3-diaryloxy distannoxanes such as 1,1,3,3-tetramethyl-1,3-diphenoxy distannoxane, 1,1,3,3-tetramethyl-1,3-di(methylphenoxy) distannoxane (including isomers), 1,1,3,3-tetramethyl-1,3-di(ethylphenoxy)distannoxane (including isomers), 1,1,3,3-tetramethyl-1,3-di(propylphenoxy)distannoxane (including isomers), 1,1,3,3-tetramethyl-1,3-di(butylphenoxy)distannoxane (including isomers), 1,1,3,3-tetramethyl-1,3-di(pentylphenoxy)distannoxane (including isomers), 1,1,3,3-tetramethyl-1,3-di(hexylphenoxy)distannoxane (including isomers), 1,1,3,3-tetramethyl-1,3-bis(dimethylphenoxy)distannoxane (including isomers), 1,1,3,3-tetramethyl-1,3-di(methylethylphenoxy)distannoxane (including isomers), 1,1,3,3-tetramethyl-1,3-di(methylpropylphenoxy)distannoxane (including isomers), 1,1,3,3-tetramethyl-1,3-di(methylbutylphenoxy)distannoxane (including isomers), 1,1,3,3-tetramethyl-1,3-di(methylpentylphenoxy)distannoxane (including isomers), 1,1,3,3-tetramethyl-1,3-bis(diethylphenoxy)distannoxane (including isomers), 1,1,3,3-tetramethyl-1,3-di(ethylpropylphenoxy)distannoxane (including isomers), 1,1,3,3-tetramethyl-1,3-di(ethylbutylphenoxy)distannoxane (including isomers), 1,1,3,3-tetramethyl-1,3-di(dipropylphenoxy)distannoxane (including isomers), 1,1,3,3-tetramethyl-1,3-di(trimethylphenoxy)distannoxane (including isomers), 1,1,3,3-tetramethyl-1,3-bis (dimethylethylphenoxy)distannoxane (including isomers), 1,1,3,3-tetramethyl-1,3-bis(dimethylpropylphenoxy)distannoxane (including isomers), 1,1,3,3-tetramethyl-1,3-bis (dimethylbutylphenoxy)distannoxane (including isomers), 1,1,3,3-tetramethyl-1,3-di(methylethylpropylphenoxy)distannoxane (including isomers), 1,1,3,3-tetramethyl-1,3-di (ethyldimethylphenoxy)distannoxane (including isomers), 1,1,3,3-tetramethyl-1,3-di(triethylphenoxy)distannoxane (including isomers), 1,1,3,3-tetrabutyl-1,3-diphenoxy distannoxane (including isomers), 1,1,3,3-tetrabutyl-1,3-di(methylphenoxy)distannoxane (including isomers), 1,1,3,3-tetrabutyl-1,3-di(ethylphenoxy)distannoxane (including isomers), 1,1,3,3-tetrabutyl-1,3-di(propylphenoxy)distannoxane (including isomers), 1,1,3,3-tetrabutyl-1,3-di(butylphenoxy)distannoxane (including isomers), 1,1,3,3-tetrabutyl-1,3-di(pentylphenoxy)distannoxane (including isomers), 1,1,3,3-tetrabutyl-1,3-di(hexylphenoxy)distannoxane (including isomers), 1,1,3,3-tetrabutyl-1,3-bis(dimethylphenoxy)distannoxane (including isomers), 1,1,3,3-tetrabutyl-1,3-di(methylethylphenoxy)distannoxane (including isomers), 1,1,3,3-tetrabutyl-1,3-di(methylpropylphenoxy)distannoxane (including isomers), 1,1,3,3-tetrabutyl-1,3-di(methylbutylphenoxy)distannoxane (including isomers), 1,1,3,3-tetrabutyl-1,3-di(methylpentylphenoxy)distannoxane (including isomers), 1,1,3,3-tetrabutyl-1,3-bis(diethylphenoxy)distannoxane (including isomers), 1,1,3,3-tetrabutyl-1,3-di(ethylpropylphenoxy)distannoxane (including isomers), 1,1,3,3-tetrabutyl-1,3-di(ethylbutylphenoxy)distannoxane (including isomers), 1,1,3,3-tetrabutyl-1,3-di(dipropylphenoxy)distannoxane (including isomers), 1,1,3,3-tetrabutyl-1,3-di(trimethylphenoxy)distannoxane (including isomers), 1,1,3,3-tetrabutyl-1,3-bis(dimethylethylphenoxy)distannoxane (including isomers), 1,1,3,3-tetrabutyl-1,3-bis(dimethylpropylphenoxy)distannoxane (including isomers), 1,1,3,3-tetrabutyl-1,3-bis(dimethylbutylphenoxy)distannoxane (including isomers), 1,1,3,3-tetrabutyl-1,3-di(methylethylpropylphenoxy)distannoxane (including isomers), 1,1,3,3-tetrabutyl-1,3-di(ethyldimethylphenoxy)distannoxane (including isomers), 1,1,3,3-tetrabutyl-1,3-di(triethylphenoxy)distannoxane (including isomers), 1,1,3,3-tetraoctyl-1,3-diphenoxy distannoxane (including isomers), 1,1,3,3-tetraoctyl-1,3-di(methylphenoxy)distannoxane (including isomers), 1,1,3,3-tetraoctyl-1,3-di(ethylphenoxy)distannoxane (including isomers), 1,1,3,3-tetraoctyl-1,3-di(propylphenoxy)distannoxane (including isomers), 1,1,3,3-tetraoctyl-1,3-di(butylphenoxy)distannoxane (including isomers), 1,1,3,3-tetraoctyl-1,3-di(pentylphenoxy)distannoxane (including isomers), 1,1,3,3-tetraoctyl-1,3-di(hexylphenoxy)distannoxane (including isomers), 1,1,3,3-tetraoctyl-1,3-bis(dimethylphenoxy)distannoxane (including isomers), 1,1,3,3-tetraoctyl-1,3-di(methylethylphenoxy)distannoxane (including isomers), 1,1,3,3-tetraoctyl-1,3-di(methylpropylphenoxy)distannoxane (including isomers), 1,1,3,3-tetraoctyl-1,3-di(methylbutylphenoxy)distannoxane (including isomers), 1,1,3,3-tetraoctyl-1,3-di(methylpentylphenoxy)distannoxane (including isomers), 1,1,3,3-tetraoctyl-1,3-bis(diethylphenoxy)distannoxane (including isomers), 1,1,3,3-tetraoctyl-1,3-di(ethylpropylphenoxy)distannoxane (including isomers), 1,1,3,3-tetraoctyl-1,3-di(ethylbutylphenoxy)distannoxane (including isomers), 1,1,3,3-tetraoctyl-1,3-di(dipropylphenoxy)distannoxane (including isomers), 1,1,3,3-tetraoctyl-1,3-di(trimethylphenoxy)distannoxane (including isomers), 1,1,3,3-tetraoctyl-1,3-bis(dimethylethylphenoxy)distannoxane (including isomers), 1,1,3,3-tetraoctyl-1,3-bis(dimethylpropylphenoxy)distannoxane (including isomers), 1,1,3,3-tetraoctyl-1,3-bis(dimethylbutylphenoxy)distannoxane (including isomers), 1,1,3,3-tetraoctyl-1,3-di(methylethylpropylphenoxy)distannoxane (including isomers), 1,1,3,3-tetraoctyl-1,3-di(ethyldimethylphenoxy)distannoxane (including isomers) or 1,1,3,3-tetraoctyl-1,3-di(triethylphenoxy)distannoxane (including isomers).

In general, organic tin compounds easily adopt an associated structure. For example, dialkyl tin dialkoxides are known to form a dimer structure, while tetraalkyl dialkoxy distannoxanes are known to exist by forming ladder structures in which two or three molecules are associated. Even in cases in which such associated states change, it is common among persons with ordinary skill in the art to express these compounds in terms of their monomer structure.

<Carbonic Acid Ester>

There are no particular limitations on the carbonic acid ester used in the present embodiment, and carbonic acid esters represented by the following formula (16) are used preferably.

$$R^2OCOOR^2 \qquad (16)$$

(wherein each of $R^2$ independently represents a linear or branched, saturated or unsaturated hydrocarbon group, a hydrocarbon group having a saturated or unsaturated cyclic hydrocarbon substituent, or a Y—$CH_2$— group (wherein Y represents an alkyl polyalkylene group, an aromatic group or a cyclic saturated or unsaturated alkylene ether group)).

In the carbonic acid esters represented by the formula (16), although $R^2$ may be an aliphatic hydrocarbon group or an aromatic hydrocarbon group, since a lower acidity of a hydroxyl compound having the structure $R^2OH$ in which an OH group is bound to an $R^2$ group constituting the carbonic acid ester facilitates elimination as $R^2OX$, among the above-mentioned $R^2$, those in which the carbon bound to oxygen has a methyl or methylene structure are preferable. Examples of such $R^2$ may include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), a hexadecyl group (including isomers) or an octadecyl group (including isomers); cycloalkyl groups such as a cyclopentyl group, a cyclohexyl group, a cycloheptyl group, a cyclooctyl group (including isomers), a methyl-cyclopentyl group, a methyl-cyclohexyl group, a methyl-cycloheptyl group, a methyl-cyclooctyl group, an ethylcyclopentyl group, an ethylcyclohexyl group, an ethylcycloheptyl group, an ethylcyclooctyl group (including isomers), a propylcyclopentyl group, a propylcyclohexyl group, a propylcycloheptyl group, a propylcyclooctyl group (including isomers), a cyclopentylmethyl group, a cyclohexylmethyl group, a cycloheptylmethyl group, a cyclooctylmethyl group (including isomers), a cyclopentylethyl group, a cyclohexylethyl group, a cycloheptylethyl group, a cyclooctylethyl group (including isomers), a cyclopentylpropyl group, a cyclohexylpropyl group, a cycloheptylpropyl group or a cyclooctylpropyl group (including isomers); hydrocarbon groups having a cyclic hydrocarbon substituent such as a cyclopentylmethyl group, a cyclopentylethyl group, a cyclohexylmethyl group or a cyclohexylethyl group; aryl-substituted hydrocarbon groups such as a phenylmethyl group, a phenylethyl group, a tolylmethyl group, a tolylethyl group (including isomers), a xylylmethyl group (including isomers) or a xylylethyl group (including isomers); and, polyoxyalkylene groups such as a methoxymethyl group, a methoxyethyl group, a methoxypropyl group (including isomers), a methoxybutyl group (including isomers), a methoxypentyl group (including isomers), a methoxyhexyl group (including isomers), an ethoxymethyl group, an ethoxyethyl group, an ethoxypropyl group (including isomers), an ethoxybutyl group (including isomers), an ethoxypentyl group (including isomers), an ethoxyhexyl group (including isomers) or a polyoxyethylene group. Among these, in consideration of fluidity and separation after reacting, the carbonic acid ester is more preferably a carbonic acid ester in which $R^2$ in the formula (16) has 1 to 8 carbon atoms. Among the hydrocarbons, carbonic acid esters in which $R^2$ is a group selected from alkyl groups and cycloalkyl groups are most preferable. Specific examples of carbonic acid esters represented by formula (16) may include dimethyl carbonate, diethyl carbonate, dipropyl carbonate (including isomers), dibutyl carbonate (including isomers), dipentyl carbonate (including isomers), dihexyl carbonate (including isomers), diheptyl carbonate (including isomers) and dioctyl carbonate (including isomers).

<Alcohol>

There are no particular limitations on the alcohol used in the present embodiment, and is an alcohol represented by the following formula (17).

$$R^2OH \quad (17)$$

(wherein
R² is the same as previously defined for R² in the formula (16)).

In the alcohol represented by the formula (17), although R² may be an aliphatic hydrocarbon group or an aromatic hydrocarbon group, alcohols in which R² is a group selected from alkyl groups and cycloalkyl groups are preferable. Examples of such R² may include alkyl groups such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), a hexadecyl group (including isomers) or an octadecyl group (including isomers); cycloalkyl groups such as a cyclopentyl group, a cyclohexyl group, a cycloheptyl group, a cyclooctyl group (including isomers), a methyl-cyclopentyl group, a methyl-cyclohexyl group, a methyl-cycloheptyl group, a methyl-cyclooctyl group (including isomers), an ethylcyclopentyl group, an ethylcyclohexyl group, an ethylcycloheptyl group, an ethylcyclooctyl group (including isomers), a propylcyclopentyl group, a propylcyclohexyl group, a propylcycloheptyl group, a propylcyclooctyl group (including isomers), a cyclopentylmethyl group, a cyclohexylmethyl group, a cycloheptylmethyl group, a cyclooctylmethyl group (including isomers), a cyclopentylethyl group, a cyclohexylethyl group, a cycloheptylethyl group, a cyclooctylethyl group (including isomers), a cyclopentylpropyl group, a cyclohexylpropyl group, a cycloheptylpropyl group or a cyclooctylpropyl group (including isomers). Among these, alcohols in which R² in the formula (17) is an alkyl group having 1 to 8 carbon atoms are more preferable. Specific examples of such alcohols may include methanol, ethanol, propyl alcohol (including isomers), butyl alcohol (including isomers), pentyl alcohol (including isomers), hexyl alcohol (including isomers), heptyl alcohol (including isomers) and octyl alcohol (including isomers).

In addition, alcohols represented by the following formula (18) are used in a different aspect of the present embodiment:

$$WOH \quad (18)$$

(wherein
W represents a linear or branched, saturated or unsaturated hydrocarbon group, a hydrocarbon group having a saturated or unsaturated cyclic hydrocarbon substituent, or a Y—CH₂— group (wherein Y represents an alkyl polyalkylene group, an aromatic group or a cyclic saturated or unsaturated alkylene ether group)).

There are no restrictions on the alcohol represented by the formula (18), and alcohols represented by the above-mentioned formula (17) can be used. Alcohols listed as preferable examples in formula (17) can also be preferably used as preferable examples of alcohols represented by formula (18). Although subsequently described, alcohols having a boiling point at normal pressure higher than that of water are more preferable to facilitate separation of water, and examples of such alcohols may include n-butanol, 3-methylpropanol, pentyl alcohol (including isomers), hexyl alcohol (including isomers), heptyl alcohol (including isomers) and octyl alcohol (including isomers).

<Reaction Between Dialkyl Tin Compound and/or Tetraalkyl Distannoxane Compound and Carbonic Acid Ester>

Next, an explanation is provided of the reaction between a dialkyl tin compound and/or a tetraalkyl distannoxane compound and carbonic acid ester in the present embodiment.

In the reaction between a dialkyl tin compound and/or a tetraalkyl distannoxane compound and carbonic acid ester, the compositional ratio of these compounds is such that the stoichiometric ratio of the dialkyl tin compound and/or tetraalkyl distannoxane compound to the carbonic acid ester is preferably 1:0.1 to 1:100. Although it is preferable to use an excess of carbonic acid ester to increase the reaction rate and complete the reaction rapidly, since the reactor becomes excessively large if an excessively large amount of carbonic acid ester is used, the reaction is carried out at a compositional ratio preferably within a range of from 1:0.3 to 1:50 and more preferably from 1:1 to 1:30.

Although varying according to the types and compositional ratio of reactants used, the reaction temperature is preferably within a range of from 20 to 250° C. Although the reaction is preferably carried out at a high temperature to complete the reaction rapidly, if the temperature is excessively high, a thermal denaturation reaction and the like of the reaction raw materials in the form of the dialkyl tin compound and/or the tetraalkyl distannoxane compound, and/or the reaction products in the form of the dialkyl tin dialkoxy compound and/or the tetralkyl dialkoxy distannoxane compound may occur, and since this may cause a decrease in the yield of the target compound in the reaction, the reaction temperature is more preferably within a range of from 30 to 230° C., and even more preferably within a range of from 50 to 200° C. In addition, the reaction does not require the use of a catalyst.

Although the use of a solvent is not required in the reaction, a solvent can be used for the purpose of improving fluidity or facilitating the reaction procedure. Any solvent may be used provided it does not react with the reaction raw materials in the form of the dialkyl tin compound and/or tetraalkyl distannoxane compound and the carbonic acid ester, or with the reaction products in the form of the dialkyl tin dialkoxide compound and/or tetraalkyl dialkoxy distannoxane compound. Examples of such solvents may include linear, branched or cyclic hydrocarbons having 5 to 16 carbon atoms, ethers composed of linear, branched or cyclic hydrocarbons having 4 to 16 carbon atoms, and linear, branched or cyclic halogenated hydrocarbons having 1 to 16 carbon atoms. More specifically, use can be made of linear or cyclic hydrocarbons selected from pentane (including isomers), hexane (including isomers), heptane (including isomers), octane (including isomers), nonane (including isomers), decane (including isomers), hexadecane (including isomers), cyclohexane, cycloheptane, cyclooctane, benzene, toluene, xylene (including isomers) or ethylbenzene; ethers selected from diethyl ether, dipropyl ether (including isomers), dibutyl ether (including isomers), dihexyl ether (including isomers), dioctyl ether (including isomers) and diphenyl ether (including isomers); or halogenated hydrocarbons selected from methylene chloride, chloroform, carbon tetrachloride, chlorobenzene, tetrachloroethane and dichlorobenzene (including isomers). In addition, in the case of using an excess of carbonic acid ester in this reaction, an excess of carbonic acid ester can also be used as a solvent. These solvents can be used alone or two or more types can be used as a mixture.

Although other additives are not required to be added in addition to the solvent, additives may be added for the purpose of adjusting fluidity or adjusting the reaction rate. Additives can be added without limitation provided they do not have a detrimental effect on the reaction. Examples of such additives may include Lewis acid compounds and Lewis base compounds. Examples of these compounds may include $SnF_2$ and $SnBr_2$.

There are no particular limitations on the pressure at which the reaction is carried out, and although the reaction can be carried out under conditions of a reduced pressure, an atmospheric pressure or an increased pressure, in the case of carrying out the reaction while removing all or a portion of the reaction products of the reaction in the form of the dialkyl tin dialkoxide compound and/or tetraalkyl dialkoxy distannoxane compound, and/or a compound represented by $XOR^2$ to be described later from the reaction system, the reaction is preferably carried out under a reduced pressure. In the case of carrying out the reaction under a reduced pressure, the reaction is carried out at a pressure preferably within a range of from 10 Pa to 1 MPa and more preferably within a range of from 1 kPa to 0.5 MPa. In addition, the reaction is preferably carried out in an inert gas atmosphere such as argon, neon or nitrogen, and these inert gases are preferably used after having been dried with a dehydration column and the like.

Although the reaction time during which the reaction is carried out (residence time in the case of a continuous process) varies according to the compounds and reactor used in the reaction, temperature and pressure, and there are no particular limitations thereon, the reaction can be carried out preferably for 0.01 to 30 hours and more preferably for 0.1 to 20 hours. In addition, the reaction can be terminated after having confirmed the formation of a desired amount of the dialkyl tin dialkoxide compound and/or tetraalkyl dialkoxy distannoxane compound. Progression of the reaction can be confirmed by sampling the reaction liquid in the reactor, and confirming the amount of the dialkyl tin dialkoxide compound and/or tetraalkyl dialkoxy distannoxane compound formed by analyzing using a method such as $^{119}$Sn-NMR or gas chromatography. For example, the reaction may be terminated once 10% or more of the dialkyl tin dialkoxide compound and/or tetraalkyl dialkoxy distannoxane compound have been formed based on the number of moles of the dialkyl tin compound and/or tetraalkyl distannoxane compound, or the reaction may be terminated after continuing until that value reaches 90% or more.

In addition, although a compound represented by the formula $XOR^2$ to be described later is also formed in the reaction between the dialkyl tin compound and/or tetraalkyl distannoxane compound and the carbonic acid ester $R^2OCOOR^2$, the reaction can also be terminated after confirming formation of the desired amounts of these compounds by quantifying the amounts thereof by a known method such as gas chromatography or liquid chromatography.

There are no particular limitations on the reactor used for each reaction of the present embodiment, and a known reactor can be used. For example, conventional reactors can be suitably combined for use, examples of which may include a stirring tank, a pressurized stirring tank, a depressurized stirring tank, a column reactor, a distillation column, a packed column and a thin film distillation still. There are also no particular limitations on the material of the reactor, and a known material can be used. For example, a reactor made of glass, stainless steel, carbon steel or Hastelloy, or a reactor made of a base material provided with a glass lining or a Teflon™-coated reactor can be used. Since there are cases in which corrosion by acid may be prominent depending on the step and conditions, in such cases a reactor made of glass, that having a glass lining, that provided with a Teflon™ coating or that made of Hastelloy may be suitably selected.

<Reaction Between Dialkyl Tin Compound and/or Tetraalkyl Distannoxane Compound and Alcohol>

Next, an explanation is provided of the reaction between the dialkyl tin compound and/or tetraalkyl distannoxane compound and an alcohol.

In the reaction between the dialkyl tin compound and/or tetraalkyl distannoxane compound and alcohol, the compositional ratio of these compounds is such that the stoichiometric ratio of the dialkyl tin compound and/or tetraalkyl distannoxane compound to the alcohol is preferably 1:0.1 to 1:100. Although it is preferable to use an excess of alcohol to increase the reaction rate and complete the reaction rapidly, since the reactor becomes excessively large if an excessively large amount of alcohol is used, the reaction is carried out at a compositional ratio preferably within a range of from 1:0.3 to 1:50 and more preferably from 1:1 to 1:30.

Although varying according to the types and compositional ratio of reactants used, the reaction temperature is preferably within a range of from 20 to 250° C. Although the reaction is preferably carried out at a high temperature to complete the reaction rapidly, if the temperature is excessively high, a thermal denaturation reaction and the like of the reaction raw materials in the form of the dialkyl tin compound and/or the tetraalkyl distannoxane compound, and/or the reaction products in the form of the dialkyl tin dialkoxy compound and/or the tetralkyl dialkoxy distannoxane compound may occur, and since this may cause a decrease in the yield of the target compound in the reaction, the reaction temperature is more preferably within a range of from 30 to 230° C., and even more preferably within a range of from 50 to 200° C. In addition, the reaction does not require the use of a catalyst.

Although the use of a solvent is not required in the reaction, a solvent can be used for the purpose of improving fluidity or facilitating the reaction procedure. Any solvent may be used provided it does not react with the reaction raw materials in the form of the dialkyl tin compound and/or tetraalkyl distannoxane compound and the carbonic acid ester, or with the reaction products in the form of the dialkyl tin dialkoxide compound and/or tetraalkyl dialkoxy distannoxane compound. Examples of such solvents may include linear, branched or cyclic hydrocarbons having 5 to 16 carbon atoms, ethers composed of linear, branched or cyclic hydrocarbons having 4 to 16 carbon atoms, and linear, branched or cyclic halogenated hydrocarbons having 1 to 16 carbon atoms. More specifically, use can be made of linear or cyclic hydrocarbons selected from pentane (including isomers), hexane (including isomers), heptane (including isomers), octane (including isomers), nonane (including isomers), decane (including isomers), hexadecane (including isomers), cyclohexane, cycloheptane, cyclooctane, benzene, toluene, xylene (including isomers) or ethylbenzene; ethers selected from diethyl ether, dipropyl ether (including isomers), dibutyl ether (including isomers), dihexyl ether (including isomers), dioctyl ether (including isomers) and diphenyl ether (including isomers); or halogenated hydrocarbons selected from methylene chloride, chloroform, carbon tetrachloride, chlorobenzene, tetrachloroethane and dichlorobenzene (including isomers). In addition, in the case of using an excess of alcohol in this reaction, an excess of alcohol can also be used as a solvent. These solvents can be used alone or two or more types can be used as a mixture.

Although other additives are not required to be added in addition to the solvent, additives may be added for the purpose of adjusting fluidity or adjusting the reaction rate. Additives can be added without limitation provided they do not have a detrimental effect on the reaction. Examples of such additives may include Lewis acid compounds and Lewis base compounds. Examples of these compounds may include $SnF_2$ and $SnBr_2$.

There are no particular limitations on the pressure at which the reaction is carried out, and although the reaction can be carried out under conditions of a reduced pressure, an atmospheric pressure or an increased pressure, in the case of carrying out the reaction while removing all or a portion of the reaction products of the reaction in the form of the dialkyl tin dialkoxide compound and/or tetraalkyl dialkoxy distannoxane compound, and/or a compound represented by $XOR^2$ to be described later from the reaction system, the reaction is preferably carried out under a reduced pressure. In the case of carrying out the reaction under a reduced pressure, the reaction is carried out at a pressure preferably within a range of from 10 Pa to 1 MPa and more preferably within a range of from 1 kPa to 0.5 MPa. In addition, the reaction is preferably carried out in an inert gas atmosphere such as argon, neon or nitrogen, and these inert gases are preferably used after having been dried with a dehydration column and the like.

Although the reaction time during which the reaction is carried out (residence time in the case of a continuous process) varies according to the compounds and reactor used in the reaction, temperature and pressure, and there are no particular limitations thereon, the reaction can be carried out preferably for 0.01 to 30 hours and more preferably for 0.1 to 20 hours. In addition, the reaction can be terminated after having confirmed the formation of a desired amount of the dialkyl tin dialkoxide compound and/or tetraalkyl dialkoxy distannoxane compound. Progression of the reaction can be confirmed by sampling the reaction liquid in the reactor, and confirming the amount of the dialkyl tin dialkoxide compound and/or tetraalkyl dialkoxy distannoxane compound formed by analyzing using a method such as $^{119}Sn$-NMR or gas chromatography. For example, the reaction may be terminated once 10% or more of the dialkyl tin dialkoxide compound and/or tetraalkyl dialkoxy distannoxane compound have been formed based on the number of moles of the dialkyl tin compound and/or tetraalkyl distannoxane compound, or the reaction may be terminated after continuing until that value reaches 90% or more.

In addition, although a compound represented by the formula $XOR^2$ to be described later is also formed in the reaction between the dialkyl tin compound and/or tetraalkyl distannoxane compound and the alcohol $R^2OH$, the reaction can also be terminated after confirming formation of the desired amounts of these compounds by quantifying the amounts thereof by a known method such as gas chromatography or liquid chromatography. Alternatively, since water is also formed as a by-product by the reaction in addition to the compound represented by $XOR^2$, the reaction can also be terminated by confirming that an amount of water has formed that is proportionate to formation of a desired amount of a target compound by quantifying the amount of water formed using a Karl Fischer moisture meter and the like.

There are no particular limitations on the reactor used for each reaction of the present embodiment, and a known reactor can be used. For example, conventional reactors can be suitably combined for use, examples of which may include a stirring tank, a pressurized stirring tank, a depressurized stirring tank, a column reactor, a distillation column, a packed column and a thin film distillation still. There are also no particular limitations on the material of the reactor, and a known material can be used. For example, a reactor made of glass, stainless steel, carbon steel or Hastelloy, or a reactor made of a base material provided with a glass lining or a Teflon™-coated reactor can be used. Since there are cases in which corrosion by acid may be prominent depending on the step and conditions, in such cases a reactor made of glass, that having a glass lining, that provided with a Teflon™ coating or that made of Hastelloy may be suitably selected.

In the production of the dialkyl tin dialkoxide compound and/or tetraalkyl dialkoxy distannoxane compound as indicated above, either the reaction between the dialkyl tin compound and/or the tetraalkyl distannoxane compound and the carbonic acid ester, or the reaction between the dialkyl tin compound and/or the tetraalkyl distannoxane compound and the alcohol may be carried out, or both reactions may be carried out simultaneously.

<Dialkyl Tin Dialkoxide Compound>

The following provides an explanation of the dialkyl tin dialkoxide compound formed by the previously described production process.

The dialkyl tin dialkoxide compound is a compound having a single tin atom, two $Sn-R^1$ bonds and two $Sn-OR^2$ bonds, and is represented by the following formula (19):

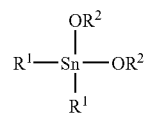

(19)

(wherein
each of $R^1$ independently represents a linear or branched alkyl group having 1 to 12 carbon atoms, which is derived from a dialkyl tin compound and/or a tetraalkyl distannoxane compound, and
each of $R^2$ independently represents a hydrocarbon group which is derived from a carbonic acid ester and/or an alcohol).

Specific examples of compounds represented by the formula (19) may include dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dimethyl-diphenoxy tin, dimethyl-di(methylphenoxy)tin, dimethyl-di(ethylphenoxy)tin, dimethyl-bis(dimethylphenoxy)tin (including isomers), dimethyl-di(phenylmethoxy) tin, dimethyl-di(phenylethoxy)tin (including isomers), dimethyl-di(methylphenylmethoxy)tin (including isomers), dibutyl-dimethoxy tin, dibutyl-diethoxy tin, dibutyl-dipropoxy tin (including isomers), dibutyl-dibutoxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dibutyl-diphenoxy tin (including isomers), dibutyl-di(methylphenoxy)tin (including isomers), dibutyl-di(ethylphenoxy)tin (including isomers), dibutyl-bis(dimethylphenoxy)tin (including isomers), dibutyl-di(phenylmethoxy)tin, dibutyl-di(phenylethoxy)tin (including isomers), dibutyl-di(methylphenylmethoxy)tin (including isomers), dioctyl-dimethoxy tin, dioctyl-diethoxy tin, dioctyl-dipropoxy tin (including isomers), dioctyl-dibutoxy tin (including isomers), dioctyl-dipentyloxy tin (including isomers), dioctyl-dihexyloxy tin (including isomers), dioctyl-diheptyloxy tin (including isomers), dioctyl-dioctyloxy tin (including isomers), dioctyl-diphenoxy tin (including isomers), dioctyl-di(methylphenoxy)tin (including isomers), dioctyl-di(ethylphenoxy)tin (including isomers), dioctyl-bis(dimethylphenoxy)tin (including isomers), dioctyl-di(phenylmethoxy)tin (including isomers), dioctyl-di(phenylethoxy)tin (including isomers) and dioctyl-di(methylphenylmethoxy)tin (including isomers).

<Tetraalkyl Dialkoxy Distannoxane Compound>

The following provides an explanation of the tetraalkyl dialkoxy distannoxane compound formed by the previously described production process.

The tetraalkyl dialkoxy distannoxane compound is a tetralkyl dialkoxy distannoxane compound having one Sn—O—Sn bond, wherein each tin atom of the tetraalkyl dialkoxy distannoxane compound has two Sn—$R^1$ bonds and one Sn—$OR^2$ bond, and more specifically, is represented by the following formula (20):

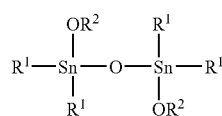

(20)

(wherein each of $R^1$ independently represents a linear or branched alkyl group having 1 to 12 carbon atoms, which is derived from a tetraalkyl distannoxane compound and/or a dialkyl tin compound, and each of $R^2$ independently represents an alkyl group which is derived from a carbonic acid ester and/or an alcohol).

Specific examples of compounds represented by the formula (20) may include 1,1,3,3-tetramethyl-1,3-diethoxy distannoxane, 1,1,3,3-tetramethyl-1,3-dipropoxy distannoxane (including isomers), 1,1,3,3-tetramethyl-1,3-dibutoxy distannoxane (including isomers), 1,1,3,3-tetramethyl-1,3-dipentyloxy distannoxane (including isomers), 1,1,3,3-tetramethyl-1,3-dihexyloxy distannoxane (including isomers), 1,1,3,3-tetramethyl-1,3-diheptyloxy distannoxane (including isomers), 1,1,3,3-tetramethyl-1,3-dioctyloxy distannoxane (including isomers), 1,1,3,3-tetramethyl-1,3-di(phenoxy)distannoxane (including isomers), 1,1,3,3-tetramethyl-1,3-di(methylphenoxy)distannoxane (including isomers), 1,1,3,3-tetramethyl-1,3-bis(dimethylphenoxy)distannoxane (including isomers), 1,1,3,3-tetramethyl-1,3-di(ethylphenoxy)distannoxane (including isomers), 1,1,3,3-tetramethyl-1,3-di(phenylmethoxy)distannoxane (including isomers), 1,1,3,3-tetramethyl-1,3-di(phenylethoxy)distannoxane (including isomers), 1,1,3,3-tetramethyl-1,3-di(methylphenylmethoxy)distannoxane (including isomers), 1,1,3,3-tetrabutyl-1,3-diethoxy distannoxane (including isomers), 1,1,3,3-tetrabutyl-1,3-dipropoxy distannoxane (including isomers), 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetrabutyl-1,3-di(phenoxy)distannoxane (including isomers), 1,1,3,3-tetrabutyl-1,3-di(methylphenoxy)distannoxane (including isomers), 1,1,3,3-tetrabutyl-1,3-bis(dimethylphenoxy)distannoxane (including isomers), 1,1,3,3-tetrabutyl-1,3-di(ethylphenoxy)distannoxane (including isomers), 1,1,3,3-tetrabutyl-1,3-di(phenylmethoxy)distannoxane (including isomers), 1,1,3,3-tetrabutyl-1,3-di(phenylethoxy)distannoxane (including isomers), 1,1,3,3-tetrabutyl-1,3-di(methylphenylmethoxy)distannoxane (including isomers), 1,1,3,3-tetraoctyl-1,3-diethoxy distannoxane (including isomers), 1,1,3,3-tetraoctyl-1,3-dipropoxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers), 1,1,3,3-tetraoctyl-1,3-dioctyloxy distannoxane (including isomers), 1,1,3,3-tetraoctyl-1,3-di(phenoxy)distannoxane (including isomers), 1,1,3,3-tetraoctyl-1,3-di(methylphenoxy)distannoxane (including isomers), 1,1,3,3-tetraoctyl-1,3-bis(dimethylphenoxy)distannoxane (including isomers), 1,1,3,3-tetraoctyl-1,3-di(ethylphenoxy)distannoxane (including isomers), 1,1,3,3-tetraoctyl-1,3-di(phenylmethoxy)distannoxane (including isomers), 1,1,3,3-tetraoctyl-1,3-di(phenylethoxy)distannoxane (including isomers), and 1,1,3,3-tetraoctyl-1,3-di(methylphenylmethoxy)distannoxane (including isomers).

Although previously described, in general organic tin compounds easily adopt an associated structure. For example, dialkyl tin dialkoxide compounds are known to form a dimer structure, while tetraalkyl dialkoxy distannoxane compounds are known to exist by forming ladder structures in which two or three molecules are associated. Even in cases in which such associated states change, it is common for the persons with ordinary skill in the art to express these compounds in terms of their monomer structure.

<Compound $XOR^2$>

In addition, in the above-mentioned production process, a compound represented by the following formula (21) is formed in addition to the dialkyl tin dialkoxide compound and/or the tetraalkyl dialkoxy distannoxane compound.

(21)

(wherein

X represents a group which is derived from a dialkyl tin compound and/or a tetraalkyl distannoxane compound, $R^2$ represents an alkyl group which is derived from a carbonic acid ester and/or an alcohol, and O represents an oxygen atom).

In the formula (21) above, the group OX is a group which is derived from the dialkyl tin compound and/or tetraalkyl distannoxane compound used in the reaction, and in the case of having used a dialkyl tin compound represented by the previously described formula (14), the group OX is a group which is derived from a group $OX^1$ or group $OX^2$, while in the case of having used a tetraalkyl distannoxane compound represented by the previously described formula (15), the group OX is a group which is derived from a group $OX^3$ or a group $OX^4$.

In addition, in the formula (21) above, the group $R^2$ is a group which is derived from the carbonic acid ester and/or the alcohol used in the reaction, and in the case of having used a carbonic ester represented by $R^2OCOOR^2$, the group $R^2$ is a group which is derived from the group $R^2$ that consitutites the carbonic acid ester, while in the case of having used an alcohol represented by $R^2OH$, the group $R^2$ is a group which is derived from the group $R^2$ that constitutes the alcohol.

More specifically, in the case the group OX is an acyloxyl group, the compound represented by the formula (21) is an ester compound, and is equivalent to compounds such as ethyl acetate, propyl acetate (including isomers), butyl acetate (including isomers), pentyl acetate (including isomers), hexyl acetate (including isomers), heptyl acetate (including isomers), octyl acetate (including isomers), ethyl propionate, propyl propionate (including isomers), butyl propionate (including isomers), pentyl propionate (including isomers), hexyl propionate (including isomers), heptyl propionate (including isomers), octyl propionate (including isomers), ethyl butyrate, propyl butyrate (including isomers), butyl butyrate (including isomers), pentyl butyrate (including isomers), hexyl butyrate (including isomers), heptyl butyrate (including isomers), octyl butyrate (including isomers), ethyl valerate, propyl valerate (including isomers), butyl valerate (including isomers), pentyl valerate (including isomers), hexyl valerate (including isomers), heptyl valerate (including isomers), octyl valerate (including isomers), ethyl laurate, propyl laurate (including isomers), butyl laurate (including isomers), pentyl laurate (including isomers), hexyl laurate (including isomers), heptyl laurate (including isomers) or octyl laurate (including isomers).

A dialkyl tin dialkoxide compound and/or a tetraalkyl dialkoxy distannoxane compound can be produced from a dialkyl tin compound and/or a tetraalkyl distannoxane compound according to the process indicated above. At that time, a desired dialkyl tin dialkoxide compound and/or a tetraalkyl dialkoxy distannoxane compound can be produced directly by a reaction between the dialkyl tin compound and/or the tetraalkyl distannoxane compound and a carbonic acid ester and/or alcohol, or a first dialkyl tin dialkoxide compound and/or a first tetraalkyl dialkoxy distannoxane compound can be produced by reacting a dialkyl tin compound and/or a tetraalkyl distannoxane compound with a first carbonic acid ester and/or first alcohol, followed by producing a desired second dialkyl tin dialkoxide compound and/or second tetraalkyl dialkoxy distannoxane compound by reacting the first dialkyl tin dialkoxide compound and/or the first tetraalkyl dialkoxy distannoxane compound with a second carbonic acid ester and/or second alcohol.

The above explanation has explained a process of the present embodiment for producing a compound represented by $XOR^2$ and a dialkyl tin dialkoxide compound and/or tetraalkyl dialkoxy distannoxane compound by reacting an alkyl tin compound with a carbonic acid ester and/or alcohol. Furthermore, a step for carrying out this production process is defined as step (Z). This production process can preferably be used in a production process of a carbonic acid ester using the dialkyl tin dialkoxide compound. The following provides an explanation of a production process of a carbonic acid ester that combines this production process.

<Process for Producing Dialkyl Tin Compound/Tetraalkyl Distannoxane Compound>

A process for producing the dialkyl tin compound and tetraalkyl distannoxane compound of the present embodiment preferably use a dialkyl tin compound and tetraalkyl distannoxane compound produced according to a process comprising a step (1) and a step (2) as explained below:

step (1): reacting an alkyl tin composition, containing a monoalkyl tin alkoxide compound and a trialkyl tin alkoxide compound formed in an alkyl group, which are produced by a disproportionation reaction of at least one alkyl tin alkoxide compound selected from the group consisting of a dialkyl tin dialkoxide compound having one tin atom, two Sn—$R^1$ bonds and two Sn—$OR^2$ bonds and/or a tetraalkyl dialkoxy distannoxane compound having one Sn—O—Sn bond, in which each tin atom of the tetraalkyl distannoxane compound has two Sn—$R^1$ bonds and one Sn—$OR^2$ bond, (wherein the number of two $R^1$ groups bound to tin is disproportionated between two molecules in the case of a dialkyl tin alkoxide compound, or disproportionated intramolecularly and/or intermolecularly in the case of a tetraalkyl dialkoxy distannoxane compound, so as to convert to a monoalkyl tin alkoxide compound having one Sn—$R^1$ bond and a trialkyl tin alkoxide compound having three Sn—$R^1$ bonds) with an acid represented by the general formula HOX (Bronsted acid having a pKa of from 0 to 6.8) and/or an acid anhydride represented by the general formula XOX (wherein OX represents a group in which HOX that is a conjugate acid of OX is a Bronsted acid having a pKa of from 0 to 6.8), so as to produce a mixture of organic tin compounds having a group (OX group), which is derived from the acid and/or the acid anhydride; and step (2): carrying out an alkyl group redistribution reaction by heat-treating the mixture of the organic tin compounds obtained in step (1), so as to obtain from the monoalkyl tin alkoxide compound and the trialkyl tin alkoxide compound in the alkyl tin composition at least one alkyl tin compound selected from the group consisting of:

i) a dialkyl tin compound having one tin atom, the one tin atom having two Sn—$R^1$ (wherein $R^1$ represents an alkyl group) bonds, and two Sn—OX bonds (wherein OX is a group in which HOX that is a conjugate acid of OX is a Bronsted acid having a pKa of from 0 to 6.8), and ii) a tetraalkyl distannoxane compound having one Sn—O—Sn bond, in which each tin atom of the tetraalkyl distannoxane compound has two Sn—$R^1$ bonds and one Sn—OX bond (wherein OX is a group in which HOX that is a conjugate acid of OX is a Bronsted acid having a pKa of from 0 to 6.8).

<Alkyl Group Disproportionation Reaction>

First, an explanation is provided of the "alkyl group disproportionation reaction of the alkyl tin alkoxide compound" of step (1) above.

The alkyl tin alkoxide compound used herein refers to the previously explained dialkyl tin dialkoxide compound and/or tetraalkyl dialkoxy distannoxane compound, and more specifically, refers to a dialkyl tin compound represented by the following formula (22) and/or a tetraalkyl dialkoxy distannoxane compound represented by the following formula (23):

(22)

(wherein, each of $R^1$ independently represents a linear or branched alkyl group having 1 to 12 carbon atoms, which is derived from a dialkyl tin compound and/or tetraalkyl distannoxane compound, and each of $R^2$ independently represents a hydrocarbon group which is derived from a carbonic acid ester and/or alcohol).

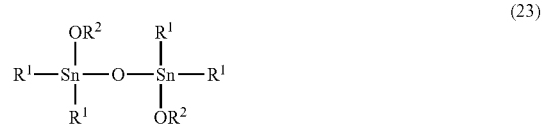

(23)

(wherein each of $R^1$ independently represents a linear or branched alkyl group having 1 to 12 carbon atoms, which is derived from a tetraalkyl distannoxane compound and/or dialkyl tin compound, and $R^2$ represents alkyl groups which are derived from a carbonic acid ester and/or alcohol).

Specific examples of compounds represented by the formula (22) may include dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dimethyl-diphenoxy tin, dimethyl-di(methylphenoxy)tin (including isomers), dimethyl-di(ethylphenoxy)tin, dimethyl-bis(dimethylphenoxy)tin (including isomers), dimethyl-di(phenylmethoxy)tin, dimethyl-di(phenylethoxy)tin (including isomers), dimethyl-di(methylphenylmethoxy)tin (including isomers), dibutyl-dimethoxy tin (including isomers), dibutyl-diethoxy tin (including isomers), dibutyl-dipropoxy tin (including isomers), dibutyl-dibutoxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dibutyl-diphenoxy tin (including isomers), dibutyl-di(methylphenoxy)tin (including isomers), dibutyl-di(ethylphenoxy)tin (including isomers), dibutyl-bis(dimethylphenoxy)tin (including isomers), dibutyl-di(phenylmethoxy)tin, dibutyl-di(phenylethoxy)tin (including isomers), dibutyl-di(methylphenylmethoxy)tin (including isomers), dioctyl-dimethoxy tin, dioctyl-diethoxy tin, dioctyl-dipropoxy tin (including isomers), dioctyl-dibutoxy tin (including isomers), dioctyl-dipentyloxy tin (including isomers), dioctyl-dihexyloxy tin (including isomers), dioctyl-diheptyloxy tin (including isomers), dioctyl-dioctyloxy tin (including isomers), dioctyl-diphenoxy tin (including isomers), dioctyl-di(methylphenoxy)tin (including isomers), dioctyl-di(ethylphenoxy)tin (including isomers), dioctyl-bis(dimethylphenoxy)tin (including isomers), dioctyl-di(phenylmethoxy)tin (including isomers), dioctyl-di(phenylethoxy)tin (including isomers) and dioctyl-di(methylphenylmethoxy)tin (including isomers).

Specific examples of compounds represented by the formula (23) may include 1,1,3,3-tetramethyl-1,3-diethoxy distannoxane, 1,1,3,3-tetramethyl-1,3-dipropoxy distannoxane (including isomers), 1,1,3,3-tetramethyl-1,3-dibutoxy distannoxane (including isomers), 1,1,3,3-tetramethyl-1,3-dipentyloxy distannoxane (including isomers), 1,1,3,3-tetramethyl-1,3-dihexyloxy distannoxane (including isomers), 1,1,3,3-tetramethyl-1,3-diheptyloxy distannoxane (including isomers), 1,1,3,3-tetramethyl-1,3-dioctyloxy distannoxane (including isomers), 1,1,3,3-tetramethyl-1,3-di(phenoxy) distannoxane (including isomers), 1,1,3,3-tetramethyl-1,3-di(methylphenoxy)distannoxane (including isomers), 1,1,3,3-tetramethyl-1,3-bis(dimethylphenoxy)distannoxane (including isomers), 1,1,3,3-tetramethyl-1,3-di(ethylphenoxy)distannoxane (including isomers), 1,1,3,3-tetramethyl-1,3-di(phenylmethoxy)distannoxane (including isomers), 1,1,3,3-tetramethyl-1,3-di(phenylethoxy)distannoxane (including isomers), 1,1,3,3-tetramethyl-1,3-di(methylphenylmethoxy)distannoxane (including isomers), 1,1,3,3-tetrabutyl-1,3-diethoxy distannoxane (including isomers), 1,1,3,3-tetrabutyl-1,3-dipropoxy distannoxane (including isomers), 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetrabutyl-1,3-di(phenoxy)distannoxane (including isomers), 1,1,3,3-tetrabutyl-1,3-di(methylphenoxy)distannoxane (including isomers), 1,1,3,3-tetrabutyl-1,3-bis(dimethylphenoxy)distannoxane (including isomers), 1,1,3,3-tetrabutyl-1,3-di(ethylphenoxy)distannoxane (including isomers), 1,1,3,3-tetrabutyl-1,3-di(phenylmethoxy)distannoxane (including isomers), 1,1,3,3-tetrabutyl-1,3-di(phenylethoxy)distannoxane (including isomers), 1,1,3,3-tetrabutyl-1,3-di(methylphenylmethoxy)distannoxane (including isomers), 1,1,3,3-tetraoctyl-1,3-diethoxy distannoxane (including isomers), 1,1,3,3-tetraoctyl-1,3-dipropoxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers), 1,1,3,3-tetraoctyl-1,3-dioctyloxy distannoxane (including isomers), 1,1,3,3-tetraoctyl-1,3-di(phenoxy)distannoxane (including isomers), 1,1,3,3-tetraoctyl-1,3-di(methylphenoxy)distannoxane (including isomers), 1,1,3,3-tetraoctyl-1,3-bis(dimethylphenoxy)distannoxane (including isomers), 1,1,3,3-tetraoctyl-1,3-di(ethylphenoxy)distannoxane (including isomers), 1,1,3,3-tetraoctyl-1,3-di(phenylmethoxy)distannoxane (including isomers), 1,1,3,3-tetraoctyl-1,3-di(phenylethoxy)distannoxane (including isomers) and 1,1,3,3-tetraoctyl-1,3-di(methylphenylmethoxy)distannoxane (including isomers).

Although previously described, in general organic tin compounds easily adopt an associated structure. For example, dialkyl tin dialkoxide compounds are known to form a dimer structure, while tetraalkyl dialkoxy distannoxane compounds are known to exist by forming ladder structures in which two or three molecules are associated. Even in cases in which such associated states change, it is common for the persons with ordinary skill in the art to express these compounds in terms of their monomer structure.

"The alkyl group disproportionation reaction of an alkyl tin alkoxide compound" of step (1) above refers to a reaction in which the number of two $R^1$ groups (wherein $R^1$ represents an alkyl group) bound to tin is disproportionated between two molecules in the case of a dialkyl tin alkoxide compound, or disproportionated intramolecularly and/or intermolecularly in the case of a tetraalkyl dialkoxy distannoxane compound, so as to convert to a monoalkyl tin alkoxide compound having one Sn—$R^1$ bond and a trialkyl tin alkoxide compound having three Sn—$R^1$ bonds.

For example, the alkyl group disproportionation reaction represented by the following formula (24) is presumed to occur in the case of a tetraalkyl dialkoxy distannoxane compound, while the alkyl group disproportionation reaction represented by the following formula (25) is presumed to occur in the case of a dialkyl tin dialkoxide compound:

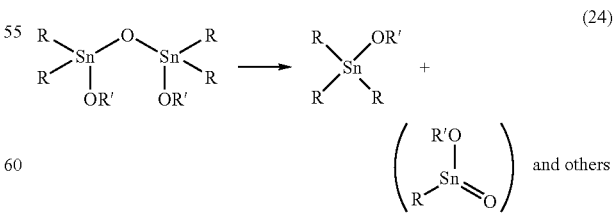

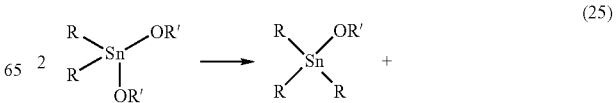

-continued

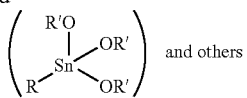

and others (wherein,
each of R and R' independently represent a linear or branched alkyl group having 1 to 12 carbons).

Although it is difficult to identify the structures of all of the products of the alkyl group disproportionation reactions, at least one of product is a trialkyl tin alkoxide compound as represented below. For example, there are many cases in which roughly half of the trialkyl tin alkoxide compound represented by the following formula (26) is formed in terms of the stoichiometric ratio thereof with respect to a decrease in the amount of the dialkyl tin dialkoxide compound and/or tetraalkyl dialkoxy distannoxane compound in this alkyl group disproportionation reaction. A trialkyl tin alkoxide compound as referred to in the present embodiment has three Sn—$R^1$ bonds, and the alkyl group $R^1$ is an alkyl group which is derived from a dialkyl tin dialkoxide compound and/or tetraalkyl dialkoxy distannoxane compound.

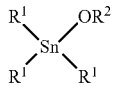

(26)

(wherein
each of $R^1$ independently represents an alkyl group which is derived from a dialkyl tin dialkoxide compound and/or tetraalkyl dialkoxy distannoxane compound, and
$R^2$ represents an alkyl group which is derived from a dialkyl tin dialkoxide compound and/or tetraalkyl dialkoxy distannoxane compound).

Examples of trialkyl tin alkoxide compounds represented by the formula (26) above may include trialkyl-alkoxy tin compounds such as trimethyl-methoxy tin, trimethyl-ethoxy tin, trimethyl-propoxy tin (including isomers), trimethyl-butoxy tin (including isomers), trimethyl-pentyloxy tin (including isomers), trimethyl-hexyloxy tin (including isomers), trimethyl-heptyloxy tin (including isomers), trimethyl-octyloxy tin (including isomers), butyl-dimethyl-methoxy tin (including isomers), butyl-dimethyl-ethoxy tin (including isomers), butyl-dimethyl-propoxy tin (including isomers), butyl-dimethyl-butoxy tin (including isomers), butyl-dimethyl-pentyloxy tin (including isomers), butyl-dimethyl-hexyloxy tin (including isomers), butyl-dimethyl-heptyloxy tin (including isomers), butyl-dimethyl-octyloxy tin (including isomers), butyl-dimethyl-nonyloxy tin (including isomers), butyl-dimethyl-decyloxy tin (including isomers), dibutyl-methyl-methoxy tin, dibutyl-methyl-ethoxy tin (including isomers), dibutyl-methyl-propoxy tin (including isomers), dibutyl-methyl-butoxy tin (including isomers), dibutyl-methyl-pentyloxy tin (including isomers), dibutyl-methyl-hexyloxy tin (including isomers), dibutyl-methyl-heptyloxy tin (including isomers), dibutyl-methyl-octyloxy tin (including isomers), butyl-diethyl-methoxy tin (including isomers), butyl-diethyl-ethoxy tin (including isomers), butyl-diethyl-propoxy tin (including isomers), butyl-diethyl-butoxy tin (including isomers), butyl-diethyl-pentyloxy tin (including isomers), butyl-diethyl-hexyloxy tin (including isomers), butyl-diethyl-heptyloxy tin (including isomers), butyl-diethyl-octyloxy tin (including isomers), dibutyl-ethyl-methoxy tin (including isomers), dibutyl-ethyl-ethoxy tin (including isomers), dibutyl-ethyl-propoxy tin (including isomers), dibutyl-ethyl-butoxy tin (including isomers), dibutyl-ethyl-pentyloxy tin (including isomers), dibutyl-ethyl-hexyloxy tin (including isomers), dibutyl-ethyl-heptyloxy tin (including isomers), dibutyl-ethyl-octyloxy tin (including isomers), butyl-dipropyl-methoxy tin (including isomers), butyl-dipropyl-ethoxy tin (including isomers), butyl-dipropyl-propoxy tin (including isomers), butyl-dipropyl-butoxy tin (including isomers), butyl-dipropyl-pentyloxy tin (including isomers), butyl-dipropyl-hexyloxy tin (including isomers), butyl-dipropyl-heptyloxy tin (including isomers), butyl-dipropyl-octyloxy tin (including isomers), dibutyl-propyl-methoxy tin (including isomers), dibutyl-propyl-ethoxy tin (including isomers), dibutyl-propyl-propoxy tin (including isomers), dibutyl-propyl-butoxy tin (including isomers), dibutyl-propyl-pentyloxy tin (including isomers), dibutyl-propyl-hexyloxy tin (including isomers), dibutyl-propyl-heptyloxy tin (including isomers), dibutyl-propyl-octyloxy tin (including isomers), tributyl-methoxy tin, tributyl-ethoxy tin, tributyl-propoxy tin (including isomers), tributyl-butoxy tin (including isomers), tributyl-pentyloxy tin (including isomers), tributyl-hexyloxy tin (including isomers), tributyl-heptyloxy tin (including isomers), tributyl-octyloxy tin (including isomers), octyl-dimethyl-methoxy tin (including isomers), octyl-dimethyl-ethoxy tin (including isomers), octyl-dimethyl-propoxy tin (including isomers), octyl-dimethyl-butoxy tin (including isomers), octyl-dimethyl-pentyloxy tin (including isomers), octyl-dimethyl-hexyloxy tin (including isomers), octyl-dimethyl-heptyloxy tin (including isomers) octyl-dimethyl-octyloxy tin (including isomers), octyl-dimethyl-nonyloxy tin (including isomers), octyl-dimethyl-decyloxy tin (including isomers), dioctyl-methyl-methoxy tin (including isomers), dioctyl-methyl-ethoxy tin (including isomers), dioctyl-methyl-propoxy tin (including isomers), dioctyl-methyl-butoxy tin (including isomers), dioctyl-methyl-pentyloxy tin (including isomers), dioctyl-methyl-hexyloxy tin (including isomers), dioctyl-methyl-heptyloxy tin (including isomers), dioctyl-methyl-octyloxy tin (including isomers), octyl-diethyl-methoxy tin (including isomers), octyl-diethyl-ethoxy tin (including isomers), octyl-diethyl-propoxy tin (including isomers), octyl-diethyl-butoxy tin (including isomers), octyl-diethyl-pentyloxy tin (including isomers), octyl-diethyl-hexyloxy tin (including isomers), octyl-diethyl-heptyloxy tin (including isomers), octyl-diethyl-octyloxy tin (including isomers), dioctyl-ethyl-methoxy tin (including isomers), dioctyl-ethyl-ethoxy tin (including isomers), dioctyl-ethyl-propoxy tin (including isomers), dioctyl-ethyl-butoxy tin (including isomers), dioctyl-ethyl-pentyloxy tin (including isomers), dioctyl-ethyl-hexyloxy tin (including isomers), dioctyl-ethyl-heptyloxy tin (including isomers), dioctyl-ethyl-octyloxy tin (including isomers), octyl-dipropyl-methoxy tin (including isomers), octyl-dipropyl-ethoxy tin (including isomers), octyl-dipropyl-propoxy tin (including isomers), octyl-dipropyl-butoxy tin (including isomers), octyl-dipropyl-pentyloxy tin (including isomers), octyl-dipropyl-hexyloxy tin (including isomers), octyl-dipropyl-heptyloxy tin (including isomers), octyl-dipropyl-octyloxy tin (including isomers), dioctyl-propyl-methoxy tin (including isomers), dioctyl-propyl-ethoxy tin (including isomers), dioctyl-propyl-propoxy tin (including isomers), dioctyl-propyl-butoxy tin (including isomers), dioctyl-propyl-pentyloxy tin (including isomers), dioctyl-propyl-hexyloxy tin (including isomers), dioctyl-propyl-heptyloxy tin (including isomers), dioctyl-propyl-octyloxy tin (including isomers), octyl-dibutyl-methoxy tin (including isomers), octyl-dibutyl-ethoxy tin (including isomers), octyldibutyl-propoxy tin (including isomers), octyl-dibutyl-butoxy tin (including isomers), octyl-dibutyl-pentyloxy tin (including isomers), octyl-dibutyl-hexyloxy tin (including isomers), octyl-dibutyl-heptyloxy tin (including isomers), octyl-dibutyl-octyloxy tin (including isomers), dioctyl-butyl-methoxy tin (including isomers), dioctyl-butyl-ethoxy tin (including isomers), dioctyl-butyl-propoxy tin (including isomers), dioctyl-butyl-butoxy tin (including isomers), dioctyl-butyl-pentyloxy tin (including isomers), dioctyl-butyl-hexyloxy tin (including isomers), dioctyl-butyl-heptyloxy tin (including isomers), dioctyl-butyl-octyloxy tin (including isomers), trioctyl-methoxy tin (including isomers), trioctyl-ethoxy tin (including isomers), trioctyl-propoxy tin (including isomers), trioctyl-butoxy tin (including isomers), trioctyl-pentyloxy tin (including isomers), trioctyl-hexyloxy tin (including isomers), trioctyl-heptyloxy tin (including isomers) or trioctyl-octyloxy tin (including isomers).

As was previously described, since the trialkyl tin alkoxide compound is formed in the alkyl group disproportionation reaction, a monoalkyl tin alkoxide compound having one Sn—R$^1$ bond is presumed to be formed simultaneous to the trialkyl tin alkoxide compound as shown in the formula (22) and/or the formula (23) above in consideration of alkyl group balance. Examples of such monoalkyl tin alkoxide compounds may include monoalkyl-alkoxy tin oxides such as methyl-methoxy tin oxide, methyl-ethoxy tin oxide, methyl-propoxy tin oxide (including isomers), methyl-butoxy tin oxide (including isomers), methyl-pentyloxy tin oxide (including isomers), methyl-hexyloxy tin oxide (including isomers), methyl-heptyloxy tin oxide (including isomers), methyl-octyloxy tin oxide (including isomers), butyl-methoxy tin oxide (including isomers), butyl-ethoxy tin oxide (including isomers), butyl-propoxy tin oxide (including isomers), butyl-butoxy tin oxide (including isomers), butyl-pentyloxy tin oxide (including isomers), butyl-hexyloxy tin oxide (including isomers), butyl-heptyloxy tin oxide (including isomers), butyl-octyloxy tin oxide (including isomers), octyl-methoxy tin oxide (including isomers), octyl-ethoxy tin oxide (including isomers), octyl-propoxy tin oxide (including isomers), octyl-butoxy tin oxide (including isomers), octyl-pentyloxy tin oxide (including isomers), octyl-hexyloxy tin oxide (including isomers), octyl-heptyloxy tin oxide (including isomers) or octyl-octyloxy tin oxide (including isomers); and monoalkyl-trialkoxy tin such as methyl-trimethoxy tin, methyl-triethoxy tin, methyl-tripropoxy tin (including isomers), methyl-tributoxy tin (including isomers), methyl-tripentyloxy tin (including isomers), methyl-trihexyloxy tin (including isomers), methyl-triheptyloxy tin (including isomers), methyl-trioctyloxy tin (including isomers), butyl-trimethoxy tin (including isomers), butyl-triethoxy tin (including isomers), butyl-tripropoxy tin (including isomers), butyl-tributoxy tin (including isomers), butyl-tripentyloxy tin (including isomers), butyl-trihexyloxy tin (including isomers), butyl-triheptyloxy tin (including isomers), butyl-trioctyloxy tin (including isomers), octyl-trimethoxy tin (including isomers), octyl-triethoxy tin (including isomers), octyl-tripropoxy tin (including isomers), octyl-tributoxy tin (including isomers), octyl-tripentyloxy tin (including isomers), octyl-trihexyloxy tin (including isomers), octyl-triheptyloxy tin (including isomers) or octyl-trioctyloxy tin (including isomers).

Although it is difficult to characterize the structure of the monoalkyl tin alkoxide compound, in addition to having "one Sn—R$^1$ bond" as previously described, it can also be characterized by its chemical shift as determined by $^{119}$Sn-NMR. Namely, at least one type of compound formed by the alkyl group disproportionation reaction of the dialkyl tin dialkoxide compound and/or tetraalkyl dialkoxy distannoxane compound is a monoalkyl tin alkoxide compound, and the monoalkyl tin alkoxide compound is characterized by the detection of a tin atom demonstrating a chemical shift of from −220 to −610 ppm based on tetramethyl tin during analysis by $^{119}$Sn-NMR in a deuterated chloroform solution.

Namely, products of the alkyl disproportionation reaction contain a trialkyl tin alkoxide compound having three Sn—R$^1$ bonds and a monoalkyl tin alkoxide compound having one Sn—R$^1$ bond, and the monoalkyl tin alkoxide compound demonstrates a chemical shift of from −220 to −610 ppm based on tetramethyl tin when analyzing by $^{119}$Sn-NMR in a deuterated chloroform solution. In the present embodiment, a composition containing the trialkyl tin alkoxide compound and monoalkyl tin alkoxide compound is referred to as a "alkyl tin composition".

In many cases, the dialkyl tin dialkoxide compound represented by the formula (22) and the tetraalkyl dialkoxy distannoxane compound represented by the formula (23) have a tin atom demonstrating a chemical shift of from 200 to −200 ppm based on tetramethyl tin when analyzed by $^{119}$Sn-NMR in a deuterated chloroform solution, and as a result of the alkyl group disproportionation reaction of the dialkyl tin dialkoxide compound and/or tetralkyl dialkoxy distannoxane compound, a tin atom is detected that demonstrates a chemical shift within a range of from −220 to −610 ppm as described above. In nearly all cases, since the product of the alkyl group disproportionation reaction has a plurality of signals within a range of from −220 to −610 ppm, in addition to the monoalkyl alkoxy tin oxide and monoalkyl tin trialkoxy tin as exemplified by formula (24) and/or formula (25), the product of the alkyl group disproportionation reaction is presumed to contain other structures as well in many cases. Although a certain product of the alkyl group disproportionation reaction is composed of compounds for which the structure is unknown in this manner, these compounds having unknown structures may be contained in the alkyl tin composition used in step (1) without problem. In addition, there are also no problems associated with a dialkyl tin dialkoxide compound and/or tetraalkyl dialkoxy distannoxane compound being contained in the alkyl tin composition.

The product resulting from the alkyl disproportionation reaction of the dialkyl tin dialkoxide compound and/or tetraalkyl dialkoxy distannoxane compound is easily presumed to adopt a structure other than the examples indicated above. Moreover, as a result of forming a stannoxane backbone, a compound may be formed containing a unit in which two alkyl groups are bound to tin and a unit in which an integral number of alkyl groups other than two are bound to tin. The presumed structures of products resulting from the alkyl group disproportionation reaction are shown below together with the previously described examples:

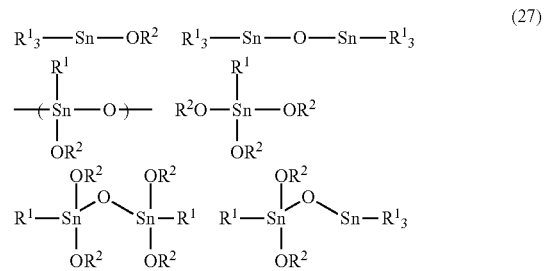

(27)

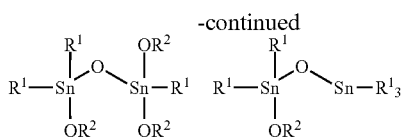

(wherein, each of $R^1$ independently represents an alkyl group which is derived from a dialkyl tin dialkoxide compound and/or tetraalkyl dialkoxy distannoxane compound, and each of $R^2$ independently represents an alkyl group which is derived from a dialkyl tin dialkoxide compound and/or tetralkyl dialkoxy distannoxane compound).

As was previously described, although the alkyl tin composition as used in the present embodiment refers to a composition containing a trialkyl tin alkoxide compound and a monoalkyl tin alkoxide compound, it may be a composition consisting essentially of the trialkyl tin alkoxide compound and the monoalkyl tin alkoxide compound, or it may be a composition also containing a tetralkyl dialkoxy distannoxane compound and/or dialkyl tin dialkoxide compound. In addition, it may also contain a product resulting from the alkyl group disproportionation reaction as previously described.

An alkyl tin composition preferably used in the present embodiment is an alkyl tin composition containing, when represented as mol %, 10 mol % or more, preferably 30 mol % or more, and more preferably 50 mol % or more, of a compound in the alkyl tin composition in which the number of alkyl groups bound to the tin atom is a number other than 2 based on the total number of moles of tin atoms contained in the alkyl tin composition.

Depending on the case, although the alkyl tin composition may contain a dialkyl tin dialkoxide compound, tetraalkyl dialkoxy distannoxane compound, tetraalkyl tin, hexaalkyl distannoxane or tin oxide ($SnO_2$) and the like, these compounds may be contained without problem provided they are contained to a degree that does not conflict with the purport of the present invention.

In addition, a composition can also be used in which a composition containing a trialkyl tin alkoxide compound and a composition containing a monoalkyl tin alkoxide compound have been separated from the alkyl tin composition. Various known methods can be used for the separation method. For example, at least one method selected from the group consisting of distillation separation, extraction separation and membrane separation can be used, and distillation separation is used particularly preferably.

Step (1) is a step for reacting the alkyl tin composition described above with an acid represented by the general formula HOX (Bronsted acid having a pKa of from 0 to 6.8) and/or an acid anhydride represented by the general formula XOX (wherein OX represents a group in which a conjugate acid of OX in the form of HOX is a Bronsted acid having a pKa of from 0 to 6.8) to produce a mixture of organic tin compounds having a group (OX group) which is derived from the acid and/or the acid anhydride.

In step (1), an organic acid is preferably used for the acid represented by the general formula HOX. Although examples of organic acids may include carboxylic acid, sulfonic acid and phenolic acid, carboxylic acid is used preferably. Examples of carboxylic acids may include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (including isomers), octanoic acid (including isomers), nonaoic acid (including isomers), decanoic acid (including isomers), undecanoic acid (including isomers), dodecanoic acid (including isomers), tetradecanoic acid (including isomers), hexadecanoic acid (including isomers), acrylic acid, crotic acid, isocrotic acid, vinylacetic acid, methacrylic acid, angelic acid, tiglic acid, allylacetic acid or undecenoic acid (including isomers); saturated or unsaturated aliphatic dicarboxylic acid such as oxalic acid, malonic acid, succinic acid, glutaric acid, adipic acid, heptanedioic acid (including isomers), octanedioic acid (including isomers), nonanedioic acid (including isomers), decanedioic acid (including isomers), maleic acid, fumaric acid, methylmaleic acid, methylfumaric acid, pentenedioic acid (including isomers), itaconic acid or allylmalonic acid; saturated or unsaturated tricarboxylic acid compounds such as 1,2,3-propanetricarboxylic acid, 1,2,3-propenetricarboxylic acid or 2,3-dimethylbutane-1,2,3-tricarboxylic acid; aromatic carboxylic acid compounds such as benzoic acid, methylbenzoic acid (including isomers), ethylbenzoic acid (including isomers), propylbenzoic acid (including isomers), dimethylbenzoic acid (including isomers) or trimethylbenzoic acid (including isomers); aromatic dicarboxylic acid compounds such as phthalic acid, isophthalic acid, terephthalic acid or methylisophthalic acid (including isomers); and, aromatic tricarboxylic acid compounds such as hemimellitic acid, trimellitic acid or trimesic acid. Among these carboxylic acids, saturated monocarboxylic acids are used preferably, saturated monocarboxylic acids having a standard boiling point of 300° C. or lower are used more preferably, and saturated monocarboxylic acids having a standard boiling point of 250° C. or lower are used even more preferably. Standard boiling point refers to the boiling point at 1 atmosphere as described in Encyclopedia Chimica (Kyoritsu Publishing Co., Ltd.). More specifically, acetic acid, propionic acid, n-butyric acid, isobutyric acid, valeric acid, isovaleric acid, 2-methylbutanoic acid, pivalic acid or hexanoic acid is used preferably.

In addition, in step (1), examples of acid anhydrides represented by the general formula XOX may include aliphatic anhydrides such as acetic anhydride, propionic anhydride, butyric anhydride, isobutyric anhydride, valeric anhydride, isovaleric anhydride, succinic anhydride, maleic anhydride, propionic anhydride or glutaric anhydride; and, aromatic anhydrides such as benzoic anhydride, phthalic anhydride or pyromellitic anhydride. Among these, acid anhydrides having a standard boiling point of 300° C. or lower are used preferably, and in order to facilitate removal of excess acid anhydride after the reaction, acid anhydrides having a standard boiling point of 200° C. or lower are used more preferably. Moreover, maleic anhydride and acetic anhydride are preferable from the viewpoint of facilitating the removal of by-products such as carboxylic acid esters and ease of industrial acquisition.

Although these acids and acid anhydrides can be used alone or by mixing a plurality of types, in the case of using an acid, there are many cases in which water is formed in the case of reacting the acid with the alkyl tin composition. Distillation separation or membrane separation may be carried out or a dehydrating agent may be used to remove the water. In addition, the combined use of an acid anhydride as a dehydrating agent is preferable. Moreover, in the case of using an acid anhydride only, since there are many cases in which water is not formed in the reaction between the alkyl tin composition and the acid anhydride, a method using an acid anhydride only is preferable.

The following provides an explanation of the reaction in step (1).

The amount of acid and/or acid anhydride used is preferably within a range of from 0.1 to 50 times in terms of the stoichiometric ratio based on the tin atoms contained in the alkyl tin composition in consideration of the reaction rate and final yield of the mixture of organic tin compounds (to be subsequently explained in detail) in step (1), and is more preferably within a range of from 0.5 to 20 times in consideration of the size of the reactor and the reaction rate. In the case the amount used is less than 0.1 in terms of the stoichiometric ratio, there are cases in which it is difficult for the reaction to proceed, while conversely even if used in an amount greater than 50 times in terms of the stoichiometric ratio, there are many cases in which this does not have an effect on reaction rate or final yield of the mixture of organic tin compounds in the reaction.

The reaction of step (1) is preferably carried out at a reaction temperature of from −20 to 300° C. and more preferably at a reaction temperature of from −10 to 250° C., and although a high reaction temperature is preferable for increasing the reaction rate, since there are also cases in which undesirable reactions such as decomposition (for example, a reaction in which alkyl groups bound to tin dissociate as alkanes and ketones) occur at high temperatures thereby lowering the yield, the reaction is even more preferably carried out a reaction temperature of from 0 to 230° C. In addition, the reaction of step (1) is preferably carried out in an inert gas atmosphere such as argon, neon or nitrogen.

Although the use of a solvent is not required in step (1), a solvent can be used for the purpose of improving fluidity, facilitating the reaction procedure or efficiently removing water outside the system in the case water is formed in the reaction. Examples of such solvents may include linear, branched or cyclic hydrocarbons having 5 to 16 carbon atoms, ethers composed of linear, branched or cyclic hydrocarbons having 4 to 16 carbon atoms, and linear, branched or cyclic halogenated hydrocarbons having 1 to 16 carbon atoms. More specifically, examples of solvents that can be used may include linear or cyclic hydrocarbons selected from the group consisting of pentane (including isomers), hexane (including isomers), heptane (including isomers), octane (including isomers), nonane (including isomers), decane (including isomers), hexadecane (including isomers), cyclohexane, cycloheptane, cyclooctane, benzene, toluene, xylene (including isomers) and ethylbenzene; ethers selected from the group consisting of diethyl ether, dipropyl ether (including isomers), dibutyl ether (including isomers), dihexyl ether (including isomers), dioctyl ether (including isomers) and diphenyl ether; and halogenated hydrocarbons selected from the group consisting of methylene chloride, chloroform, carbon tetrachloride, chlorobenzene, tetrachloroethane and dichlorobenzene (including isomers). These solvents can be used alone or used by mixing two or more types.

Although subsequently described, the alkyl group redistribution reaction of step (2) is an equilibrium reaction, and based on the typical properties of equilibrium reactions, the alkyl group redistribution reaction of step (2) is preferably carried out by carrying out the reaction of step (1) using an alkyl tin composition in which the monoalkyl tin alkoxide compound and trialkyl tin alkoxide compound are accumulated and/or concentrated at a high concentration (for example, the content of the monoalkyl tin alkoxide compound and the trialkyl tin alkoxide compound in the alkyl tin composition based on the total number of moles of tin atoms in the alkyl tin composition, when represented as mol %, is 10 mol % or more, preferably 30 mol % or more and more preferably 50 mol % or more).

<Case of Separating Trialkyl Tin Alkoxide Compound from Alkyl Tin Composition>

The composition containing the trialkyl tin alkoxide compound and the composition containing the monoalkyl tin alkoxide compound can be separated from the alkyl tin composition before carrying out step (1). Furthermore, in the case of separating the composition containing the trialkyl tin alkoxide compound and the composition containing the monoalkyl tin alkoxide compound from the alkyl tin composition, each composition can be reacted with acid and/or acid anhydride under different temperature conditions.

Although various known methods can be used for this separation, such as distillation separation, crystallization, membrane separation, filtration or solvent extraction, separation is preferably carried out by distillation separation.

<Removal of Unreacted Substances and By-Products>

The mixture of organic tin compounds obtained in step (1) may be used directly for the raw material of step (2), or it may be used for the raw material of step (2) after having removed unreacted acid and/or acid anhydride and/or organic compounds not containing tin atoms formed by the reaction. It is preferably used for the raw material of step (2) after having removed unreacted acid and/or acid anhydride. This is because if step (2) is carried out without removing unreacted acid and/or acid anhydride, there are many cases in which a dealkylation reaction to be described later occurs, and the yield of the dialkyl tin compound and/or tetraalkyl distannoxane compound formed decreases due to this dealkylation reaction. A known method such as filtration, distillation separation, membrane separation, crystallization or solvent extraction can be used for removing unreacted acid and/or acid anhydride and/or organic compounds not containing tin atoms formed by the reaction.

In addition, although the dealkylation reaction to be described later may also occur simultaneously during the step (1) or during the procedure for removing unreacted acid and/or acid anhydride, this does not present a problem provided it is within the range of the gist of the present embodiment.

Moreover, a solid compound containing tin atoms may also be formed in step (1). According to studies conducted by the inventors of the present invention, in the case of reacting the alkyl tin composition with acetic acid, for example, there were cases in which a subliming white solid is formed depending on the compounds contained in the alkyl tin composition, the reaction conditions and the like. Although this white solid was presumed to be divalent diacetoxy tin based on the results of NMR analysis and the like, step (2) may be carried out after removing this compound from the mixture obtained in step (1), or step (2) may be carried out without removing this compound.

In addition, an alcohol which is derived from the alkoxy group contained in the alkyl tin composition may be formed in addition to the mixture of organic tin compounds having a group (OX group) which is derived from the acid and/or acid anhydride in step (1) depending on the reaction conditions of step (1), and this alcohol is preferably separated and recovered. The recovered alcohol can be used as alcohol in other steps of the present embodiment (for example, as the alcohol of formula (17), formula (18) or formula (36)). Although a known method can be used to separate and recover the alcohol, such as distillation separation or membrane separation, distillation separation is preferable.

After reacting the acid and/or acid anhydride with the alkyl tin composition, the temperature during separation and recovery of the by-product alcohol by distillation separation is preferably within a range of from 0 to 100° C. and more preferably within a range of from 0 to 80° C. The use of a high temperature may cause decomposition or a dehydration condensation reaction between the acid and alcohol and the yield of the recovered alcohol may decrease, while at low temperatures, the organic tin compound may become a solid resulting in poor fluidity. Thus, separation and recovery of the alcohol is more preferably carried out within a temperature range of from 20 to 60° C. Although varying according to the types of compounds used, reaction temperature and the like, the pressure is preferably within a range of from 1 Pa to 1 MPa and more preferably within a range of from 10 Pa to 10 kPa. If the pressure is excessively high, considerable time is required for distillation separation of the alcohol or a dehydration condensation reaction may occur between the acid and alcohol, and since this may cause a decrease in the yield of the recovered alcohol, the pressure is even more preferably within a range of from 10 Pa to 1 kPa.

The procedure for recovering the alcohol by distillation may be carried out after having completed the reaction procedure between the acid and/or acid anhydride and the alkyl tin composition, or may be carried out simultaneous to the reaction between the acid and/or acid anhydride and the alkyl tin composition.

There are no particular limitations on the reactor used for the reaction between the acid and/or acid anhydride and the alkyl tin composition and the reactor used for distillation separation of the alcohol, and a known reactor can be used. Conventionally known reactors can be suitably combined for use, examples of which may include a stirring tank, a pressurized stirring tank, a depressurized stirring tank, a column reactor, a distillation column, a packed column and a thin film distiller. There are also no particular limitations on the material of the reactor, and a known material can be used. For example, a reactor made of glass, stainless steel, carbon steel or Hastelloy, or a reactor made of a base material provided with a glass lining or a Teflon™-coated reactor can be used. Since there are cases in which corrosion by acid may be prominent depending on the step and conditions, in such cases a reactor made of glass, that having a glass lining, that provided with a Teflon™ coating or that made of Hastelloy may be suitably selected.

<Organic Tin Compounds>

The following provides an explanation of the mixture of organic tin compounds formed by the reaction of step (1).

The term "Organic tin compounds" as used in the present embodiment refers to organic tin compounds having a group (OX group) which is derived from the acid and/or acid anhydride formed by the reaction of step (1). As was previously described, although the raw material of step (1) in the form of an alkyl tin compound contains a trialkyl tin alkoxide compound represented by the formula (25), a compound having three Sn—$R^1$ bonds (wherein $R^1$ represents an alkyl group) and one Sn—OX bond (wherein OX represents a group which is derived from an acid and/or acid anhydride) is formed from the trialkyl tin alkoxide compound by the reaction of step (1). More specifically, this is a compound represented by the following formula (28):

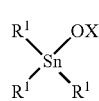

(28)

(wherein
each of $R^1$ independently represents an alkyl group;
X represents a group which is derived from an acid and/or acid anhydride; and
O represents an oxygen atom).

On the other hand, compounds having one Sn—$R^1$ bond and one to three Sn—OX groups are formed from the above-mentioned monoalkyl tin alkoxide compound by the reaction of step (1). It was previously described that when these monoalkyl tin alkoxide compounds were analyzed by $^{119}$Sn-NMR in a deuterated chloroform solution, the compounds were found to have a tin atom demonstrating a chemical shift at 200 to −200 ppm based on tetramethyl tin, thereby making it difficult to identify all of the structures of these compounds. Thus, it is also difficult to identify all of the structures of compounds formed from these monoalkyl tin alkoxide compounds. However, since there are many cases in which the reaction between a monoalkyl tin alkoxide compound and an acid and/or acid anhydride is mainly a reaction that combines 1) a reaction in which the $R^{20}$ group of the Sn—$OR^2$ bond of the monoalkyl tin alkoxide compound is replaced with an XO group, and 2) a reaction in which distannoxane bonds represented by Sn—O—Sn are cleaved resulting in the formation of Sn—OX bonds, there are many cases in which a compound represented by the following formula (29) is formed:

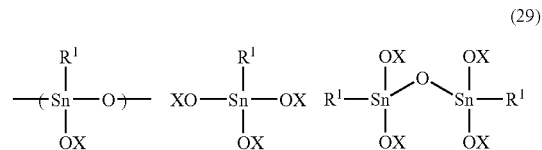

(29)

(wherein
each of $R^1$ independently represents an alkyl group;
X represents a group which is derived from an acid and/or acid anhydride; and
O represents an oxygen atom).

In addition, as was stated above, the products resulting from the alkyl group disproportionation reaction of a dialkyl tin dialkoxide compound and/or a tetraalkyl dialkoxy distannoxane compound are presumed to adopt various structures, and compounds having the structure represented by the above-mentioned formula (27) are presumed to be products of the alkyl group disproportionation reaction. These compounds represented by formula (27) are also predicted to react with acid and/or acid anhydride in step (1), and the reaction is presumed to proceed as represented by the following formula (30):

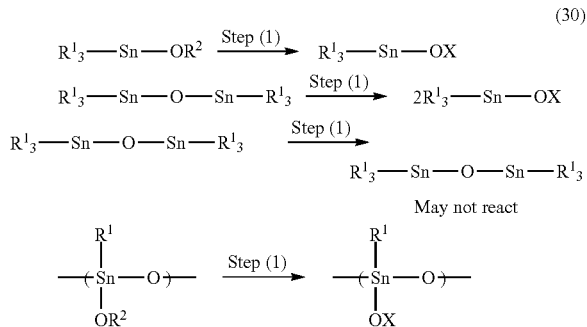

(30)

-continued

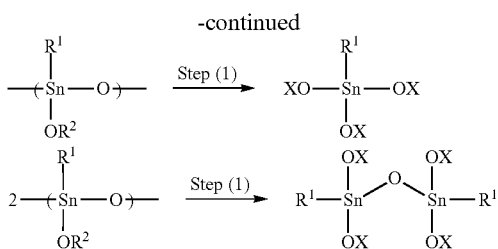

(wherein
R¹ and R² are the same as defined in formula (27), and
O represents an oxygen atom).
<Step (2)>
The following provides an explanation of step (2).
Step (2) is a step for obtaining at least one alkyl tin compound selected from the group consisting of:
i) a dialkyl tin compound having one tin atom wherein the one tin atom has two Sn—R¹ bonds (wherein R¹ represents an alkyl group) and two Sn—OX bonds (wherein OX is a group in which a conjugate acid of OX in the form of HOX is a Bronsted acid having a pKa of from 0 to 6.8), and
ii) a tetraalkyl distannoxane compound having one Sn—O—Sn bond wherein each tin atom of the tetraalkyl distannoxane compound has two Sn—R¹ bonds and one Sn—OX bond (wherein OX is a group in which a conjugate acid of OX in the form of HOX is a Bronsted acid having a pKa of from 0 to 6.8), from a monoalkyl tin alkoxide compound and a trialkyl tin alkoxide compound in an alkyl tin composition by heat-treating the mixture of organic tin compounds obtained in step (1) and carrying out an alkyl group redistribution reaction.

An alkyl group redistribution reaction as used herein refers to a reaction in which the number of alkyl groups bound to a single tin atom is equilibrated by reacting two or more types of organic tin compounds having two or more different numbers of alkyl groups bound to a single tin atom, and the alkyl group redistribution reaction is an equilibrium reaction. Although the detailed reaction mechanism is unclear, it is presumed to involve the formation of organic tin compounds having two alkyl groups bound to a single tin atom by the reaction of an organic tin compound having three alkyl groups bound to a single tin atom and an organic tin compound having one alkyl group bound to a single tin atom as indicated in the following formula (31):

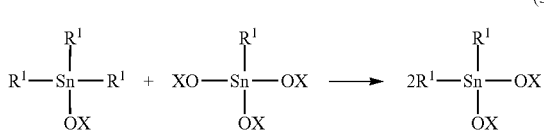

(wherein
each of R¹ independently represents an alkyl group,
X represents a group which is derived from an acid and/or acid anhydride, and
O represents an oxygen atom).

The alkyl group redistribution reaction proceeds by heat-treating a mixture of two or more types of organic tin compounds having two or more different numbers of alkyl groups bound to a single tin atom.

This heat treatment is preferably carried out within a temperature range of from 20 to 300° C., and in the case of desiring to accelerate the reaction or in the case of desiring to obtain a higher concentration of a dialkyl form (tin compound having two Sn—R¹ bonds), since a high reaction temperature is advantageous for shifting the equilibrium to the right, the temperature is more preferably 50 to 280° C. Although a high temperature for the heat treatment temperature is preferable for increasing the reaction rate, since undesirable reactions such as decomposition can occur at high temperatures thereby resulting in a decrease in yield, the reaction is even more preferably carried out within a temperature range of from 80 to 260° C. If the temperature is lower than 20° C., the reaction time may become excessively long, while in the case the temperature exceeds 300° C., the yield of dialkyl tin compound may decrease as a result of denaturation of organic tin compounds due to decomposition and the like. Although varying according to the compounds used and heat treatment temperature, the reaction time is 0.001 to 50 hours, preferably 0.01 to 10 hours, and in consideration of industrial productivity, the reaction temperature and the like is set to that the reaction time is 0.1 to 2 hours. The reaction may be terminated when the desired dialkyl tin compound has been obtained as determined using ¹¹⁹Sn-NMR and the like. As will be described later, since the alkyl group redistribution reaction of the present embodiment is presumed to be an equilibrium reaction, in order to obtain a tin compound having two alkyl groups bound to a single tin atom at a higher concentration than the reactants, the reaction is carried out within a temperature range such that the concentration of the products is greater than that of the reactants by measuring the equilibrium concentrations of compounds used relative to temperature, or by increasing the dialkyl tin compound concentration in the products by converting substituents by a method to be described later. In addition, in the case of carrying out heat treatment at a high temperature (for example, 150° C. or higher), the yield of dialkyl tin compound may decrease if time is required for cooling following the reaction. This is because the reaction system attempts to approach the equilibrium concentration at a low temperature during the course of cooling, thus making it preferable to carry out heat treatment at a high temperature followed by cooling rapidly. A known method can be preferably used to cool the reaction liquid, and a method such as the use of brine or flushing into a reactor at a lower pressure than the heat treatment tank can be used preferably.

The alkyl group redistribution reaction can be carried out in the presence or absence of a metal halide catalyst. Examples of metal halide catalysts may include tin(II)chloride, mercury(II)chloride, lead(II)chloride, mercury(II)fluoride, lead(II)fluoride, tin(II)fluoride, tin(II)iodide, lead(II)iodide, mercury(II)iodide, tin(II)bromide, mercury(II)bromide and lead(II)bromide, and these metal halides can be used alone or two or more types can be used as a mixture. These metal halides can be preferably used within a range of from 0.1 to 10% by weight based on the solution used for heat treatment.

Although the use of a solvent is not required in the alkyl group redistribution reaction, a solvent can be used for the purpose of improving fluidity or facilitating the reaction procedure. Examples of such solvents may include linear, branched or cyclic hydrocarbons having 5 to 16 carbon atoms, ethers composed of linear, branched or cyclic hydrocarbons having 4 to 16 carbon atoms and linear, branched or cyclic halogenated hydrocarbons having 1 to 16 carbon atoms. Specific examples may include linear and cyclic hydrocarbons selected from pentane (including isomers), hexane (including isomers), heptane (including isomers), octane (including isomers), nonane (including isomers), decane (including isomers), hexadecane (including isomers), cyclohexane, cycloheptane, cyclooctane, benzene, toluene, xylene (including isomers) and ethylbenzene; ethers selected from diethyl ether, dipropyl ether (including isomers), dibutyl ether (including isomers), dihexyl ether (including isomers), dioctyl ether (including isomers) and diphenyl ether; and halogenated hydrocarbons selected from methylene chloride, chloroform, carbon tetrachloride, chlorobenzene, tetrachloroethane and dichlorobenzene (including isomers). These solvents can be used alone or two or more types can be used as a mixture. Solvents can be used for the purpose of improving fluidity, facilitating the reaction procedure, or efficiently removing water outside the system in the case water is formed in the reaction. Examples of such solvents may include linear, branched or cyclic hydrocarbons having 5 to 16 carbons, ethers composed of linear, branched or cyclic hydrocarbons having 4 to 16 carbon atoms and linear, branched or cyclic halogenated hydrocarbons having 1 to 16 carbon atoms. Specific examples thereof may include linear and cyclic hydrocarbons selected from pentane (including isomers), hexane (including isomers), heptane (including isomers), octane (including isomers), nonane (including isomers), decane (including isomers), hexadecane (including isomers), cyclohexane, cycloheptane, cyclooctane, benzene, toluene, xylene (including isomers) and ethylbenzene; ethers selected from diethyl ether, dipropyl ether (including isomers), dibutyl ether (including isomers), dihexyl ether (including isomers), dioctyl ether (including isomers) and diphenyl ether; and, halogenated hydrocarbons selected from methylene chloride, chloroform, carbon tetrachloride, chlorobenzene, tetrachloroethane and dichlorobenzene (including isomers). These solvents can be used alone or two or more types can be used as a mixture.

In addition, a dealkylation reaction to be described later may also simultaneously occur in step (2).

As was previously described, the alkyl group redistribution reaction is presumed to be an equilibrium reaction. As a result of extensive studies conducted by the inventors of the present invention, it was found that this alkyl group redistribution reaction is dependent on the substituents bound to the tin atom and/or the temperature at which the alkyl group redistribution reaction is carried out. With respect to substituents bound to the tin atom, in the case of a group (for example, a group equivalent to the OX group in the previously described formula (31)) bound to the tin atom other than an alkyl group (for example, a group equivalent to $R^1$ in the formula (31)), in many cases the equilibrium is bias towards the products in the case the conjugate acid of the group has a pKa of from 0 to 6.8, while conversely, there are many cases in which equilibrium shifts towards the reactants in the case the pKa of the conjugate acid of the group is 6.8 to 25. In addition, it was also found that the equilibrium is bias towards the products at higher temperatures in the case the pKa of the conjugate acid is 0 to 6.8.

Namely, in general the alkyl group redistribution reaction in step (2) can occur as a result of the $OR^2$ group in the above-mentioned formulas (24) and (25) having a pKa of greater than 6.8 and by converting the $OR^2$ group to an OX group in step (1).

Although the term "dealkylation reaction" was previously used, this dealkylation reaction refers to a reaction in which an organic tin compound having an Sn—OX bonds, in which an OX group which is derived from an acid or acid anhydride is bound to a tin atom, is formed by reacting a compound having at least one Sn—$R^1$ bond (wherein $R^1$ represents an alkyl group) and an acid represented by HOX and/or an acid anhydride represented by XOX (wherein OX is group in which a conjugate acid of OX in the form of HOX is a Bronsted acid having a pKa of from 0 to 6.8) followed by elimination of the alkyl group ($R^1$) bound to the tin atom. Although the detailed reaction mechanism of this dealkylation reaction is unclear, a compound having a Sn—OX bond is presumed to be formed by a reaction between a trialkyl tin compound and an acid HOX as shown, for example, in the following formula (32):

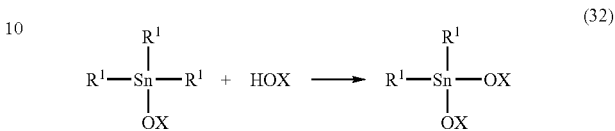

(wherein
each of $R^1$ independently represents an alkyl group,
X represents a group which is derived from an acid and/or acid anhydride, and
O represents an oxygen atom).

In addition, a substitution reaction of an alkoxy group of a trialkyl tin alkoxide compound may also occur simultaneous to the above-mentioned dealkylation reaction due to a reaction between the trialkyl tin alkoxide compound and an acid HOX as shown in the following formula (33):

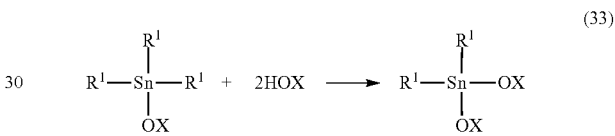

(wherein
each of $R^1$ independently represents an alkyl group,
$R^2$ represents an alkyl group,
X represents a group which is derived from an acid and/or acid anhydride, and
O represents an oxygen atom).

The dealkylation reaction as described above may occur in step (1) or step (2) depending on the reaction conditions. However, since the alkyl group eliminated in the dealkylation reaction does not rebond with a tin atom in many cases, thereby resulting in a decrease in the yield of the dialkyl tin compound and/or tetraalkyl distannoxane compound in the alkyl group redistribution reaction of step (2), it is preferable to set the reaction conditions of step (1) and step (2) so that it is difficult for the dealkylation reaction to occur.

A method can also be adopted for regenerating, for example, a monoalkyl tin dialkoxide compound and a trialkyl tin alkoxide compound, formed by an alkyl group disproportionation reaction of a dialkyl tin dialkoxide compound and/or tetraalkyl dialkoxy distannoxane compound, in the form of a dialkyl tin dialkoxide compound and/or tetraalkyl dialkoxy distannoxane compound by combining the previously explained steps (1) and (2) with the step (Z) (see FIG. 1).

<Process for Producing Alkyl Tin Composition>

The following provides an explanation of a process for producing the alkyl tin composition in the previously described step (1).

Although there are no particular limitations on the alkyl tin composition provided it is an alkyl tin composition containing a monoalkyl tin alkoxide compound and a trialkyl tin alkoxide compound, it is preferably an alkyl tin composition formed during the course of production of carbonic acid ester that is obtained by sequentially carrying out the following steps (a) to (c):

step (a): obtaining a reaction liquid containing a carbonic acid ester and the tetraalkyl dialkoxy distannoxane represented by the following general formula (35) and/or a conjugate of the tetraalkyl dialkoxy distannoxane and carbon dioxide by reacting the dialkyl tin dialkoxide represented by the following general formula (34) and carbon dioxide:

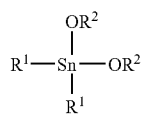

(34)

(wherein each of $R^1$ independently represents a linear or branched alkyl group having 1 to 12 carbon atoms, and each of $R^2$ independently represents a linear or branched, unsaturated or saturated hydrocarbon group, a hydrocarbon group having a saturated or unsaturated cyclic hydrocarbon substituent, or a Y—$CH_2$— group (wherein Y represents an alkyl polyalkylene group, an aromatic group, or a cyclic saturated or unsaturated alkylene ether group));

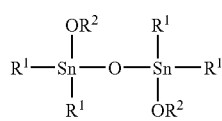

(35)

(wherein each of $R^1$ represents a linear or branched alkyl group having 1 to 12 carbon atoms, and each of $R^2$ represents a linear or branched, unsaturated or saturated hydrocarbon group, a hydrocarbon group having a saturated or unsaturated cyclic hydrocarbon substituent, or a Y—$CH_2$— group (wherein Y represents an alkyl polyalkylene group, an aromatic group, or a cyclic saturated or unsaturated alkylene ether group));

step (b): obtaining a residual liquid containing the tetraalkyl dialkoxy distannoxane and/or a conjugate of the tetraalkyl dialkoxy distannoxane and carbon dioxide by separating the carbonic acid ester from the reaction liquid by distillation; and step (c): reacting the residual liquid with an alcohol represented by the following general formula (36), so as to remove a water formed as a by-product to regenerate the dialkyl tin dialkoxide, and using the dialkyl tin dialkoxide as the dialkyl tin dialkoxide of step (a):

$R^2OH$ (36)

(wherein $R^2$ represents a linear or branched alkyl group having 2 to 8 carbon atoms).

An explanation is first provided of step (a).

Examples of $R^1$ in the formula (34) above used in step (a) may include alkyl groups in the form of aliphatic hydrocarbon groups in which the number of carbon atoms that constitute the groups is a number selected from an integer of from 1 to 12, such as a methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof may include linear or branched alkyl groups in which the number of carbon atoms that constitute the groups is a number selected from an integer of from 1 to 8. Although a dialkyl tin compound can be used in which the groups are alkyl groups in which the number of carbon atoms that constitutes the groups is outside the indicated range, fluidity may become poor and productivity may be impaired. The alkyl groups are more preferably a n-butyl group or a n-octyl group in consideration of ease of acquisition during industrial production.

Examples of a group $R^2$ in the formula (34) may include alkyl groups in the form of aliphatic hydrocarbon groups in which the number of carbon atoms that constitute the groups is a number selected from an integer of from 1 to 12, such as a methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof may include linear or branched alkyl groups in which the number of carbon atoms that constitute the groups is a number selected from an integer of from 2 to 8. Thus, preferable examples of the $OR^2$ group in the formula (34) above may include alkoxy groups such as a methoxy group, an ethoxy group, a propyloxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers) or a dodecyloxy group (including isomers), while more preferable examples thereof may include an ethoxy group, a propyloxy group (including isomers), a butyloxy group (including isomers), a pentyloxy group (including isomers), a hexyloxy group (including isomers), a heptyloxy group (including isomers) or an octyloxy group (including isomers).

Specific examples of dialkyl tin dialkoxide represented by the formula (34) may include dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dibutyl-dimethoxy tin (including isomers), dibutyl-diethoxy tin (including isomers), dibutyl-dipropoxy tin (including isomers), dibutyl-dibutoxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dioctyl-dimethoxy tin, dioctyl-diethoxy tin, dioctyl-dipropoxy tin (including isomers), dioctyl-dibutoxy tin (including isomers), dioctyl-dipentyloxy tin (including isomers), dioctyl-dihexyloxy tin (including isomers), dioctyl-diheptyloxy tin (including isomers), dioctyl-dioctyloxy tin (including isomers).

Although previously described, in general organic tin compounds easily adopt an associated structure. For example, dialkyl tin dialkoxide compounds are known to form a dimer structure, while tetraalkyl dialkoxy distannoxane compounds are known to exist by forming ladder structures in which two or three molecules are associated. Even in cases in which such associated states change, it is common for the persons with ordinary skill in the art to express these compounds in terms of their monomer structure.

Although there are no particular limitations on the production process of the dialkyl tin dialkoxide compound used in step (a), a previously disclosed dialkyl tin dialkoxide production process (such as that disclosed in WO 2005/111049) can be used preferably. This step is a step for producing a dialkyl tin dialkoxide from a dialkyl tin oxide and an alcohol. The following provides an explanation of this production process.

Examples of alcohols used preferably in this step may include alcohols in which the number of carbon atoms that constitute the alcohol is selected from an integer of from 1 to 12, such as methanol, ethanol, propanol (including isomers), butanol (including isomers), pentanol (including isomers), hexanol (including isomers), heptanol (including isomers), octanol (including isomers), nonanol (including isomers) or decanol (including isomers). More preferable examples thereof may include alcohols in which the number of carbon atoms that constitute the alcohol is selected from an integer of from 2 to 8, such as ethanol, propanol (including isomers), butanol (including isomers), pentanol (including isomers), hexanol (including isomers), heptanol (including isomers) or octanol (including isomers).

The dialkyl tin oxide used in the production of the dialkyl tin dialkoxide uses a dialkyl tin oxide represented by the following formula (37):

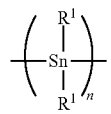

(37)

(wherein
each of $R^1$ independently represents a linear or branched alkyl group having 1 to 12 carbon atoms).

Examples of $R^1$ in the formula (37) may include alkyl groups in the form of aliphatic hydrocarbon groups having 1 to 12 carbon atoms, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers) or a dodecyl group (including isomers). More preferable examples thereof may include linear or branched saturated alkyl groups having 1 to 8 carbon atoms, while even more preferable examples thereof may include a n-butyl group and a n-octyl group.

A tetraalkyl dialkoxy distannoxane and/or dialkyl tin dialkoxide is obtained by a dehydration reaction of the alcohol and the dialkyl tin oxide while removing the water formed from the system. The temperature at which the reaction is carried out is, for example, within a range of from 80 to 180° C., and in order to distill off the water formed from the system, although varying according to the reaction pressure, a temperature of from 100 to 180° C. is preferable. Although a high temperature is preferable for the reaction temperature to accelerate the reaction rate, since undesirable reactions such as decomposition may also occur at high temperatures thereby decreasing yield, the reaction temperature is more preferably within a range of from 100 to 160° C. The reaction pressure is a pressure that allows water formed to be removed from the system, and the reaction is carried out at a pressure of from 20 to $1\times10^6$ Pa, although varying according to the reaction temperature. There are no particular limitations on the reaction time of the dehydration reaction, and is generally 0.001 to 50 hours, preferably 0.01 to 10 hours and more preferably 0.1 to 2 hours. The reaction may be terminated once a composition containing the desired amount of dialkyl tin dialkoxide has been obtained. Progression of the reaction is also determined by measuring the amount of water extracted outside the system, and can also be determined by a method using $^{119}$Sn-NMR by sampling the reaction liquid.

Although a composition containing a dialkyl tin dialkoxide mainly contains a dialkyl tin dialkoxide and a tetraalkyl dialkoxy distannoxane, the reaction is terminated after confirming that a composition has been obtained in which the molar ratio of the tetraalkyl dialkoxy distannoxane to the dialkyl tin dialkoxide contained in the composition, as represented by the combined mol % of both, is preferably within a range of from 0:100 to 80:20 and more preferably within a range of from 10:90 to 70:30. The alcohol used may be used while still present in the reaction system, and the alcohol may also be used by distilling off the alcohol depending on the case. Since there is the advantage of being able to reduce the size of the reaction vessels of the other steps, it is preferable to remove as much of the alcohol as possible. Removal by known distillation is preferable for the removal method, and known distillation equipment can be used for the distiller used for distillation. A thin film distillation apparatus is preferably used for the distillation apparatus since the alcohol can be removed in a short period of time. There are no particular limitations on the type of reaction vessel of the dehydration reaction, and a known tank type or column type reaction vessel can be used. A low boiling point reaction mixture containing water is extracted in gaseous form from the reaction vessel by distillation, while a high boiling point reaction mixture containing a produced dialkyl tin dialkoxide is extracted in the form of a liquid from the lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a columnar reactor are preferable from the viewpoint of efficiently shifting the equilibrium to the products side, while a structure having a large gas-liquid contact area is preferable for being able to rapidly transfer the water formed to the gaseous phase. Although continuous methods using a multitubular reactor, a multistage distillation column or a packed column packed with a packing can also be used, since the dialkyl tin oxide used in this step is generally a solid, it is preferable to employ a method in which the reaction is first carried out in a tank-type reaction vessel followed by increasing the content of dialkyl tin dialkoxide in a column-type reaction vessel. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Furthermore, although the composition containing a dialkyl tin dialkoxide obtained with the above-mentioned production process mainly contains dialkyl tin dialkoxide and tetraalkyl dialkoxy distannoxane, the tetraalkyl dialkoxy distannoxane is a compound represented by the above-mentioned formula (35).

Examples of $R^1$ in the formula (35) may include alkyl groups in the form of aliphatic hydrocarbon groups having 1 to 12 carbon atoms, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers) or a dodecyl group (including isomers). More preferable examples thereof may include linear or branched saturated alkyl groups having 1 to 8 carbon atoms, while even more preferable examples thereof may include a n-butyl group and a n-octyl group.

Specific examples of compounds represented by the formula (35) may include 1,1,3,3-tetramethyl-1,3-diethoxy distannoxane, 1,1,3,3-tetramethyl-1,3-dipropoxy distannoxane (including isomers), 1,1,3,3-tetramethyl-1,3-dibutoxy distannoxane (including isomers), 1,1,3,3-tetramethyl-1,3-dipentyloxy distannoxane (including isomers), 1,1,3,3-tetramethyl-1,3-dihexyloxy distannoxane (including isomers), 1,1,3,3-tetramethyl-1,3-diheptyloxy distannoxane (including isomers), 1,1,3,3-tetramethyl-1,3-dioctyloxy distannoxane (including isomers), 1,1,3,3-tetrabutyl-1,3-diethoxy distannoxane (including isomers), 1,1,3,3-tetrabutyl-1,3-dipropoxy distannoxane (including isomers), 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetraoctyl-1,3-diethoxy distannoxane (including isomers), 1,1,3,3-tetraoctyl-1,3-dipropoxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers) and 1,1,3,3-tetraoctyl-1,3-dioctyloxy distannoxane (including isomers).

Although previously described, in general organic tin compounds easily adopt an associated structure. For example, dialkyl tin dialkoxide compounds are known to form a dimer structure, while tetraalkyl dialkoxy distannoxane compounds are known to exist by forming ladder structures in which two or three molecules are associated. Even in cases in which such associated states change, it is common for the persons with ordinary skill in the art to express these compounds in terms of their monomer structure.

Step (a) is a step for reacting the dialkyl tin dialkoxide represented by formula (34) above with carbon dioxide to obtain a reaction liquid containing carbonic acid ester and a tetraalkyl dialkoxy distannoxane represented by formula (35) above and/or a conjugate of the tetraalkyl dialkoxy distannoxane and carbon dioxide.

This step preferably uses a previously disclosed carbonic acid ester production process (such as that disclosed in WO 03/055840 or WO 04/014840).

The dialkyl tin dialkoxide used in this step may be the dialkyl tin dialkoxide produced by the reaction between the dialkyl tin oxide and the alcohol as previously described, or a dialkyl tin dialkoxide regenerated in step (c) to be described later during continuous production. In addition, it may also be supplied from a step in which dialkyl tin dialkoxide and/or tetraalkyl dialkoxy distannoxane are regenerated as will be described later.

In step (a), gaseous carbon dioxide is absorbed by the above-mentioned dialkyl tin dialkoxide to cause a chemical reaction to obtain a mixture containing a conjugate of dialkyl tin dialkoxide and carbon dioxide.

When carrying out this chemical reaction, the dialkyl tin dialkoxide is reacted in a liquid state or by putting into a liquid state with a solvent and the like. When putting into a liquid state, the dialkyl tin dialkoxide is preferably put into a liquid state by heating. It may also be put into a liquid state with a solvent. Although varying according to the reaction temperature, the reaction pressure is preferably within a range of from a normal pressure to 1 MPa and more preferably within a range of from a normal pressure to 0.6 MPa. Although varying according to the reaction pressure, the reaction temperature is preferably within a range of from −40 to 80° C., and in consideration of fluidity during transfer, more preferably from 0 to 80° C. and most preferably within a range of from a normal temperature (e.g., 20° C.) to 80° C. The reaction time may be within a range of from several seconds to 100 hours, and in consideration of productivity and the like, is preferably several minutes to 10 hours. A known tank type reaction vessel or column type reaction vessel can be used for the reaction vessel. In addition, a plurality of reaction vessels may be used in combination. Since the reaction is a reaction between carbon dioxide gas (gas) and the dialkyl tin dialkoxide (liquid), in order to carry out the reaction efficiently, it is preferable to increase the contact surface area between the gas and liquid by increasing the gas-liquid interface. Known findings can be used for the method for reacting while increasing the gas-liquid interface in this manner, and examples of preferable methods thereof may include increasing the stirring speed or generating bubbles in the liquid in the case of a tank type reaction vessel, and using a packed column or using a plate column in the case of a column type reaction vessel. Examples of such column type reaction vessels may include plate column types using a tray such as a bubble tray, a porous plate tray, a valve tray or counter-current tray, and packed column types packed with various types of packing materials such as a raschig ring, a lessing ring, a pole ring, a Berl saddle, an Interlock saddle, a Dixon packing, a McMahon packing, Helipack, a Sulzer packing or Mellapak. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling. Since the reaction is generally an exothermic reaction, the reaction vessel may be cooled or it may be cooled by dissipation of heat there from. Alternatively, the reaction vessel may also be heated if the purpose is combining with a carbonic acid esterification reaction. A known method such as a method using a heat jacket or a method using an internal coil can be used to heat and cool the reaction vessel. The carbon dioxide gas and dialkyl tin dialkoxides composition supplied to the reaction vessel may be supplied separately to the reaction vessel or they may be mixed prior to supplying to the reaction vessel. These components may also be supplied from a plurality of locations in the reaction vessel. Completion of the reaction can be determined by, for example, $^{119}$Sn-NMR analysis.

Next, a reaction liquid containing carbonic acid ester is obtained from the conjugate of the dialkyl tin dialkoxide obtained in the above and the carbon dioxide according to the method described below.

Although the reaction temperature is within a range of from 110 to 200° C., and a high temperature is preferable for the reaction temperature in order to accelerate the reaction rate, since undesirable reactions such as decomposition also occur at high temperatures thereby decreasing yield, the reaction temperature is more preferably within a range of from 120 to 180° C., the reaction time is preferably within a range of from 0.1 to 10 hours, and the reaction pressure is within a range of from 1.5 to 20 MPa and preferably from 2.0 to 10 MPa. The reaction is terminated after the desired carbonic acid ester has formed in the reaction vessel. Progression of the reaction can be confirmed by, for example, sampling the reaction liquid in the reaction vessel, and analyzing the carbonic acid ester formed by a method such as $^1$H-NMR or gas chromatography. For example, the reaction may be terminated after the carbonic acid ester has been formed at a molar ratio of 10% or more of the dialkyl tin dialkoxide and/or carbon dioxide-bonded form of the dialkyl tin dialkoxide contained in the dialkyl tin dialkoxide and/or carbon dioxide-bonded form of the dialkyl tin dialkoxide, and in the case of desiring to increase the yield of the carbonic acid ester, the reaction may be terminated after allowing to continue until the value reaches 90% or more. A known reaction vessel can be used for the reaction vessel, and a column type reaction vessel or a tank type reaction vessel can be used preferably. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Next, an explanation is provided of step (b). This step is a step for separating carbonic acid ester from the reaction liquid containing carbonic acid ester obtained in step (a) to obtain a residual liquid containing a tetraalkyl dialkoxy distannoxane and/or a conjugate of the tetraalkyl dialkoxy distannoxane and carbon dioxide. A known method and apparatus can be preferably used for the separation method. A preferable separation method is separation by distillation.

Carbonic acid ester and distillation residue are obtained by batch or semi-batch, or continuous distillation of the reaction liquid transferred from step (a). A preferable example of a distillation method may include supplying the reaction liquid to a distiller, separating the carbonic acid ester in the form of a gaseous phase component from the top of the distiller outside the system, and extracting the distillation residue in the form of a liquid component from the bottom of the distiller. Although varying according to the boiling point of the carbonic acid ester and pressure, the temperature in this step is within a range of from a normal temperature (e.g., 20° C.) to 200° C., and since there are cases in which denaturation of tin compounds in the distillation residue may occur or the amount of carbonic acid ester may decrease due to a reverse reaction at high temperatures, the reaction temperature is preferably within a range of from a normal temperature (e.g. 20° C.) to 150° C. Although varying according to the type of carbonic acid ester and temperature at which the reaction is carried out, the reaction is generally carried out at normal pressure to reduced pressure conditions, and in consideration of productivity, the pressure is more preferably within a range of from 100 Pa to 80 KPa and most preferably within a range of from 100 Pa to 50 KPa. The reaction can be carried out a reaction time within a range of from 0.01 to 10 hours, and since there are cases in which tin compounds contained in the reaction liquid are denatured and cases in which the amount of carbonic acid ester decreases due to a reverse reaction when the reaction is carried out for a long period of time at high temperatures, the reaction time is preferably within a range of from 0.01 to 0.5 hours and most preferably within a range of from 0.01 to 0.3 hours. A known distiller can be used for the distiller, a column type distiller or a tank type distiller can be used preferably, or a plurality of types can be used in combination. More preferable distillers may include a thin film evaporator and a thin film distiller, and a thin film evaporator provided with a distillation column or a thin film distiller is most preferable. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Although the terms "conjugate of the dialkyl tin dialkoxide and carbon dioxide" and "conjugate of the tetraalkyl dialkoxy distannoxane and carbon dioxide" are used in the above-mentioned explanations of step (a) and step (b), the following provides an explanation thereof.

A conjugate of a dialkyl tin dialkoxide and carbon dioxide as used herein refers to a structure in which the alkoxide group portion of the dialkyl tin dialkoxide is partially or completely substituted (or transformed) with a carbonate bond. Similarly, a conjugate of a tetraalkyl dialkoxy distannoxane and carbon dioxide refers to a structure in which the alkoxy group portion of the tetraalkyl dialkoxy distannoxane is partially or completely substituted (or transformed) with a carbonate bond.

Moreover, the following provides an explanation of a conjugate of a dialkyl tin dialkoxide and carbon dioxide and a conjugate of a tetraalkyl dialkoxy distannoxane and carbon dioxide in the present embodiment using the following examples. As was previously described, a conjugate of a dialkyl tin dialkoxide and carbon dioxide refers to a structure in which the alkoxy group portion of the dialkyl tin dialkoxide is partially or completely substituted (or transformed) with a carbonate group. Although the presence of bonds of this conjugate with carbon dioxide can be confirmed by combining known methods such as $^{119}$Sn-NMR, $^{13}$C-NMR, $^1$H-NMR and X-ray structural analysis, since there are many cases in which the structure of the conjugate of the dialkyl tin dialkoxide and carbon dioxide is complex and may be unable to be identified with current analytical techniques, the conjugate of the dialkyl tin dialkoxide and carbon dioxide of the present embodiment is not limited to the structural examples indicated below. Similarly, since there also many cases in which the conjugate of the tetraalkyl dialkoxy distannoxane and carbon dioxide also has a complex structure and may be unable to be identified with current analytical techniques, the conjugate of the tetralkyl dialkoxy distannoxane and carbon dioxide of the present embodiment is also not limited to the structural examples indicated below.

Examples of conjugates of the dialkyl tin dialkoxide and carbon dioxide corresponding to the dialkyl tin dialkoxide represented by the above-mentioned formula (34) may include those having the structural formulas represented by the following formulas (38), (39) and (40). Furthermore, these compounds may be monomers or associated forms, and may be multimers or polymers:

(38)

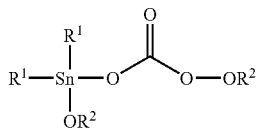

(39)

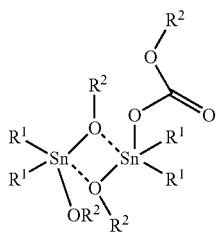

(40)

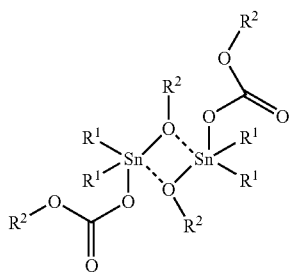

(wherein
each of $R^1$ independently represents a linear or branched alkyl group having 1 to 12 carbon atoms, and
each of $R^2$ independently represents a linear or branched, unsaturated or saturated hydrocarbon group, a hydrocarbon group having a saturated or unsaturated cyclic hydrocarbon substituent, or a Y—$CH_2$— group (wherein Y represents an alkyl polyalkylene group, an aromatic group, or a cyclic saturated or unsaturated alkylene ether group)).

Examples of conjugates of the tetraalkyl dialkoxy distannoxane and carbon dioxide corresponding to the tetraalkyl dialkoxy distannoxane represented by the above-mentioned formula (35) may include those having the structural formulas represented by the following formulas (41), (42) and (43). Furthermore, these compounds may be monomers or associated forms, and may be multimers or polymers:

(41)

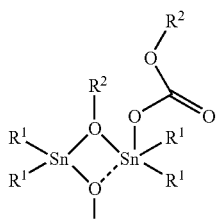

(42)

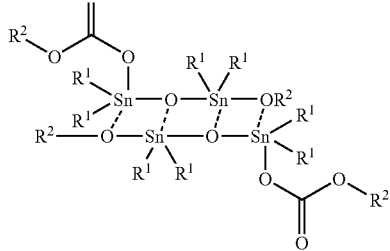

(43)

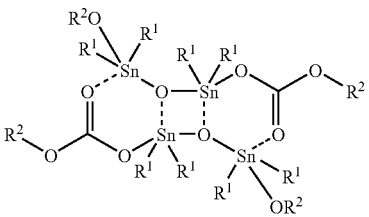

(wherein
each of $R^1$ independently represents a linear or branched alkyl group having 1 to 12 carbon atoms, and
each of $R^2$ independently represents a linear or branched, unsaturated or saturated hydrocarbon group, a hydrocarbon group having a saturated or unsaturated cyclic hydrocarbon substituent, or a Y—$CH_2$— group (wherein Y represents an alkyl polyalkylene group, an aromatic group, or a cyclic saturated or unsaturated alkylene ether group)).

Examples of $R^1$ and $R^2$ of the conjugates represented by formulas (38) to (43) above may include those as previously described, and examples of such conjugates with carbon dioxide may include alkoxy-alkylcarbonato-dialkyl tin and aralkyloxy-aralkylcarbonato-dialkyl tin such as methoxy-methylcarbonato-dibutyl tin, ethoxy-ethylcarbonato-dibutyl tin, propoxy-propylcarbonato-dibutyl tin (including isomers), butoxy-butylcarbonato-dibutyl tin (including isomers), pentyloxy-pentylcarbanato-dibutyl tin (including isomers), hexyloxy-hexylcarbonato-dibutyl tin (including isomers), heptyloxy-heptylcarbonato-dibutyl tin (including isomers), benzyloxy-benzylcarbonato-dibutyl tin (including isomers), methoxy-methylcarbonato-dioctyl tin, ethoxy-ethylcarbonato-dioctyl tin, propoxy-propylcarbonato-dioctyl tin (including isomers), butoxy-butylcarbonato-dioctyl tin (including isomers), pentyloxy-pentylcarbanato-dioctyl tin (including isomers), hexyloxy-hexylcarbonato-dioctyl tin (including isomers), heptyloxy-heptylcarbonato-dioctyl tin (including isomers) or benzyloxy-benzylcarbonato-dioctyl tin (including isomers); and, 1-alkoxy-3-alkylcarbonato-1,1,3,3-tetraalkyl distannoxanes and 1-aralkyloxy-3-aralkylcarbonato-1,1,3,3-tetraalkyl distannoxanes such as 1-methoxy-3-methylcarbonato-1,1,3,3-tetrabutyl distannoxane, 1-ethoxy-3-ethylcarbonato-1,1,3,3-tetrabutyl distannoxane, 1-propoxy-3-propylcarbonato-1,1,3,3-tetrabutyl distannoxane (including isomers), 1-butoxy-3-butylcarbonato-1,1,3,3-tetrabutyl distannoxane (including isomers), 1-pentyloxy-3-pentylcarbonato-1,1,3,3-tetrabutyl distannoxane (including isomers), 1-hexyloxy-3-hexylcarbonato-1,1,3,3-tetrabutyl distannoxane (including isomers), 1-heptyloxy-3-heptylcarbonato-1,1,3,3-tetrabutyl distannoxane (including isomers), 1-benzyloxy-3-benzylcarbonato-1,1,3,3-tetrabutyl distannoxane (including isomers), 1-methoxy-3-methylcarbonato-1,1,3,3-tetraoctyl distannoxane, 1-ethoxy-3-ethylcarbonato-1,1,3,3-tetraoctyl distannoxane, 1-propoxy-3-propylcarbonato-1,1,3,3-tetraoctyl distannoxane (including isomers), 1-butoxy-3-butylcarbonato-1,1,3,3-tetraoctyl distannoxane (including isomers), 1-pentyloxy-3-pentylcarbonato-1,1,3,3-tetraoctyl distannoxane (including isomers), 1-hexyloxy-3-hexylcarbonato-1,1,3,3-tetraoctyl distannoxane (including isomers), 1-heptyloxy-3-heptylcarbonato-1,1,3,3-tetraoctyl distannoxane (including isomers) or 1-benzyloxy-3-benzylcarbonato-1,1,3,3-tetraoctyl distannoxane (including isomers). A compound of the above-mentioned group may be selected alone or a mixture of compounds may be selected from the above-mentioned group.

Among the conjugates with carbon dioxide represented by formulas (38) to (43) above, those in which $R^1$ is selected from a n-butyl group and a n-octyl group are preferable.

As was previously described, although the alkyl tin composition contains a tetraalkyl tin alkoxide compound and a monoalkyl tin alkoxide compound, there are cases in which conjugates thereof with carbon dioxide are formed.

For example, an example of the conjugate of the trialkyl tin alkoxide compound represented by the above-mentioned formula (26) and carbon dioxide is represented by the following formula (44):

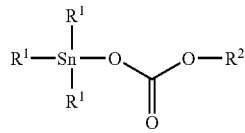

(44)

(wherein
each of $R^1$ independently represents a linear or branched alkyl group having 1 to 12 carbon atoms, and
$R^2$ independently represents a linear or branched, unsaturated or saturated hydrocarbon group, a hydrocarbon group having a saturated or unsaturated cyclic hydrocarbon substituent or a Y—$CH_2$— group (wherein Y represents an alkyl polyalkylene group, an aromatic group, or a cyclic saturated or unsaturated alkylene ether group)).

Examples of $R^1$ and $R^2$ of conjugates represented by the formula (44) above may include those as previously described, and examples of such conjugates with carbon dioxide may include trialkyl-alkylcarbonato tin and trialkyl-aralkylcarbonato tin such as tributyl-methylcarbonato tin, tributyl-ethylcarbonato tin, tributyl-propylcarbonato tin (including isomers), tributyl-butylcarbonato tin (including isomers), tributyl-pentylcarbonato tin (including isomers), tributyl-hexylcarbonato tin (including isomers), tributyl-heptylcarbonato tin (including isomers), tributyl-benzylcarbonato tin (including isomers), trioctyl-methylcarbonato tin, trioctyl-ethylcarbonato tin, trioctyl-propylcarbonato tin (including isomers), trioctyl-butylcarbonato tin (including isomers), trioctyl-pentylcarbonato tin (including isomers), trioctyl-hexylcarbonato tin (including isomers), trioctyl-heptylcarbonato tin (including isomers) or trioctyl-benzylcarbonato tin (including isomers). A compound of the above-mentioned group may be selected alone or a mixture of compounds may be selected from the above-mentioned group.

In addition, examples of structures of conjugates of a monoalkyl tin alkoxide compound represented by the above-mentioned formula (27) and carbon dioxide may include those represented by the following formulas (45), (46) and (47). The carbon dioxide conjugates of the compounds represented by the formulas (45), (46) and (47) easily adopt various structures, and are not limited to the following formulas (45), (46) and (47):

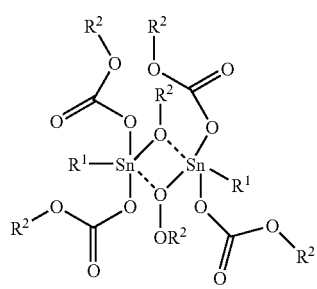

(45)

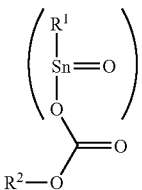

(46)

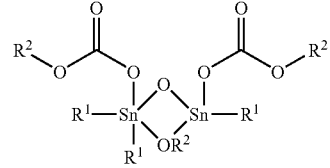

(47)

(wherein
each of $R^1$ independently represents a linear or branched alkyl group having 1 to 12 carbon atoms, and
each of $R^2$ independently represents a linear or branched, unsaturated or saturated hydrocarbon group, a hydrocarbon group having a saturated or unsaturated cyclic hydrocarbon substituent, or a Y—$CH_2$— group (wherein Y represents an alkyl polyalkylene group, an aromatic group, or a cyclic saturated or unsaturated alkylene ether group)).

Examples of these conjugates of monoalkyl tin alkoxide compounds and carbon dioxide may include alkyl-alkoxy-di-alkylcarbonato tin and alkyl-aralkyloxy-di-aralkylcarbonato tin such as butyl-methoxy-di-methylcarbonato tin, butyl-ethoxy-di-ethylcarbonato tin, butyl-propoxy-di-propylcarbonato tin (including isomers), butyl-butoxy-di-butylcarbonato tin (including isomers), butyl-pentyloxy-di-pentylcarbonato tin ((including isomers), butyl-hexyloxy-di-hexylcarbonato tin (including isomers), butyl heptyloxy-di-heptylcarbonato tin (including isomers), butyl-benzyloxy-di-benzylcarbonato tin (including isomers), octyl-methoxy-di-methylcarbonato tin, octyl-ethoxy-di-ethylcarbonato tin, octyl-propoxy-di-propylcarbonato tin (including isomers), octyl-butoxy-di-butylcarbonato tin (including isomers), octyl-pentyloxy-di-pentylcarbonato tin ((including isomers), octyl-hexyloxy-di-hexylcarbonato tin (including isomers), octyl-heptyloxy-di-heptylcarbonato tin (including isomers), octyl-benzyloxy-di-benzylcarbonato tin (including isomers); alkyl-alkylcarbonato tin oxides and alkyl-aralkylcarbonato tin oxides such as butyl-methylcarbonato tin oxide, butyl-ethylcarbonato tin oxide, butyl-propylcarbonato tin oxide (including isomers), butyl-butylcarbonato tin oxide (including isomers), butyl-pentylcarbonato tin oxide (including isomers), butyl-hexylcarbonato tin oxide (including isomers), butyl-heptylcarbonato tin oxide (including isomers), butyl-benzylcarbonato tin oxide (including isomers), octyl-methylcarbonato tin oxide, octyl-ethylcarbonato tin oxide, octyl-propylcarbonato tin oxide (including isomers), octyl-butylcarbonato tin oxide (including isomers), octyl-pentylcarbonato tin oxide (including isomers), octyl-hexylcarbonato tin oxide (including isomers), octyl-heptylcarbonato tin oxide (including isomers), octyl-benzylcarbonato tin oxide (including isomers); and, trialkyl-di-alkylcarbonato-alkoxy distannoxanes and trialkyl-diaralkylcarbonato-aralkyloxy distannoxanes such as 1,1,3-tributyl-1,3-di-methylcarbonato-3-methoxy distannoxane, 1,1,3-tributyl-1,3-di-ethylcarbonato-3-ethoxy distannoxane, 1,1,3-tributyl-1,3-di-propylcarbonato-3-propoxy distannoxane (including isomers), 1,1,3-tributyl-1,3-di-butylcarbonato-3-butoxy distannoxane (including isomers), 1,1,3-tributyl-1,3-di-pentylcarbonato-3-pentyloxy distannoxane (including isomers), 1,1,3-tributyl-1,3-di-hexylcarbonato-3-hexyloxy distannoxane (including isomers), 1,1,3-tributyl-1,3-di-heptylcarbonato-3-heptyloxy distannoxane (including isomers), 1,1,3-tributyl-1,3-di-benzylcarbonato-3-benzyloxy distannoxane (including isomers), 1,1,3-trioctyl-1,3-di-methylcarbonato-3-methoxy distannoxane, 1,1,3-trioctyl-1,3-di-ethylcarbonato-3-ethoxy distannoxane, 1,1,3-trioctyl-1,3-di-propylcarbonato-3-propoxy distannoxane (including isomers), 1,1,3-trioctyl-1,3-di-butylcarbonato-3-butoxy distannoxane (including isomers), 1,1,3-trioctyl-1,3-di-pentylcarbonato-3-pentyloxy distannoxane (including isomers), 1,1,3-trioctyl-1,3-di-hexylcarbonato-3-hexyloxy distannoxane (including isomers), 1,1,3-trioctyl-1,3-di-heptylcarbonato-3-heptyloxy distannoxane (including isomers) or 1,1,3-trioctyl-1,3-di-benzylcarbonato-3-benzyloxy distannoxane (including isomers). A compound of the above-mentioned group may be selected alone or a mixture of compounds may be selected from the above-mentioned group.

Most preferable examples thereof may include (n-butyl)-di-(n-butylcarbonato)-(n-butoxy)tin, (n-butyl)-di-(n-pentylcarbonato)-(n-pentyloxy)tin, (n-butyl)-bis-(3-methylbutyl-carbonato)-(3-methylbutoxy)tin, (n-butyl)-di-(n-hexylcarbonato)-(n-hexyloxy)tin, (n-butyl)-bis-(2-ethylbutylcarbonato)-(2-ethylbutoxy)tin, (n-octyl)-di-(n-butylcarbonato)-(n-butoxy)tin, (n-octyl)-di-(n-pentylcarbonato)-(n-pentyloxy)tin, (n-octyl)-di-(n-hexylcarbonato)-(n-hexyloxy)tin, (n-octyl)-bis-(3-methylbutylcarbonato)-(3-methylbutoxy)tin, (n-octyl)-bis-(2-ethylbutylcarbonato)-(2-ethylbutoxy)tin, (n-butyl)-(n-butylcarbonato)tin oxide, (n-butyl)-(n-pentylcarbonato)tin oxide, (n-butyl)-(3-methylbutylcarbonato)tin oxide, (n-butyl)-(n-hexylcarbonato)tin oxide, (n-butyl)-(2-ethylbutylcarbonato)tin oxide, (n-octyl)-(n-butylcarbonato)tin oxide, (n-octyl)-(n-pentylcarbonato)tin oxide, (n-octyl)-(n-hexylcarbonato)tin oxide, (n-octyl)-(3-methylbutylcarbonato)tin oxide, (n-octyl)-(2-ethylbutylcarbonato)tin oxide, 1,1,3-tri-(n-butyl)-1,3-di-(n-butylcarbonato)-3-(n-butoxy)distannoxane, 1,1,3-tri-(n-butyl)-1,3-di-(n-pentylcarbonato)-3-(n-pentyloxy)distannoxane, 1,1,3-tri-(n-butyl)-1,3-bis-(3-methylbutylcarbonato)-3-(3-methylbutoxy)distannoxane, 1,1,3-tri-(n-butyl)-1,3-di-(n-hexylcarbonato)-3-(n-hexyloxy)distannoxane, 1,1,3-tri-(n-butyl)-1,3-bis-(2-ethylbutyl-carbonato)-3-(2-ethylbutoxy)distannoxane, 1,1,3-tri-(n-octyl)-1,3-di-(n-butylcarbonato)-3-(n-butoxy)distannoxane, 1,1,3-tri-(n-octyl)-1,3-di-(n-pentylcarbonato)-3-(n-pentyloxy)distannoxane, 1,1,3-tri-(n-octyl)-1,3-bis-(3-methylbutylcarbonato)-3-(3-methylbutoxy)distannoxane, 1,1,3-tri-(n-octyl)-1,3-di-(n-hexylcarbonato)-3-(n-hexyloxy) distannoxane and 1,1,3-tri-(n-octyl)-1,3-bis-(2-ethyl butylcarbonato)-3-(2-ethylbutoxy)distannoxane.

Conjugates of carbon dioxide and the above-mentioned dialkyl tin dialkoxides, tetraalkyl dialkoxy distannoxanes and trialkyl tin alkoxide compounds may each be mixtures, may be used alone, or may be mutually coordinated or associated. In general, it is difficult to identify the structures of alkyl tin alkoxides since their ligands are easily exchanged, and other coordinated or associated conjugates with carbon dioxide other than those indicated above may be present. However, since this is merely due to being unable identify them with the current analytical techniques, conjugates of carbon dioxide and dialkyl tin dialkoxides, tetraalkyl dialkoxy distannoxanes, trialkyl tin alkoxide compounds, and monoalkyl tin alkoxide compounds based on the definitions of alkyl groups, alkoxy groups and carbonato groups as described above can also be used in the present embodiment.

Next, an explanation is provided of step (c). Step (c) is a step for reacting the residual liquid obtained in step (b) with an alcohol represented by the above-mentioned formula (36), and removing the water formed as a by-product by distillation and regenerating dialkyl tin dialkoxide to use the dialkyl tin dialkoxide as the dialkyl tin dialkoxide of step (a).

Examples of alcohols represented by the formula (36) may include methanol, ethanol, propanol (including isomers), butanol (including isomers), pentanol (including isomers), hexanol (including isomers), heptanol (including isomers), octanol (including isomers), nonanol (including isomers) and decanol (including isomers), and alcohols in which the number of carbon atoms that constitute the alcohol is a number selected from an integer of from 1 to 12 are used preferably. More preferable examples thereof may include ethanol, propanol (including isomers), butanol (including isomers), pentanol (including isomers), hexanol (including isomers), heptanol (including isomers) and octanol (including isomers), while even more preferable examples thereof may include the same alcohols as those used in the production of dialkyl tin dialkoxide as previously described.

Removal of water formed as a by-product in the reaction by distillation is preferably carried out under the same conditions as distillation of water in the production of dialkyl tin dialkoxide as previously described. The reaction may be terminated once a composition containing the desired amount of dialkyl tin dialkoxide has been obtained. Progression of the reaction is also determined by measuring the amount of water extracted outside the system, and can also be determined by a method using $^{119}$Sn-NMR by sampling the reaction liquid. In the use of the composition containing the dialkyl tin dialkoxide in step (a), the reaction is terminated after confirming the obtaining of a composition in which the molar ratio of tetraalkyl dialkoxy distannoxane and dialkyl tin dialkoxide contained in the alkyl tin alkoxide composition obtained in the above reaction, when expressed as the combined molar ratio of both, is within a range of from 0:100 to 80:20 and more preferably within a range of from 10:90 to 70:30. The alcohol used may be used while still present in the reaction system, and the alcohol may also be used by distilling off the alcohol depending on the case. Since there is the advantage of being able to reduce the size of the reaction vessels of the other steps, it is preferable to remove as much of the alcohol as possible. Removal by known distillation is preferable for the removal method, and known distillation equipment can be used for the distiller used for distillation. A thin film distillation apparatus is preferably used for the distillation apparatus since the alcohol can be removed in a short period of time.

There are few restrictions on the reactor used in step (c) since, differing from the production process of dialkyl tin dialkoxide by a reaction between dialkyl tin oxide and alcohol, dialkyl tin oxide, which is generally in the form of a solid, is not used. Namely, there are no particular limitations on the type of reaction vessel of the dehydration reaction, and a known tank type or a column type reaction vessel can be used. A low boiling point reaction mixture containing water is extracted in gaseous form from the reaction vessel by distillation, while a high boiling point reaction mixture containing a produced dialkyl tin dialkoxide and/or tetraalkyl dialkoxy distannoxane is extracted in the form of a liquid from the lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a columnar reactor are preferable from the viewpoint of efficiently shifting the equilibrium to the products side, while a structure having a large gas-liquid contact area is preferable for being able to rapidly transfer the water formed to the gaseous phase. Continuous methods using a multitubular reactor, a multistage distillation column or a packed column packed with a packing are particularly preferable. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Although the above description has indicated a production example of carbonic acid ester using dialkyl tin dialkoxide, during the course of the production of this carbonic acid ester, monoalkyl tin alkoxide compounds and trialkyl tin alkoxide compounds are formed. These monoalkyl tin alkoxide compounds and trialkyl tin alkoxide compounds gradually accumulate in the reaction system as the production of carbonic acid ester is repeated, and may cause a decrease in the reaction rate or a decrease in the yield of carbonic acid ester. Thus, it is preferable to extract a portion of the alkyl tin composition containing monoalkyl tin alkoxide compounds and trialkyl tin alkoxide compounds from the reaction system, use this extracted alkyl tin composition as the alkyl tin composition of the above-mentioned step (1), obtain an alkyl tin composition from step (2), and regenerate dialkyl tin dialkoxide and/or tetraalkyl dialkoxy distannoxane by a reaction between the alkyl tin composition and a carbonic acid ester and/or alcohol. This regeneration of dialkyl tin alkoxide and/or tetraalkyl dialkoxy distannoxane is preferably carried out after the step (b) and/or step (c), and the regenerated dialkyl tin dialkoxide and/or tetraalkyl dialkoxy distannoxane is used as the dialkyl tin dialkoxide of step (a) and/or the raw material of step (c) by mixing with the residual liquid of step (b).

Figure 2:
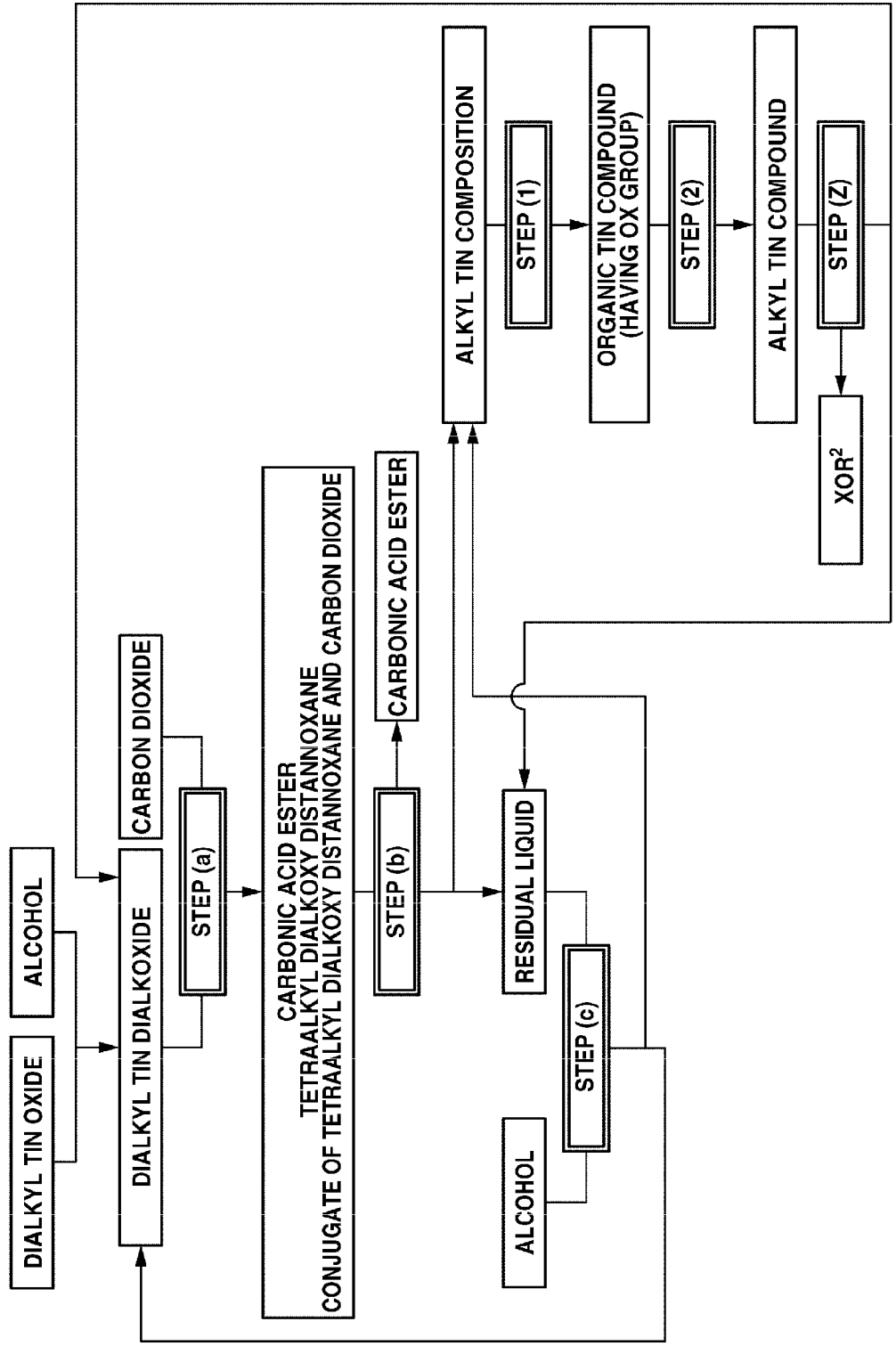
FIG. 2 shows a flow chart for explaining an improved carbonic acid ester production process that combines a carbonic acid ester production process and a dialkyl tin compound production process according the present embodiment.

FIG. 2 illustrates a flow chart for explaining an improved process for producing carbonic acid ester that combines a carbonic acid ester production process and the dialkyl tin compound production process according to the present embodiment. As was previously described, a portion or all of the alkyl tin composition extracted from step (b) and/or step (c) of the carbonic acid ester production process is used as the raw material of step (1). The dialkyl tin dialkoxide and/or tetraalkyl dialkoxy distannoxane obtained by going through steps (1) to (2) and step (Z) may be used as the dialkyl tin dialkoxide of step (a), or may be used as the raw material of step (c) by mixing with the residual liquid of step (b). In the production of carbonic acid ester, the monoalkyl tin alkoxide compound and trialkyl tin alkoxide compound formed by the alkyl group disproportionation reaction of the dialkyl tin dialkoxide and/or the tetraalkyl dialkoxy distannoxane does not have activity as a catalyst for producing carbonic acid ester and was required to be removed outside the system as a so-called deactivated form, thus making it necessary to dispose of the removed deactivated form outside the system. According to the improved carbonic acid ester production process of the present embodiment, the monoalkyl tin alkoxide and trialkyl tin alkoxide are regenerated in the form of dialkyl tin dialkoxide and/or tetraalkyl dialkoxy distannoxane, thereby offering the advantages of being able to be reused as catalysts for producing carbonic acid ester while also dramatically reducing the amount of waste products formed.

As has been explained above, although the production process of the dialkyl tin dialkoxide compound and/or tetraalkyl dialkoxy distannoxane compound (step (Z)) of the present embodiment has as aspect of a single step in a process for regenerating dialkyl tin dialkoxide and/or tetraalkyl dialkoxy distannoxane from the monoalkyl tin alkoxide compound and/or the trialkyl tin alkoxide compound formed in the carbonic acid ester production process, separate from this, it also has the aspect of being a single step in the carbonic acid ester production process differing from the above-mentioned process in the form of the carbonic acid ester production process for carrying out the following steps (A) and (B) by using the dialkyl tin dialkoxide compound and/or tetraalkyl dialkoxy distannoxane compound produced in the process of the present embodiment as raw materials:

step (A): reacting a dialkyl tin dialkoxide compound and/or tetraalkyl dialkoxy distannoxane compound produced in the production process of the present embodiment with carbon dioxide to obtain a reaction liquid containing a carbonic acid ester and a tetraalkyl dialkoxy distannoxane compound and/or a conjugate of the tetraalkyl dialkoxy distannoxane compound and carbon dioxide; and, step (B): separating the carbonic acid ester from the reaction liquid by distillation so as to obtain a residual liquid containing tetraalkyl dialkoxy distannoxane and/or a conjugate of the tetraalkyl dialkoxy distannoxane and carbon dioxide.

Step (A) is the similar to the above-mentioned step (a) with the exception of using the dialkyl tin dialkoxide compound produced in step (Z) instead of a dialkyl tin dialkoxide, and can be carried out according to the process indicated below. A dialkyl tin dialkoxide compound produced in step (Z) in the flow charts shown in FIGS. 1 and 2, for example, or a dialkyl tin dialkoxide compound produced by carrying out step (Z) using an alkyl tin compound obtained in step (C) to be described later may be used for the dialkyl tin dialkoxide compound produced in step (Z).

In step (A), gaseous carbon dioxide is absorbed into the dialkyl tin dialkoxide compound and/or tetraalkyl dialkoxy distannoxane compound produced in step (Z) and allowing to chemically react to obtain a mixture containing a conjugate of a dialkyl tin dialkoxide compound and carbon dioxide.

During this chemical reaction, the dialkyl tin dialkoxide compound is reacted in liquid form or by putting into liquid form with a solvent and the like. A method in which the compound is put into liquid form by heating is preferably used for putting the compound into liquid form, and the compound may also be put into liquid form with a solvent and the like. Although varying according to the reaction temperature, the pressure at which the reaction is carried out is preferably within a range of from a normal pressure to 1 MPa, and more preferably within a range of from a normal pressure to 0.6 MPa. Although varying according to the reaction pressure, the temperature at which the reaction is carried out is preferably within a range of from −40 to 80° C., and in consideration of fluidity during transfer, is more preferably 0 to 80° C. and most preferably within a range of from a normal temperature (for example, 20° C.) to 80° C. The reaction is carried out within a range of from several seconds to 100 hours, and in consideration of productivity and the like, is preferably carried out for several minutes to 10 hours. A known tank-type reactor or a column-type reaction reactor can be used for the reactor. In addition, a plurality of reactors may be used in combination. Since the reaction is a reaction of a composition containing carbon dioxide (gas) and a dialkyl tin dialkoxide compound (liquid), in order to carry out the reaction efficiently, it is preferable to increase the contact surface area between the gas and liquid by increasing the size of the gas-liquid interface. A known method can be used for reacting while increasing the size of the gas-liquid interface in this manner, preferable examples of which may include increasing the stirring rate or generating air bubbles in the liquid in the case of a tank-type reactor, and using a packed column or a tray-type distillation column in the case of a column-type reactor. Examples of such column-type reactors may include tray-type distillation column types such as a bubble tray, a porous plate tray, a valve tray or a countercurrent tray, and packed column types packed with various types of packing materials such as a Raschig ring, a Lessing ring, a pole ring, a Berl saddle, an Interlock saddle, a Dixon packing, a McMahon packing, Helipack, a Sulzer packing or Mellapak. Although a known material may be used for the materials of the reactor and lines provided it does not have a detrimental effect, materials such as SUS304, SUS316 and SUS316L are inexpensive and can be used preferably. Known processing equipment including instruments such as flow meters and thermometers, reboilers, pumps and condensers may be added as necessary, a known method such as steam heating or a heater may be used for heating, and a known method such as air cooling, cold water or brine can be used for cooling. Since the reaction is ordinarily an exothermic reaction, the reactor may be cooled directly or the reactor may be cooled by dissipating heat of the reactor. Alternatively, the reactor may also be heated if the reaction is carried out for the purpose of simultaneously carrying out carbonic acid esterification. A known method can be used for cooling and heating the reactor, such as a method using a jacket or a method using internal coils. The composition containing carbon dioxide gas and dialkyl tin dialkoxide compound supplied to the reactor may also be supplied by supplying each reactant separately or by mixing prior to supplying to the reactor. The reactants may also be supplied from multiple locations in the reactor. Following completion of the reaction, the reaction products can be determined by $^{119}$Sn-NMR analysis and the like.

Next, a reaction liquid containing carbonic acid ester is obtained according to the process described below from the conjugate of dialkyl tin dialkoxide compound and carbon dioxide obtained above.

The reaction conditions are such that the reaction is carried out within a range of from 110 to 200° C., and although a high reaction temperature is preferable for increasing the reaction rate, since there are cases in which undesirable reactions such as decomposition occur at high temperatures thereby resulting in a decrease in yield, the reaction temperature is preferably 120 to 180° C., the reaction time is within a range of from 0.1 to 10 hours, and the reaction pressure is within a range of from 1.5 to 20 MPa and preferably within a range of from 2.0 to 10 MPa. The reaction is completed after forming the desired carbonic acid ester in the reactor. The progression of the reaction can be confirmed by, for example, sampling the reaction liquid in the reactor and analyzing the carbonic acid ester formed by a method such as $^1$H-NMR or gas chromatography. For example, the reaction may be completed once 10% or more of the dialkyl tin dialkoxide compound and/or conjugate of the dialkyl tin dialkoxide compound and carbon dioxide has formed based on the molar ratio thereof, or in the case of desiring to increase the yield of carbonic acid ester, the reaction may be completed after continuing until this value is 90% or more. A known reactor can be used for the reactor, and a column-type reactor or a tank-type reactor can be used preferably. Although a known material may be used for the materials of the reactor and lines provided it does not have a detrimental effect, materials such as SUS304, SUS316 and SUS316L are inexpensive and can be used preferably. Known processing equipment including instruments such as flow meters and thermometers, reboilers, pumps and condensers may be added as necessary, a known method such as steam heating or a heater may be used for heating, and a known method such as air cooling, cold water or brine can be used for cooling.

Next, an explanation is provided of step (B). This step is a step for separating carbonic acid ester from the reaction liquid containing carbonic acid ester obtained in step (A), so as to obtain a residual liquid containing a tetraalkyl dialkoxy distannoxane compound and/or a conjugate of the tetraalkyl dialkoxy distannoxane compound and carbon dioxide. A known method and apparatus can be preferably used for the separation method. A preferable separation method is separation by distillation.

Carbonic acid ester and residual liquid are obtained by batch, semi-batch or continuous distillation of the reaction liquid transferred from step (A). A preferable distillation method comprising supplying the reaction liquid to a distiller, separating carbonic acid ester from the top of the distiller outside the system in the form of a gas phase component, and extracting the residual liquid from the bottom of the distiller in the form of a liquid component. Although varying according to the boiling point of the carbonic acid ester and pressure, the temperature of this step is within a range of from a normal temperature (for example, 20° C.) to 200° C., and since there are cases in which denaturation of tin compounds in the residual liquid occurs at high temperatures as well as cases in which the carbonic acid ester ends up decreasing due to a reverse reaction, the temperature is preferably within a range of from a normal temperature (for example, 20° C.) to 150° C. Although varying according to the type of carbonic acid ester and temperature at which this step is carried out, pressure is generally from a normal pressure to a reduced pressure, and in consideration of productivity, pressure is more preferably within a range of from 100 Pa to 80 KPa and most preferably within a range of from 100 Pa to 50 KPa. This step can be carried out within a range of from 0.01 to 10 hours, and since there are cases in which tin compounds contained in the reaction liquid may be denatured or carbonic acid ester may decrease due to a reverse reaction if this step is carried out at a high temperature for an extended period of time, the reaction time is preferably within a range of from 0.01 to 0.5 hours and most preferably within a range of from 0.01 to 0.3 hours. A known distiller can be used for the distiller, a column-type distiller or a tank-type distiller can be used preferably, or a plurality of types may be used in combination. More preferably, the distiller is a thin film evaporator or a thin film distiller, while a thin film evaporator equipped with a distillation column or a thin film distiller is the most preferable. Although known materials may be used for the distiller and lines provided they do not have detrimental effects, materials such as SUS304, SUS316 or SUS316L are inexpensive and can be used preferably. Known processing equipment including instruments such as flow meters and thermometers, reboilers, pumps and condensers may be added as necessary, a known method such as steam heating or a heater may be used for heating, and a known method such as air cooling, cold water or brine can be used for cooling.

Moreover, in the present embodiment, a step (C) described below can be added to the above-mentioned steps (A) and (B), and an alkyl tin compound produced in the step (C) can be used as an alkyl tin compound of step (Z).

step (C): producing at least one alkyl tin compound selected from the group consisting of the following i) and ii) by reacting the residual liquid of the step (B) with an acid represented by the general formula HOX (Bronsted acid having a pKa of from 0 to 6.8) and/or an acid anhydride represented by the general formula XOX (wherein OX represents a group in which HOX that is a conjugate acid of OX is a Bronsted acid having a pKa of from 0 to 6.8);

i) a dialkyl tin compound having one tin atom, two Sn—$R^1$ (wherein $R^1$ represents an alkyl group), and two Sn—OX bonds (wherein OX is a group in which HOX that is a conjugate acid of OX is a Bronsted acid having a pKa of from 0 to 6.8); and
  ii) a tetraalkyl distannoxane compound having one Sn—O—Sn bond, in which each tin atom of the tetraalkyl distannoxane compound has two Sn—$R^1$ bonds and one Sn—OX bond (wherein OX is a group in which HOX that is a conjugate acid of OX is a Bronsted acid having a pKa of from 0 to 6.8).

This step (C) resembles the previously explained step (1) and is carried out by a method like that described below.

In step (C), an organic acid is preferably used for the acid represented by the general formula HOX. Although examples of these organic acids may include carboxylic acid, sulfonic acid and phenol, carboxylic acid is used preferably. Examples of carboxylic acids may include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (including isomers), octanoic acid (including isomers), nonaoic acid (including isomers), decanoic acid (including isomers), undecanoic acid (including isomers), dodecanoic acid (including isomers), tetradecanoic acid (including isomers), hexadecanoic acid (including isomers), acrylic acid, crotic acid, isocrotic acid, vinylacetic acid, methacrylic acid, angelic acid, tiglic acid, allylacetic acid or undecenoic acid (including isomers); saturated or unsaturated aliphatic dicarboxylic acids such as oxalic acid, malonic acid, succinic acid, glutaric acid, adipic acid, heptanedioic acid (including isomers), octanedioic acid (including isomers), nonanedioic acid (including isomers), decanedioic acid (including isomers), maleic acid, fumaric acid, methylmaleic acid, methylfumaric acid, pentenedioic acid (including isomers), itaconic acid or allylmalonic acid; saturated or unsaturated tricarboxylic acid compounds such as 1,2,3-propanetricarboxylic acid, 1,2,3-propenetricarboxylic acid or 2,3-dimethylbutane-1,2,3-tricarboxylic acid; aromatic carboxylic acid compounds such as benzoic acid, methylbenzoic acid (including isomers), ethylbenzoic acid (including isomers), propylbenzoic acid (including isomers), dimethylbenzoic acid (including isomers) or trimethylbenzoic acid (including isomers); aromatic dicarboxylic acid compounds such as phthalic acid, isophthalic acid, terephthalic acid or methylisophthalic acid (including isomers); and, aromatic tricarboxylic acid compounds such as hemimellitic acid, trimellitic acid or trimesic acid. Among these carboxylic acids, saturated monocarboxylic acids are used preferably, saturated monocarboxylic acids having a standard boiling point of 300° C. or lower are used more preferably, and saturated monocarboxylic acids having a standard boiling point of 250° C. or lower are used even more preferably. Standard boiling point refers to the boiling point at 1 atmosphere as described in Encyclopedia Chimica (issued on Oct. 1, 2003 by Kyoritsu Publishing Co., Ltd.). More specifically, acetic acid, propionic acid, n-butyric acid, isobutyric acid, valeric acid, isovaleric acid, 2-methylbutanoic acid, pivalic acid or hexanoic acid is used preferably.

In addition, in step (C), examples of acid anhydrides represented by the general formula XOX may include aliphatic anhydrides such as acetic anhydride, propionic anhydride, butyric anhydride, isobutyric anhydride, valeric anhydride, isovaleric anhydride, succinic anhydride, maleic anhydride, propionic anhydride or glutaric anhydride; and, aromatic anhydrides such as benzoic anhydride, phthalic anhydride or pyromellitic anhydride. Among these, acid anhydrides having a standard boiling point of 300° C. or lower are used preferably, and in order to facilitate removal of excess acid anhydride after the reaction, acid anhydrides having a standard boiling point of 200° C. or lower are used more preferably. Moreover, maleic anhydride and acetic anhydride are preferable from the viewpoint of facilitating the removal of by-products such as carboxylic acid esters and ease of industrial acquisition.

Although these acids and acid anhydrides can be used alone or by mixing a plurality of types, in the case of using an acid, there are many cases in which water is formed in the case of reacting the acid with the tetraalkyl dialkoxy distannoxane compound. Distillation separation or membrane separation may be carried out or a dehydrating agent may be used to remove the water. In addition, the combined use of an acid anhydride as a dehydrating agent is preferable. Moreover, in the case of using an acid anhydride only, since there are many cases in which water is not formed in the reaction between the tetraalkyl dialkoxy distannoxane compound and the acid anhydride, a method using an acid anhydride only is preferable.

The amount of acid and/or acid anhydride used is preferably within a range of from 0.1 to 50 times in terms of the stoichiometric ratio based on the tin atoms contained in the residua liquid obtained in step (B) in consideration of the reaction rate in step (C) and the final yield of the dialkyl tin compound, and is more preferably within a range of from 0.5 to 20 times in consideration of the size of the reactor and the reaction rate. In the case the amount used is less than 0.1 in terms of the stoichiometric ratio, there are cases in which it is difficult for the reaction to proceed, while conversely even if used in an amount greater than 50 times in terms of the stoichiometric ratio, there are many cases in which this does not have an effect on reaction rate or final yield of the dialkyl tin compound in this step.

The reaction of step (C) is preferably carried out at a reaction temperature of from −20 to 300° C. and more preferably at a reaction temperature of from −10 to 250° C., and although a high reaction temperature is preferable for increasing the reaction rate, since there are also cases in which undesirable reactions such as decomposition occur at high temperatures thereby lowering the yield, the reaction is even more preferably carried out a reaction temperature of from 0 to 230° C. In addition, the reaction of step (C) is preferably carried out in an inert gas atmosphere such as argon, neon or nitrogen.

Although the use of a solvent is not required in step (C), a solvent can be used for the purpose of improving fluidity, facilitating the reaction procedure or efficiently removing water outside the system in the case water is formed in the reaction. Examples of such solvents may include linear, branched or cyclic hydrocarbons having 5 to 16 carbon atoms, ethers composed of linear, branched or cyclic hydrocarbons having 4 to 16 carbon atoms, and linear, branched or cyclic halogenated hydrocarbons having 1 to 16 carbon atoms. More specifically, examples of solvents that can be used may include linear or cyclic hydrocarbons selected from the group consisting of pentane (including isomers), hexane (including isomers), heptane (including isomers), octane (including isomers), nonane (including isomers), decane (including isomers), hexadecane (including isomers), cyclohexane, cycloheptane, cyclooctane, benzene, toluene, xylene (including isomers) and ethylbenzene; ethers selected from the group consisting of diethyl ether, dipropyl ether (including isomers), dibutyl ether (including isomers), dihexyl ether (including isomers), dioctyl ether (including isomers) and diphenyl ether; and halogenated hydrocarbons selected from the group consisting of methylene chloride, chloroform, carbon tetrachloride, chlorobenzene, tetrachloroethane and dichlorobenzene (including isomers). These solvents can be used alone or used by mixing two or more types.

The alkyl tin compound produced in this step (C) is at least one alkyl tin compound selected from the group consisting of dialkyl tin compounds represented by the following formula (48) and tetraalkyl distannoxane compounds represented by the following formula (49):

(48)

(wherein, each of $R^1$ independently represents a linear or branched alkyl group having 1 to 12 carbon atoms, O represents an oxygen atom, $OX^1$ and $OX^2$ are $OX^1$ and $OX^2$ in which conjugate acids of $OX^1$ and $OX^2$ in the form of $HOX^1$ and $HOX^2$ are Bronsted acids having a pKa of from 0 to 6.8, and a and b are integers of 0 to 2, respectively, and a+b=2);

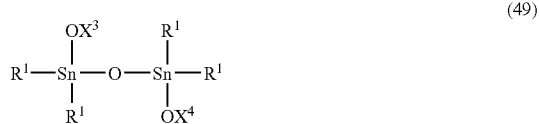

(49)

(wherein, each of $R^1$ independently represents a linear or branched alkyl group having 1 to 12 carbon atoms, O represents an oxygen atom, and $OX^3$ and $OX^4$ are $OX^3$ and $OX^4$ in which conjugate acids of $OX^3$ and $OX^4$ in the form of $HOX^3$ and $HOX^4$ are Bronsted acids having a pKa of from 0 to 6.8).

Examples of $R^1$ in the formula (48) may include alkyl groups in the form of aliphatic hydrocarbon groups in which the number of carbon atoms that constitute the groups is a number selected from an integer of from 1 to 12, such as methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples may include linear or branched alkyl groups in which the number of carbon atoms that constitute the groups is a number selected from an integer of from 1 to 8. Although a dialkyl tin compound can be used in which the groups are alkyl groups in which the number of carbon atoms that constitute the groups is outside the indicated range, fluidity may become poor and productivity may be impaired. The alkyl groups are more preferably n-butyl groups or n-octyl groups in consideration of ease of acquisition during industrial production.

Although there are no particular limitations on $OX^1$ and $OX^2$ in the formula (48) provided their conjugate acids in the form of $HOX^1$ and $HOX^2$ are Bronsted acids and the pKa of the conjugate acids are 0 to 6.8, they are preferably at least one type of substituent selected from the group consisting of acyloxyl groups and aryloxy groups, and the pKa of conjugate acids thereof are 0 to 6.8. More preferably, $OX^1$ and $OX^2$ are groups in which the number of carbon atoms that constitute the groups is a number selected from integers of 0 to 12. Specific examples of such groups may include acyloxyl groups composed of a linear or branched, saturated alkyl group, a carbonyl group and an oxygen atom, such as an acetoxy group, a propionyloxy group, a butyryloxy group, a valeryloxy group or a lauroyloxy group; and aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a dimethylphenoxy group (including isomers), a methylethylphenoxy group (including isomers), a methylpropylphenoxy group (including isomers), a methylbutylphenoxy group (including isomers), a methylpentylphenoxy group (including isomers), a diethylphenoxy group (including isomers), an ethylpropylphenoxy group (including isomers), an ethylbutylphenoxy group (including isomers), a dipropylphenoxy group (including isomers), a trimethylphenoxy group (including isomers), a dimethylethylphenoxy group (including isomers), a dimethylpropylphenoxy group (including isomers), a dimethylbutylphenoxy group (including isomers), a methylethylpropylphenoxy group, a methyldimethylphenoxy group or a triethylphenoxy group (including isomers).

Specific examples of dialkyl tin compounds represented by the formula (48) may include dialkyl-diacyloxy tin compounds such as dimethyl-diacetoxy tin, dimethyl-dipropionyloxy tin (including isomers), dimethyl-dibutyryloxy tin (including isomers), dimethyl-valeryloxy tin (including isomers), dimethyl-dilauroyloxy tin (including isomers), dibutyl-diacetoxy tin (including isomers), dibutyl-dipropionyloxy tin (including isomers), dibutyl-dibutyryloxy tin (including isomers), dibutyl-divaleryloxy tin (including isomers), dibutyl-dilauroyloxy tin (including isomers), dioctyl-diacetoxy tin (including isomers), dioctyl-dipropionyloxy tin (including isomers), dioctyl-butyryloxy tin (including isomers), dioctyl-valeryloxy tin (including isomers) or dioctyl-dilauroyloxy tin (including isomers); and, alkyl-diaryloxy tin compounds such as dimethyl-diphenoxy tin, dimethyl-di(methylphenoxy)tin (including isomers), dimethyl-di(ethylphenoxy)tin (including isomers), dimethyl-di(propylphenoxy) tin (including isomers), dimethyl-di(butylphenoxy)tin (including isomers), dimethyl-di(pentylphenoxy)tin (including isomers), dimethyl-di(hexylphenoxy)tin (including isomers), dimethyl-bis(dimethylphenoxy)tin (including isomers), dimethyl-di(methylethylphenoxy)tin (including isomers), dimethyl-di(methylpropylphenoxy)tin (including isomers), dimethyl-di(methylbutylphenoxy)tin (including isomers), dimethyl-di(methylpentylphenoxy)tin (including isomers), dimethyl-bis(diethylphenoxy)tin (including isomers), dimethyl-di(ethylpropylphenoxy)tin (including isomers), dimethyl-di(ethylbutylphenoxy)tin (including isomers), dimethyl-di(dipropylphenoxy)tin (including isomers), dimethyl-di(trimethylphenoxy)tin (including isomers), dimethyl-bis(dimethylethylphenoxy)tin (including isomers), dimethyl-bis(diethylpropylphenoxy)tin (including isomers), dimethyl-bis(dimethylbutylphenoxy)tin (including isomers), dimethyl-di(methylethylpropylphenoxy)tin (including isomers), dimethyl-di(ethyldimethylphenoxy)tin (including isomers), dimethyl-di(triethylphenoxy)tin (including isomers), dibutyl-diphenoxy tin (including isomers), dibutyl-di(methylphenoxy)tin (including isomers), dibutyl-di(ethylphenoxy) tin (including isomers), dibutyl-di(propylphenoxy)tin (including isomers), dibutyl-di(butylphenoxy)tin (including isomers), dibutyl-di(pentylphenoxy)tin (including isomers), dibutyl-di(hexylphenoxy)tin (including isomers), dibutyl-bis(dimethylphenoxy)tin (including isomers), dibutyl-di(methylethylphenoxy)tin (including isomers), dibutyl-di(methylpropylphenoxy)tin (including isomers), dibutyl-di(methylbutylphenoxy)tin (including isomers), dibutyl-di(methylpentylphenoxy)tin (including isomers), dibutyl-bis(diethylphenoxy)tin (including isomers), dibutyl-di(ethylpropylphenoxy)tin (including isomers), dibutyl-di(ethylbutylphenoxy)tin (including isomers), dibutyl-di(dipropylphenoxy)tin (including isomers), dibutyl-di(trimethylphenoxy)tin (including isomers), dibutyl-bis(dimethylethylphenoxy)tin (including isomers), dibutyl-bis(dimethylpropylphenoxy)tin (including isomers), dibutyl-bis(dimethylbutylphenoxy)tin (including isomers), dibutyl-di(methylethylpropylphenoxy)tin (including isomers), dibutyl-di(ethyldimethylphenoxy)tin (including isomers), dibutyl-di(triethylphenoxy)tin (including isomers), dioctyl-diphenoxy tin (including isomers), dioctyl-di(methylphenoxy)tin (including isomers), dioctyl-di(ethylphenoxy)tin (including isomers), dioctyl-di(propylphenoxy)tin (including isomers), dioctyl-di(butylphenoxy)tin (including isomers), dioctyl-di(pentylphenoxy)tin (including isomers), dioctyl-di(hexylphenoxy)tin (including isomers), diocty-bis(dimethylphenoxy)tin (including isomers), dioctyl-di(methylethylphenoxy)tin (including isomers), dioctyl-di(methylpropylphenoxy)tin (including isomers), dioctyl-di(methylbutylphenoxy)tin (including isomers), dioctyl-di(methylpentylphenoxy)tin (including isomers), dioctyl-bis(diethylphenoxy)tin (including isomers), dioctyl-di(ethylpropylphenoxy)tin (including isomers), dioctyl-di(ethylbutylphenoxy)tin (including isomers), dioctyl-di(dipropylphenoxy)tin (including isomers), dioctyl-di(trimethylphenoxy)tin (including isomers), dioctyl-bis(dimethylethylphenoxy)tin (including isomers), dioctyl-bis(dimethylpropylphenoxy)tin (including isomers), dioctyl-bis(dimethylbutylphenoxy)tin (including isomers), dioctyl-di(methylethylpropylphenoxy)tin (including isomers), dioctyl-di(ethyldimethylphenoxy)tin (including isomers) or dioctyl-di(triethylphenoxy)tin (including isomers).

Examples of $R^1$ in the formula (49) may include alkyl groups in the form of aliphatic hydrocarbon groups in which the number of carbon atoms that constitute the groups is a number selected from an integer of from 1 to 12, such as methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof may include linear or branched alkyl groups in which the number of carbon atoms that constitute the groups is a number selected from an integer of from 1 to 8. Although a tetraalkyl dialkoxy distannoxane compound can be used in which the groups are alkyl groups in which the number of carbon atoms that constitute the groups is outside the indicated range, fluidity may become poor and productivity may be impaired. The alkyl groups are more preferably n-butyl groups or n-octyl groups in consideration of ease of acquisition during industrial production.

Although there are no particular limitations on $OX^3$ and $OX^4$ in the formula (49) provided their conjugate acids in the form of $HOX^3$ and $HOX^4$ are Bronsted acids and the pKa of the conjugate acids are 0 to 6.8, they are preferably at least one type of substituent selected from the group consisting of acyloxyl groups and aryloxy groups, and the pKa of conjugate acids thereof are 0 to 6.8. More preferably, $OX^1$ and $OX^2$ are groups in which the number of carbon atoms that consitute the groups is a number selected from integers of from 0 to 12. Specific examples of such groups may include acyloxyl groups composed of a linear or branched, saturated alkyl group, a carbonyl group and an oxygen atom, such as an acetoxy group, a propionyloxy group, a butyryloxy group, a valeryloxy group or a lauroyloxy group; and aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a dimethylphenoxy group (including isomers), a methylethylphenoxy group (including isomers), a methylpropylphenoxy group (including isomers), a methylbutylphenoxy group (including isomers), a methylpentylphenoxy group (including isomers), a diethylphenoxy group (including isomers), an ethylpropylphenoxy group (including isomers), an ethylbutylphenoxy group (including isomers), a dipropylphenoxy group (including isomers), a trimethylphenoxy group (including isomers), a dimethylethylphenoxy group (including isomers), a dimethylpropylphenoxy group (including isomers), a dimethylbutylphenoxy group (including isomers), a methylethylpropylphenoxy group, a methyldimethylphenoxy group or a triethylphenoxy group (including isomers).

Specific examples of compounds represented by the formula (49) may include 1,1,3,3-tetraallkyl-1,3-diacyloxy distannoxanes such as 1,1,3,3-tetramethyl-1,3-diacetoxy distannoxane, 1,1,3,3-tetramethyl-1,3-dipropionyloxy distannoxane (including isomers), 1,1,3,3-tetramethyl-1,3-dibutyryloxy distannoxane (including isomers), 1,1,3,3-tetramethyl-1,3-divaleryloxy distannoxane (including isomers), 1,1,3,3-tetramethyl-1,3-dilauroyloxy distannoxane (including isomers), 1,1,3,3-tetrabutyl-1,3-diacetoxy distannoxane (including isomers), 1,1,3,3-tetrabutyl-1,3-dipropionyloxy distannoxane (including isomers), 1,1,3,3-tetrabutyl-1,3-dibutyryloxy distannoxane (including isomers), 1,1,3,3-tetrabutyl-1,3-divaleryloxy distannoxane (including isomers), 1,1,3,3-tetrabutyl-1,3-dilauroyloxy distannoxane (including isomers), 1,1,3,3-tetraoctyl-1,3-diacetoxy distannoxane (including isomers), 1,1,3,3-tetraoctyl-1,3-dipropionyloxy distannoxane (including isomers), 1,1,3,3-tetraoctyl-1,3-dibutyryloxy distannoxane (including isomers), 1,1,3,3-tetraoctyl-1,3-divaleryloxy distannoxane (including isomers) or 1,1,3,3-tetraoctyl-1,3-dilauroyloxy distannoxane (including isomers); and 1,1,3,3-tetraalkyl-1,3-diaryloxy distannoxanes such as 1,1,3,3-tetramethyl-1,3-diphenoxy distannoxane, 1,1,3,3-tetramethyl-1,3-di(methylphenoxy) distannoxane (including isomers), 1,1,3,3-tetramethyl-1,3-di(ethylphenoxy)distannoxane (including isomers), 1,1,3,3-tetramethyl-1,3-di(propylphenoxy)distannoxane (including isomers), 1,1,3,3-tetramethyl-1,3-di(butylphenoxy)distannoxane (including isomers), 1,1,3,3-tetramethyl-1,3-di(pentylphenoxy)distannoxane (including isomers), 1,1,3,3-tetramethyl-1,3-di(hexylphenoxy)distannoxane (including isomers), 1,1,3,3-tetramethyl-1,3-bis(dimethylphenoxy)distannoxane (including isomers), 1,1,3,3-tetramethyl-1,3-di(methylethylphenoxy)distannoxane (including isomers), 1,1,3,3-tetramethyl-1,3-di(methylpropylphenoxy)distannoxane (including isomers), 1,1,3,3-tetramethyl-1,3-di(methylbutylphenoxy)distannoxane (including isomers), 1,1,3,3-tetramethyl-1,3-di(methylpentylphenoxy)distannoxane (including isomers), 1,1,3,3-tetramethyl-1,3-bis(diethylphenoxy)distannoxane (including isomers), 1,1,3,3-tetramethyl-1,3-di(ethylpropylphenoxy)distannoxane (including isomers), 1,1,3,3-tetramethyl-1,3-di(ethylbutylphenoxy)distannoxane (including isomers), 1,1,3,3-tetramethyl-1,3-di(dipropylphenoxy)distannoxane (including isomers), 1,1,3,3-tetramethyl-1,3-di(trimethylphenoxy)distannoxane (including isomers), 1,1,3,3-tetramethyl-1,3-bis(dimethylethylphenoxy)distannoxane (including isomers), 1,1,3,3-tetramethyl-1,3-bis(dimethylpropylphenoxy)distannoxane (including isomers), 1,1,3,3-tetramethyl-1,3-bis(dimethylbutylphenoxy)distannoxane (including isomers), 1,1,3,3-tetramethyl-1,3-di(methylethylpropylphenoxy)distannoxane (including isomers), 1,1,3,3-tetramethyl-1,3-di(ethyldimethylphenoxy)distannoxane (including isomers), 1,1,3,3-tetramethyl-1,3-di(triethylphenoxy)tin (including isomers), 1,1,3,3-tetrabutyl-1,3-diphenoxy distannoxane (including isomers), 1,1,3,3-tetrabutyl-1,3-di(methylphenoxy)distannoxane (including isomers), 1,1,3,3-tetrabutyl-1,3-di(ethylphenoxy)distannoxane (including isomers), 1,1,3,3-tetrabutyl-1,3-di(propylphenoxy)distannoxane (including isomers), 1,1,3,3-tetrabutyl-1,3-di(butylphenoxy)distannoxane (including isomers), 1,1,3,3-tetrabutyl-1,3-di(pentylphenoxy)distannoxane (including isomers), 1,1,3,3-tetrabutyl-1,3-di(hexylphenoxy)distannoxane (including isomers), 1,1,3,3-tetrabutyl-1,3-bis(dimethylphenoxy)distannoxane (including isomers), 1,1,3,3-tetrabutyl-1,3-di(methylethylphenoxy)distannoxane (including isomers), 1,1,3,3-tetrabutyl-1,3-di(methylpropylphenoxy)distannoxane (including isomers), 1,1,3,3-tetrabutyl-1,3-di(methylbutylphenoxy)distannoxane (including isomers), 1,1,3,3-tetrabutyl-1,3-di(methylpentylphenoxy)distannoxane (including isomers), 1,1,3,3-tetrabutyl-1,3-bis(diethylphenoxy)distannoxane (including isomers), 1,1,3,3-tetrabutyl-1,3-di(ethylpropylphenoxy)distannoxane (including isomers), 1,1,3,3-tetrabutyl-1,3-di(ethylbutylphenoxy)distannoxane (including isomers), 1,1,3,3-tetrabutyl-1,3-di(dipropylphenoxy)distannoxane (including isomers), 1,1,3,3-tetrabutyl-1,3-di(trimethylphenoxy)distannoxane (including isomers), 1,1,3,3-tetrabutyl-1,3-bis(dimethylethylphenoxy)distannoxane (including isomers), 1,1,3,3-tetrabutyl-1,3-bis(dimethylpropylphenoxy)distannoxane (including isomers), 1,1,3,3-tetrabutyl-1,3-bis(dimethylbutylphenoxy)distannoxane (including isomers), 1,1,3,3-tetrabutyl-1,3-di(methylethylpropylphenoxy)distannoxane (including isomers), 1,1,3,3-tetrabutyl-1,3-di(ethyldimethylphenoxy)tin (including isomers), 1,1,3,3-tetrabutyl-1,3-di(triethylphenoxy)distannoxane (including isomers), 1,1,3,3-tetraoctyl-1,3-diphenoxy distannoxane (including isomers), 1,1,3,3-tetraoctyl-1,3-di(methylphenoxy)distannoxane (including isomers), 1,1,3,3-tetraoctyl-1,3-di(ethylphenoxy)distannoxane (including isomers), 1,1,3,3-tetraoctyl-1,3-di(propylphenoxy)distannoxane (including isomers), 1,1,3,3-tetraoctyl-1,3-di(butylphenoxy)distannoxane (including isomers), 1,1,3,3-tetraoctyl-1,3-di(pentylphenoxy)distannoxane (including isomers), 1,1,3,3-tetraoctyl-1,3-di(hexylphenoxy)distannoxane (including isomers), 1,1,3,3-tetraoctyl-1,3-bis(dimethylphenoxy)distannoxane (including isomers), 1,1,3,3-tetraoctyl-1,3-di(methylethylphenoxy)distannoxane (including isomers), 1,1,3,3-tetraoctyl-1,3-di(methylpropylphenoxy)distannoxane (including isomers), 1,1,3,3-tetraoctyl-1,3-di(methylbutylphenoxy)distannoxane (including isomers), 1,1,3,3-tetraoctyl-1,3-di(methylpentylphenoxy)distannoxane (including isomers), 1,1,3,3-tetraoctyl-1,3-bis(diethylphenoxy)distannoxane (including isomers), 1,1,3,3-tetraoctyl-1,3-di(ethylpropylphenoxy)distannoxane (including isomers), 1,1,3,3-tetraoctyl-1,3-di(ethylbutylphenoxy)distannoxane (including isomers), 1,1,3,3-tetraoctyl-1,3-di(dipropylphenoxy)distannoxane (including isomers), 1,1,3,3-tetraoctyl-1,3-di(trimethylphenoxy)distannoxane (including isomers), 1,1,3,3-tetraoctyl-1,3-bis(dimethylethylphenoxy)distannoxane (including isomers), 1,1,3,3-tetraoctyl-1,3-bis(dimethylpropylphenoxy)distannoxane (including isomers), 1,1,3,3-tetraoctyl-1,3-bis(dimethylbutylphenoxy)distannoxane (including isomers), 1,1,3,3-tetraoctyl-1,3-di(methylethylpropylphenoxy)distannoxane (including isomers), 1,1,3,3-tetraoctyl-1,3-di(ethyldimethylphenoxy)distannoxane (including isomers) or 1,1,3,3-tetraoctyl-1,3-di(triethylphenoxy)tin (including isomers).

In general, organic tin compounds easily adopt an associated structure, and although, for example, dialkyl tin dialkoxides are known to form a dimer structure, and tetraalkyl dialkoxy distannoxanes are known to be present by forming a ladder structure in which two or three molecules are associated, even in cases in which there are changes in this associated state, the representation of a compound in the form of a monomer structure is common for the persons with ordinary skill in the art.

Figure 3:
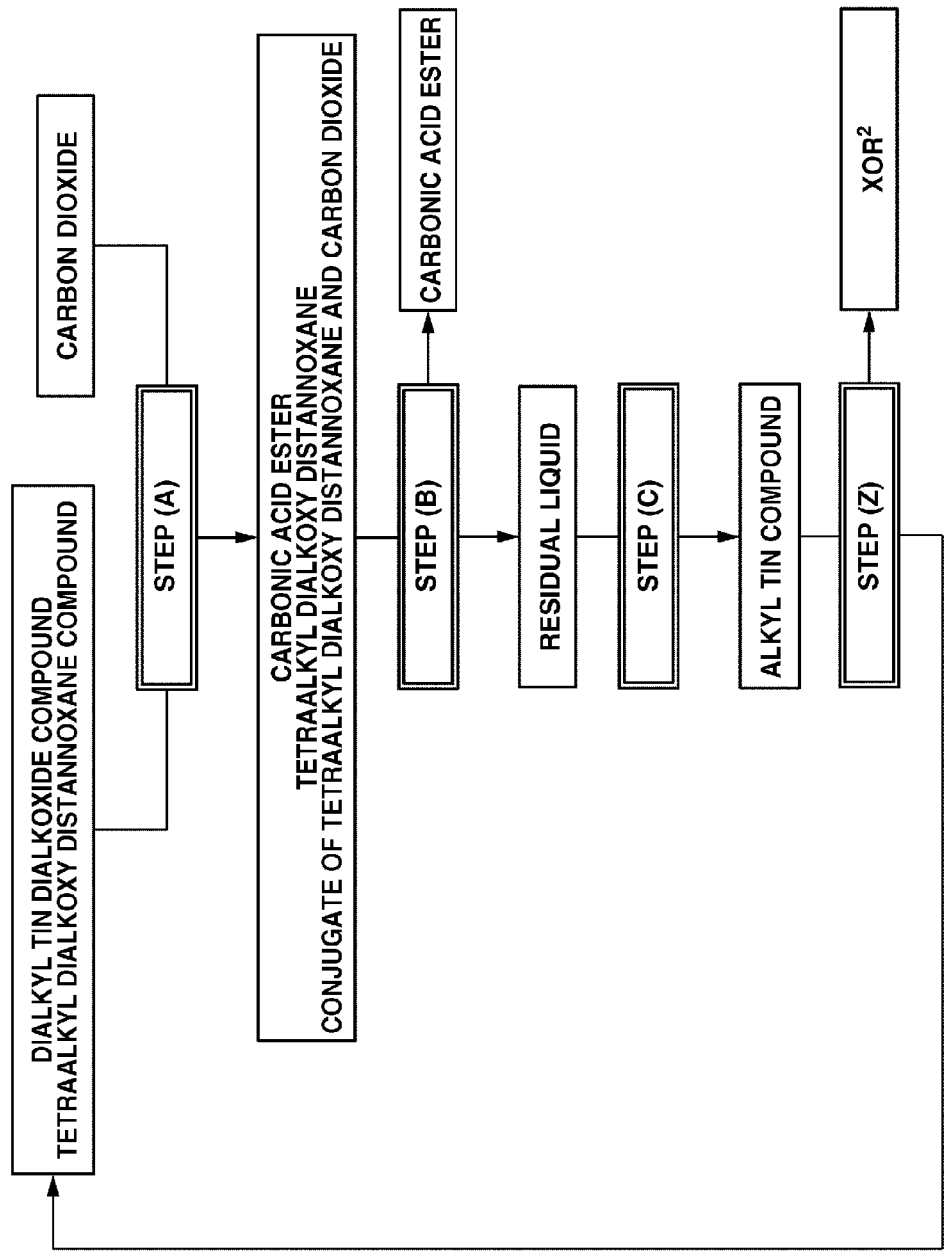
FIG. 3 shows a flow chart for explaining a carbonic acid ester production process that combines steps (A) to (C) with a step (Z) in the present embodiment.

FIG. 3 illustrates a flow chart for explaining a novel process for producing carbonic acid ester by combining steps (A) to (C) and step (Z) as explained above.

Moreover, as an alternative to the novel carbonic acid ester production process indicated in FIG. 3, an explanation is provided of a process in which a dialkyl tin compound and/or tetraalkyl distannoxane compound is produced by a process that includes the steps (I) to (III) below, and step (Z) is carried out by using the dialkyl tin compound and/or the tetraalkyl distannoxane compound.

step (I): reacting a dialkyl tin dialkoxide represented by the following general formula (50) with carbon dioxide, so as to obtain a reaction liquid containing carbonic acid ester and a tetraalkyl dialkoxy distannoxane represented by the following general formula (51) and/or a conjugate of the tetraalkyl dialkoxiy distannoxane and carbon dioxide;

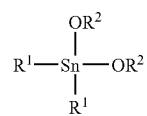

(50)

(wherein
each of $R^1$ independently represents a linear or branched alkyl group having 1 to 12 carbon atoms, and
$R^2$ respectively and independently represents a linear or branched alkyl group having 2 to 8 carbon atoms);

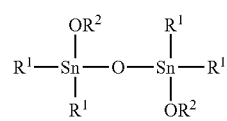

(51)

(wherein
each of $R^1$ independently represents a linear or branched alkyl group having 1 to 12 carbon atoms, and
$R^2$ respectively and independently represents a linear or branched alkyl group having 2 to 8 carbon atoms);

step (II): separating the carbonic acid ester from the reaction liquid by distillation so as to obtain a residual liquid containing the tetraalkyl dialkoxy distannoxane and/or a conjugate of the tetraalkyl dialkoxy distannoxane and carbon dioxide; and step (III): reacting the residual liquid of the step (II) with an acid represented by the general formula HOX (Bronsted acid having a pKa of from 0 to 6.8) and/or acid anhydride represented by the general formula XOX (wherein OX represents a group in which HOX that is a conjugate acid of OX is a Bronsted acid having a pKa of from 0 to 6.8), so as to produce a compound having a group (OX group), which is derived from the acid and/or the acid anhydride, and which is a dialkoxy tin compound represented by the following general formula (52) and/or a tetraalkyl distannoxane compound represented by the following general formula (53):

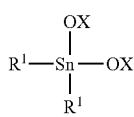
(52)

(wherein
each of $R^1$ independently represents a linear or branched alkyl group having 1 to 12 carbon atoms,
O represents an oxygen atom, and
OX represents a group OX in which HOX that is a conjugate acid of OX is a Bronsted acid having a pKa of from 0 to 6.8);

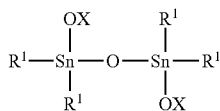
(11)

(wherein
each of $R^1$ independently represents a linear or branched alkyl group having 1 to 12 carbon atoms,
O represents an oxygen atom, and
OX represents a group OX in which HOX that is a conjugate acid of OX is a Bronsted acid having a pKa of from 0 to 6.8).

An explanation is first provided of the compounds indicated above.

Examples of $R^1$ in the formula (50) may include alkyl groups in the form of aliphatic hydrocarbon groups in which the number of carbon atoms that constitute the groups is a number selected from an integer of from 1 to 12, such as methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof may include linear or branched alkyl groups in which the number of carbon atoms that constitute the groups is a number selected from an integer of from 1 to 8. Although a dialkyl tin compound can be used in which the groups are alkyl groups in which the number of carbon atoms that constitute the groups is outside the indicated range, fluidity may become poor and productivity may be impaired. The alkyl groups are more preferably n-butyl groups or n-octyl groups in consideration of ease of acquisition during industrial production.

Examples of $R^2$ in the formula (50) may include alkyl groups in the form of aliphatic hydrocarbon groups in which the number of carbon atoms that constitute the groups is a number selected from an integer of from 1 to 12, such as methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof include linear or branched alkyl groups in which the number of carbon atoms that constitute the groups is a number selected from an integer of from 2 to 8. Thus, preferable examples of the $OR^2$ group in the formula (50) above may include alkoxy groups such as a methoxy group, an ethoxy group, a propyloxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers) or a dodecyloxy group (including isomers), while more preferable examples thereof may include an ethoxy group, a propyloxy group (including isomers), a butyloxy group (including isomers), a pentyloxy group (including isomers), a hexyloxy group (including isomers), a heptyloxy group (including isomers) or an octyloxy group (including isomers).

Specific examples of compounds represented by the formula (50) may include dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dibutyl-dimethoxy tin (including isomers), dibutyl-diethoxy tin (including isomers), dibutyl-dipropoxy tin (including isomers), dibutyl-dibutoxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dioctyl-dimethoxy tin, dioctyl-diethoxy tin, dioctyl-dipropoxy tin (including isomers), dioctyl-dibutoxy tin (including isomers), dioctyl-dipentyloxy tin (including isomers), dioctyl-dihexyloxy tin (including isomers), dioctyl-diheptyloxy tin (including isomers) and dioctyl-dioctyloxy tin (including isomers).

Examples of $R^1$ in the formula (51) may include alkyl groups in the form of aliphatic hydrocarbon groups in which the number of carbon atoms that constitute the groups is a number selected from an integer of from 1 to 12, such as methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof may include linear or branched alkyl groups in which the number of carbon atoms that constitute the groups is a number selected from an integer of from 1 to 8. Although a tetraalkyl dialkoxy distannoxane compound can be used in which the groups are alkyl groups in which the number of carbon atoms that constitute the groups is outside the indicated range, fluidity may become poor and productivity may be impaired. The alkyl groups are more preferably n-butyl groups or n-octyl groups in consideration of ease of acquisition during industrial production.

Although there are no particular limitations on $OX^3$ and $OX^4$ in the formula (51) provided their conjugate acids in the form of $HOX^3$ and $HOX^4$ are Bronsted acids and the pKa of the conjugate acids are 0 to 6.8, they are preferably at least one type of substituent selected from the group consisting of acyloxyl groups and aryloxy groups, and the pKa of conjugate acids thereof are 0 to 6.8. More preferably, $OX^1$ and $OX^2$ are groups in which the number of carbon atoms that constitute the groups is a number selected from integers of from 0 to 12. Specific examples of such groups may include acyloxyl groups composed of a linear or branched, saturated alkyl group, a carbonyl group and an oxygen atom, such as an acetoxy group, a propionyloxy group, a butyryloxy group, a valeryloxy group or a lauroyloxy group; and aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a dimethylphenoxy group (including isomers), a methylethylphenoxy group (including isomers), a methylpropylphenoxy group (including isomers), a methylbutylphenoxy group (including isomers), a methylpentylphenoxy group (including isomers), a diethylphenoxy group (including isomers), an ethylpropylphenoxy group (including isomers), an ethylbutylphenoxy group (including isomers), a dipropylphenoxy group (including isomers), a trimethylphenoxy group (including isomers), a dimethylethylphenoxy group (including isomers), a dimethylpropylphenoxy group (including isomers), a dimethylbutylphenoxy group (including isomers), a methylethylpropylphenoxy group, a methyldimethylphenoxy group or a triethylphenoxy group (including isomers).

Specific examples of compounds represented by the formula (51) may include 1,1,3,3-tetraallyl-1,3-diacyloxy distannoxanes such as 1,1,3,3-tetramethyl-1,3-diacetoxy distannoxane, 1,1,3,3-tetramethyl-1,3-dipropionyloxy distannoxane (including isomers), 1,1,3,3-tetramethyl-1,3-dibutyryloxy distannoxane (including isomers), 1,1,3,3-tetramethyl-1,3-divaleryloxy distannoxane (including isomers), 1,1,3,3-tetramethyl-1,3-dilauroyloxy distannoxane (including isomers), 1,1,3,3-tetrabutyl-1,3-diacetoxy distannoxane (including isomers), 1,1,3,3-tetrabutyl-1,3-dipropionyloxy distannoxane (including isomers), 1,1,3,3-tetrabutyl-1,3-dibutyryloxy distannoxane (including isomers), 1,1,3,3-tetrabutyl-1,3-divaleryloxy distannoxane (including isomers), 1,1,3,3-tetrabutyl-1,3-dilauroyloxy distannoxane (including isomers), 1,1,3,3-tetraoctyl-1,3-diacetoxy distannoxane (including isomers), 1,1,3,3-tetraoctyl-1,3-dipropionyloxy distannoxane (including isomers), 1,1,3,3-tetraoctyl-1,3-dibutyryloxy distannoxane (including isomers), 1,1,3,3-tetraoctyl-1,3-divaleryloxy distannoxane (including isomers) or 1,1,3,3-tetraoctyl-1,3-dilauroyloxy distannoxane (including isomers); and 1,1,3,3-tetraalkyl-1,3-diaryloxy distannoxanes such as 1,1,3,3-tetramethyl-1,3-diphenoxy distannoxane, 1,1,3,3-tetramethyl-1,3-di(methylphenoxy)distannoxane (including isomers), 1,1,3,3-tetramethyl-1,3-di(ethylphenoxy)distannoxane (including isomers), 1,1,3,3-tetramethyl-1,3-di(propylphenoxy)distannoxane (including isomers), 1,1,3,3-tetramethyl-1,3-di(butylphenoxy)distannoxane (including isomers), 1,1,3,3-tetramethyl-1,3-di(pentylphenoxy)distannoxane (including isomers), 1,1,3,3-tetramethyl-1,3-di(hexylphenoxy)distannoxane (including isomers), 1,1,3,3-tetramethyl-1,3-bis(dimethylphenoxy)distannoxane (including isomers), 1,1,3,3-tetramethyl-1,3-di(methylethylphenoxy)distannoxane (including isomers), 1,1,3,3-tetramethyl-1,3-di(methylpropylphenoxy)distannoxane (including isomers), 1,1,3,3-tetramethyl-1,3-di(methylbutylphenoxy)distannoxane (including isomers), 1,1,3,3-tetramethyl-1,3-di(methylpentylphenoxy)distannoxane (including isomers), 1,1,3,3-tetramethyl-1,3-bis(diethylphenoxy)distannoxane (including isomers), 1,1,3,3-tetramethyl-1,3-di(ethylpropylphenoxy)distannoxane (including isomers), 1,1,3,3-tetramethyl-1,3-di(ethylbutylphenoxy)distannoxane (including isomers), 1,1,3,3-tetramethyl-1,3-di(dipropylphenoxy)distannoxane (including isomers), 1,1,3,3-tetramethyl-1,3-di(trimethylphenoxy)distannoxane (including isomers), 1,1,3,3-tetramethyl-1,3-bis(dimethylethylphenoxy)distannoxane (including isomers), 1,1,3,3-tetramethyl-1,3-bis(dimethylpropylphenoxy)distannoxane (including isomers), 1,1,3,3-tetramethyl-1,3-bis(dimethylbutylphenoxy)distannoxane (including isomers), 1,1,3,3-tetramethyl-1,3-di(methylethylpropylphenoxy)distannoxane (including isomers), 1,1,3,3-tetramethyl-1,3-di(ethyldimethylphenoxy)distannoxane (including isomers), 1,1,3,3-tetramethyl-1,3-di(triethylphenoxy)tin (including isomers), 1,1,3,3-tetrabutyl-1,3-diphenoxy distannoxane (including isomers), 1,1,3,3-tetrabutyl-1,3-di(methylphenoxy)distannoxane (including isomers), 1,1,3,3-tetrabutyl-1,3-di(ethylphenoxy)distannoxane (including isomers), 1,1,3,3-tetrabutyl-1,3-di(propylphenoxy)distannoxane (including isomers), 1,1,3,3-tetrabutyl-1,3-di(butylphenoxy)distannoxane (including isomers), 1,1,3,3-tetrabutyl-1,3-di(pentylphenoxy)distannoxane (including isomers), 1,1,3,3-tetrabutyl-1,3-di(hexylphenoxy)distannoxane (including isomers), 1,1,3,3-tetrabutyl-1,3-bis(dimethylphenoxy)distannoxane (including isomers), 1,1,3,3-tetrabutyl-1,3-di(methylethylphenoxy)distannoxane (including isomers), 1,1,3,3-tetrabutyl-1,3-di(methylpropylphenoxy)distannoxane (including isomers), 1,1,3,3-tetrabutyl-1,3-di(methylbutylphenoxy)distannoxane (including isomers), 1,1,3,3-tetrabutyl-1,3-di(methylpentylphenoxy)distannoxane (including isomers), 1,1,3,3-tetrabutyl-1,3-bis(diethylphenoxy)distannoxane (including isomers), 1,1,3,3-tetrabutyl-1,3-di(ethylpropylphenoxy)distannoxane (including isomers), 1,1,3,3-tetrabutyl-1,3-di(ethylbutylphenoxy)distannoxane (including isomers), 1,1,3,3-tetrabutyl-1,3-di(dipropylphenoxy)distannoxane (including isomers), 1,1,3,3-tetrabutyl-1,3-di(trimethylphenoxy)distannoxane (including isomers), 1,1,3,3-tetrabutyl-1,3-bis(dimethylethylphenoxy)distannoxane (including isomers), 1,1,3,3-tetrabutyl-1,3-bis(dimethylpropylphenoxy)distannoxane (including isomers), 1,1,3,3-tetrabutyl-1,3-bis(dimethylbutylphenoxy)distannoxane (including isomers), 1,1,3,3-tetrabutyl-1,3-di(methylethylpropylphenoxy)distannoxane (including isomers), 1,1,3,3-tetrabutyl-1,3-di(ethyldimethylphenoxy)tin (including isomers), 1,1,3,3-tetrabutyl-1,3-di(triethylphenoxy)distannoxane (including isomers), 1,1,3,3-tetraoctyl-1,3-diphenoxy distannoxane (including isomers), 1,1,3,3-tetraoctyl-1,3-di(methylphenoxy)distannoxane (including isomers), 1,1,3,3-tetraoctyl-1,3-di(ethylphenoxy)distannoxane (including isomers), 1,1,3,3-tetraoctyl-1,3-di(propylphenoxy)distannoxane (including isomers), 1,1,3,3-tetraoctyl-1,3-di(butylphenoxy)distannoxane (including isomers), 1,1,3,3-tetraoctyl-1,3-di(pentylphenoxy)distannoxane (including isomers), 1,1,3,3-tetraoctyl-1,3-di(hexylphenoxy)distannoxane (including isomers), 1,1,3,3-tetraoctyl-1,3-bis(dimethylphenoxy)distannoxane (including isomers), 1,1,3,3-tetraoctyl-1,3-di(methylethylphenoxy)distannoxane (including isomers), 1,1,3,3-tetraoctyl-1,3-di(methylpropylphenoxy)distannoxane (including isomers), 1,1,3,3-tetraoctyl-1,3-di(methylbutylphenoxy)distannoxane (including isomers), 1,1,3,3-tetraoctyl-1,3-di(methylpentylphenoxy)distannoxane (including isomers), 1,1,3,3-tetraoctyl-1,3-bis(diethylphenoxy)distannoxane (including isomers), 1,1,3,3-tetraoctyl-1,3-di(ethylpropylphenoxy)distannoxane (including isomers), 1,1,3,3-tetraoctyl-1,3-di(ethylbutylphenoxy)distannoxane (including isomers), 1,1,3,3-tetraoctyl-1,3-di(dipropylphenoxy)distannoxane (including isomers), 1,1,3,3-tetraoctyl-1,3-di(trimethylphenoxy)distannoxane (including isomers), 1,1,3,3-tetraoctyl-1,3-bis(dimethylethylphenoxy)distannoxane (including isomers), 1,1,3,3-tetraoctyl-1,3-bis(dimethylpropylphenoxy)distannoxane (including isomers), 1,1,3,3-tetraoctyl-1,3-bis(dimethylbutylphenoxy)distannoxane (including isomers), 1,1,3,3-tetraoctyl-1,3-di(methylethylpropylphenoxy)distannoxane (including isomers), 1,1,3,3-tetraoctyl-1,3-di(ethyldimethylphenoxy)distannoxane (including isomers) or 1,1,3,3-tetraoctyl-1,3-di(triethylphenoxy)tin (including isomers).

In general, organic tin compounds easily adopt an associated structure, and although, for example, dialkyl tin dialkoxy tin is known to form a dimer structure, and tetraalkyl dialkoxy distannoxanes are known to be present by forming a ladder structure in which two or three molecules are associated. However, even in cases in which there are changes in this associated state, the representation of a compound in the form of a monomer structure is common for the persons with ordinary skill in the art.

Explanations of the dialkyl tin compound represented by the above-mentioned formula (52) and the tetraalkyl distannoxane compound represented by the above-mentioned formula (53) will be subsequently provided.

Next, an explanation is provided of each step.

Step (I) is a step for reacting a dialkyl tin alkoxide represented by the above-mentioned formula (50) with carbon dioxide to obtain a reaction liquid containing carbonic acid ester and a tetraalkyl dialkoxy distannoxane represented by the above-mentioned formula (51) and/or a conjugate of the tetraalkyl dialkoxy distannoxane and carbon dioxide.

This step (I) resembles the previously described step (a) and can be carried out by the same method.

The dialkyl tin dialkoxide used in step (I) can be produced according to the previously explained process, and a dialkyl tin dialkoxide produced by a reaction between dialkyl tin oxide and alcohol is preferable for the dialkyl tin dialkoxide used in this step. The following provides a description of that production process.

Examples of alcohols used preferably in this step may include alcohols in which the number of carbon atoms that constitute the alcohol is selected from an integer of from 1 to 12, such as methanol, ethanol, propanol (including isomers), butanol (including isomers), pentanol (including isomers), hexanol (including isomers), heptanol (including isomers), octanol (including isomers), nonanol (including isomers) or decanol (including isomers). More preferable examples thereof may include alcohols in which the number of carbon atoms that constitute the alcohol is selected from an integer of from 2 to 8, such as ethanol, propanol (including isomers), butanol (including isomers), pentanol (including isomers), hexanol (including isomers), heptanol (including isomers) or octanol (including isomers).

A dialkyl tin oxide represented by the following formula (54) is used for the dialkyl tin oxide used in the production of dialkyl tin dialkoxide:

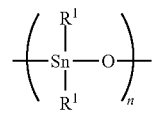

(54)

(wherein
each of $R^1$ independently represents a linear or branched alkyl group having 1 to 12 carbon atoms).

Examples of $R^1$ in the formula (54) may include alkyl groups in the form of aliphatic hydrocarbon groups having 1 to 12 carbon atoms, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers) or a dodecyl group (including isomers). More preferable examples thereof may include linear or branched saturated alkyl groups having 1 to 8 carbon atoms, while even more preferable examples thereof may include an n-butyl group and n-octyl group.

The alcohol and dialkyl tin oxide are subjected to a dehydration reaction to obtain a tetraalkyl dialkoxy distannoxane and/or dialkyl tin dialkoxide while removing the formed water outside the system. The temperature at which the reaction is carried out is, for example, within a range of from 80 to 180° C., the temperature is preferably 100 to 180° C., although varying according to the reaction pressure, for removing formed water outside the system by distillation, and although a high temperature is preferable for the reaction temperature in order to increase the reaction rate, since undesirable reactions such as decomposition may occur at high temperatures causing a decrease in yield, the reaction temperature is even more preferably within a range of from 100 to 160° C. The pressure of the reaction is a pressure at which formed water can be removed outside the system, and although varying according to the reaction temperature, is generally 20 to $1 \times 10^6$ Pa. There are no particular limitations on the reaction time of the dehydration reaction, and the reaction time is generally 0.001 to 50 hours, preferably 0.01 to 10 hours and even more preferably 0.1 to 2 hours. The reaction may be terminated once a composition containing a desired amount of dialkyl tin dialkoxide has been obtained. Progression of the reaction can be determined by measuring the amount of water extracted outside the system, or can be determined by a method using $^{119}$Sn-NMR by sampling the reaction liquid.

Although the composition containing dialkyl tin dialkoxide mainly contains dialkyl tin dialkoxide and tetraalkyl dialkoxy distannoxane, the reaction is terminated after confirming that a composition has been obtained in which the molar ratio of the tetraalkyl dialkoxy distannoxane to the dialkyl tin dialkoxide contained in the composition, as represented by the combined mol % of both, is preferably within a range of from 0:100 to 80:20 and more preferably within a range of from 10:90 to 70:30. The alcohol used may be allowed to remain present or may be removed by distillation depending on the case. It is preferable to remove as much of the alcohol as possible since this offers the advantage of being able to reduce the size of the reactors of the other steps. Removal by a known distillation method is preferable for the removal method, and a known distillation apparatus can be used for the distiller used to distill off the alcohol. A thin film distillation apparatus can be preferably used for the distillation apparatus since it allows alcohol to be removed in a short period of time. There are no particular limitations on the type of reactor of the dehydration reaction, and a known tank-type or a column-type reactor can be used. A low boiling point reaction mixture containing water is extracted from the reactor by distillation in the form of a gas, while a high boiling point reaction mixture containing the produced dialkyl tin dialkoxide is extracted from the bottom of the reactor in the form of a liquid. Various known methods are used for such a reactor, such as methods using reactors including any of, for example, a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a narrow flow phase reactor or a bubble column as well as combinations thereof. Methods using a column-type reactor are preferable in terms of efficiently shifting the equilibrium to the products side, and a structure having a large gas-liquid contact area enabling formed water to promptly move into the gaseous phase is preferable. Although a continuous method using a multitubular reactor, multistage distillation column or a packed column packed with a packing material can also be used, since the dialkyl tin oxide used in this step is ordinarily a solid, a method in which this step is first carried out in a tank-type reactor followed by increasing the content of dialkyl tin dialkoxide in a column-type reactor is the most preferable. Although known materials may be used for the reactor and lines provided they do not have detrimental effects, materials such as SUS304, SUS316 or SUS316L are inexpensive and can be used preferably. Known processing equipment including instruments such as flow meters and thermometers, reboilers, pumps and condensers may be added as necessary, a known method such as steam heating or a heater may be used for heating, and a known method such as air cooling, cold water or brine can be used for cooling.

In step (I), gaseous carbon dioxide is absorbed by the dialkyl tin dialkoxide to cause a chemical reaction to obtain a mixture containing a dialkyl tin dialkoxide and carbon dioxide.

During this chemical reaction, the dialkyl tin dialkoxide compound is reacted in liquid form or by putting into liquid form with a solvent and the like. A method in which the compound is put into liquid form by heating is preferably used for putting the compound into liquid form, and the compound may also be put into liquid form with a solvent and the like. Although varying according to the reaction temperature, the pressure at which the reaction is carried out is preferably within a range of from a normal pressure to 1 MPa, and more preferably within a range of from a normal pressure to 0.6 MPa. Although varying according to the reaction pressure, the temperature at which the reaction is carried out is preferably within a range of from −40 to 80° C., and in consideration of fluidity during transfer, is more preferably 0 to 80° C. and most preferably within a range of from a normal temperature (for example, 20° C.) to 80° C. The reaction is carried out within a range of from several seconds to 100 hours, and in consideration of productivity and the like, is preferably carried out for several minutes to 10 hours. A known tank-type reactor or a column-type reaction reactor can be used for the reactor. In addition, a plurality of reactors may be used in combination. Since the reaction is a reaction of a composition containing carbon dioxide (gas) and a dialkyl tin dialkoxide (liquid), in order to carry out the reaction efficiently, it is preferable to increase the contact surface area between the gas and liquid by increasing the size of the gas-liquid interface. A known method can be used for reacting while increasing the size of the gas-liquid interface in this manner, preferable examples of which may include increasing the stirring rate or generating air bubbles in the liquid in the case of a tank-type reactor, and using a packed column or a tray-type distillation column in the case of a column-type reactor. Examples of such column-type reactors may include tray-type distillation column types such as a bubble tray column, a porous plate tray, a valve tray or a counter-current tray, and packed column types packed with various types of packing materials such as a Raschig ring, a Lessing ring, a pole ring, a Berl saddle, an Interlock saddle, a Dixon packing, a McMahon packing, Helipack, a Sulzer packing or Mellapak. Although a known material may be used for the materials of the reactor and lines provided it does not have a detrimental effect, materials such as SUS304, SUS316 and SUS316L are inexpensive and can be used preferably. Known processing equipment including instruments such as flow meters and thermometers, reboilers, pumps and condensers may be added as necessary, a known method such as steam heating or a heater may be used for heating, and a known method such as air cooling, cold water or brine can be used for cooling. Since the reaction is ordinarily an exothermic reaction, the reactor may be cooled directly or the reactor may be cooled by dissipating heat of the reactor. Alternatively, the reactor may also be heated if the reaction is carried out for the purpose of simultaneously carrying out carbonic acid esterification. A known method can be used for cooling and heating the reactor, such as a method using a jacket or a method using internal coils. The composition containing carbon dioxide gas and dialkyl tin dialkoxide supplied to the reactor may also be supplied by supplying each reactant separately or by mixing prior to supplying to the reactor. The reactants may also be supplied from multiple locations in the reactor. Following completion of the reaction, the reaction products can be determined by $^{119}$Sn-NMR analysis and the like.

Next, a reaction liquid containing carbonic acid ester is obtained according to the process described below from the conjugate of dialkyl tin dialkoxide compound and carbon dioxide obtained above.

The reaction conditions are such that the reaction is carried out within a range of from 110 to 200° C., and although a high reaction temperature is preferable for increasing the reaction rate, since there are cases in which undesirable reactions such as decomposition occur at high temperatures thereby resulting in a decrease in yield, the reaction temperature is preferably 120 to 180° C., the reaction time is within a range of from 0.1 to 10 hours, and the reaction pressure is within a range of from 1.5 to 20 MPa and preferably within a range of from 2.0 to 10 MPa. The reaction is completed after forming the desired carbonic acid ester in the reactor. The progression of the reaction can be confirmed by, for example, sampling the reaction liquid in the reactor and analyzing the carbonic acid ester formed by a method such as $^1$H-NMR or gas chromatography. For example, the reaction may be completed once 10% or more of the dialkyl tin dialkoxide compound and/or conjugate of the dialkyl tin dialkoxide compound and carbon dioxide has formed based on the molar ratio thereof, or in the case of desiring to increase the yield of carbonic acid ester, the reaction may be completed after continuing until this value is 90% or more. A known reactor can be used for the reactor, and a column-type reactor or a tank-type reactor can be used preferably. Although a known material may be used for the materials of the reactor and lines provided it does not have a detrimental effect, materials such as SUS304, SUS316 and SUS316L are inexpensive and can be used preferably. Known processing equipment including instruments such as flow meters and thermometers, reboilers, pumps and condensers may be added as necessary, a known method such as steam heating or a heater may be used for heating, and a known method such as air cooling, cold water or brine can be used for cooling.

Next, an explanation is provided of step (II). This step (II) resembles the previously described step (b) and can be carried out by the same method.

Step (II) is a step for separating carbonic acid ester from the reaction liquid containing carbonic acid ester obtained in step (I) to obtain a residual liquid containing tetraalkyl dialkoxy distannoxane and/or a conjugate of the tetraalkyl dialkoxy distannoxane and carbon dioxide. A known method and apparatus can be preferably used for the separation method. A preferable separation method is separation by distillation.

Carbonic acid ester and residual liquid are obtained by batch, semi-batch or continuous distillation of the reaction liquid transferred from step (a). A preferable distillation method comprises supplying the reaction liquid to a distiller, separating carbonic acid ester from the top of the distiller outside the system in the form of a gas phase component, and extracting the residual liquid from the bottom of the distiller in the form of a liquid component. Although varying according to the boiling point of the carbonic acid ester and pressure, the temperature of this step is within a range of from a normal temperature (for example, 20° C.) to 200° C., and since there are cases in which denaturation of tin compounds in the residual liquid occurs at high temperatures as well as cases in which the carbonic acid ester ends up decreasing due to a reverse reaction, the temperature is preferably within a range of from a normal temperature (for example, 20° C.) to 150° C. Although varying according to the type of carbonic acid ester and temperature at which this step is carried out, pressure is generally from a normal pressure to a reduced pressure, and in consideration of productivity, the pressure is more preferably within a range of from 100 Pa to 80 KPa and most preferably within a range of from 100 Pa to 50 KPa. This step can be carried out within a range of from 0.01 to 10 hours, and since there are cases in which tin compounds contained in the reaction liquid may be denatured or carbonic acid ester may decrease due to a reverse reaction if this step is carried out at a high temperature for an extended period of time, the reaction time is preferably within a range of from 0.01 to 0.5 hours and most preferably within a range of from 0.01 to 0.3 hours. A known distiller can be used for the distiller, a column-type distiller or a tank-type distiller can be used preferably, or a plurality of types may be used in combination. More preferably, the distiller is a thin film evaporator or a thin film distiller, while a thin film evaporator equipped with a distillation column or a thin film distiller is the most preferable. Although known materials may be used for the distiller and lines provided they do not have detrimental effects, materials such as SUS304, SUS316 or SUS316L are inexpensive and can be used preferably. Known processing equipment including instruments such as flow meters and thermometers, reboilers, pumps and condensers may be added as necessary, a known method such as steam heating or a heater may be used for heating, and a known method such as air cooling, cold water or brine can be used for cooling.

The next step (III) resembles the previously described step (C) and can be carried out by the same method.

In this step (III), an organic acid is preferably used for the acid represented by the general formula HOX. Although examples of these organic acids may include carboxylic acid, sulfonic acid and phenol, carboxylic acid is used preferably. Examples of carboxylic acids may include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (including isomers), octanoic acid (including isomers), nonanoic acid (including isomers), decanoic acid (including isomers), undecanoic acid (including isomers), dodecanoic acid (including isomers), tetradecanoic acid (including isomers), hexadecanoic acid (including isomers), acrylic acid, crotic acid, isocrotic acid, vinylacetic acid, methacrylic acid, angelic acid, tiglic acid, allylacetic acid or undecenoic acid (including isomers); saturated or unsaturated aliphatic dicarboxylic acids such as oxalic acid, malonic acid, succinic acid, glutaric acid, adipic acid, heptanedioic acid (including isomers), octanedioic acid (including isomers), nonanedioic acid (including isomers), decanedioic acid (including isomers), maleic acid, fumaric acid, methylmaleic acid, methylfumaric acid, pentenedioic acid (including isomers), itaconic acid or allylmalonic acid; saturated or unsaturated tricarboxylic acid compounds such as 1,2,3-propanetricarboxylic acid, 1,2,3-propenetricarboxylic acid or 2,3-dimethylbutane-1,2,3-tricarboxylic acid; aromatic carboxylic acid compounds such as benzoic acid, methylbenzoic acid (including isomers), ethylbenzoic acid (including isomers), propylbenzoic acid (including isomers), dimethylbenzoic acid (including isomers) or trimethylbenzoic acid (including isomers); aromatic dicarboxylic acid compounds such as phthalic acid, isophthalic acid, terephthalic acid or methylisophthalic acid (including isomers); and, aromatic tricarboxylic acid compounds such as hemimellitic acid, trimellitic acid or trimesic acid. Among these carboxylic acids, saturated monocarboxylic acids are used preferably, saturated monocarboxylic acids having a standard boiling point of 300° C. or lower are used more preferably, and saturated monocarboxylic acids having a standard boiling point of 250° C. or lower are used even more preferably. Standard boiling point refers to the boiling point at 1 atmosphere as described in Encyclopedia Chimica (issued on Oct. 1, 2003 by Kyoritsu Publishing Co., Ltd.). More specifically, acetic acid, propionic acid, n-butyric acid, isobutyric acid, valeric acid, isovaleric acid, 2-methylbutanoic acid, pivalic acid or hexanoic acid is used preferably.

In addition, in step (III), examples of acid anhydrides represented by the general formula XOX may include aliphatic anhydrides such as acetic anhydride, propionic anhydride, butyric anhydride, isobutyric anhydride, valeric anhydride, isovaleric anhydride, succinic anhydride, maleic anhydride, propionic anhydride or glutaric anhydride; and, aromatic anhydrides such as benzoic anhydride, phthalic anhydride or pyromellitic anhydride. Among these, acid anhydrides having a standard boiling point of 300° C. or lower are used preferably, and in order to facilitate removal of excess acid anhydride after the reaction, acid anhydrides having a standard boiling point of 200° C. or lower are used more preferably. Moreover, maleic anhydride and acetic anhydride are preferable from the viewpoint of facilitating the removal of by-products such as carboxylic acid esters outside the system and ease of industrial acquisition.

Although these acids and acid anhydrides can be used alone or by mixing a plurality of types thereof, in the case of using an acid, there are many cases in which water is formed in the case of reacting the acid with a tetraalkyl dialkoxy distannoxane compound. Distillation separation or membrane separation may be carried out or a dehydrating agent may be used to remove the water. In addition, the combined use of an acid anhydride as a dehydrating agent is preferable. Moreover, in the case of using an acid anhydride only, since there are many cases in which water is not formed in the reaction between the tetraalkyl dialkoxy distannoxane compound and the acid anhydride, a method using an acid anhydride only is preferable.

The amount of acid and/or acid anhydride used is preferably within a range of from 0.1 to 50 times in terms of the stoichiometric ratio based on the tin atoms contained in the residua liquid obtained in step (II) in consideration of the reaction rate in step (III) and the final yield of the dialkyl tin compound, and is more preferably within a range of from 0.5 to 20 times in consideration of the size of the reactor and the reaction rate. In the case the amount used is less than 0.1 in terms of the stoichiometric ratio, there are cases in which it is difficult for the reaction to proceed, while conversely even if used in an amount greater than 50 times in terms of the stoichiometric ratio, there are many cases in which this does not have an effect on reaction rate or final yield of the dialkyl tin compound in this step.

The reaction of step (III) is preferably carried out at a reaction temperature of from −20 to 300° C. and more preferably at a reaction temperature of from −10 to 250° C., and although a high reaction temperature is preferable for increasing the reaction rate, since there are also cases in which undesirable reactions such as decomposition occur at high temperatures thereby lowering the yield, the reaction is even more preferably carried out a reaction temperature of from 0 to 230° C. In addition, the reaction of step (III) is preferably carried out in an inert gas atmosphere such as argon, neon or nitrogen.

Although the use of a solvent is not required in step (III), a solvent can be used for the purpose of improving fluidity, facilitating the reaction procedure or efficiently removing water outside the system in the case water is formed in the reaction. Examples of such solvents may include linear, branched or cyclic hydrocarbons having 5 to 16 carbon atoms, ethers composed of linear, branched or cyclic hydrocarbons having 4 to 16 carbon atoms, and linear, branched or cyclic halogenated hydrocarbons having 1 to 16 carbon atoms. More specifically, examples of solvents that can be used may include linear or cyclic hydrocarbons selected from the group consisting of pentane (including isomers), hexane (including isomers), heptane (including isomers), octane (including isomers), nonane (including isomers), decane (including isomers), hexadecane (including isomers), cyclohexane, cycloheptane, cyclooctane, benzene, toluene, xylene (including isomers) and ethylbenzene; ethers selected from the group consisting of diethyl ether, dipropyl ether (including isomers), dibutyl ether (including isomers), dihexyl ether (including isomers), dioctyl ether (including isomers) and diphenyl ether; and halogenated hydrocarbons selected from the group consisting of methylene chloride, chloroform, carbon tetrachloride, chlorobenzene, tetrachloroethane and dichlorobenzene (including isomers). These solvents can be used alone or used by mixing two or more types.

The alkyl tin compound produced in this step (III) is at least one alkyl tin compound selected from the group consisting of dialkyl tin compounds represented by the following formula (52) and tetraalkyl distannoxane compounds represented by the following formula (53):

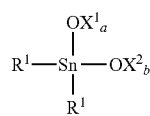

(52)

(wherein
each of $R^1$ independently represents a linear or branched alkyl group having 1 to 12 carbon atoms,
O represents an oxygen atom,
$OX^1$ and $OX^2$ are $OX^1$ and $OX^2$ in which conjugate acids of $OX^1$ and $OX^2$ in the form of $HOX^1$ and $HOX^2$ are Bronsted acids having a pKa of from 0 to 6.8, and
a and b are integers of 0 to 2, respectively, and a+b=2);

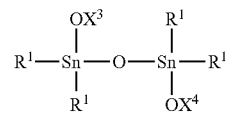

(53)

(wherein
each of $R^1$ independently represents a linear or branched alkyl group having 1 to 12 carbon atoms,
O represents an oxygen atom, and
$OX^3$ and $OX^4$ are $OX^3$ and $OX^4$ in which conjugate acids of $OX^3$ and $OX^4$ in the form of $HOX^3$ and $HOX^4$ are Bronsted acids having a pKa of from 0 to 6.8).

Examples of $R^1$ in the formula (52) may include alkyl groups in the form of aliphatic hydrocarbon groups in which the number of carbon atoms that constitute the groups is a number selected from an integer of from 1 to 12, such as methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof may include linear or branched alkyl groups in which the number of carbon atoms that constitute the groups is a number selected from an integer of from 1 to 8. Although a dialkyl tin compound can be used in which the groups are alkyl groups in which the number of carbon atoms that constitute the groups is outside the indicated range, fluidity may become poor and productivity may be impaired. The alkyl groups are more preferably n-butyl groups or n-octyl groups in consideration of ease of acquisition during industrial production.

Although there are no particular limitations on $OX^1$ and $OX^2$ in the formula (52) provided their conjugate acids in the form of $HOX^1$ and $HOX^2$ are Bronsted acids and the pKa of the conjugate acids are 0 to 6.8, they are preferably at least one type of substituent selected from the group consisting of acyloxyl groups and aryloxy groups, and the pKa of conjugate acids thereof are 0 to 6.8. More preferably, $OX^1$ and $OX^2$ are groups in which the number of carbon atoms that constitute the groups is a number selected from integers of from 0 to 12. Specific examples of such groups may include acyloxyl groups composed of a linear or branched, saturated alkyl group, a carbonyl group and an oxygen atom, such as an acetoxy group, a propionyloxy group, a butyryloxy group, a valeryloxy group or a lauroyloxy group; and aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a dimethylphenoxy group (including isomers), a methylethylphenoxy group (including isomers), a methylpropylphenoxy group (including isomers), a methylbutylphenoxy group (including isomers), a methylpentylphenoxy group (including isomers), a diethylphenoxy group (including isomers), an ethylpropylphenoxy group (including isomers), an ethylbutylphenoxy group (including isomers), a dipropylphenoxy group (including isomers), a trimethylphenoxy group (including isomers), a dimethylethylphenoxy group (including isomers), a dimethylpropylphenoxy group (including isomers), a dimethylbutylphenoxy group (including isomers), a methylethylpropylphenoxy group, a methyldimethylphenoxy group or a triethylphenoxy group (including isomers).

Specific examples of dialkyl tin compounds represented by the formula (52) may include dialkyl-diacyloxy tin compounds such as dimethyl-diacetoxy tin, dimethyl-dipropionyloxy tin (including isomers), dimethyl-dibutyryloxy tin (including isomers), dimethyl-valeryloxy tin (including isomers), dimethyl-dilauroyloxy tin (including isomers), dibutyl-diacetoxy tin (including isomers), dibutyl-dipropionyloxy tin (including isomers), dibutyl-dibutyryloxy tin (including isomers), dibutyl-divaleryloxy tin (including isomers), dibutyl-dilauroyloxy tin (including isomers), dioctyl-diacetoxy tin (including isomers), dioctyl-dipropionyloxy tin (including isomers), dioctyl-butyryloxy tin (including isomers), dioctyl-valeryloxy tin (including isomers) or dioctyl-dilauroyloxy tin (including isomers); and, alkyl-diaryloxy tin compounds such as dimethyl-diphenoxy tin, dimethyl-di(methylphenoxy)tin (including isomers), dimethyl-di(ethylphenoxy)tin (including isomers), dimethyl-di(propylphenoxy) tin (including isomers), dimethyl-di(butylphenoxy)tin (including isomers), dimethyl-di(pentylphenoxy)tin (including isomers), dimethyl-di(hexylphenoxy)tin (including isomers), dimethyl-bis(dimethylphenoxy)tin (including isomers), dimethyl-di(methylethylphenoxy)tin (including isomers), dimethyl-di(methylpropylphenoxy)tin (including isomers), dimethyl-di(methylbutylphenoxy)tin (including isomers), dimethyl-di(methylpentylphenoxy)tin (including isomers), dimethyl-bis(diethylphenoxy)tin (including isomers), dimethyl-di(ethylpropylphenoxy)tin (including isomers), dimethyl-di(ethylbutylphenoxy)tin (including isomers), dimethyl-di(dipropylphenoxy)tin (including isomers), dimethyl-di(trimethylphenoxy)tin (including isomers), dimethyl-bis(dimethylethylphenoxy)tin (including isomers), dimethyl-bis(diethylpropylphenoxy)tin (including isomers), dimethyl-bis(dimethylbutylphenoxy)tin (including isomers), dimethyl-di(methylethylpropylphenoxy)tin (including isomers), dimethyl-di(ethyldimethylphenoxy)tin (including isomers), dimethyl-di(triethylphenoxy)tin (including isomers), dibutyl-diphenoxy tin (including isomers), dibutyl-di(methylphenoxy)tin (including isomers), dibutyl-di(ethylphenoxy) tin (including isomers), dibutyl-di(propylphenoxy)tin (including isomers), dibutyl-di(butylphenoxy)tin (including isomers), dibutyl-di(pentylphenoxy)tin (including isomers), dibutyl-di(hexylphenoxy)tin (including isomers), dibutyl-bis(dimethylphenoxy)tin (including isomers), dibutyl-di(methylethylphenoxy)tin (including isomers), dibutyl-di(methylpropylphenoxy)tin (including isomers), dibutyl-di(methylbutylphenoxy)tin (including isomers), dibutyl-di(methylpentylphenoxy)tin (including isomers), dibutyl-bis(diethylphenoxy)tin (including isomers), dibutyl-di(ethylpropylphenoxy)tin (including isomers), dibutyl-di(ethylbutylphenoxy)tin (including isomers), dibutyl-di(dipropylphenoxy)tin (including isomers), dibutyl-di(trimethylphenoxy)tin (including isomers), dibutyl-bis(dimethylethylphenoxy)tin (including isomers), dibutyl-bis(dimethylpropylphenoxy)tin (including isomers), dibutyl-bis(dimethylbutylphenoxy)tin (including isomers), dibutyl-di(methylethylpropylphenoxy)tin (including isomers), dibutyl-di(ethyldimethylphenoxy)tin (including isomers), dibutyl-di(triethylphenoxy)tin (including isomers), dioctyl-diphenoxy tin (including isomers), dioctyl-di(methylphenoxy)tin (including isomers), dioctyl-di(ethylphenoxy)tin (including isomers), dioctyl-di(propylphenoxy)tin (including isomers), dioctyl-di(butylphenoxy)tin (including isomers), dioctyl-di(pentylphenoxy)tin (including isomers), dioctyl-di(hexylphenoxy)tin (including isomers), diocty-bis(dimethylphenoxy)tin (including isomers), dioctyl-di(methylethylphenoxy)tin (including isomers), dioctyl-di(methylpropylphenoxy)tin (including isomers), dioctyl-di(methylbutylphenoxy)tin (including isomers), dioctyl-di(methylpentylphenoxy)tin (including isomers), dioctyl-bis(diethylphenoxy)tin (including isomers), dioctyl-di(ethylpropylphenoxy)tin (including isomers), dioctyl-di(ethylbutylphenoxy)tin (including isomers), dioctyl-di(dipropylphenoxy)tin (including isomers), dioctyl-di(trimethylphenoxy) tin (including isomers), dioctyl-bis(dimethylethylphenoxy) tin (including isomers), dioctyl-bis(dimethylpropylphenoxy) tin (including isomers), dioctyl-bis(dimethylbutylphenoxy) tin (including isomers), dioctyl-di(methylethylpropylphenoxy)tin (including isomers), dioctyl-di(ethyldimethylphenoxy)tin (including isomers) or dioctyl-di(triethylphenoxy)tin (including isomers).

Examples of $R^1$ in the formula (53) may include alkyl groups in the form of aliphatic hydrocarbon groups in which the number of carbon atoms that constitute the groups is a number selected from an integer of from 1 to 12, such as methyl, ethyl, propyl (including isomers), butyl (including isomers), pentyl (including isomers), hexyl (including isomers), heptyl (including isomers), octyl (including isomers), nonyl (including isomers), decyl (including isomers) or dodecyl (including isomers) group. Preferable examples thereof may include linear or branched alkyl groups in which the number of carbon atoms that constitute the groups is a number selected from an integer of from 1 to 8. Although a tetraalkyl dialkoxy distannoxane compound can be used in which the groups are alkyl groups in which the number of carbon atoms that constitute the groups is outside the indicated range, fluidity may become poor and productivity may be impaired. The alkyl groups are more preferably n-butyl groups or n-octyl groups in consideration of ease of acquisition during industrial production.

Although there are no particular limitations on $OX^3$ and $OX^4$ in the formula (53) provided their conjugate acids in the form of $HOX^3$ and $HOX^4$ are Bronsted acids and the pKa of the conjugate acids are 0 to 6.8, they are preferably at least one type of substituent selected from the group consisting of acyloxyl groups and aryloxy groups, and the pKa of conjugate acids thereof are 0 to 6.8. More preferably, $OX^1$ and $OX^2$ are groups in which the number of carbon atoms that constitute the groups is a number selected from integers of from 0 to 12. Specific examples of such groups may include acyloxyl groups composed of a linear or branched, saturated alkyl group, a carbonyl group and an oxygen atom, such as an acetoxy group, a propionyloxy group, a butyryloxy group, a valeryloxy group or a lauroyloxy group; and aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a dimethylphenoxy group (including isomers), a methylethylphenoxy group (including isomers), a methylpropylphenoxy group (including isomers), a methylbutylphenoxy group (including isomers), a methylpentylphenoxy group (including isomers), a diethylphenoxy group (including isomers), an ethylpropylphenoxy group (including isomers), an ethylbutylphenoxy group (including isomers), a dipropylphenoxy group (including isomers), a trimethylphenoxy group (including isomers), a dimethylethylphenoxy group (including isomers), a dimethylpropylphenoxy group (including isomers), a dimethylbutylphenoxy group (including isomers), a methylethylpropylphenoxy group, a methyldimethylphenoxy group or a triethylphenoxy group (including isomers).

Specific examples of compounds represented by the formula (53) may include 1,1,3,3-tetraallyl-1,3-diacyloxy distannoxanes such as 1,1,3,3-tetramethyl-1,3-diacetoxy distannoxane, 1,1,3,3-tetramethyl-1,3-dipropionyloxy distannoxane (including isomers), 1,1,3,3-tetramethyl-1,3- dibutyryloxy distannoxane (including isomers), 1,1,3,3-tetramethyl-1,3-divaleryloxy distannoxane (including isomers), 1,1,3,3-tetramethyl-1,3-dilauroyloxy distannoxane (including isomers), 1,1,3,3-tetrabutyl-1,3-diacetoxy distannoxane (including isomers), 1,1,3,3-tetrabutyl-1,3-dipropionyloxy distannoxane (including isomers), 1,1,3,3-tetrabutyl-1,3-dibutyryloxy distannoxane (including isomers), 1,1,3,3-tetrabutyl-1,3-divaleryloxy distannoxane (including isomers), 1,1,3,3-tetrabutyl-1,3-dilauroyloxy distannoxane (including isomers), 1,1,3,3-tetraoctyl-1,3-diacetoxy distannoxane (including isomers), 1,1,3,3-tetraoctyl-1,3-dipropionyloxy distannoxane (including isomers), 1,1,3,3-tetraoctyl-1,3-dibutyryloxy distannoxane (including isomers), 1,1,3,3-tetraoctyl-1,3-divaleryloxy distannoxane (including isomers) or 1,1,3,3-tetraoctyl-1,3-dilauroyloxy distannoxane (including isomers); and 1,1,3,3-tetraalkyl-1,3-diaryloxy distannoxanes such as 1,1,3,3-tetramethyl-1,3-diphenoxy distannoxane, 1,1,3,3-tetramethyl-1,3-di(methylphenoxy)distannoxane (including isomers), 1,1,3,3-tetramethyl-1,3-di(ethylphenoxy)distannoxane (including isomers), 1,1,3,3-tetramethyl-1,3-di(propylphenoxy)distannoxane (including isomers), 1,1,3,3-tetramethyl-1,3-di(butylphenoxy)distannoxane (including isomers), 1,1,3,3-tetramethyl-1,3-di(pentylphenoxy)distannoxane (including isomers), 1,1,3,3-tetramethyl-1,3-di(hexylphenoxy)distannoxane (including isomers), 1,1,3,3-tetramethyl-1,3-bis(dimethylphenoxy)distannoxane (including isomers), 1,1,3,3-tetramethyl-1,3-di(methylethylphenoxy)distannoxane (including isomers), 1,1,3,3-tetramethyl-1,3-di(methylpropylphenoxy)distannoxane (including isomers), 1,1,3,3-tetramethyl-1,3-di(methylbutylphenoxy)distannoxane (including isomers), 1,1,3,3-tetramethyl-1,3-di(methylpentylphenoxy)distannoxane (including isomers), 1,1,3,3-tetramethyl-1,3-bis(diethylphenoxy)distannoxane (including isomers), 1,1,3,3-tetramethyl-1,3-di(ethylpropylphenoxy)distannoxane (including isomers), 1,1,3,3-tetramethyl-1,3-di(ethylbutylphenoxy)distannoxane (including isomers), 1,1,3,3-tetramethyl-1,3-di(dipropylphenoxy)distannoxane (including isomers), 1,1,3,3-tetramethyl-1,3-di(trimethylphenoxy)distannoxane (including isomers), 1,1,3,3-tetramethyl-1,3-bis(dimethylethylphenoxy)distannoxane (including isomers), 1,1,3,3-tetramethyl-1,3-bis(dimethylpropylphenoxy)distannoxane (including isomers), 1,1,3,3-tetramethyl-1,3-bis(dimethylbutylphenoxy)distannoxane (including isomers), 1,1,3,3-tetramethyl-1,3-di(methylethylpropylphenoxy)distannoxane (including isomers), 1,1,3,3-tetramethyl-1,3-di(ethyldimethylphenoxy)distannoxane (including isomers), 1,1,3,3-tetramethyl-1,3-di(triethylphenoxy)tin (including isomers), 1,1,3,3-tetrabutyl-1,3-diphenoxy distannoxane (including isomers), 1,1,3,3-tetrabutyl-1,3-di(methylphenoxy)distannoxane (including isomers), 1,1,3,3-tetrabutyl-1,3-di(ethylphenoxy)distannoxane (including isomers), 1,1,3,3-tetrabutyl-1,3-di(propylphenoxy)distannoxane (including isomers), 1,1,3,3-tetrabutyl-1,3-di(butylphenoxy)distannoxane (including isomers), 1,1,3,3-tetrabutyl-1,3-di(pentylphenoxy)distannoxane (including isomers), 1,1,3,3-tetrabutyl-1,3-di(hexylphenoxy)distannoxane (including isomers), 1,1,3,3-tetrabutyl-1,3-bis(dimethylphenoxy)distannoxane (including isomers), 1,1,3,3-tetrabutyl-1,3-di(methylethylphenoxy)distannoxane (including isomers), 1,1,3,3-tetrabutyl-1,3-di(methylpropylphenoxy)distannoxane (including isomers), 1,1,3,3-tetrabutyl-1,3-di(methylbutylphenoxy)distannoxane (including isomers), 1,1,3,3-tetrabutyl-1,3-di(methylpentylphenoxy)distannoxane (including isomers), 1,1,3,3-tetrabutyl-1,3-bis(diethylphenoxy)distannoxane (including isomers), 1,1,3,3-tetrabutyl-1,3-di(ethylpropylphenoxy)distannoxane (including isomers), 1,1,3,3-tetrabutyl-1,3-di(ethylbutylphenoxy)distannoxane (including isomers), 1,1,3,3-tetrabutyl-1,3-di(dipropylphenoxy)distannoxane (including isomers), 1,1,3,3-tetrabutyl-1,3-di(trimethylphenoxy)distannoxane (including isomers), 1,1,3,3-tetrabutyl-1,3-bis(dimethylethylphenoxy)distannoxane (including isomers), 1,1,3,3-tetrabutyl-1,3-bis(dimethylpropylphenoxy)distannoxane (including isomers), 1,1,3,3-tetrabutyl-1,3-bis(dimethylbutylphenoxy)distannoxane (including isomers), 1,1,3,3-tetrabutyl-1,3-di(methylethylpropylphenoxy)distannoxane (including isomers), 1,1,3,3-tetrabutyl-1,3-di(ethyldimethylphenoxy)tin (including isomers), 1,1,3,3-tetrabutyl-1,3-di(triethylphenoxy)distannoxane (including isomers), 1,1,3,3-tetraoctyl-1,3-diphenoxy distannoxane (including isomers), 1,1,3,3-tetraoctyl-1,3-di(methylphenoxy)distannoxane (including isomers), 1,1,3,3-tetraoctyl-1,3-di(ethylphenoxy)distannoxane (including isomers), 1,1,3,3-tetraoctyl-1,3-di(propylphenoxy)distannoxane (including isomers), 1,1,3,3-tetraoctyl-1,3-di(butylphenoxy)distannoxane (including isomers), 1,1,3,3-tetraoctyl-1,3-di(pentylphenoxy)distannoxane (including isomers), 1,1,3,3-tetraoctyl-1,3-di(hexylphenoxy)distannoxane (including isomers), 1,1,3,3-tetraoctyl-1,3-bis(dimethylphenoxy)distannoxane (including isomers), 1,1,3,3-tetraoctyl-1,3-di(methylethylphenoxy)distannoxane (including isomers), 1,1,3,3-tetraoctyl-1,3-di(methylpropylphenoxy)distannoxane (including isomers), 1,1,3,3-tetraoctyl-1,3-di(methylbutylphenoxy)distannoxane (including isomers), 1,1,3,3-tetraoctyl-1,3-di(methylpentylphenoxy)distannoxane (including isomers), 1,1,3,3-tetraoctyl-1,3-bis(diethylphenoxy)distannoxane (including isomers), 1,1,3,3-tetraoctyl-1,3-di(ethylpropylphenoxy)distannoxane (including isomers), 1,1,3,3-tetraoctyl-1,3-di(ethylbutylphenoxy)distannoxane (including isomers), 1,1,3,3-tetraoctyl-1,3-di(dipropylphenoxy)distannoxane (including isomers), 1,1,3,3-tetraoctyl-1,3-di(trimethylphenoxy)distannoxane (including isomers), 1,1,3,3-tetraoctyl-1,3-bis(dimethylethylphenoxy)distannoxane (including isomers), 1,1,3,3-tetraoctyl-1,3-bis(dimethylpropylphenoxy)distannoxane (including isomers), 1,1,3,3-tetraoctyl-1,3-bis(dimethylbutylphenoxy)distannoxane (including isomers), 1,1,3,3-tetraoctyl-1,3-di(methylethylpropylphenoxy)distannoxane (including isomers), 1,1,3,3-tetraoctyl-1,3-di(ethyldimethylphenoxy)distannoxane (including isomers) or 1,1,3,3-tetraoctyl-1,3-di(triethylphenoxy)tin (including isomers).

In general, organic tin compounds easily adopt an associated structure, and for example, dialkyl tin dialkoxides are known to form a dimer structure, and tetraalkyl dialkoxy distannoxanes are known to be present by forming a ladder structure in which two or three molecules are associated. Even in cases in which there are changes in this associated state, the representation of a compound in the form of a monomer structure is common for the persons with ordinary skill in the art.

Figure 4:
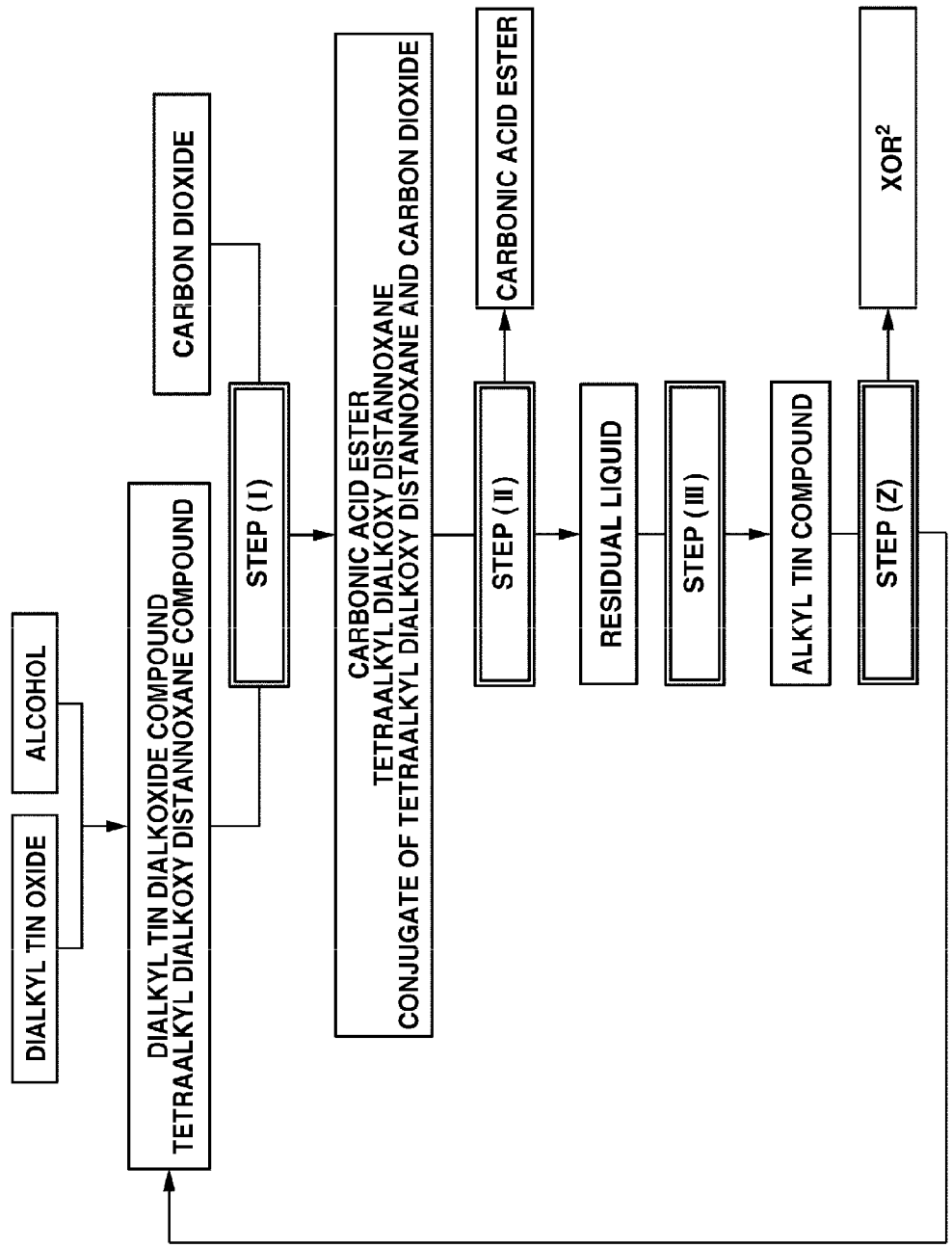
FIG. 4 shows a flow chart for explaining a carbonic acid ester production process that combines steps (I) to (III) with a step (Z) in the present embodiment.

Although a dialkyl tin dialkoxide compound and/or tetraalkyl dialkoxy distannoxane compound can be produced by using the dialkyl tin compound and/or tetraalkyl distannoxane compound obtained by carrying out the above-mentioned steps (I) to (III) as the dialkyl tin compound and/or tetraalkyl distannoxane compound of step (Z), the dialkyl tin dialkoxide compound and/or tetraalkyl dialkoxy distannoxane compound can be preferably used as the dialkyl tin dialkoxide compound of the above-mentioned step (I). FIG. 4 shows a flow chart for explaining a novel process for producing carbonic acid ester by combining steps (I) to (III) and step (Z) as explained above.

Since the production process (z) of a dialkyl tin dialkoxide compound and/or tetraalkyl dialkoxy distannoxane compound of the present embodiment allows the production of a dialkyl tin dialkoxide compound and/or tetraalkyl dialkoxy distannoxane compound without involving the handling of solid tin compounds by reacting a dialkyl tin compound and/or a tetraalkyl distannoxane compound with an acid and/or acid anhydride, the production process is more convenient than conventional processes.

In addition, as previously described, step (Z) can be used as a portion of novel processes for producing carbonic acid esters by combining various steps with step (Z). Since these novel processes for producing carbonic acid ester contain a step for regenerating monoalkyl tin alkoxide compounds and trialkyl tin alkoxide compounds, formed in the production process of the carbonic acid ester and which have lost catalytic activity during the course of that carbonic acid ester production, into dialkyl tin dialkoxide compounds and/or tetraalkyl dialkoxy distannoxane compounds, problems associated with costs and waste encountered in the carbonic acid ester production process can be solved. Thus, the production process as claimed in the present embodiment is industrially extremely important.

EXAMPLES

Although the following provides a more detailed explanation of the present embodiment using Examples and Comparative Examples thereof, the present embodiment is not limited to these Examples only.

Furthermore, analytical methods used in the present embodiment are as described below.
<Analytical Methods>
1) NMR Analysis
   Apparatus: JNM-A400 FT-NMR system, JEOL Ltd.
(1) Preparation of $^1$H-, $^{13}$C- and $^{119}$Sn-NMR Analysis Samples About 0.3 g of sample solution were weighed followed by the addition of about 0.7 g of heavy chloroform (99.8%, Aldrich Corp.) and 0.05 g of internal standard in the form of tetramethyl tin (guaranteed reagent, Wako Pure Chemical Industries, Ltd.) and mixing to uniformity to obtain solutions used as NMR analysis samples.
2) Gas Chromatography
   Apparatus: GC-2010, Shimadzu Corp., Japan
   Column: DB-1 column, Agilent Technologies Corp., USA, length: 30 m, inner diameter: 0.250 mm, film thickness: 1.00 µM
   Column temperature: Held at 50° C. for 5 minutes followed by increasing at the rate of 10° C./min to 200° C.; held at 200° C. for 5 minutes followed by increasing at the rate of 10° C./min to 300° C.
   Detector: FID
(1) Gas Chromatography Analysis Samples About 0.05 g of sample were weighed followed by the addition of about 1 g of acetone (dehydrated, Wako Pure Chemical Industries, Ltd., Japan) and about 0.02 g of internal standard in the form of toluene (dehydrated, Wako Pure Chemical Industries, Ltd., Japan) and mixing to uniformity to obtain solutions used as gas chromatography analysis samples.
(2) Quantitative Analysis Analyses were performed for each standard and quantitative analyses were performed on the analysis sample solutions based on the resulting calibration curve.
3) Inductively-Coupled Plasma Mass Spectrometry
   Apparatus: SPQ-8000, Seiko Electronics Corp., Japan (1) Inductively-Coupled Plasma Mass Spectrometry Analysis Samples About 0.15 g of sample were ashed with dilute sulfuric acid followed by dissolving in dilute nitric acid.
(2) Quantitative Analysis Analyses were performed for each standard and quantitative analyses were performed on the analysis sample solutions based on the resulting calibration curve.

Reference Example 1

Production of Bis(3-methylbutyl)Carbonate

Step (A-1): Production of Dialkyl Tin Catalyst 627 g (2.7 mol) of dibutyl tin oxide (Sankyo Organic Chemicals Co., Ltd., Japan) and 2000 g (22.7 mol) of 3-methyl-1-butanol (Kuraray Co., Ltd., Japan) were placed in a 5000 mL volumetric eggplant-shaped flask. The flask was attached to an evaporator (R-144, Shibata Co., Ltd., Japan) to which was connected an oil bath (OBH-24, Masuda Corp., Japan) equipped with a temperature controller, a vacuum pump (G-50A, Ulvac Inc., Japan) and a vacuum controller (VC-10S, Okano Seisakusho Co., Ltd.). The purge valve outlet of the evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 145° C., the flask was immersed in the oil bath and rotation of the evaporator was started. After heating for about 40 minutes in the presence of atmospheric pressure nitrogen with the purge valve of the evaporator left open, distillation of 3-methyl-1-butanol containing water began. After maintaining in this state for 7 hours, the purge valve was closed, pressure inside the system was gradually reduced, and excess 3-methyl-1-butanol was distilled with the pressure inside the system at 74 to 35 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 1173 g of reaction liquid were obtained in the flask. Based on the results of $^{119}$Sn-, $^1$H- and $^{13}$C-NMR analyses, 1,1,3,3-tetra-n-butyl-1,3-bis(3-methylbutyloxy)distannoxane was confirmed to have been obtained at a yield of 99% based on dibutyl tin oxide. The same procedure was then repeated 12 times to obtain a total of 10345 g of 1,1,3,3-tetra-n-butyl-1,3-bis(3-methylbutyloxy)distannoxane.

Step (A-2): Production of Carbonic Acid Ester and Recovery of Alkyl Tin Composition Carbonic acid ester was produced in a continuous production apparatus like that shown in FIG. 5. 1,1,3,3-Tetra-butyl-1,3-bis(3-methylbutyloxy)distannoxane produced in the manner described above was supplied at the rate of 4388 g/hr from a transfer line 4 into a column-type reactor 102 packed with Metal Gauze CY Packing (Sulzer Chemtech Ltd., Switzerland) and having an inner diameter of 151 mm and effective length of 5040 mm, and 3-methyl-1-butanol purified with a distillation column 101 was supplied at the rate of 14953 g/hr from a transfer line 2. The liquid temperature inside the reactor 102 was adjusted to 160° C. by a heater and a reboiler 112, and the pressure was adjusted to about 120 kPa-G with a pressure control valve. The residence time in the reactor was about 17 minutes. 3-Methyl-1-butanol containing water at the rate of 15037 g/hr from the top of the reactor via a transfer line 6, and 3-methyl-1-butanol (Kuraray Co., Ltd., Japan) at the rate of 825 g/hr via feed line 1, were pumped to the distillation column 101 packed with Metal Gauze CY Packing (Sulzer Chemtech Ltd., Switzerland) and provided with a reboiler 111 and a condenser 121 to carry out distillative purification. In the top of the distillation column 101, a fraction containing a high concentration of water was condensed by the condenser 121 and recovered from a recovery line 3. Purified 3-methyl-1-butanol was pumped to the column-type reactor 102 via the transfer line 2 located in the bottom of the distillation column 101. A composition (to be referred to as a catalyst composition) containing di-n-butyl-bis(3-methylbutyloxy)tin and 1,1,3,3-tetra-n-butyl-1,3-bis(3-methylbutyloxy)distannoxane was obtained from the bottom of column-type reactor 102, and supplied to a thin film evaporator 103 (Kobelco Eco-Solutions Co., Ltd., Japan) via a transfer line 5. The 3-methyl-1-butanol was distilled off in the thin film evaporator 103 and returned to the column-type reactor 102 via a condenser 123, a transfer line 8 and the transfer line 4. The catalyst composition was pumped from the bottom of the thin film evaporator 103 via a transfer line 7 and supplied to an autoclave 104 while adjusting the flow rate of di-n-butyl-bis(3-methylbutyloxy)tin and 1,1,3,3-tetra-butyl-1,3-bis(3-methylbutyloxy)distannoxane to about 5130 g/hr. Carbon dioxide was supplied to the autoclave by a transfer line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the catalyst composition was carried out to obtain a reaction liquid containing bis(3-methylbutyl)carbonate. This reaction liquid was transferred to a decarbonization tank 105 via a transfer line 10 and a control valve to remove residual carbon dioxide, and the carbon dioxide was recovered from a transfer line 11. Subsequently, the reaction liquid was transferred to a thin film evaporator (Kobelco Eco-Solutions Co., Ltd., Japan) 106 set to about 142° C. and about 0.5 kPa via a transfer line 12 and supplied while adjusting the flow rate of 1,1,3,3-tetra-n-butyl-1,3-bis(3-methylbutyloxy)distannoxane to about 4388 g/hr to obtain a fraction containing bis(3-methylbutyl) carbonate. On the other hand, the evaporation residue was circulated to the column-type reactor 102 via the transfer line 13 and the transfer line 4 while adjusting the flow rate of 1,1,3,3-tetra-n-butyl-1,3-bis(3-methylbutyloxy)distannoxane to about 4388 g/hr. The fraction containing bis(3-methylbutyl)carbonate was supplied to a distillation column 107 packed with Metal Gauze CY Packing (Sulzer Chemtech Ltd., Switzerland) and equipped with a reboiler 117 and a condenser 127 via a condenser 126 and a transfer line 14 at the rate of 959 g/hr followed by distillative purification to obtain 99% by weight of bis(3-methylbutyl)carbonate from a recovery line 15 at the rate of 944 g/hr.

Reference Example 2

Production of Bis(2-ethylbutyl)Carbonate

Step (B-1): Production of Dialkyl Tin Catalyst 893 g (2.48 mol) of di-n-octyl tin oxide (Sankyo Organic Chemicals Co., Ltd., Japan) and 2403 g (23.6 mol) of 2-ethyl-1-butanol were placed in a 5000 mL volumetric eggplant-shaped flask. The flask was attached to an evaporator to which was connected an oil bath equipped with a temperature controller, a vacuum pump and a vacuum controller. The purge valve outlet of the evaporator was connected to a line containing nitrogen gas flowing at normal pressure. After closing the purge valve of the evaporator to reduce pressure inside the system, the purge valve was opened gradually to allow nitrogen to flow into the system and return to a normal pressure. The oil bath temperature was set to about 165° C., the flask was immersed in the oil bath and rotation of the evaporator was started. After heating for about 40 minutes in the presence of atmospheric pressure nitrogen with the purge valve of the evaporator left open, distillation of 2-ethyl-1-butanol containing water began. After maintaining in this state for 7 hours, the purge valve was closed, pressure inside the system was gradually reduced, and excess 2-ethyl-1-butanol was distilled with the pressure inside the system at 74 to 25 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 1114 g of reaction liquid were obtained in the flask. Based on the results of $^{119}$Sn-, $^{1}$H- and $^{13}$C-NMR analyses, 1,1,3,3-tetra-n-octyl-1,3-bis(2-ethylbutyloxy)distannoxane was confirmed to have been obtained at a yield of 99% based on di-n-octyl tin oxide. The same procedure was then repeated 12 times to obtain a total of 13380 g of 1,1,3,3-tetra-n-octyl-1,3-bis(2-ethylbutyloxy)distannoxane.

Step (B-2): Production of Carbonic Acid Ester and Recovery of Alkyl Tin Composition Carbonic acid ester was produced in a continuous production apparatus like that shown in FIG. 5. 1,1,3,3-Tetra-n-octyl-1,3-bis(2-ethylbutyloxy)distannoxane produced in the manner described above was supplied at the rate of 6074 g/hr from the transfer line 4 into the column-type reactor 102 packed with Metal Gauze CY Packing and having an inner diameter of 151 mm and effective length of 5040 mm, and 2-ethyl-1-butanol purified with the distillation column 101 was supplied at the rate of 12260 g/hr from the transfer line 2. The liquid temperature inside the reactor 102 was adjusted to 160° C. by a heater and the reboiler 112, and the pressure was adjusted to about 120 kPa-G with a pressure control valve. The residence time in the reactor was about 17 minutes. 2-Ethyl-1-butanol containing water at the rate of 12344 g/hr from the top of the reactor via the transfer line 6, and 2-ethyl-1-butanol at the rate of 958 g/hr via the feed line 1, were pumped to the distillation column 101 packed with Metal Gauze CY Packing and provided with the reboiler 111 and the condenser 121 to carry out distillative purification. In the top of the distillation column 101, a fraction containing a high concentration of water was condensed by the condenser 121 and recovered from the recovery line 3. Purified 2-ethyl-1-butanol was pumped to the column-type reactor 102 via the transfer line 2 located in the bottom of the distillation column 101. A composition (to be referred to as a catalyst composition) containing di-n-octyl-bis(2-ethylbutyloxy)tin and 1,1,3,3-tetra-n-octyl-1,3-bis(2-ethylbutyloxy)distannoxane was obtained from the bottom of the column-type reactor 102, and supplied to the thin film evaporator 103 via the transfer line 5. The 2-ethyl-1-butanol was distilled off in the thin film evaporator 103 and returned to the column-type reactor 102 via the condenser 123, the transfer line 8 and the transfer line 4. The catalyst composition was pumped from the bottom of the thin film evaporator 103 via the transfer line 7 and supplied to the autoclave 104 while adjusting the flow rate of di-n-octyl-bis(2-ethylbutyloxy)tin and 1,1,3,3-tetra-n-octyl-1,3-bis(2-ethylbutyloxy)distannoxane to about 6945 g/hr. Carbon dioxide was supplied to the autoclave by the transfer line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the catalyst composition was carried out to obtain a reaction liquid containing bis(2-ethylbutyl)carbonate. This reaction liquid was transferred to the decarbonization tank 105 via the transfer line 10 and a control valve to remove residual carbon dioxide, and the carbon dioxide was recovered from the transfer line 11. Subsequently, the reaction liquid was transferred to the thin film evaporator 106 set to about 142° C. and about 0.5 kPa via the transfer line 12 and supplied while adjusting the flow rate of 1,1,3,3-tetra-n-octyl-1,3-bis(2-ethylbutyloxy)distannoxane to about 6074 g/hr to obtain a fraction containing bis(2-ethylbutyl)carbonate. On the other hand, the evaporation residue was circulated to the column-type reactor 102 via the transfer line 13 and the transfer line 4 while adjusting the flow rate of 1,1,3,3-tetra-n-octyl-1,3-bis(2-ethylbutyloxy)distannoxane to about 6074 g/hr. The fraction containing bis(2-ethylbutyl)carbonate was supplied to the distillation column 107 packed with Metal Gauze CY Packing (Sulzer Chemtech Ltd., Switzerland) and equipped with the reboiler 117 and the condenser 127 via the condenser 126 and the transfer line 14 at the rate of 959 g/hr followed by distillative purification to obtain 99% by weight of bis(2-ethylbutyl)carbonate from a recovery line 16 at the rate of 1075 g/hr.

Reference Example 3

Production of Di(n-butyl)Carbonate

Step (C-1): Production of Tetraalkyl Dialkoxy Distannoxane 692 g (2.78 mol) of di-n-butyl tin oxide and 2000 g (27 mol) of 1-butanol (Wako Pure Chemical Industries, Ltd., Japan) were placed in a 3000 mL volumetric eggplant-shaped flask. The flask containing the white, slurry-like mixture was attached to an evaporator to which was connected an oil bath equipped with a temperature controller, a vacuum pump and a vacuum controller. The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to 126° C., the flask was immersed in the oil bath and rotation of the evaporator was started. After heating and agitating by rotation for about 30 minutes at normal pressure with the purge valve of the evaporator left open, the mixture boiled and distillation of low boiling point components began. After maintaining in this state for 8 hours, the purge valve was closed, pressure inside the system was gradually reduced, and residual low boiling point components were distilled with the pressure inside the system at 76 to 54 kPa. After the low boiling point components no longer appeared, the flask was taken out of the oil bath. The reaction liquid was in the form of a clear liquid. Subsequently, the flask was taken out of the oil bath, the purge valve was opened gradually and the pressure inside the system was returned to normal pressure. 952 g of reaction liquid were obtained in the flask. Based on the results of $^{119}$Sn-, $^1$H- and $^{13}$C-NMR analyses, a product in the form of 1,1,3,3-tetra-n-butyl-1,3-di(n-butyloxy)distannoxane was obtained at a yield of 99% based on di-n-butyl tin oxide. The same procedure was then repeated 12 times to obtain a total of 11488 g of 1,1,3,3-tetra-n-butyl-1,3-di(butyloxy)distannoxane.

Step (C-2): Production of Carbonic Acid Ester

Figure 5:
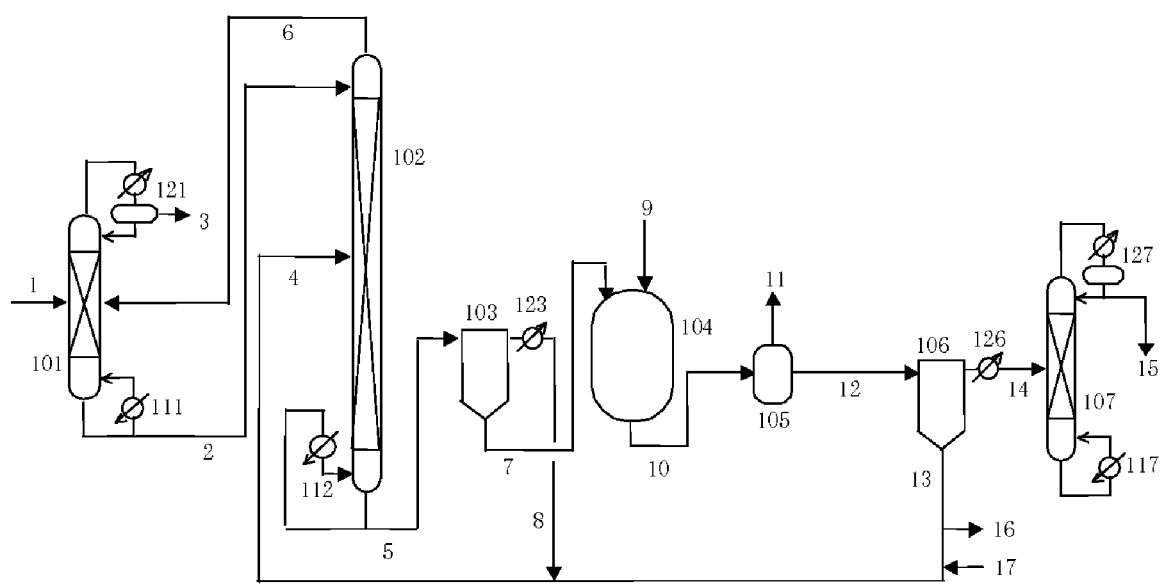
FIG. 5 shows a schematic drawing representing a carbonic acid ester production apparatus in an example.

Carbonic acid ester was produced in a continuous production apparatus like that shown in FIG. 5. 1,1,3,3-Tetra-butyl-1,3-di(butyloxy)distannoxane produced in step 1 was supplied at the rate of 4201 g/hr from the transfer line 4 into a column-type reactor packed with Mellapak 750Y packing and having an inner diameter of 151 mm and effective length of 5040 mm, and 1-butanol purified with the distillation column 101 was supplied to the column-type reactor 102 at the rate of 24717 g/hr from the feed line 2. The liquid temperature inside the reaction vessel was adjusted to 160° C. by a heater and the reboiler 112, and the pressure was adjusted to about 250 kPa-G with a pressure control valve. The residence time in the reaction vessel was about 10 minutes. 1-Butanol containing water at the rate of 24715 g/hr from the top of the reactor via the transfer line 6, and 1-butanol at the rate of 824 g/hr via the feed line 1, were pumped to the distillation column 101 packed with Metal Gauze CY packing and provided with the reboiler 111 and the condenser 121 to carry out distillative purification. In the top of the distillation column 101, a fraction containing a high concentration of water was condensed by the condenser 121 and recovered from the transfer line 3. Purified 1-butanol was pumped via the transfer line 2 located in the bottom of the distillation column 101. A composition (to be referred to as a catalyst composition) containing dibutyl tin dibutoxide and 1,1,3,3-tetra-n-butyl-1,3-di(butyloxy)distannoxane was obtained from the bottom of the column-type reactor 102, and supplied to the thin film evaporator 103 via the transfer line 5. The 1-butanol was distilled off in the thin film evaporator 103 and returned to the column-type reaction vessel 102 via the condenser 123, the transfer line 8 and the transfer line 4. The catalyst composition was pumped from the bottom of the thin film evaporator 103 via the transfer line 7 and supplied to the autoclave 104 while adjusting the flow rate of the active components in the form of dibutyl tin dibutoxide and 1,1,3,3-tetra-n-butyl-1,3-di(butyloxy)distannoxane to about 4812 g/hr. Carbon dioxide was supplied to the autoclave by the feed line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the catalyst composition was carried out to obtain a reaction liquid containing dibutyl carbonate. This reaction liquid was transferred to the decarbonization tank 105 via the transfer line 10 and a control valve to remove residual carbon dioxide, and the carbon dioxide was recovered from the transfer line 11. Subsequently, the reaction liquid was pumped to the thin film evaporator 106 set to about 140° C. and about 1.4 kPa via the transfer line 12 and supplied while adjusting the flow rate of the 1,1,3,3-tetra-n-butyl-1,3-di(butyloxy)distannoxane to about 4201 g/hr to obtain a fraction containing dibutyl carbonate. On the other hand, the evaporation residue was circulated to the column-type reaction vessel 102 via the transfer line 13 and the transfer line 4 while adjusting the flow rate of 1,1,3,3-tetra-n-butyl-1,3-di(butyloxy)distannoxane to about 4201 g/hr. The fraction containing dibutyl carbonate was supplied to the distillation column 107 packed with Metal Gauze CY packing and equipped with the reboiler 117 and the condenser 127 via the condenser 126 and the transfer line 14 at the rate of 830 g/hr followed by distillative purification to obtain 99% by weight bis(3-methylbutyl)carbonate from the recovery line 16 at the rate of 814 g/hr.

Example 1

240 g of di-n-butyl tin diacetate (Aldrich Corp., USA) and 692 g of the bis(3-methylbutyl)carbonate produced in step (A-2) of Reference Example 1 were placed in a 2 L volumetric eggplant-shaped flask in a nitrogen atmosphere at atmospheric pressure, and a Dimroth condenser and three-way valve were attached to the flask. The flask was immersed in an oil bath heated to 150° C. and heated for 5 hours while stirring the contents. The flask was attached to a rotary evaporator to which was connected an oil bath equipped with a temperature controller, a vacuum pump and a vacuum controller. The purge valve outlet of the rotary evaporator was connected to a line containing nitrogen gas flowing at atmospheric pressure. After replacing the inside of the system with nitrogen, the temperature of the oil bath was set to be 150° C., the flask was immersed in the oil bath and rotation of the rotary evaporator was started. A low boiling point component was distilled off for about 7 hours in the presence of nitrogen at atmospheric pressure with the purge valve of the rotary evaporator left open, after which the pressure in the system was gradually reduced, and residual low boiling point component was distilled off with the pressure inside the system at 76 to 10 kPa. When the low boiling point component fraction no longer appeared, the flask was removed from the oil bath and allowed to cool. 287 g of residual liquid were obtained in the flask. Based on the results of $^1$H-, $^{13}$C- and $^{119}$Sn-NMR analyses, the residual liquid in the flask was a solution containing 92.0% by weight of di-n-butyl-bis(3-methylbutyloxy) tin.

On the other hand, 598 g of low boiling point component were recovered. When analyzed by gas chromatography, the low boiling point component contained about 28% by weight of isoamyl acetate.

Example 2

399 g of a residual liquid were obtained by carrying out the same method as Example 1 with the exception of using 310 g of 1,1,3,3-tetra-n-butyl-1,3-diacetoxy distannoxane (Aldrich Corp., USA) instead of di-n-butyl tin diacetate, and using 900 g of di(n-butyl)carbonate instead of bis(3-methylbutyl)carbonate. The residual liquid contained 93.4% by weight of di-n-butyl-di(n-butyloxy)tin. In addition, the low boiling point component contained 29.4% by weight of butyl acetate.

Example 3

165 g of a residual liquid were obtained by carrying out the same method as Example 1 with the exception of using 290 g of di-n-butyl tin dilaurate (Aldrich Corp., USA) instead of di-n-butyl tin diacetate, using 326 g of diethyl carbonate (Aldrich Corp., USA) instead of bis(3-methylbutyl)carbonate, and setting the oil bath temperature to 130° C. The residual liquid contained 83.5% by weight of di-n-butyl-diethyl tin. In addition, the low boiling point component contained 47.3% by weight of ethyl laurate.

Example 4

206 g of a residual liquid were obtained by carrying out the same method as Example 1 with the exception of using 300 g of di-n-butyl tin dilaurate instead of di-n-butyl tin diacetate, using 343 g of dimethyl carbonate (Aldrich Corp., USA) instead of bis(3-methylbutyl)carbonate, setting the oil bath temperature to be 90° C. and heating for 20 hours. The residual liquid contained 40.8% by weight of di-n-butyl-dimethyl tin. In addition, the low boiling point component contained 30% by weight of methyl laurate.

Example 5

162 g of a residual liquid were obtained by carrying out the same method as Example 1 with the exception of using 135 g of di-n-butyl tin diacetate and using 494 g of diphenyl carbonate (Aldrich Corp., USA) instead of bis(3-methylbutyl) carbonate. The residual liquid contained 95.4% by weight of di-n-butyl-diphenyl tin. In addition, the low boiling point component contained 23% by weight of phenyl acetate.

Example 6

221 g of di-n-butyl tin diacetate and 515 g of 2-ethyl-1-butanol (guaranteed reagent, Wako Pure Chemical Industries, Ltd., Japan) were placed in a 2 L volumetric eggplant-shaped flask in a nitrogen atmosphere at atmospheric pressure, and the flask was attached to a rotary evaporator to which was connected an oil bath equipped with a temperature controller, a vacuum pump and a vacuum controller. The purge valve outlet of the rotary evaporator was connected to a line containing nitrogen gas flowing at atmospheric pressure. After replacing the inside of the system with nitrogen, the temperature of the oil bath was set to be 140° C., the flask was immersed in the oil bath and rotation of the rotary evaporator was started. A low boiling point component was distilled off for about 7 hours in the presence of nitrogen at atmospheric pressure with the purge valve of the rotary evaporator left open, after which the pressure in the system was gradually reduced, and residual low boiling point component was distilled off with the pressure inside the system at 76 to 10 kPa. When the low boiling point component fraction no longer appeared, the flask was removed from the oil bath and allowed to cool. 274 g of residual liquid were obtained in the flask. Based on the results of $^1$H-, $^{13}$C- and $^{119}$Sn-NMR analyses, the residual liquid in the flask was a solution containing 96.0% by weight of di-n-butyl-bis(2-ethylbutyloxy) tin.

On the other hand, 563 g of low boiling point component were recovered. When analyzed by gas chromatography, the low boiling point component contained about 30.9% by weight of (2-ethylbutyl)acetate.

Example 7

306 g of a residual liquid were obtained by carrying out the same method as Example 6 with the exception of using 255 g of di-n-butyl tin diacetate, and using 961 g of 3-methyl-1-butanol (Tokyo Chemical Industry Co., Ltd., Japan) instead of 2-ethyl-1-butanol. The residual liquid contained 92.7% by weight of di-n-butyl-bis(3-methylbutyloxy)tin. In addition, the low boiling point component contained 18.0% by weight of isoamyl acetate.

Example 8

424 g of a residual liquid were obtained by carrying out the same method as Example 6 with the exception of using 322 g of 1,1,3,3-tetra-n-butyl-1,3-diacetoxy distannoxane instead of di-n-butyl tin diacetate, and using 1034 g of n-butanol instead of 2-ethyl-1-butanol. The residual liquid contained 77.3% by weight of di-n-butyl-di(n-butyloxy)tin and 19.9% by weight of 1,1,3,3-tetra-n-butyl-1,3-di(n-butyloxy)distannoxane. In addition, the low boiling point component contained 17.2% by weight of butyl acetate.

Example 9

206 g of a residual liquid were obtained by carrying out the same method as Example 6 with the exception of using 341 g of di-n-butyl tin dilaurate instead of di-n-butyl tin diacetate, and using 363 g of methanol (Aldrich Corp., USA) instead of 2-ethyl-1-butanol. The residual liquid contained 59.5% by weight of di-n-butyl-dimethoxy tin and 38.1% by weight of di-n-butyl tin dilaurate. In addition, the low boiling point component contained 34.8% by weight of methyl laurate.

Example 10

389 g of a residual liquid were obtained by carrying out the same method as Example 6 with the exception of using 320 g of di-n-butyl tin diacetate, and using 1029 g of phenol (for nucleic acid extraction, Wako Pure Chemical Industries, Ltd., Japan) instead of 2-ethyl-1-butanol. The residual liquid contained 95.3% by weight of di-n-butyl-diphenoxy tin. In addition, the low boiling point component contained 22% by weight of phenyl acetate.

Example 11

289 g of di-n-butyl tin diacetate and 1024 g of bis(2-ethylbutyl)carbonate were placed in a 2 L volumetric eggplant-shaped flask in a nitrogen atmosphere at atmospheric pressure, and the flask was attached to a rotary evaporator to which was connected an oil bath equipped with a temperature controller, a vacuum pump and a vacuum controller. The purge valve outlet of the rotary evaporator was connected to a line containing nitrogen gas flowing at atmospheric pressure. After replacing the inside of the system with nitrogen, the temperature of the oil bath was set to 280° C., the flask was immersed in the oil bath and rotation of the rotary evaporator was started. A low boiling point component was distilled off for about 7 hours in the presence of nitrogen at atmospheric pressure with the purge valve of the rotary evaporator left open, after which the pressure in the system was gradually reduced, and residual low boiling point component was distilled off with the pressure inside the system at 76 to 10 kPa. When the low boiling point component fraction no longer appeared, the flask was removed from the oil bath and allowed to cool. 365 g of residual liquid were obtained in the flask. Based on the results of $^1$H-, $^{13}$C- and $^{119}$Sn-NMR analyses, the residual liquid in the flask was a solution containing 79.7% by weight of di-n-butyl-bis(2-ethylbutyloxy) tin and 7.6% by weight of tri-n-butyl-(2-ethylbutyloxy)tin.

On the other hand, 888 g of low boiling point component were recovered. When analyzed by gas chromatography, the low boiling point component contained about 25.2% by weight of (2-ethylbutyl)acetate.

Example 12

356 g of a residual liquid were obtained by carrying out the same method as Example 11 with the exception of using 310 g of di-n-butyl tin diacetate, using 934 g of 3-methyl-1-butanol and setting the oil bath temperature to 30° C. The residual liquid contained 53.5% by weight of di-n-butyl-bis (3-methylbutyl)tin. In addition, the low boiling point component contained 12.8% by weight of isoamyl acetate.

Example 13

Step (13-1): Production of Dialkyl Tin Catalyst 972 g (2.7 mol) of di-n-octyl tin oxide (Sankyo Organic Chemicals Co., Ltd., Japan) and 2100 g (23.9 mol) of 3-methyl-1-butanol were placed in a 5000 mL volumetric eggplant-shaped flask. The flask was attached to an evaporator to which was connected an oil bath equipped with a temperature controller, a vacuum pump and a vacuum controller. The purge valve outlet of the evaporator was connected to a line containing nitrogen gas flowing at a normal pressure. After closing the purge valve of the evaporator to reduce pressure inside the system, the purge valve was opened gradually to allow nitrogen to flow into the system and return to normal pressure. The oil bath temperature was set to about 145° C., the flask was immersed in the oil bath and rotation of the evaporator was started. After heating for about 40 minutes in the presence of atmospheric pressure nitrogen with the purge valve of the evaporator left open, distillation of 3-methyl-1-butanol containing water began. After maintaining in this state for 7 hours, the purge valve was closed, pressure inside the system was gradually reduced, and excess 3-methyl-1-butanol was distilled with the pressure inside the system at 74 to 35 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 1176 g of reaction liquid were obtained in the flask. Based on the results of $^{119}$Sn-, $^1$H- and $^{13}$C-NMR analyses, 1,1,3,3-tetra-n-octyl-1,3-bis(3-methylbutyloxy)distannoxane was confirmed to have been obtained at a yield of 99% based on di-n-octyl tin oxide. The same procedure was then repeated 12 times to obtain a total of 14120 g of 1,1,3,3-tetra-n-octyl-1,3-bis(3-methylbutyloxy)distannoxane.

Step (13-2): Production of Carbonic Acid Ester and Recovery of Alkyl Tin Composition Carbonic acid ester was produced in a continuous production apparatus like that shown in FIG. 5. 1,1,3,3-tetra-n-octyl-1,3-bis(3-methylbutyloxy)distannoxane produced in the manner described above was supplied at the rate of 5887 g/hr from the transfer line 4 into the column-type reactor 102 packed with Metal Gauze CY Packing and having an inner diameter of 151 mm and effective length of 5040 mm, and 3-methyl-1-butanol purified with the distillation column 101 was supplied at the rate of 14953 g/hr from the transfer line 2. The liquid temperature inside the reactor 102 was adjusted to 160° C. by a heater and the reboiler 112, and the pressure was adjusted to about 120 kPa-G with a pressure control valve. The residence time in the reactor was about 17 minutes. 3-Methyl-1-butanol containing water at the rate of 15037 g/hr from the top of the reactor via the transfer line 6, and 3-methyl-1-butanol at the rate of 824 g/hr via the feed line 1, were pumped to the distillation column 101 packed with Metal Gauze CY Packing and provided with the reboiler 111 and the condenser 121 to carry out distillative purification. In the top of the distillation column 101, a fraction containing a high concentration of water was condensed by the condenser 121 and recovered from the recovery line 3. Purified 3-methyl-1-butanol was pumped to the column-type reactor 102 via the transfer line 2 located in the bottom of the distillation column 101. A composition (to be referred to as a catalyst composition) containing di-n-octyl-bis(3-methylbutyloxy)tin and 1,1, 3,3-tetra-n-octyl-1,3-bis(3-methylbutyloxy)distannoxane was obtained from the bottom of the column-type reactor 102, and supplied to the thin film evaporator 103 via the transfer line 5. The 3-methyl-1-butanol was distilled off in the thin film evaporator 103 and returned to the column-type reactor 102 via the condenser 123, the transfer line 8 and the transfer line 4. The catalyst composition was pumped from the bottom of the thin film evaporator 103 via the transfer line 7 and supplied to the autoclave 104 while adjusting the flow rate of di-n-octyl-bis(3-methylbutyloxy)tin and 1,1,3,3-tetra-n-octyl-1,3-bis(3-methylbutyloxy)distannoxane to about 6627 g/hr. Carbon dioxide was supplied to the autoclave by the transfer line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the catalyst composition was carried out to obtain a reaction liquid containing bis(3-methylbutyl)carbonate. This reaction liquid was transferred to the decarbonization tank 105 via the transfer line 10 and a control valve to remove residual carbon dioxide, and the carbon dioxide was recovered from the transfer line 11. Subsequently, the reaction liquid was transferred to the thin film evaporator 106 set to about 142° C. and about 0.5 kPa via the transfer line 12 and supplied while adjusting the flow rate of 1,1,3,3-tetra-n-octyl-1,3-bis(3-methylbutyloxy)distannoxane to about 5887 g/hr to obtain a fraction containing bis(3-methylbutyl)carbonate. On the other hand, the evaporation residue was circulated to the column-type reactor 102 via the transfer line 13 and the transfer line 4 while adjusting the flow rate of 1,1,3,3-tetra-n-octyl-1,3-bis(3-methylbutyloxy)distannoxane to about 5887 g/hr. The fraction containing bis(3-methylbutyl)carbonate was supplied to the distillation column 107 packed with Metal Gauze CY Packing and equipped with the reboiler 117 and the condenser 127 via the condenser 126 and the transfer line 14 at the rate of 959 g/hr followed by distillative purification to obtain 99% by weight of bis(3-methylbutyl)carbonate from the recovery line 15 at the rate of 944 g/hr. When the alkyl tin alkoxide catalyst composition of the transfer line 13 was analyzed by $^{119}$Sn-, $^1$H- and $^{13}$C-NMR analysis, it was found to contain 1,1,3,3-tetra-n-octyl-1,3-bis(3-methylbutyloxy)distannoxane but not contain di-n-octyl-bis(3-methylbutyloxy)tin. After carrying out the above-mentioned continuous operation for about 240 hours, catalyst composition was extracted from an extraction line 16 at the rate of 18 g/hr, while 1,1,3,3-tetra-n-octyl-1,3-bis(3-methylbutyloxy)distannoxane produced according to the above process was supplied from a feed line 17 at the rate of 18 g/hr, and 200 g of alkyl tin composition containing 1,1,3,3-tetra-n-octyl-1,3-bis(3-methylbutyloxy)distannoxane was extracted from the extraction line 16. When the alkyl tin composition was analyzed by $^{119}$Sn-NMR, in addition to containing about 60% by weight of 1,1,3,3-tetra-n-octyl-1,3-bis(3-methylbutyloxy)distannoxane, tri-n-octyl(3-methylbutyloxy)tin along with a plurality of NMR shifts of deactivated components of 1,1,3,3-tetra-n-octyl-1,3-bis(3-methylbutyloxy)distannoxane were observed at −240 to −605 ppm.

Step (13-3): Substituent Exchange Reaction of Alkyl Tin Composition Containing 1,1,3,3-tetra-n-octyl-1,3-bis(3-methylbutyloxy)Distannoxane 350 g of the alkyl tin composition containing 1,1,3,3-tetra-n-octyl-1,3-bis(3-methylbutyloxy)distannoxane obtained in step (13-2) were placed on a 1 L eggplant-shaped flask in a nitrogen atmosphere followed by the addition of 95 g of acetic acid (guaranteed reagent, Wako Pure Chemical Industries, Ltd., Japan) and 325 g of acetic anhydride (guaranteed reagent, Wako Pure Chemical Industries, Ltd., Japan) and stirring for 1 hour at 25° C. A fractionation head equipped with a reflux condenser connected to a distillate collector and a thermometer which were attached to the flask, and after replacing the inside of the flask with nitrogen in a vacuum, the flask was immersed in an oil bath heated to 50° C. The pressure inside the vessel was gradually reduced and excess acetic acid, acetic anhydride and the like were distilled off to obtain a distillate. When the distillate was analyzed by gas chromatography, the distillate was found to contain acetic acid, acetic anhydride and 3-methyl-1-butanol. 368 g of residue were obtained in the flask. When the residue was measured by $^1$H- and $^{119}$Sn-NMR, the residue was found to be a mixture of tri-n-octyl acetoxy tin, di-n-octyl diacetoxy tin and organic tin compounds containing tin atoms demonstrating a plurality of chemical shifts of −240 to −605 ppm in $^{119}$Sn-NMR. This mixture contained 27.9% by weight of tri-n-octyl acetoxy tin and 50.0% by weight of di-n-octyl diacetoxy tin.

Step (13-4): Alkyl Group Redistribution Reaction 365 g of the mixture obtained in step (13-3) were placed in a 500 mL metal pressure vessel (Model TSV-N2, Taiatsu Techno Corp., Japan) in a nitrogen atmosphere. The metal pressure vessel was immersed in an oil bath heated to 200° C. and heated for 3 hours. After allowing the metal pressure vessel to cool to the vicinity of room temperature, the reaction liquid was recovered. When $^1$H- and $^{119}$Sn-NMR measurement were carried out on the reaction liquid, the reaction liquid was determined to be a mixture of organic tin compounds containing di-n-octyl diacetoxy tin and tri-n-octyl acetoxy tin, and contained 94.0% by weight of di-n-octyl-diacetoxy tin and about 3% by weight of tri-n-octyl acetoxy tin.

Step (13-5): Alkoxylation of Dialkyl Tin Compound 363 g of the mixture obtained in step (13-4) and 366 g of 3-methyl-1-butanol were placed in a 2 L four-mouth flask. A fractionation head equipped with a reflux condenser connected to a distillate collector and a thermometer which were attached to the flask, and after replacing the inside of the flask with nitrogen in a vacuum, the flask was immersed in an oil bath heated to 140° C. After heating while stirring for about 5 hours, the pressure inside the system was gradually reduced and a low boiling point component was distilled off to obtain 410 g of residue in the flask. When the residue was measured by $^1$H- and $^{119}$Sn-NMR, the residue was found to be a mixture of organic tin compounds containing di-n-octyl-bis(3-methylbutyloxy)tin, tri-n-octyl-(3-methylbutyloxy)tin, and contained 93.3% by weight of di-n-octyl-bis(3-methylbutyloxy)tin and about 3.1% by weight of tri-n-octyl-(3-methylbutyloxy)tin.

On the other hand, 453 g of the low boiling point component were recovered, and the low boiling point component contained 45% by weight of isoamyl acetate.

Example 14

Step (14-1): Separation of Tri-n-octyl(3-methylbutyloxy)Tin 180 g of an alkyl tin composition obtained containing 1,1,3,3-tetra-n-octyl-1,3-bis(3-methylbutyloxy)distannoxane obtained in the same manner as step (13-2) of Example 13 were placed in a 500 mL eggplant-shaped flask, a three-way valve, a distillation column packed with Helipack No. 3 and measuring 45 cm in length, a fractionation head equipped with a reflux condenser connected to a distillate collector and a thermometer were attached to the flask, and the inside of the vessel was replaced with nitrogen in a vacuum. The inside of the vessel was returned to atmospheric pressure and the flask was immersed in an oil bath heated to about 230° C. After about 20 minutes, the pressure inside the vessel was gradually reduced and the distilled components were recovered when the temperature of the contents of the flask reached about 210° C. Finally, distillation was terminated when the pressure inside the vessel reached about 0.01 kPa. The distillate and residue inside the flask were subjected to $^1$H- and $^{119}$Sn-NMR measurement. The distillate was tri-n-octyl(3-methylbutyloxy)tin. The residue inside the flask contained 73.5% by weight of 1,1,3,3-tetra-n-octyl-1,3-bis(3-methylbutyloxy) distannoxane, and according to $^{119}$Sn-NMR, was a mixture of organic tin compounds containing tin atoms demonstrating a plurality of chemical shifts at −240 to −605 ppm. There were 33.2 g of the resulting distillate and 146.8 g of residue inside the flask.

Step (14-2): Substituent Exchange Reaction 32.1 g of the tri-n-octyl(3-methylbutyloxy)tin obtained in step (14-1) were placed on a 300 mL eggplant-shaped flask followed by the addition of 27.2 g of acetic anhydride and stirring for 1 hour at 25° C. A fractionation head equipped with a reflux condenser connected to a distillate collector and a thermometer which were attached to the flask, and after replacing the inside of the flask with nitrogen in a vacuum, the flask was immersed in an oil bath heated to 50° C. The pressure inside the vessel was gradually reduced and excess acetic anhydride and the like were distilled off to obtain 30.5 g of a residue inside the flask. When the residue was measured by $^1$H- and $^{119}$Sn-NMR, the residue was determined to be tri-n-octyl acetoxy tin.

On the other hand, 145 g of the residue containing 73.5% by weight of 1,1,3,3-tetra-n-octyl-1,3-bis(3-methylbutyloxy) distannoxane obtained in step (14-1) were placed in a 500 mL metal pressure vessel followed by the addition of 180.6 g of acetic anhydride and stirring. The metal pressure vessel was immersed in an oil bath heated to 200° C. and heated for 3 hours. After allowing the metal pressure vessel to cool to the vicinity of room temperature (25° C.), the contents were transferred to a 500 mL eggplant-shaped flask. A fractionation head equipped with a reflux condenser connected to a distillate collector and a thermometer which were attached to the flask, and after replacing the inside of the flask with nitrogen in a vacuum, the flask was immersed in an oil bath heated to 50° C. The pressure inside the vessel was gradually reduced, and isoamyl acetate and excess acetic anhydride were distilled off to obtain 155 g of a residue in the flask. When the residue was measured by $^1$H- and $^{119}$Sn-NMR, the residue was found to be a mixture containing di-n-octyl diacetoxy tin and n-octyl triacetoxy tin, and the content of di-n-octyl diacetoxy tin in the mixture was 78.5% by weight while the content of n-octyl triacetoxy tin was 21.3% by weight. This mixture was mixed with the previously obtained tri-n-octyl acetoxy tin and used as the raw material of the subsequent step (14-3).

Step (14-3): Alkyl Group Redistribution Reaction

A reaction liquid was recovered by carrying out the same method as step (13-4) of Example 13 with the exception of using 183 g of the mixture obtained in step (14-2) instead of the mixture obtained in step (13-3) in a nitrogen atmosphere. When the reaction liquid was measured by $^1$H- and $^{119}$Sn-NMR, the reaction liquid was determined to be a mixture containing di-n-octyl diacetoxy tin and n-octyl triacetoxy tin, and the content of di-n-octyl diacetoxy tin in the mixture was 94.5% by weight.

Step (14-4): Alkoxylation of Dialkyl Tin Compound 210 g of a residue were obtained by carrying out the same method as step (13-5) of Example 13 with the exception of using 182 g of the mixture obtained in step (14-3) instead of the mixture obtained in step (13-4) and using 213 g of 3-methyl-1-butanol. When the residue was measured by $^1$H- and $^{119}$Sn-NMR, the residue contained 91% by weight of di-n-octyl-bis(3-methylbutyloxy)tin. On the other hand, 239 g of a low boiling point component were recovered, and the low boiling point component contained 42.2% by weight of isoamyl acetate.

Example 15

Step (15-1): Production of Dialkyl Tin Catalyst 893 g (2.48 mol) of di-n-octyl tin oxide (Sankyo Organic Chemicals Co., Ltd., Japan) and 2403 g (23.6 mol) of 2-ethyl-1-butanol were placed in a 5000 mL volumetric eggplant-shaped flask. The flask was attached to an evaporator to which was connected an oil bath equipped with a temperature controller, a vacuum pump and a vacuum controller. The purge valve outlet of the evaporator was connected to a line containing nitrogen gas flowing at a normal pressure. After closing the purge valve of the evaporator to reduce pressure inside the system, the purge valve was opened gradually to allow nitrogen to flow into the system and return to normal pressure. The oil bath temperature was set to about 165° C., the flask was immersed in the oil bath and rotation of the evaporator was started. After heating for about 40 minutes in the presence of atmospheric pressure nitrogen with the purge valve of the evaporator left open, distillation of 2-ethyl-1-butanol containing water began. After maintaining in this state for 7 hours, the purge valve was closed, pressure inside the system was gradually reduced, and excess 2-ethyl-1-butanol was distilled with the pressure inside the system at 74 to 25 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 1114 g of reaction liquid were obtained in the flask. Based on the results of $^{119}$Sn-, $^1$H- and $^{13}$C-NMR analyses, 1,1,3,3-tetra-n-octyl-1,3-bis(2-ethylbutyloxy)distannoxane was confirmed to have been obtained at a yield of 99% based on di-n-octyl tin oxide. The same procedure was then repeated 12 times to obtain a total of 13380 g of 1,1,3,3-tetra-n-octyl-1,3-bis(2-ethylbutyloxy)distannoxane.

Step (15-2): Production of Carbonic Acid Ester and Recovery of Alkyl Tin Composition Carbonic acid ester was produced in a continuous production apparatus like that shown in FIG. 5. 1,1,3,3-Tetra-n-octyl-1,3-bis(2-ethylbutyloxy)distannoxane produced in the manner described above was supplied at the rate of 6074 g/hr from the transfer line 4 into the column-type reactor 102 packed with Metal Gauze CY Packing and having an inner diameter of 151 mm and effective length of 5040 mm, and 2-ethyl-1-butanol purified with the distillation column 101 was supplied at the rate of 12260 g/hr from the transfer line 2. The liquid temperature inside the reactor 102 was adjusted to 160° C. by a heater and the reboiler 112, and the pressure was adjusted to about 120 kPa-G with a pressure control valve. The residence time in the reactor was about 17 minutes. 2-Ethyl-1-butanol containing water at the rate of 12344 g/hr from the top of the reactor via the transfer line 6, and 2-ethyl-1-butanol at the rate of 958 g/hr via the feed line 1, were pumped to the distillation column 101 packed with Metal Gauze CY Packing and provided with the reboiler 111 and the condenser 121 to carry out distillative purification. In the top of the distillation column 101, a fraction containing a high concentration of water was condensed by the condenser 121 and recovered from the recovery line 3. Purified 2-ethyl-1-butanol was pumped to the column-type reactor 102 via the transfer line 2 located in the bottom of the distillation column 101. A composition (to be referred to as a catalyst composition) containing di-n-octyl-bis(2-ethylbutyloxy)tin and 1,1,3,3-tetra-n-octyl-1,3-bis(2-ethylbutyloxy)distannoxane was obtained from the bottom of the column-type reactor 102, and supplied to the thin film evaporator 103 via the transfer line 5. The 2-ethyl-1-butanol was distilled off in the thin film evaporator 103 and returned to the column-type reactor 102 via the condenser 123, the transfer line 8 and the transfer line 4. The catalyst composition was pumped from the bottom of the thin film evaporator 103 via the transfer line 7 and supplied to the autoclave 104 while adjusting the flow rate of di-n-octyl-bis(2-ethylbutyloxy)tin and 1,1,3,3-tetra-n-octyl-1,3-bis(2-ethylbutyloxy)distannoxane to about 6945 g/hr. Carbon dioxide was supplied to the autoclave by the transfer line 9 at the rate of 973 g/hr, and the pressure inside the autoclave was maintained at 4 MPa-G. The temperature inside the autoclave was set to be 120° C., the residence time was adjusted to about 4 hours, and a reaction between the carbon dioxide and the catalyst composition was carried out to obtain a reaction liquid containing bis(2-ethylbutyl)carbonate. This reaction liquid was transferred to the decarbonization tank 105 via the transfer line 10 and a control valve to remove residual carbon dioxide, and the carbon dioxide was recovered from the transfer line 11. Subsequently, the reaction liquid was transferred to the thin film evaporator 106 set to about 142° C. and about 0.5 kPa via the transfer line 12 and supplied while adjusting the flow rate of 1,1,3,3-tetra-n-octyl-1,3-bis(2-ethylbutyloxy)distannoxane to about 6074 g/hr to obtain a fraction containing bis(2-ethylbutyl)carbonate. On the other hand, the evaporation residue was circulated to the column-type reactor 102 via the transfer line 13 and the transfer line 4 while adjusting the flow rate of 1,1,3,3-tetra-n-octyl-1,3-bis(2-ethylbutyloxy)distannoxane to about 6074 g/hr. The fraction containing bis(2-ethylbutyl)carbonate was supplied to the distillation column 107 packed with Metal Gauze CY Packing and equipped with the reboiler 117 and the condenser 127 via the condenser 126 and the transfer line 14 at the rate of 959 g/hr followed by distillative purification to obtain 99% by weight of bis(2-ethylbutyl)carbonate from the recovery line 15 at the rate of 1075 g/hr. When the catalyst composition of the transfer line 13 was analyzed by $^{119}$Sn-, $^{1}$H- and $^{13}$C-NMR analysis, it was found to contain 1,1,3,3-tetra-n-octyl-1,3-bis(2-ethylbutyloxy)distannoxane but not contain di-n-octyl-bis(2-ethylbutyloxy)tin. After carrying out the above-mentioned continuous operation for about 220 hours, catalyst composition was extracted from the extraction line 16 at the rate of 18 g/hr, while 1,1,3,3-tetra-n-octyl-1,3-bis(2-ethylbutyloxy)distannoxane produced according to the above process was supplied from the feed line 17 at the rate of 18 g/hr, and 180 g of alkyl tin composition containing 1,1,3,3-tetra-n-octyl-1,3-bis(2-ethylbutyloxy)distannoxane was extracted from the extraction line 16. When the alkyl tin composition was analyzed by $^{119}$Sn-NMR, in addition to containing about 55% by weight of 1,1,3,3-tetra-n-octyl-1,3-bis(2-ethylbutyloxy)distannoxane, tri-n-octyl(2-ethylbutyloxy)tin along with a plurality of NMR shifts of deactivated components of 1,1,3,3-tetra-n-octyl-1,3-bis(2-ethylbutyloxy)distannoxane were observed at −240 to −605 ppm.

Step (15-3): Substituent Exchange Reaction of Alkyl Tin Composition Containing 1,1,3,3-tetra-n-octyl-1,3-bis(2-ethylbutyloxy)Distannoxane 198 g of a mixture tri-n-octyl acetoxy tin, di-n-octyl diacetoxy tin and organic tin compounds containing tin atoms demonstrating a plurality of chemical shifts at −240 to −605 ppm in $^{119}$Sn-NMR were obtained by carrying out the same method as step (13-3) of Example 13 with the exception of using 195 g of the alkyl tin composition containing 1,1,3,3-tetra-n-octyl-1,3-bis(2-ethylbutyloxy)distannoxane obtained in step (15-2) instead of the alkyl tin composition obtained in step (13-2) and using 220 g of acetic anhydride (acetic acid was not used). In this mixture, the content of tri-n-octyl acetoxy tin was 25.1% by weight and the content of di-n-octyl diacetoxy tin was 54.9% by weight.

Step (15-4): Alkyl Group Redistribution Reaction

A reaction liquid was recovered by carrying out the same method as step (13-4) of Example 13 with the exception of using 196 g of the mixture obtained in step (15-3) instead of the mixture obtained in step (13-3). When $^{1}$H- and $^{119}$Sn-NMR measurement were carried out on the reaction liquid, the reaction liquid was determined to be a mixture of di-n-octyl diacetoxy tin and n-octyl triacetoxy tin, and the content of di-n-octyl diacetoxy tin in the mixture was 96.3% by weight.

Step (15-5): Alkoxylation of Dialkyl Tin Compound 232 g of a residue were obtained by carrying out the same method as step (13-5) of Example 13 with the exception of using 195 g of the mixture obtained in step (15-4) instead of the mixture obtained in step (13-4) and using 258 g of 2-ethyl-1-butanol instead of 3-methyl-1-butanol. When the residue was measured by $^{1}$H- and $^{119}$Sn-NMR, the residue was found to contain 95.7% by weight of di-n-octyl-bis(2-ethylbutyloxy)tin.

Example 16

Step (16-1): Substituent Exchange Reaction

Figure 6:
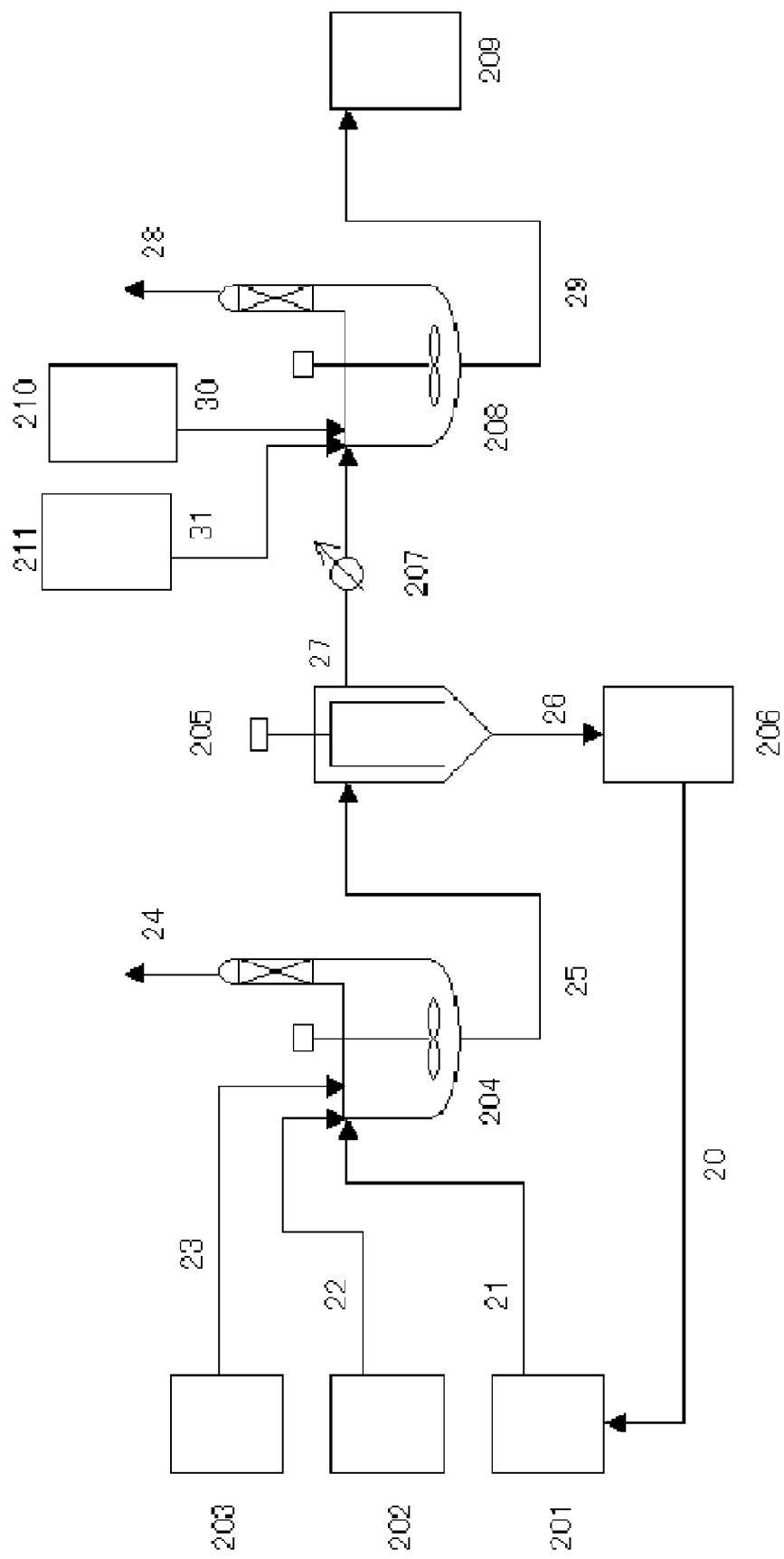
FIG. 6 shows a schematic drawing representing a dialkyl tin dialkoxide and/or tetraalkyl dialkoxy distannoxane production apparatus in an example.

A reaction was carried out using an apparatus like that shown in FIG. 6.

A composition of deactivated forms obtained in the same manner as step (13-2) of Example 13 was stored in a storage tank 201. 4.27 kg of the deactivated form composition was loaded into a stirring tank 204 equipped with a distillation column from the storage tank 201 via a line 21. The stirring tank 204 was heated to about 40° C. and 0.93 kg of acetic acid was added to the stirring tank 204 from a storage tank 202 via a line 22. After stirring for about 1 hour, the pressure inside the stirring tank 204 was reduced to about 0.13 kPa, the stirring tank 204 was heated to about 80° C. and a low boiling point component was distilled to recover 0.94 kg of the low boiling point component from a line 24. Next, the pressure inside the stirring tank 204 was returned to atmospheric pressure with nitrogen and the stirring tank 204 was then heated to about 100° C. followed by the addition of 1.87 kg of acetic anhydride from a storage tank 203 via a line 23. After stirring for about 3 hours, the pressure inside the stirring tank 204 was reduced to about 1 kPa, the stirring tank 204 was heated to about 120° C. and low boiling point components such as unreacted acetic anhydride were distilled to recover about 1.76 kg of low boiling point component from the line 24. A residue was obtained in the stirring tank 204. When this residue was sampled by analyzed by $^{119}$Sn- and $^{1}$H-NMR, the residue was found to contain 45.2% by weight of di-n-octyl tin diacetate and 25.4% by weight of tri-n-octyl tin acetate.

Step (16-2): Alkyl Group Redistribution Reaction

Next, a reaction was carried out using an apparatus like that shown in FIG. 6.

The stirring tank 204 containing the residue was returned to atmospheric pressure with nitrogen followed by heating to about 200° C. and stirring for about 2 hours. When the residue obtained in the stirring tank 204 was sampled and analyzed by $^{119}$Sn- and $^1$H-NMR, the residue was found to contain 90.2% by weight of di-n-octyl tin diacetate and about 0.5% by weight of tri-n-octyl tin acetate. Next, the residue heated to about 200° C. was fed to a thin film evaporator 205 in which the pressure in the system had been reduced to about 0.26 kPa via a line 25 to carry out distillative separation. A liquid phase component was condensed in a condenser 207 via a line 27 and recovered in a stirring tank 208. A liquid phase component was recovered in a storage tank 206 via a line 26. When the compound recovered in the stirring tank 208 was analyzed by $^{119}$Sn- and $^1$H-NMR, the residue was found to contain 98.4% by weight of di-n-octyl tin diacetate and about 0.3% by weight of tri-n-octyl tin acetate. On the other hand, there was 0.28 kg of the liquid phase component recovered in the storage tank 206. This liquid phase component was transferred to the storage tank 201 via a line 20 and recycled for use as a raw material of step (16-1).

Step (16-3): Alkoxylation of Dialkyl Tin Compound 15.33 kg of n-propanol (dehydrated, Wako Pure Chemical Industries, Ltd., Japan) were loaded into a stirring tank 208 equipped with a distillation column from a storage tank 210 via a line 30. After heating to about 100° C. with the stirring tank 208 sealed and reacting for about 40 hours, unreacted n-propanol was recovered by distillation from a line 28. There was about 15.33 kg of the distilled component and the content of n-propanol was 86.8% by weight while the content of propyl acetate was 11.2% by weight.

Next, 3.74 kg of 3-methyl-1-butanol were loaded into the stirring tank 208 from a storage tank 211 via a line 31. After heating the stirring tank 208 to about 130° C. and stirring for about 3 hours, the pressure inside the stirring tank 208 was reduced, and a low boiling point component containing unreacted 3-methyl-1-butanol and the like was recovered from the line 28. 3.28 kg of the low boiling point component were recovered, and the low boiling point component contained 69.5% by weight of 3-methyl-1-butanol and 30.5% by weight of n-propanol.

A residue obtained in the stirring tank 208 was recovered in a storage tank 209 via a line 29. When the recovered product was sampled and analyzed by $^{119}$Sn- and $^1$H-NMR, the recovered product was found to contain 97.1% by weight of di-n-octyl-bis(3-methylbutyloxy)tin.

Example 17

Step (17-1): Substituent Exchange Reaction

A reaction was carried out using an apparatus like that shown in FIG. 6.

An alkyl tin composition containing 1,1,3,3-tetra-n-octyl-1,3-bis(3-methylbutyloxy)distannoxane obtained using the same method as step (13-2) of Example 13 was stored in the storage tank 201. About 2.37 kg of a low boiling point component was recovered from the line 24 by distilling low boiling point components such as unreacted propionic anhydride by carrying out the same method as step (16-1) of Example 16 with the exception of loading 4.56 kg of the alkyl tin composition containing 1,1,3,3-tetra-n-octyl-1,3-bis(3-methylbutyloxy)distannoxane into the stirring tank 204 equipped with a distillation column from the storage tank 201 via the line 21, using 1.23 kg of propionic acid (Wako Pure Chemical Industries, Ltd., Japan) instead of acetic acid, and using 2.54 kg of propionic anhydride instead of acetic anhydride. When the low boiling point component was analyzed by gas chromatography, the low boiling point component was found to contain propionic acid, propionic anhydride and 3-methyl-1-butanol. A residue was obtained in the stirring tank 204. When this residue was sampled and analyzed by $^{119}$Sn- and $^1$H-NMR, the residue was found to contain 46.8% by weight of di-n-octyl-di(propionyloxy)tin and 25.3% by weight of tri-n-octyl-(propionyloxy)tin.

Step (17-2): Alkyl Group Redistribution Reaction

Next, a reaction was carried out using an apparatus like that shown in FIG. 6.

A mixture was obtained in the stirring tank 208 containing 98.5% by weight of di-n-octyl-di(propionyloxy)tin and about 0.4% by weight of tri-n-octyl-propionyloxy tin by carrying out the same method as step (16-2) of Example 16 with the exception of setting the pressure of the thin film evaporator 205 to about 0.13 kPa. On the other hand, 0.31 kg of a liquid phase component were recovered in the storage tank 206, and this liquid phase component was transferred to the storage tank 201 via the line 20 and recycled as a raw material of step (17-1).

Step (17-3): Alkoxylation of Dialkyl Tin Compound

Unreacted ethanol was recovered by distillation from the line 28 by carrying out the same method as step (16-3) of Example 16 with the exception of using 12.73 kg of ethanol (dehydrated, Wako Pure Chemical Industries, Ltd., Japan) instead of n-propanol, heating the stirring tank 208 to about 80° C. and carrying out the reaction for about 80 hours. There were about 13.21 kg of the distilled component, and the distilled component contained 83.7% by weight of ethanol and 13.9% by weight of ethyl propionate.

Next, a low boiling point component containing unreacted 3-methyl-1-butanol and the like was recovered from the line 28 by loading 3.99 kg of 3-methyl-1-butanol into the stirring tank 208 and carrying out the same method as step (16-3) of Example 16. There were 3.26 kg of the low boiling point component, and the low boiling point component contained 74.5% by weight of 3-methyl-1-butanol and 25.5% by weight of ethanol.

A residue obtained in the stirring tank 208 was recovered in the storage tank 209 via the line 29. When the recovered product was sampled and analyzed by $^{119}$Sn- and $^1$H-NMR, the recovered product was found to contain 97.9% by weight of di-n-octyl-bis(3-methylbutyloxy)tin.

Example 18

Step (18-1): Substituent Exchange Reaction

A reaction was carried out using an apparatus like that shown in FIG. 6.

An alkyl tin composition containing 1,1,3,3-tetra-n-octyl-1,3-bis(2-ethylbutyloxy)distannoxane obtained using the same method as step (15-2) of Example 15 was stored in the storage tank 201 instead of an alkyl tin composition containing 1,1,3,3-tetra-n-octyl-1,3-bis(3-methylbutyloxy)distannoxane obtained using the same method as step (13-2) of Example 13. About 1.59 kg of a low boiling point component was recovered from the line 24 by distilling low boiling point components such as unreacted acetic anhydride by carrying out the same method as step (16-1) of Example 16 with the exception of loading 3.95 kg of the alkyl tin composition containing 1,1,3,3-tetra-n-octyl-1,3-bis(2-ethylbutyloxy)

distannoxane into the stirring tank 204 equipped with a distillation column from the storage tank 201 via the line 21, using 0.83 kg of acetic acid, and using 1.68 kg of acetic anhydride. When the low boiling point component was analyzed by gas chromatography, the low boiling point component was found to contain acetic acid, acetic anhydride and 2-ethyl-1-butanol. A residue was obtained in the stirring tank 204. When this residue was sampled and analyzed by $^{119}$Sn- and $^1$H-NMR, the residue was found to contain 44.8% by weight of di-n-octyl tin diacetate and 25.2% by weight of tri-n-octyl tin acetate.

Step (18-2): Alkyl Group Redistribution Reaction

Next, a reaction was carried out using an apparatus like that shown in FIG. 6.

A mixture was obtained in the stirring tank 208 containing 98.9% by weight of di-n-octyl tin diacetate by carrying out the same method as step (16-2) of Example 16. On the other hand, 0.24 kg of a liquid phase component were recovered in the storage tank 206, and this liquid phase component was transferred to the storage tank 201 via the line 20 and recycled as a raw material of step (18-1).

Step (18-3): Alkoxylation of Dialkyl Tin Compound

Unreacted ethanol was recovered by distillation from the line 28 by carrying out the same method as step (16-3) of Example 16 with the exception of using 10.75 kg of ethanol instead of n-propanol, heating the stirring tank 208 to about 80° C. and carrying out the reaction for about 150 hours. There were 10.94 kg of the distilled component, and the distilled component contained 85.2% by weight of ethanol and 12.2% by weight of ethyl acetate.

Next, a low boiling point component containing unreacted 2-ethyl-1-butanol and the like was recovered from the line 28 by loading 3.91 kg of 2-ethyl-1-butanol instead of 3-methyl-1-butanol into the stirring tank 208 and carrying out the same method as step (16-3) of Example 16. There were 3.29 kg of the low boiling point component, and the low boiling point component contained 72.3% by weight of 2-ethyl-1-butanol and 21.3% by weight of ethanol.

A residue obtained in the stirring tank 208 was recovered in the storage tank 209 via the line 29. When the recovered product was sampled and analyzed by $^{119}$Sn- and $^1$H-NMR, the recovered product was found to contain 97.4% by weight of di-n-octyl-bis(2-ethylbutyloxy)tin.

Example 19

Step (19-1): Substituent Exchange Reaction

A reaction was carried out using an apparatus like that shown in FIG. 6.

An alkyl tin composition containing 1,1,3,3-tetra-n-butyl-1,3-dibutyloxy distannoxane obtained using the same method as step (3-2) of Reference Example 3 was stored in the storage tank 201 instead of an alkyl tin composition containing 1,1,3,3-tetra-n-octyl-1,3-bis(3-methylbutyloxy)distannoxane obtained using the same method as step (13-2) of Example 13. About 6.29 kg of a low boiling point component were recovered from the line 24 by distilling low boiling point components such as unreacted hexanoic anhydride by carrying out the same method as step (16-1) of Example 16 with the exception of loading 5.41 kg of the alkyl tin composition containing 1,1,3,3-tetra-n-butyl-1,3-dibutyloxy distannoxane into the stirring tank 204 equipped with a distillation column from the storage tank 201 via the line 21, using 3.21 kg of hexanoic acid instead of acetic acid, and using 6.81 kg of hexanoic anhydride instead of acetic anhydride. When the low boiling point component was analyzed by gas chromatography, the low boiling point component was found to contain hexanoic acid, hexanoic anhydride and n-butanol. A residue was obtained in the stirring tank 204. When this residue was sampled and analyzed by $^{119}$Sn- and $^1$H-NMR, the residue was found to contain 47.3% by weight of di-n-butyl-dipropionyloxy tin and 20.7% by weight of tri-n-butyl-propionyloxy tin.

Step (19-2): Alkyl Group Redistribution Reaction

Next, a reaction was carried out using an apparatus like that shown in FIG. 6.

A mixture was obtained in the stirring tank 208 containing 90.2% by weight of di-n-butyl dipropionyloxy tin by carrying out the same method as step (16-2) of Example 16. On the other hand, 0.46 kg of a liquid phase component were recovered in the storage tank 206, and this liquid phase component was transferred to the storage tank 201 via the line 20 and recycled as a raw material of step (19-1).

Step (19-3): Alkoxylation of Dialkyl Tin Compound

Unreacted n-butanol was recovered by distillation from the line 28 by carrying out the same method as step (16-3) of Example 16 with the exception of using 32.57 kg of n-butanol instead of n-propanol, heating the stirring tank 208 to about 120° C. and carrying out the reaction for about 80 hours. There were 33.97 kg of the distilled component, and the distilled component contained 83.8% by weight of n-butanol and 14.7% by weight of butyl hexanoate.

A residue obtained in the stirring tank 208 was recovered in the storage tank 209 via the line 29. When the recovered product was sampled and analyzed by $^{119}$Sn- and $^1$H-NMR, the recovered product was found to contain 76.1% by weight of di-n-butyl-di(n-butyloxy)tin and 10.9% by weight of tri-n-butyl-(n-butyloxy)tin.

Example 20

Step (20-1): Substituent Exchange Reaction

A reaction was carried out using an apparatus like that shown in FIG. 6. An alkyl tin composition containing 1,1,3,3-tetra-n-butyl-1,3-dibutyloxy distannoxane obtained using the same method as step (3-2) of Reference Example 3 was stored in the storage tank 201 instead of an alkyl tin composition containing 1,1,3,3-tetra-n-octyl-1,3-bis(3-methylbutyloxy)distannoxane obtained using the same method as step (13-2) of Example 13. About 6.29 kg of a low boiling point component were recovered from the line 24 by distilling low boiling point components such as unreacted hexanoic anhydride by carrying out the same method as step (16-1) of Example 16 with the exception of loading 5.41 kg of the alkyl tin composition containing 1,1,3,3-tetra-n-butyl-1,3-dibutyloxy distannoxane into the stirring tank 204 equipped with a distillation column from the storage tank 201 via the line 21, using 3.21 kg of hexanoic acid instead of acetic acid, and using 6.81 kg of hexanoic anhydride instead of acetic anhydride. When the low boiling point component was analyzed by gas chromatography, the low boiling point component was found to contain hexanoic acid, hexanoic anhydride and n-butanol. A residue was obtained in the stirring tank 204. When this residue was sampled and analyzed by $^{119}$Sn- and ¹H-NMR, the residue was found to contain 47.3% by weight of di-n-butyl-dipropionyloxy tin and 20.7% by weight of tri-n-butyl-propionyloxy tin.

Step (20-2): Alkyl Group Redistribution Reaction

Next, a reaction was carried out using an apparatus like that shown in FIG. 6.

A mixture was obtained in the stirring tank 208 containing 90.2% by weight of di-n-butyl dipropionyloxy tin by carrying out the same method as step (16-2) of Example 16. On the other hand, 0.46 kg of a liquid phase component were recovered in the storage tank 206, and this liquid phase component was transferred to the storage tank 201 via the line 20 and recycled as a raw material of step (20-1).

Step (20-3): Alkoxylation of Dialkyl Tin Compound

Unreacted n-butanol was recovered by distillation from the line 28 by carrying out the same method as step (16-3) of Example 16 with the exception of using 32.57 kg of n-butanol instead of n-propanol, heating the stirring tank 208 to about 120° C. and carrying out the reaction for about 80 hours. There were 33.97 kg of the distilled component, and the distilled component contained 83.8% by weight of n-butanol and 14.7% by weight of butyl hexanoate.

A residue obtained in the stirring tank 208 was recovered in the storage tank 209 via the line 29. When the recovered product was sampled and analyzed by $^{119}$Sn- and ¹H-NMR, the recovered product was found to contain 76.1% by weight of di-n-butyl-di(n-butyloxy)tin and 10.9% by weight of tri-n-butyl-(n-butyloxy)tin.

Example 21

Step (21-1): Production of Carbonic Acid Ester Using Regenerated Dialkyl Tin Dialkoxide Compound In step (15-2) of Example 15, an alkyl tin alkoxide catalyst composition was extracted at the rate of 18 g/hr from the extraction line 16 while a mixture containing 97.4% by weight of the di-n-octyl-bis(2-ethylbutyloxy)tin obtained in step (18-3) of Example 18 was supplied from the feed line 17 at the rate of 18 g/hr. The regenerated di-n-octyl-bis(2-ethylbutyloxy)tin was supplied to the column-type reactor 102 via the line 4. 99% by weight of bis(2-ethylbutyl)carbonate was recovered from the line 15 by carrying out operation using the same method as step (15-2) of Example 15. The recovered amount of the bis(2-ethylbutyl)carbonate did not change before and after use of the regenerated di-n-octyl-bis(2-ethylbutyloxy)tin.

Example 22

Step (22-1): Production of Carbonic Acid Ester

Figure 7:
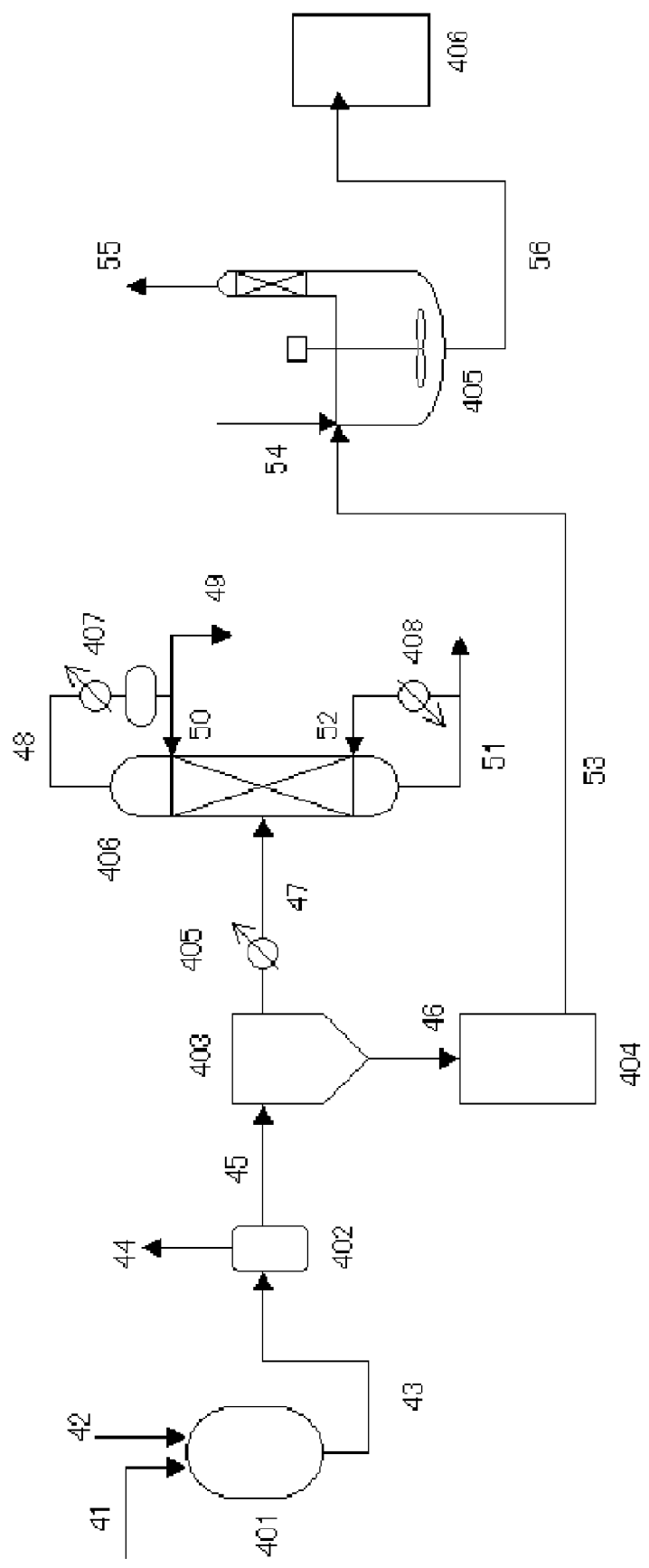
FIG. 7 shows a schematic drawing representing a carbonic acid ester and dialkyl tin dialkoxide and/or tetraalkyl dialkoxy distannoxane production apparatus in an example.

Carbonic acid ester was produced in a continuous production apparatus like that shown in FIG. 7.

The mixture containing 97.1% by weight of di-n-octyl-bis(3-methylbutyloxy)tin obtained in step (16-3) of Example 16 was fed to an autoclave 401 via a line 41 at the rate of 6944 g/hr. Carbon dioxide was supplied to the autoclave from a line 42 at the rate of 1390 g/hr, and the pressure inside the autoclave was maintained at 4 MPa-G. The temperature inside the autoclave was set to be 120° C., the residence time was adjusted to about 4 hours, and a reaction between the carbon dioxide and the di-n-octyl-bis(3-methylbutyloxy)tin was carried out to obtain a reaction liquid containing bis(3-methylbutyl)carbonate. This reaction liquid was transferred to a decarbonization tank 402 via a line 43 and a control valve at the rate of 7253 g/hr to remove residual carbon dioxide, and the carbon dioxide was recovered from a line 44. Subsequently, the reaction liquid was transferred to a thin film evaporator 403 set to about 142° C. and about 0.5 kPa via a line 45 to obtain a fraction containing bis(3-methylbutyl) carbonate. The fraction containing bis(3-methylbutyl)carbonate was supplied to a distillation column 406 packed with Metal Gauze CY Packing and equipped with a reboiler 408 and a condenser 407 via a condenser 405 and a line 47 followed by distillative purification. 99% by weight of bis(3-methylbutyl)carbonate was obtained from a line 49 at the rate of 1351 g/hr. On the other hand, a liquid phase component separated in the thin film evaporator 403 was recovered in a storage tank 404 via a line 46 at the rate of about 58990 g/hr. When this liquid phase component was sampled and analyzed by $^{119}$Sn- and ¹H-NMR, the liquid phase component was found to be a mixture containing about 98% by weight of 1,1,3,3-tetra-n-octyl-1,3-bis(3-methylbutyloxy)distannoxane.

Step (22-2): Substituent Exchange Reaction 4.11 kg of the liquid phase component recovered in the storage tank 404 in step (22-1) were fed to a stirring tank 405 equipped with a distillation column via a line 53. The stirring tank 405 was heated to about 40° C. and 1.18 kg of acetic acid was added to the stirring tank 405 via a line 55. After stirring for about 1 hour, the pressure inside the stirring tank 405 was reduced to about 0.13 kPa, the stirring tank 405 was heated to about 80° C. and a low boiling point component was distilled to recover 0.98 kg of the low boiling component from the line 55. Next, the pressure inside the stirring tank 405 was returned to atmospheric pressure with nitrogen followed by heating to about 100° C. and adding 1.67 kg of acetic anhydride via the line 55. After stirring for about 3 hours, the pressure inside the stirring tank 405 was reduced to about 1 kPa, the stirring tank 405 was heated to about 120° C. and a low boiling point component such as unreacted acetic anhydride was distilled to recover about 1.82 kg of the low boiling point component from the line 55. When the low boiling point component was analyzed by gas chromatography, the low boiling point component was found to contain acetic acid, acetic anhydride and 3-methyl-1-butanol. A residue was obtained in the stirring tank 405. When this residue was sampled and analyzed by $^{119}$Sn- and ¹H-NMR, the residue was found to contain 90.7% by weight of di-n-octyl tin diacetate.

Step (22-3): Alkoxylation of Dialkyl Tin Compound 14.56 kg of n-propanol were loaded into the stirring tank 405 equipped with a distillation column from the line 55. After heating to about 100° C. with the stirring tank 405 sealed and reacting for about 40 hours, unreacted n-propanol was recovered by distillation from the line 55. There was about 14.56 kg of the distilled component and the content of n-propanol was 86.9% by weight while the content of propyl acetate was 11.2% by weight.

Next, 3.55 kg of 3-methyl-1-butanol were loaded into the stirring tank 405 from the line 55. After heating the stirring tank 405 to about 130° C. and stirring for about 3 hours, the pressure inside the stirring tank 405 was reduced, and a low boiling point component containing unreacted 3-methyl-1- butanol and the like was recovered from the line 55. 3.11 kg of the low boiling point component were recovered, and the low boiling point component contained 69.5% by weight of 3-methyl-1-butanol and 30.5% by weight of n-propanol.

A residue obtained in the stirring tank 405 was recovered in a storage tank 406 via a line 56. When the recovered product was sampled and analyzed by $^{119}$Sn- and $^1$H-NMR, the recovered product was found to contain 96.0% by weight of di-n-octyl-bis(3-methylbutyloxy)tin.

Step (22-4): Production of Carbonic Acid Ester

99% by weight of bis(3-methylbutyl)carbonate was obtained from a line 49 at the rate of 1350 g/hr by carrying out the same method as step (21-1) with the exception of using the recovered product containing di-n-octyl-bis(3-methylbutyloxy)tin obtained in step (22-3) instead of the mixture containing 97.1% by weight of di-n-octyl-bis(3-methylbutyloxy)tin obtained in step (16-3) of Example 16.

Example 23

Step (23-1): Production of Carbonic Acid Ester

Carbonic acid ester was produced in a continuous production apparatus like that shown in FIG. 7.

The mixture containing 97.4% by weight of di-n-octyl-bis(2-ethylbutyloxy)tin obtained in step (18-3) of Example 18 was fed to the autoclave 401 via the line 41 at the rate of 7318 g/hr. Carbon dioxide was supplied to the autoclave from the line 42 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the di-n-octyl-bis(2-ethylbutyloxy)tin was carried out to obtain a reaction liquid containing bis(2-ethylbutyl)carbonate. This reaction liquid was transferred to the decarbonization tank 402 via the line 43 and a control valve at the rate of 8188 g/hr to remove residual carbon dioxide, and the carbon dioxide was recovered from the line 44. Subsequently, the reaction liquid was transferred to the thin film evaporator 403 set to about 150° C. and about 0.5 kPa via the line 45 to obtain a fraction containing bis(2-ethylbutyl)carbonate. The fraction containing bis(2-ethylbutyl)carbonate was supplied to the distillation column 406 packed with Metal Gauze CY Packing and equipped with the reboiler 408 and the condenser 407 via the condenser 405 and the line 47 followed by distillative purification. 99% by weight of bis(2-ethylbutyl)carbonate was obtained from the line 49 at the rate of 1351 g/hr. On the other hand, a liquid phase component separated in the thin film evaporator 403 was recovered in the storage tank 404 via the line 46 at the rate of about 6074 g/hr. When this liquid phase component was sampled and analyzed by $^{119}$Sn- and $^1$H-NMR, the liquid phase component was found to be a mixture containing about 98% by weight of 1,1,3,3-tetra-n-octyl-1,3-bis(2-ethylbutyloxy)distannoxane.

Step (23-2): Substituent Exchange Reaction

About 0.86 kg of a low boiling point component was recovered from the line 55 by carrying out the same method as step (22-2) of Example 22 with the exception of feeding 2.04 kg of the liquid phase component recovered in the storage tank 404 in step (23-1) instead of the liquid phase component recovered in storage tank 404 in step (21-1), using 0.55 kg of acetic acid and using 0.78 kg of acetic anhydride. When the low boiling point component was analyzed by gas chromatography, the low boiling point component was found to contain acetic acid, acetic anhydride and 2-ethyl-1-butanol. A residue was obtained in the stirring tank 405. When this residue was sampled and analyzed by $^{119}$Sn- and $^1$H-NMR, the residue was found to contain 88.1% by weight of di-n-octyl tin diacetate.

Step (23-3): Alkoxylation of Dialkyl Tin Compound 5.38 kg of a distilled component were recovered from the line 55 by carrying out the same method as step (22-3) of Example 22 with the exception of using 5.28 kg of ethanol instead of n-propanol. The distilled component contained 85.3% by weight of ethanol and 12.3% by weight of ethyl acetate.

Next, 1.52 kg of a low boiling point component were obtained by carrying out the same method as step (22-3) of Example 22 with the exception of using 1.92 kg of 2-ethyl-1-butanol instead of 3-methyl-1-butanol. A residue obtained in the stirring tank 405 was recovered in the storage tank 406 via the line 56. When the recovered product was sampled and analyzed by $^{119}$Sn- and $^1$H-NMR, the recovered product was found to contain 96.5% by weight of di-n-octyl-bis(2-ethylbutyloxy)tin.

Step (23-4): Production of Carbonic Acid Ester

99% by weight of bis(2-ethylbutyl)carbonate was obtained from a line 49 at the rate of 1350 g/hr by carrying out the same method as step (22-1) with the exception of using the recovered product containing di-n-octyl-bis(2-ethylbutyloxy)tin obtained in step (23-3) instead of the mixture containing 97.4% by weight of di-n-octyl-bis(2-ethylbutyloxy)tin obtained in step (16-3) of Example 16.

Example 24

Step (24-1): Production of Carbonic Acid Ester

Carbonic acid ester was produced in a continuous production apparatus like that shown in FIG. 7.

The mixture containing 76.1% by weight of di-n-butyl-di(n-butyloxy)tin obtained in step (19-3) of Example 19 was fed to the autoclave 401 via the line 41 at the rate of 6666 g/hr. Carbon dioxide was supplied to the autoclave from the line 42 at the rate of 970 g/hr, and the pressure inside the autoclave was maintained at 4 MPa-G. The temperature inside the autoclave was set to 120° C., the residence time was adjusted to about 4 hours, and a reaction between the carbon dioxide and the di-n-butyl-di(n-butyloxy)tin was carried out to obtain a reaction liquid containing di(n-butyl)carbonate. This reaction liquid was transferred to the decarbonization tank 402 via the line 43 and a control valve at the rate of 7722 g/hr to remove residual carbon dioxide, and the carbon dioxide was recovered from the line 44. Subsequently, the reaction liquid was transferred to the thin film evaporator 403 set to about 150° C. and about 0.5 kPa via the line 45 to obtain a fraction containing di(n-butyl)carbonate. The fraction containing di(n-butyl)carbonate was supplied to the distillation column 406 packed with Metal Gauze CY Packing and equipped with the reboiler 408 and the condenser 407 via the condenser 405 and the line 47 followed by distillative purification. 99% by weight of di(n-butyl)carbonate was obtained from the line 49 at the rate of 1165 g/hr. On the other hand, a liquid phase component separated in the thin film evaporator 403 was recovered in the storage tank 404 via the line 46. When this liquid phase component was sampled and analyzed by 119Sn- and $^1$H-NMR, the liquid phase component was found to be a mixture containing about 77% by weight of 1,1,3,3-tetra-n-butyl-1,3-di(n-butyloxy)distannoxane.

Step (24-2): Substituent Exchange Reaction

About 4.74 kg of a low boiling point component were recovered from the line 55 by carrying out the same method as step (22-2) of Example 22 with the exception of feeding 4.06 kg of the liquid phase component recovered in the storage tank 404 in step (24-1) instead of the liquid phase component recovered in storage tank 404 in step (21-1), using 2.55 kg of hexanoic acid instead of acetic acid and using 4.99 kg of hexanoic anhydride instead of acetic anhydride. When the low boiling point component was analyzed by gas chromatography, the low boiling point component was found to contain hexanoic acid, hexanoic anhydride and n-butanol. A residue was obtained in the stirring tank 405. When this residue was sampled and analyzed by $^{119}$Sn- and $^1$H-NMR, the residue was found to contain 56.4% by weight of di-n-butyl-dipropionyloxy tin.

Step (24-3): Alkoxylation of Dialkyl Tin Compound 25.51 kg of a distilled component were recovered from the line 55 by carrying out the same method as step (22-3) of Example 22 with the exception of using 24.59 kg of n-butanol instead of n-propanol. The distilled component contained 83.7% by weight of n-butanol and 14.8% by weight of butyl hexanoate. On the other hand, a residue obtained in the storage tank 405 was recovered in the storage tank 406 via the line 56. When the recovered product was sampled and analyzed by $^{119}$Sn- and $^1$H-NMR, the recovered product was found to contain 77.2% by weight of di-n-butyl-di(n-butyloxy)tin.

Step (24-4): Production of Carbonic Acid Ester

99% by weight of di(n-butyl)carbonate was obtained from the line 49 at the rate of 1165 g/hr by carrying out the same method as step (24-1) with the exception of using the recovered product containing di-n-butyl-di(n-butyloxy)tin obtained in step (24-3) instead of the mixture containing di-n-butyl-di(n-butyloxy)tin obtained in step (16-3) of Example 16.

Example 25

Step (25-1): Production of Dialkyl Tin Catalyst

A solution containing 1,1,3,3-tetra-n-octyl-1,3-bis(2-ethylbutyloxy)distannoxane was obtained by carrying out the same method as step (15-1) of Example 15 with the exception of using 2803 g of 2-ethyl-1-butanol and 890 g of di-n-octyl tin oxide. The 1,1,3,3-tetra-n-octyl-1,3-bis(2-ethylbutyloxy) distannoxane was obtained at a yield of 99% based on di-n-octyl tin oxide. The same procedure was then repeated 12 times to obtain a total of 13400 g of 1,1,3,3-tetra-n-octyl-1, 3-bis(2-ethylbutyloxy)distannoxane.

Step (25-2): Production of Carbonic Acid Ester

Figure 8:
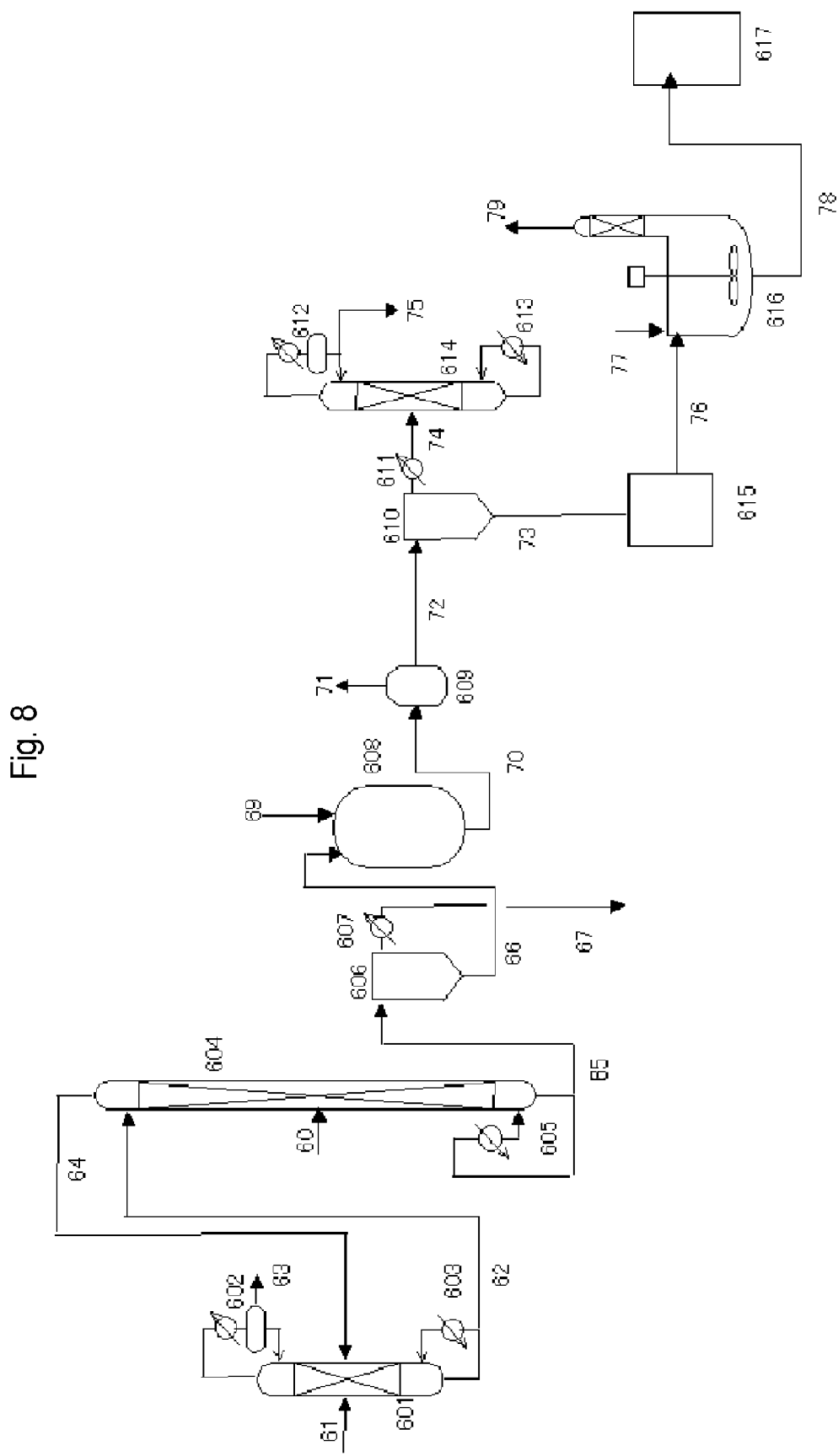
FIG. 8 shows a schematic drawing representing a carbonic acid ester and dialkyl tin dialkoxide and/or tetraalkyl dialkoxy distannoxane production apparatus in an example.

Carbonic acid ester was produced in a continuous production apparatus like that shown in FIG. 8. 1,1,3,3-tetra-n-octyl-1,3-bis(2-ethylbutyloxy)distannoxane produced in the manner described above was supplied at the rate of 6074 g/hr from a line 60 into a column-type reactor 604 packed with Metal Gauze CY Packing and having an inner diameter of 151 mm and effective length of 5040 mm, and 2-ethyl-1-butanol purified with a distillation column 601 was supplied at the rate of 12260 g/hr from a line 62. The liquid temperature inside the reactor 604 was adjusted to 160° C. by a heater and a reboiler 605, and the pressure was adjusted to about 120 kPa-G with a pressure control valve. 2-Ethyl-1-butanol containing water at the rate of 12344 g/hr from the top of the reactor via a line 64, and 2-ethyl-1-butanol at the rate of 958 g/hr via a line 61, were pumped to the distillation column 601 packed with Metal Gauze CY Packing and provided with a reboiler 603 and a condenser 602 to carry out distillative purification. In the top of the distillation column 601, a fraction containing a high concentration of water was condensed by a condenser 602 and recovered from a line 63. Purified 2-ethyl-1-butanol was pumped to a column-type reactor 604 via the line 62 located in the bottom of the distillation column 601. An alkyl tin alkoxide catalyst composition containing di-n-octyl-bis(2-ethylbutyloxy)tin and 1,1,3,3-tetra-n-octyl-1,3-bis(2-ethylbutyloxy)distannoxane was obtained from the bottom of the column-type reactor 604, and supplied to a thin film evaporator 606 via a line 65. The 2-ethyl-1-butanol was distilled off in the thin film evaporator 606. The alkyl tin alkoxide catalyst composition was pumped from the bottom of the thin film evaporator 606 via a line 66 and supplied to an autoclave 608 while adjusting the flow rate of di-n-octyl-bis(2-ethylbutyloxy)tin and 1,1,3,3-tetra-n-octyl-1,3-bis(2-ethylbutyloxy) distannoxane to about 6945 g/hr. Carbon dioxide was supplied to the autoclave by a line 69 at the rate of 973 g/hr, and the pressure inside the autoclave was maintained at 4 MPa-G. The temperature inside the autoclave was set to be 120° C., the residence time was adjusted to about 4 hours, and a reaction between the carbon dioxide and the alkyl tin alkoxide catalyst composition was carried out to obtain a reaction liquid containing bis(2-ethylbutyl)carbonate. This reaction liquid was transferred to a decarbonization tank 609 via a line 70 and a control valve to remove residual carbon dioxide, and the carbon dioxide was recovered from a line 71. Subsequently, the reaction liquid was transferred to a thin film evaporator 610 set to about 142° C. and about 0.5 kPa via a line 72 and supplied while adjusting the flow rate of 1,1,3,3-tetra-n-octyl-1,3-bis(2-ethylbutyloxy)distannoxane to about 6074 g/hr to obtain a fraction containing bis(2-ethylbutyl) carbonate. On the other hand, the evaporation residue was recovered in a storage tank 615 via a line 73. The recovered component was 1,1,3,3-tetra-n-octyl-1,3-bis(2-ethylbutyloxy)distannoxane. The fraction containing bis(2-ethylbutyl) carbonate was supplied to a distillation column 614 packed with Metal Gauze CY Packing and equipped with a reboiler 613 and a condenser 612 via a condenser 611 and a line 74 at the rate of 959 g/hr followed by distillative purification to obtain 99% by weight of bis(2-ethylbutyl)carbonate from a line 75 at the rate of 1075 g/hr.

Step (25-3): Substituent Exchange Reaction 3.16 kg of the evaporation residue recovered in the storage tank 615 in step (25-2) were fed to a stirring tank 616 equipped with a distillation column via a line 76. The stirring tank 616 was heated to about 40° C. and 1.03 kg of acetic acid was added to the stirring tank 616 via a line 77. After stirring for about 1 hour, the pressure inside the stirring tank 616 was reduced to about 0.13 kPa, the stirring tank 616 was heated to about 80° C. and a low boiling point component was distilled to recover 0.85 kg of the low boiling component from a line 79. When gas chromatographer analysis was performed on the low boiling point component, the component was found to contain 2-methyl-1-butanol. Then, the pressure inside the stirring tank 616 was returned to atmospheric pressure with nitrogen followed by heating to about 100° C. and adding 1.46 kg of acetic anhydride via the line 77. After stirring for about 3 hours, the pressure inside the stirring tank 616 was reduced to about 1 kPa, the stirring tank 616 was heated to about 120° C. and a low boiling point component such as unreacted acetic anhydride was distilled to recover about 1.59 kg of the low boiling point component from the line 79. A residue was obtained in the stirring tank 616. When this residue was sampled and analyzed by $^{119}$Sn- and $^{1}$H-NMR, the residue was found to contain 90.5% by weight of di-n-octyl tin diacetate.

Step (25-4): Alkoxylation of Dialkyl Tin Compound 13.73 kg of n-propanol were loaded into the stirring tank 616 equipped with a distillation column from the line 77. After heating to about 100° C. with the stirring tank 616 sealed and reacting for about 40 hours, unreacted n-propanol was recovered by distillation from the line 79. There was 13.73 kg of the distilled component and the content of n-propanol was 87.8% by weight while the content of propyl acetate was 10.4% by weight.

Next, 3.11 kg of 2-ethyl-1-butanol were loaded into the stirring tank 616 from the line 77. After heating the stirring tank 616 to about 130° C. and stirring for about 3 hours, the pressure inside the stirring tank 616 was reduced, and a low boiling point component containing unreacted 2-ethyl-1-butanol and the like was recovered from the line 79. 2.80 kg of the low boiling point component were recovered, and the low boiling point component contained 70.1% by weight of 2-ethyl-1-butanol and 28.9% by weight of n-propanol.

A residue obtained in the stirring tank 616 was recovered in a storage tank 617 via a line 78. When the recovered product was sampled and analyzed by $^{119}$Sn- and $^{1}$H-NMR, the recovered product was found to contain 97.0% by weight of di-n-octyl-bis(2-ethylbutyloxy)tin.

Step (25-5): Production of Carbonic Acid Ester

99% by weight of bis(2-ethylbutyl)carbonate was obtained from the line 75 at the rate of 1075 g/hr by carrying out the same method as step (24-1) with the exception of using the recovered product containing di-n-octyl-bis(2-ethylbutyloxy)tin obtained in step (25-4) instead of the mixture containing 1,1,3,3-tetra-n-octyl-1,3-bis(2-ethylbutyloxy)distannoxane obtained in step (25-1).

Example 26

Step (26-1): Production of Dialkyl Tin Catalyst 1120 g of a reaction liquid were obtained by carrying out the same method as step (13-1) of Example 13 with the exception of using 963 g of di-n-octyl tin oxide and 2120 g of 3-methyl-1-butanol. 1,1,3,3-Tetra-n-octyl-1,3-bis(3-methylbutyloxy)distannoxane was confirmed to have been obtained at a yield of 99% based on di-n-octyl tin oxide based on the results of $^{119}$Sn-, $^{1}$H- and $^{13}$C-NMR analyses. The same procedure was then repeated 12 times to obtain a total of 13990 g.

Step (26-2): Production of Carbonic Acid Ester

Carbonic acid ester was produced in a continuous production apparatus like that shown in FIG. 8.

99% by weight of bis(3-methylbutyl)carbonate was obtained from the line 75 at the rate of 940 g/hr by carrying out the same method as step (24-2) of Example 24 with the exception of using the 1,1,3,3-tetra-n-octyl-1,3-bis(3-methylbutyloxy)distannoxane obtained in step (26-1) instead of 1,1,3,3-tetra-n-octyl-1,3-bis(2-ethylbutyloxy)distannoxane from the line 60, and using 3-methyl-1-butanol instead of 2-ethyl-1-butanol. On the other hand, the evaporation residue in the thin film evaporator 610 was stored in the storage tank 615 via the line 73. The evaporation residue was 1,1,3,3-tetra-n-octyl-1,3-bis(3-methylbutyloxy)distannoxane.

Step (26-3): Substituent Exchange Reaction

A residue was obtained in the stirring tank 616 by carrying out the same method as step (24-3) of Example 24 with the exception of feeding 2.86 kg of the evaporation residue recovered in the storage tank 615 in step (26-2) into the stirring tank 616 equipped with a distillation column via the line 76, using 1.00 kg of propionic acid instead of acetic acid, and using 1.47 kg of propionic anhydride instead of acetic anhydride. When the residue was sampled and analyzed by $^{119}$Sn- and $^{1}$H-NMR, the residue was found to contain 90.2% by weight of di-n-octyl-dipropionyloxy tin.

Step (26-4): Alkoxylation of Dialkyl Tin Compound

A distilled component was recovered by distillation from the line 79 by carrying out the same method as step (24-4) of Example 24 with the exception of using 7.78 kg of ethanol instead of n-propanol. 8.07 kg of the distilled component were obtained, and the distilled component contained 83.0% by weight of ethanol and 14.0% by weight of ethyl propionate.

Next, a low boiling point component containing unreacted 3-methyl-butanol and the like was recovered from the line 79 by using 2.44 kg of 3-methyl-1-butanol instead of 2-ethyl-1-butanol. 2.05 kg of the low boiling point component were recovered, and the low boiling point component contained 72.2% by weight of 3-methyl-1-butanol and 24.9% by weight of ethanol.

A residue obtained in the stirring tank 616 was recovered in the storage tank 617 via the line 78. When this recovered product was sampled and analyzed by $^{119}$Sn- and $^{1}$H-NMR, the recovered product was found to contain 95.0% by weight of di-n-octyl-bis(3-methylbutyloxy)tin.

Step (26-5): Production of Carbonic Acid Ester

99% by weight of bis(3-methylbutyl)carbonate was obtained from the line 75 at the rate of 940 g/hr by carrying out the same method as step (26-1) with the exception of using the recovered product containing di-n-octyl-bis(3-methylbutyloxy)tin obtained in step (26-4) instead of the mixture containing 1,1,3,3-tetra-n-octyl-1,3-bis(2-ethylbutyloxy)distannoxane obtained in step (26-1).

Example 27

Step (27-1): Recovery of Alkyl Tin Composition Containing 1,1,3,3-tetra-n-butyl-1,3-bis(3-methylbutyloxy)Distannoxane After carrying out the continuous operation of step (A-2) of Reference Example 1 for about 230 hours, the alkyl tin composition containing 1,1,3,3-tetra-n-butyl-1,3-bis(3-methylbutyloxy)distannoxane was extracted from the extraction line 16 at the rate of 18 g/hr, while 1,1,3,3-tetra-n-butyl-1,3-bis(3-methylbutyloxy)distannoxane produced in step (A-1) of Reference Example 1 was supplied from the feed line 17 at the rate of 18 g/hr. When analyzed by $^{119}$Sn-NMR, in addition to containing about 50% by weight of 1,1,3,3-tetra-n-butyl-1,3-bis(3-methylbutyloxy)distannoxane, tri-n-butyl(3-methylbutyloxy)tin along with a plurality of NMR shifts of deactivated components of 1,1,3,3-tetra-n-butyl-1,3-bis(3-methylbutyloxy)distannoxane were observed at −240 to −605 ppm.

Step (27-2): Substituent Exchange Reaction

A reaction was carried out using an apparatus like that shown in FIG. 6.

An alkyl tin composition containing 1,1,3,3-tetra-n-butyl-1,3-bis(3-methylbutyloxy)distannoxane obtained using the same method as step (27-1) was stored in the storage tank 201 instead of the alkyl tin composition containing 1,1,3,3-tetra-n-butyl-1,3-bis(3-methylbutyloxy)distannoxane obtained by the same method as step (13-2) of Example 13. About 3.08 kg of a low boiling point component were recovered from the line 24 by distilling low boiling point components such as unreacted acetic anhydride by carrying out the same method as step (16-1) of Example 16 with the exception of loading 5.96 kg of the alkyl tin composition containing 1,1,3,3-tetra-n-butyl-1,3-bis(3-methylbutyloxy)distannoxane into the stirring tank 204 equipped with a distillation column from the storage tank 201 via the line 21, using 1.66 kg of acetic acid, and using 3.24 kg of acetic anhydride. A residue was obtained in the stirring tank 204. When this residue was sampled and analyzed by $^{119}$Sn- and $^1$H-NMR, the residue was found to contain 46.1% by weight of di-n-butyl tin acetate and 23.0% by weight of tri-n-butyl tin acetate.

Step (27-3): Alkyl Group Redistribution Reaction

Next, a reaction was carried out using an apparatus like that shown in FIG. 6.

A mixture was obtained in the stirring tank 208 containing 87.7% by weight of di-n-butyl tin acetate by carrying out the same method as step (16-2) of Example 16. On the other hand, 0.44 kg of a liquid phase component were recovered in the storage tank 206, and this liquid phase component was transferred to the storage tank 201 via the line 20 and recycled as a raw material of step (27-2).

Step (27-4): Alkoxylation of Dialkyl Tin Compound

Unreacted bis(3-methylbutyl)carbonate was recovered by distillation from the line 28 by carrying out the same method as step (16-3) of Example 16 with the exception of using 11.89 kg of bis(3-methylbutyl)carbonate instead of n-propanol, heating the stirring tank 208 to about 80° C. and carrying out the reaction for about 150 hours. There were about 13.17 kg of the distilled component, and the distilled component contained 67.4% by weight of bis(3-methylbutyl) carbonate and 42.3% by weight of isoamyl acetate.

A residue obtained in the stirring tank 208 was recovered in the storage tank 209 via the line 29. When the recovered product was sampled and analyzed by $^{119}$Sn- and $^1$H-NMR, the recovered product was found to contain 98.4% by weight of di-n-butyl-bis(3-methylbutyloxy)tin.

Example 28

Step (28-1): Recovery of Alkyl Tin Composition Containing 1,1,3,3-tetra-n-butyl-1,3-bis(2-ethylbutyloxy)Distannoxane After carrying out the continuous operation of step (B-2) of Reference Example 2 for about 210 hours, the alkyl tin composition containing 1,1,3,3-tetra-n-butyl-1,3-bis(2-ethylbutyloxy)distannoxane was extracted from the extraction line 16 at the rate of 18 g/hr, while 1,1,3,3-tetra-n-butyl-1,3-bis(2-ethylbutyloxy)distannoxane produced in step (B-1) of Reference Example 1 was supplied from the feed line 17 at the rate of 18 g/hr. When analyzed by $^{119}$Sn-NMR, in addition to containing about 50% by weight of 1,1,3,3-tetra-n-butyl-1,3-bis(2-ethylbutyloxy)distannoxane, tri-n-butyl(2-ethylbutyloxy)tin along with a plurality of NMR shifts of deactivated components of 1,1,3,3-tetra-n-butyl-1,3-bis(2-ethylbutyloxy)distannoxane were observed at −240 to −605 ppm.

Step (28-2): Substituent Exchange Reaction

A reaction was carried out using an apparatus like that shown in FIG. 6.

An alkyl tin composition containing 1,1,3,3-tetra-n-butyl-1,3-bis(2-ethylbutyloxy)distannoxane obtained using the same method as step (28-1) was stored in the storage tank 201 instead of the alkyl tin composition containing 1,1,3,3-tetra-n-octyl-1,3-bis(3-methylbutyloxy)distannoxane obtained by the same method as step (13-2) of Example 13. About 2.75 kg of a low boiling point component were recovered from the line 24 by distilling low boiling point components such as unreacted acetic anhydride by carrying out the same method as step (16-1) of Example 16 with the exception of loading 4.42 kg of a composition of deactivated forms into the stirring tank 204 equipped with a distillation column from the storage tank 201 via the line 21, using 1.43 kg of propionic acid instead of acetic acid, and using 2.94 kg of propionic anhydride instead of acetic anhydride. A residue was obtained in the stirring tank 204. When this residue was sampled and analyzed by $^{119}$Sn- and $^1$H-NMR, the residue was found to contain 45.3% by weight of di-n-butyl-dipropionyloxy tin and 21.8% by weight of tri-n-butyl-propionyloxy tin.

Step (28-3): Alkyl Group Redistribution Reaction

Next, a reaction was carried out using an apparatus like that shown in FIG. 6.

A mixture was obtained in the stirring tank 208 containing 88.4% by weight of di-n-butyl-dipropionyloxy tin by carrying out the same method as step (16-2) of Example 16. On the other hand, 0.32 kg of a liquid phase component were recovered in the storage tank 206, and this liquid phase component was transferred to the storage tank 201 via the line 20 and recycled as a raw material of step (28-2).

Step (28-4): Alkoxylation of Dialkyl Tin Compound

Unreacted bis(2-ethylbutyl)carbonate was recovered by distillation from the line 28 by carrying out the same method as step (16-3) of Example 16 with the exception of using 23.30 kg of bis(2-ethylbutyl)carbonate instead of n-propanol, heating the stirring tank 208 to about 80° C. and carrying out the reaction for about 150 hours. There were about 18.29 kg of the distilled component, and the distilled component contained 79.2% by weight of bis(2-ethylbutyl)carbonate and 16.3% by weight of (2-ethylbutyl)propionate.

A residue obtained in the stirring tank 208 was recovered in the storage tank 209 via the line 29. When the recovered product was sampled and analyzed by $^{119}$Sn- and $^1$H-NMR, the recovered product was found to contain 98.4% by weight of di-n-butyl-bis(2-ethylbutyloxy)tin.

Example 29

Step (29-1): Substituent Exchange Reaction

A reaction was carried out using an apparatus like that shown in FIG. 6.

An alkyl tin composition containing 1,1,3,3-tetra-n-octyl-1,3-bis(2-ethylbutyloxy)distannoxane obtained using the same method as step (15-2) of Example 15 was stored in the storage tank 201 instead of the alkyl tin composition containing 1,1,3,3-tetra-n-octyl-1,3-bis(3-methylbutyloxy)distannoxane obtained by the same method as step (13-2) of Example 13. About 2.09 kg of a low boiling point component were recovered from the line 24 by distilling low boiling point components such as unreacted acetic anhydride by carrying out the same method as step (18-1) of Example 18 with the exception of loading 3.95 kg of an alkyl tin composition containing 1,1,3,3-tetra-n-octyl-1,3-bis(2-ethylbutyloxy)distannoxane into the stirring tank 204 equipped with a distillation column from the storage tank 201 via the line 21, using 0.99 kg of acetic acid, and using 2.19 kg of acetic anhydride. A residue was obtained in the stirring tank 204. When this residue was sampled and analyzed by $^{119}$Sn- and $^1$H-NMR, the residue was found to contain 49.1% by weight of di-n-octyl tin diacetate and 25.5% by weight of tri-n-octyl tin acetate.

Step (29-2): Alkyl Group Redistribution Reaction

Next, a reaction was carried out using an apparatus like that shown in FIG. 6.

A mixture was obtained in the stirring tank 208 containing 89.8% by weight of di-n-octyl tin diacetate by carrying out the same method as step (16-2) of Example 16. On the other hand, 0.30 kg of a liquid phase component were recovered in the storage tank 206, and this liquid phase component was transferred to the storage tank 201 via the line 20 and recycled as a raw material of step (29-1).

Step (29-3): Alkoxylation of Dialkyl Tin Compound

Unreacted ethanol was recovered by distillation from the line 28 by carrying out the same method as step (16-3) of Example 16 with the exception of using 14.85 kg of ethanol instead of n-propanol, heating the stirring tank 208 to about 80° C. and carrying out the reaction for about 150 hours. There were about 15.08 kg of the distilled component, and the distilled component contained 87.4% by weight of ethanol and 10.4% by weight of ethyl acetate.

A residue obtained in the stirring tank 208 was recovered in the storage tank 209 via the line 29. When the recovered product was sampled and analyzed by $^{119}$Sn- and $^1$H-NMR, the recovered product was found to contain 91.1% by weight of di-n-octyl-diethoxy tin.

Step (29-4): Production of Carbonic Acid Ester

Carbonic acid ester was produced in a continuous production apparatus like that shown in FIG. 7.

The mixture containing 91.1% by weight of di-n-octyl-diethoxy tin obtained in step (29-3) was fed to the autoclave 401 via the line 41 at the rate of 5073 g/hr. Carbon dioxide was supplied to the autoclave from the line 42 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the di-n-octyl-diethoxy tin was carried out to obtain a reaction liquid containing diethyl carbonate. This reaction liquid was transferred to the decarbonization tank 402 via the line 43 and a control valve at the rate of 6129 g/hr to remove residual carbon dioxide, and the carbon dioxide was recovered from the line 44. Subsequently, the reaction liquid was transferred to the thin film evaporator 403 set to about 150° C. and about 0.5 kPa via the line 45 to obtain a fraction containing diethyl carbonate. The fraction containing diethyl carbonate was supplied to the distillation column 406 packed with Metal Gauze CY Packing and equipped with the reboiler 408 and the condenser 407 via the condenser 405 and the line 47 followed by distillative purification. 99% by weight of diethyl carbonate was obtained from the line 49 at the rate of 1165 g/hr. On the other hand, a liquid phase component separated in the thin film evaporator 403 was recovered in the storage tank 404 via the line 46. When this liquid phase component was sampled and analyzed by $^{119}$Sn- and $^1$H-NMR, the liquid phase component was found to be a mixture containing about 98% by weight of 1,1,3,3-tetra-n-octyl-1,3-diethoxy distannoxane.

Comparative Example 1

Step (I-1): Substituent Exchange Reaction 390 g of the alkyl tin composition containing 1,1,3,3-tetra-n-octyl-1,3-bis(3-methylbutyloxy)distannoxane obtained in step (13-2) of Example 13 were placed on a 1 L eggplant-shaped flask in a nitrogen atmosphere followed by the addition of 106 g of acetic acid and 361 g of acetic anhydride and stirring for 1 hour at 25° C. A fractionation head equipped with a reflux condenser connected to a distillate collector and a thermometer which were attached to the flask, and after replacing the inside of the flask with nitrogen in a vacuum, the flask was immersed in an oil bath heated to 50° C. The pressure inside the vessel was gradually reduced and excess acetic acid, acetic anhydride and the like were distilled off to obtain 410 g of a residue in the flask. When the residue was measured by $^1$H- and $^{119}$Sn-NMR, the residue was found to be a mixture of tri-n-octyl acetoxy tin, di-n-octyl diacetoxy tin and organic tin compounds containing tin atoms demonstrating a plurality of chemical shifts of −240 to −605 ppm in $^{119}$Sn-NMR. This mixture contained 27.9% by weight of tri-n-octyl acetoxy tin and 49.9% by weight of di-n-octyl diacetoxy tin.

Step (I-2): Alkyl Group Redistribution Reaction 408 g of the mixture obtained in step (1-2) were placed in a 500 mL metal pressure vessel in a nitrogen atmosphere. The metal pressure vessel was immersed in an oil bath heated to 200° C. and heated for 3 hours. After allowing the metal pressure vessel to cool to the vicinity of room temperature, the reaction liquid was recovered. When $^1$H- and $^{119}$Sn-NMR measurement were carried out on the reaction liquid, the reaction liquid was determined to be a mixture of organic tin compounds containing di-n-octyl diacetoxy tin and tri-n-octyl acetoxy tin, and contained 91.5% by weight of di-n-octyl-diacetoxy tin and about 5% by weight of tri-n-octyl acetoxy tin.

Step (I-3): Alkoxylation of Dialkyl Tin Compound 405 g of the mixture obtained in step (I-2) were placed in a 1 L volumetric eggplant-shaped flask followed by immersing the flask in an oil bath heated to 50° C. A white precipitate formed when 500 mL of 0.1 mol/L aqueous potassium hydroxide solution (Wako Pure Chemical Industries, Ltd.) were added while stirring the contents thereof. The mixture was filtered with filter paper, and the filtration residue was dried at 80° C. to recover 302 g of a white precipitate. This white precipitate was dioctyl tin oxide.

300 g of the white precipitate and 1836 g of 3-methyl-1-butanol were placed in a 3 L volumetric eggplant-shaped flask. The flask was attached to a rotary evaporator to which was connected an oil bath equipped with a temperature controller, a vacuum pump and a vacuum controller. The purge valve outlet of the rotary evaporator was connected to a line containing nitrogen gas flowing at atmospheric pressure. After replacing the inside of the system with nitrogen, the temperature of the oil bath was set to be 146° C., the flask was immersed in the oil bath and rotation of the rotary evaporator was started. After distilling off a low boiling point component for about 7 hours in the presence of nitrogen at atmospheric pressure with the purge valve of the rotary evaporator open, the pressure inside the system was gradually reduced, and the remaining low boiling point component was distilled off at an internal pressure of 76 to 30 kPa. Once distillation of the low boiling point component was no longer observed, the flask was taken out of the oil bath and allowed to cool. 366 g of a residue liquid were obtained in the flask. Based on the results of $^1$H-, $^{13}$C- and $^{119}$Sn-NMR analyses, the content of 1,1,3,3-tetra-n-octyl-1,3-bis(3-methylbutyloxy)distannoxane in the residue liquid in the flask was found to be 96.4% by weight.

Although 1,1,3,3-tetra-n-octyl-1,3-bis(3-methylbutyloxy)distannoxane was obtained by reacting di-n-octyl-diacetoxy tin and aqueous alkaline solution (aqueous potassium hydroxide solution) instead of directly reacting the di-n-octyl-diacetoxy tin obtained in step (I-2) with 3-methyl-1-butanol in step (I-3) to obtain dioctyl tin oxide, followed by reacting the dioctyl tin oxide with 3-methyl-1-butanol, since the dioctyl tin oxide was a solid thereby requiring the procedure of recovering the solid by filtration, the procedure is excessively complex in terms of industrial application.

Comparative Example 2

Step (II-1): Reaction of Tetrakis(Dimethylamino)Tin and Carbonic Acid Ester 290 g of tetrakis(dimethylamino)tin (Gelest Corp., USA) and 1010 g of the bis(3-methylbutyl)carbonate produced in step (A-2) of Reference Example 1 were placed in a 2 L volumetric eggplant-shaped flask in a nitrogen atmosphere at atmospheric pressure, and a Dimroth condenser and three-way valve were attached to the flask. The flask was immersed in an oil bath heated to 150° C. and heated for 5 hours while stirring the contents thereof. The flask was attached to a rotary evaporator to which was connected an oil bath equipped with a temperature controller, a vacuum pump and a vacuum controller. The purge valve outlet of the rotary evaporator was connected to a line containing nitrogen gas flowing at atmospheric pressure. After replacing the inside of the system with nitrogen, the temperature of the oil bath was set to be 150° C., the flask was immersed in the oil bath and rotation of the rotary evaporator was started. A low boiling point component was distilled off for about 7 hours in the presence of nitrogen at atmospheric pressure with the purge valve of the rotary evaporator left open, after which the pressure in the system was gradually reduced, and residual low boiling point component was distilled off with the pressure inside the system at 76 to 10 kPa. When the low boiling point component fraction no longer appeared, the flask was removed from the oil bath and allowed to cool. 292 g of residual liquid were obtained in the flask. Based on the results of $^1$H-, $^{13}$C- and $^{119}$Sn-NMR analyses, the residual liquid in the flask was a solution containing 98.0% by weight of tetrakis(dimethylamino)tin, and tin alkoxide was not obtained.

Comparative Example 3

Step (III-1): Reaction of Tetrakis(Dimethylamino)Tin and Alcohol 285 g of tetrakis(dimethylamino)tin and 1320 g of the 3-methyl-1-butanol were placed in a 2 L volumetric eggplant-shaped flask in a nitrogen atmosphere at atmospheric pressure, and a Dimroth condenser and three-way valve were attached to the flask. The flask was immersed in an oil bath heated to 135° C. and heated for 5 hours while stirring the contents thereof. The flask was attached to a rotary evaporator to which was connected an oil bath equipped with a temperature controller, a vacuum pump and a vacuum controller. The purge valve outlet of the rotary evaporator was connected to a line containing nitrogen gas flowing at atmospheric pressure. After replacing the inside of the system with nitrogen, the temperature of the oil bath was set to be 150° C., the flask was immersed in the oil bath and rotation of the rotary evaporator was started. A low boiling point component was distilled off for about 7 hours in the presence of nitrogen at atmospheric pressure with the purge valve of the rotary evaporator left open, after which the pressure in the system was gradually reduced, and residual low boiling point component was distilled off with the pressure inside the system at 76 to 10 kPa. When the low boiling point component fraction no longer appeared, the flask was removed from the oil bath and allowed to cool. 288 g of residual liquid were obtained in the flask. Based on the results of $^1$H-, $^{13}$C- and $^{119}$Sn-NMR analyses, the residual liquid in the flask was a solution containing 98.0% by weight of tetrakis(dimethylamino)tin, and tin alkoxide was not obtained.

INDUSTRIAL APPLICABILITY

The process for producing a dialkyl tin dialkoxide compound and/or tetraalkyl dialkoxy distannoxane compound of the present embodiment (Step (Z)) enables the production of a dialkyl tin dialkoxy compound and/or tetraalkyl dialkoxy distannoxane compound without involving the handling of solid tin compounds by reacting a dialkyl tin compound and/or a tetraalkyl distannoxane compound with an acid and/or acid anhydride, thereby making it a more convenient production process than conventional processes.

In addition, as was previously described, the step (Z) can be used as a portion of novel carbonic acid ester production processes by combining various steps with the step (Z). Since these novel carbonic acid ester production processes include a step for regenerating a monoalkyl tin alkoxide compound and trialkyl tin alkoxide, which are formed in these carbonic acid ester production processes and which have lost catalytic activity during the course of carbonic acid ester synthesis, into a dialkyl tin dialkoxide compound and/or tetraalkyl dialkoxy distannoxane compound, problems of costs and waste in the production process of carbonic acid ester can be solved. Thus, the present invention is industrially extremely important.

DESCRIPTION OF REFERENCE NUMERALS (In FIG. 5)
101, 107: distillation column
102: column-type reactor
103, 106: thin film evaporator
104: autoclave
105: decarbonization tank
121, 123, 126, 127: condenser
111, 112, 117: reboiler
1, 2, 3, 4, 5, 6, 7, 8, 9, 10, 11, 12, 13, 14, 15, 16, 17: line
(In FIG. 6)
201, 202, 203, 206, 209, 210, 211: storage tank
204, 208: stirring tank equipped with a distillation column
205: thin film evaporator
207: condenser
20, 21, 22, 23, 24, 25, 26, 27, 28, 29, 30, 31: line
(In FIG. 7)
401: autoclave
402: decarbonization tank
403: thin film evaporator
404, 409: storage tank
406: distillation column
405, 407: condenser
408: reboiler
41, 42, 43, 44, 45, 46, 47, 48, 49, 50, 51, 52, 53, 54, 55, 56: line
(In FIG. 8)
601, 614: distillation column
604: column-type reactor
606, 610: thin film evaporator
608: autoclave
609: decarbonization tank
615, 617: storage tank
616: stirring tank equipped with a distillation column
602, 605, 611, 612: condenser
603, 605, 613: reboiler
61, 62, 63, 64, 65, 66, 67, 68, 69, 70, 71, 72, 73, 74, 75, 76, 77, 78, 79: line

We claim:

1. A process for producing a compound represented by $XOR^2$;
   a dialkyl tin dialkoxide compound having one tin atom, two Sn—$R^1$ bonds and two Sn—$OR^2$ bonds; and/or
   a tetraalkyl dialkoxy distannoxane compound having one Sn—O—Sn bond, in which each tin atom of the tetraalkyl dialkoxy distannoxane compound has two Sn—$R^1$ bonds and one Sn—$OR^2$ bond,
   comprising reacting in the absence of a catalyst at least one alkyl tin compound selected from the group consisting of i) and ii) below:
   i) a dialkyl tin compound having one tin atom, two Sn—$R^1$ (wherein $R^1$ represents an alkyl group) bonds, and two Sn—OX bonds (wherein OX is a group in which HOX that is a conjugate acid of OX is a Bronsted acid having a pKa of from 0 to 6.8); and
   ii) a tetraalkyl distannoxane compound having one Sn—O—Sn bond, in which each tin atom of the tetraalkyl distannoxane compound has two Sn—$R^1$ bonds and one Sn—OX bond (wherein OX is a group in which HOX that is a conjugate acid of OX is a Bronsted acid having a pKa of from 0 to 6.8); and
   a carbonic acid ester represented by $R^2OCOOR^2$ (wherein $R^2$ represents a linear or branched, saturated or unsaturated hydrocarbon group, a hydrocarbon group having a saturated or unsaturated cyclic hydrocarbon substituent, or a Y—$CH_2$— group (wherein Y represents an alkyl polyalkylene group, an aromatic group or a cyclic saturated or unsaturated alkylene ether group)), and/or
   an alcohol represented by $R^2OH$ (wherein $R^2$ is the same as defined above).

2. The process according to claim 1, wherein, in the carbonic acid ester $R^2OCOOR^2$ and/or the alcohol $R^2OH$, $R^2$ represents a linear or branched, saturated or unsaturated hydrocarbon group, or a hydrocarbon group having an unsaturated or saturated cyclic hydrocarbon substituent.

3. The process according to claim 2, wherein, in the carbonic dialkyl ester $R^2OCOOR^2$ and/or the alcohol $R^2OH$, $R^2$ represents a linear or branched alkyl group having 1 to 8 carbon atoms.

4. The process according to claim 1, wherein the dialkyl tin compound is a compound represented by the following formula (1):

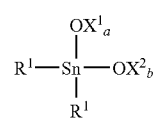

(1)

(wherein each of $R^1$ independently represents a linear or branched alkyl group having 1 to 12 carbon atoms,
O represents an oxygen atom,
$OX^1$ and $OX^2$ are $OX^1$ and $OX^2$ in which $HOX^1$ and $HOX^2$ that are conjugate acids of $OX^1$ and $OX^2$ are Bronsted acids having a pKa of from 0 to 6.8, and
a and b are integers of from 0 to 2, respectively, and a+b=2).

5. The process according to claim 1, wherein the tetraalkyl distannoxane compound is a compound represented by the following formula (2):

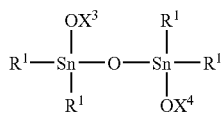

(2)

(wherein each of $R^1$ independently represents a linear or branched alkyl group having 1 to 12 carbon atoms,
O represents an oxygen atom, and
$OX^3$ and $OX^4$ are $OX^3$ and $OX^4$ in which $HOX^3$ and $HOX^4$ that are conjugate acids of $OX^3$ and $OX^4$ are Bronsted acids having a pKa of from 0 to 6.8).

6. The process according to claim 1, wherein the group OX represents an acyloxyl group.

7. The process according to claim 1, wherein the reaction of the dialkyl tin compound and/or the tetraalkyl distannoxane compound and the carbonic acid ester and/or the alcohol is carried out at a temperature of from 20 to 250° C.

8. The process according to claim 1, wherein the dialkyl tin dialkoxide compound is a compound represented by the following formula (3):

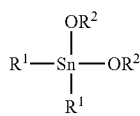

(3)

(wherein each of $R^1$ independently represents a linear or branched alkyl group having 1 to 12 carbon atoms, which is derived from a dialkyl tin compound and/or a tetraalkyl distannoxane compound, and each of $R^2$ independently represents a linear or branched, unsaturated or saturated hydrocarbon group, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group), which is derived from a carbonic acid ester and/or an alcohol).

9. The process according to claim 1, wherein the tetraalkyl dialkoxy distannoxane compound is a compound represented by the following formula (4):

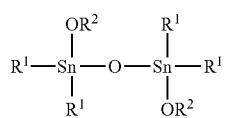

(4)

(wherein each of $R^1$ independently represents a linear or branched alkyl group having 1 to 12 carbon atoms, which is derived from a dialkyl tin compound and/or a tetraalkyl distannoxane compound, and each of $R^2$ independently represents a linear or branched, unsaturated or saturated hydrocarbon group, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group), which is derived from a carbonic acid ester and/or an alcohol).

10. The process according to claim 1, wherein the dialkyl tin compound and/or the tetraalkyl distannoxane compound are compounds produced according to a process which comprises:

a step (1) of reacting an alkyl tin composition, containing a monoalkyl tin alkoxide compound and a trialkyl tin alkoxide compound, which are produced by a disproportionation reaction of at least one alkyl tin alkoxide compound selected from the group consisting of a dialkyl tin dialkoxide compound having one tin atom, two Sn—$R^1$ bonds and two Sn—$OR^2$ bonds and/or a tetraalkyl dialkoxy distannoxane compound having one Sn—O—Sn bond, in which each tin atom of the tetraalkyl distannoxane compound has two Sn—$R^1$ bonds and one Sn—$OR^2$ bond, (wherein the number of two $R^1$ groups bound to tin is disproportionated between two molecules in the case of a dialkyl tin alkoxide compound, or disproportionated intramolecularly and/or intermolecularly in the case of a tetraalkyl dialkoxy distannoxane compound, so as to convert to a monoalkyl tin alkoxide compound having one Sn—$R^1$ bond and a trialkyl tin alkoxide compound having three Sn—$R^1$ bonds) with an acid represented by the general formula HOX (Bronsted acid having a pKa of from 0 to 6.8) and/or an acid anhydride represented by the general formula XOX (wherein OX represents a group in which HOX that is a conjugate acid of OX is a Bronsted acid having a pKa of from 0 to 6.8), so as to produce a mixture of organic tin compounds having a group (OX group), which is derived from the acid and/or the acid anhydride; and a step (2) of carrying out an alkyl group redistribution reaction by heat-treating the mixture of the organic tin compounds obtained in step (1), so as to obtain from the monoalkyl tin alkoxide compound and the trialkyl tin alkoxide compound in the alkyl tin composition at least one alkyl tin compound selected from the group consisting of:

i) a dialkyl tin compound having one tin atom, the one tin atom having two Sn—$R^1$ (wherein $R^1$ represents an alkyl group) bonds, and two Sn—OX bonds (wherein OX is a group in which HOX that is a conjugate acid of OX is a Bronsted acid having a pKa of from 0 to 6.8), and ii) a tetraalkyl distannoxane compound having one Sn—O—Sn bond, in which each tin atom of the tetraalkyl distannoxane compound has two Sn—$R^1$ bonds and one Sn—OX bond (wherein OX is a group in which HOX that is a conjugate acid of OX is a Bronsted acid having a pKa of from 0 to 6.8); provided that, $R^1$ which directly bound to tin of the dialkyl tin compound, the tetraalkyl distannoxane compound, the dialkyl tin dialkoxide compound, the tetraalkyl dialkoxy distannoxane compound, the monoalkyl tin alkoxide compound and the trialkyl tin alkoxide, is the same alkyl group.

11. The process according to claim 10, wherein the alkyl tin composition is an alkyl tin composition formed during the production of the carbonic acid ester obtained by sequentially carrying out:

a step (a) of obtaining a reaction liquid containing a carbonic acid ester and the tetraalkyl dialkoxy distannoxane represented by the following general formula (6) and/or a conjugate of the tetraalkyl dialkoxy distannoxane and carbon dioxide by reacting the dialkyl tin dialkoxide represented by the following general formula (5) and carbon dioxide:

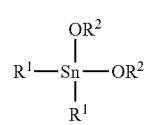

(5)

(wherein each of $R^1$ independently represents a linear or branched alkyl group having 1 to 12 carbon atoms, and each of $R^2$ independently represents a linear or branched, unsaturated or saturated hydrocarbon group, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group));

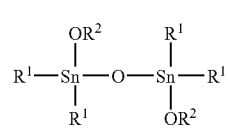

(6)

(wherein $R^1$ represents a linear or branched alkyl group having 1 to 12 carbon atoms, and $R^2$ represents a linear or branched, unsaturated or saturated hydrocarbon group, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group));

a step (b) of obtaining a residual liquid containing the tetraalkyl dialkoxy distannoxane and/or a conjugate of the tetraalkyl dialkoxy distannoxane and carbon dioxide by separating the carbonic acid ester from the reaction liquid by distillation; and a step (c) of reacting the residual liquid with an alcohol represented by the following general formula (7), so as to remove a water formed as a by-product to regenerate the dialkyl tin dialkoxide, and using the dialkyl tin dialkoxide as the dialkyl tin dialkoxide of step (a):

WOH     (7)

(wherein W represents a linear or branched, unsaturated or saturated hydrocarbon groups, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group)).

12. The process according to claim 11, wherein the step for carrying out the process according to claim 10 for regenerating the dialkyl tin dialkoxide and/or tetraalkyl dialkoxy distannoxane from the alkyl tin composition formed during the production of the carbonic acid ester is carried out after step (b) and/or step (c) according to claim 11, and uses the regenerated dialkyl tin dialkoxide and/or tetraalkyl dialkoxy distannoxane as the dialkyl tin dialkoxide of step (a), and as the raw material of step (c) by mixing with the residual liquid of step (b).

13. A process for producing a carbonic acid ester comprising following steps (A) to (B) further into the process according to claim 1:

step (A): obtaining a reaction liquid containing a carbonic acid ester and a tetraalkyl dialkoxy distannoxane compound and/or a conjugate of the tetraalkyl dialkoxy distannoxane compound and carbon dioxide by reacting the dialkyl tin dialkoxide compound and/or tetraalkyl dialkoxy distannoxane compound according to claim 1 with carbon dioxide; and step (B): obtaining a residual liquid containing a tetraalkyl dialkoxy distannoxane and/or a conjugate of the tetraalkyl dialkoxy distannoxane and carbon dioxide by separating the carbonic acid ester from the reaction liquid by distillation.

14. A process for producing the carbonic acid ester further comprising a following step (C) into the process according to claim 13 and using an alkyl tin compound produced in the step (C) for the alkyl tin compound according to claim 1:

step (C): producing at least one alkyl tin compound selected from the group consisting of the following i) and ii) by reacting the residual liquid of the step (B) with an acid represented by the general formula HOX (Bronsted acid having a pKa of from 0 to 6.8) and/or an acid anhydride represented by the general formula XOX (wherein OX represents a group in which HOX that is a conjugate acid of OX is a Bronsted acid having a pKa of from 0 to 6.8);

i) a dialkyl tin compound having one tin atom, two Sn—R$^1$ (wherein R$^1$ represents an alkyl group), and two Sn—OX bonds (wherein OX is a group in which HOX that is a conjugate acid of OX is a Bronsted acid having a pKa of from 0 to 6.8); and ii) a tetraalkyl distannoxane compound having one Sn—O—Sn bond, in which each tin atom of the tetraalkyl distannoxane compound has two Sn—R$^1$ bonds and one Sn—OX bond (wherein OX is a group in which HOX that is a conjugate acid of OX is a Bronsted acid having a pKa of from 0 to 6.8).

15. The process according to claim 1, wherein the dialkyl tin compound and/or the tetraalkyl distannoxane compound are compounds produced according to a process comprising:

a step (I) of reacting a dialkyl tin dialkoxide represented by the following general formula (8) with carbon dioxide, so as to obtain a reaction liquid containing carbonic acid ester and a tetraalkyl dialkoxy distannoxane represented by the following general formula (9) and/or a conjugate of the tetraalkyl dialkoxiy distannoxane and carbon dioxide;

(8)

(wherein each of R$^1$ independently represents a linear or branched alkyl group having 1 to 12 carbon atoms, and each of R$^2$ independently represents a linear or branched, unsaturated or saturated hydrocarbon group, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group));

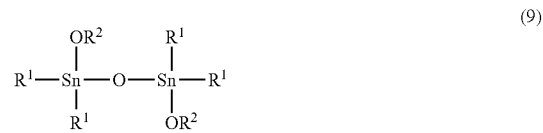

(9)

(wherein each of R$^1$ independently represents a linear or branched alkyl group having 1 to 12 carbon atoms, and each of R$^2$ independently represents a linear or branched, unsaturated or saturated hydrocarbon group, a hydrocarbon group having a saturated or unsaturated cyclic hydrocarbon substituent, or a Y—CH$_2$— group (wherein Y represents an alkyl polyalkylene group, an aromatic group, or a cyclic saturated or unsaturated alkylene ether group));

a step (II) of separating the carbonic acid ester from the reaction liquid by distillation so as to obtain a residual liquid containing the tetraalkyl dialkoxy distannoxane and/or a conjugate of the tetraalkyl dialkoxy distannoxane and carbon dioxide; and a step (III) of reacting the residual liquid of the step (II) with an acid represented by the general formula HOX (Bronsted acid having a pKa of from 0 to 6.8) and/or acid anhydride represented by the general formula XOX (wherein OX represents a group in which HOX that is a conjugate acid of OX is a Bronsted acid having a pKa of from 0 to 6.8), so as to produce a compound having a group (OX group), which is derived from the acid and/or the acid anhydride, and which is a dialkoxy tin compound represented by the following general formula (10) and/or a tetraalkyl distannoxane compound represented by the following general formula (11):

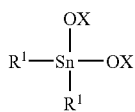

(10)

(wherein
each of $R^1$ independently represents a linear or branched alkyl group having 1 to 12 carbon atoms,
O represents an oxygen atom, and
OX represents a group OX in which HOX that is a conjugate acid of OX is a Bronsted acid having a pKa of from 0 to 6.8);

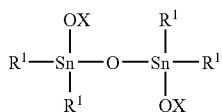

(11)

(wherein each of $R^1$ independently represents a linear or branched alkyl group having 1 to 12 carbon atoms,
O represents an oxygen atom, and
OX represents a group OX in which HOX that is a conjugate acid of OX is a Bronsted acid having a pKa of from 0 to 6.8).

16. The process according to claim 1, wherein the alkyl group $R^1$ represents a linear alkyl group having 1 to 8 carbon atoms.

17. The process according to claim 16, wherein the alkyl group $R^1$ represents an n-butyl group or an n-octyl group.

18. The process according to claim 10, wherein the acid HOX represents a carboxylic acid.

19. The process according to claim 18, wherein the carboxylic acid is selected from the group consisting of acetic acid, propionic acid and maleic acid.

20. The process according to claim 10, wherein the acid anhydride XOX represents an acid anhydride selected from the group consisting of acetic anhydride, propionic anhydride and maleic anhydride.

* * * * *